US012577255B2

(12) United States Patent
Crew et al.

(10) Patent No.: US 12,577,255 B2
(45) Date of Patent: Mar. 17, 2026

(54) MDM2-BASED MODULATORS OF PROTEOLYSIS AND ASSOCIATED METHODS OF USE

(71) Applicant: Arvinas Operations, Inc., New Haven, CT (US)

(72) Inventors: Andrew P. Crew, Chester, CT (US); Craig M. Crews, New Haven, CT (US); Hanqing Dong, Madison, CT (US); Yimin Qian, Plainsboro, NJ (US); Jing Wang, Milford, CT (US)

(73) Assignee: Arvinas Operations, Inc., New Haven, CT (US)

( * ) Notice: Subject to any disclaimer, the term of this patent is extended or adjusted under 35 U.S.C. 154(b) by 969 days.

(21) Appl. No.: 17/570,197

(22) Filed: Jan. 6, 2022

(65) Prior Publication Data

US 2022/0127279 A1 Apr. 28, 2022

Related U.S. Application Data

(63) Continuation of application No. 15/206,497, filed on Jul. 11, 2016, now abandoned.

(60) Provisional application No. 62/191,193, filed on Jul. 10, 2015.

(51) Int. Cl.

| | |
|---|---|
| ***C07D 495/14*** | (2006.01) |
| ***A61K 31/337*** | (2006.01) |
| ***A61K 31/4184*** | (2006.01) |
| ***A61K 31/436*** | (2006.01) |
| ***A61K 31/4545*** | (2006.01) |
| ***A61K 31/4995*** | (2006.01) |
| ***A61K 31/506*** | (2006.01) |
| ***A61K 31/593*** | (2006.01) |
| ***A61K 31/664*** | (2006.01) |
| ***A61K 31/704*** | (2006.01) |
| ***A61K 45/06*** | (2006.01) |
| ***A61K 47/55*** | (2017.01) |
| ***C07D 207/16*** | (2006.01) |
| ***C07D 401/12*** | (2006.01) |
| ***C07D 401/14*** | (2006.01) |
| ***C07D 405/14*** | (2006.01) |
| ***C07D 417/12*** | (2006.01) |

(52) U.S. Cl.

CPC .......... *C07D 495/14* (2013.01); *A61K 31/337* (2013.01); *A61K 31/4184* (2013.01); *A61K 31/436* (2013.01); *A61K 31/4545* (2013.01); *A61K 31/4995* (2013.01); *A61K 31/506* (2013.01); *A61K 31/593* (2013.01); *A61K 31/664* (2013.01); *A61K 31/704* (2013.01); *A61K 45/06* (2013.01); *A61K 47/55* (2017.08); *C07D 207/16* (2013.01); *C07D 401/12* (2013.01); *C07D 401/14* (2013.01); *C07D 405/14* (2013.01); *C07D 417/12* (2013.01)

(58) Field of Classification Search

CPC .................................................. C07D 495/14

USPC ........................................................ 514/183

See application file for complete search history.

(56) References Cited

U.S. PATENT DOCUMENTS

| | | | |
|---|---|---|---|
| 6,306,663 | B1 | 10/2001 | Kenten et al. |
| 6,670,348 | B1 | 12/2003 | Rosen et al. |
| 7,041,298 | B2 | 5/2006 | Deshaies et al. |
| 7,208,157 | B2 | 4/2007 | Sakamoto et al. |
| 7,915,293 | B2 | 3/2011 | Ramesh |
| 9,500,653 | B2 | 11/2016 | Crews et al. |
| 9,632,089 | B2 | 4/2017 | Crews et al. |
| 2008/0214501 | A1 | 9/2008 | Zhengying et al. |
| 2010/0286127 | A1 | 11/2010 | Miyoshi |
| 2012/0270800 | A1 | 10/2012 | Verdine et al. |
| 2014/0088143 | A1 | 3/2014 | Jain |
| 2014/0235629 | A1 | 8/2014 | Bartberger et al. |
| 2014/0243372 | A1 | 8/2014 | Rew |
| 2014/0256700 | A1 | 9/2014 | Poss |

(Continued)

FOREIGN PATENT DOCUMENTS

| | | |
|---|---|---|
| EP | 2985285 | 2/2016 |
| JP | 2009-517439 | 4/2009 |

(Continued)

OTHER PUBLICATIONS

Ding et al., Discovery of RG7388, a Potent and Selective p53-MDM2 Inhibitor in Clinical Development, Journal of Medicinal Chemistry, 2013, vol. 56, pp. 5979-5983 (Year: 2013).*

(Continued)

*Primary Examiner* — Jeffrey H Murray

*Assistant Examiner* — Rilla Marie Samsell

(74) *Attorney, Agent, or Firm* — McCarter & English, LLP; Michael J. DeGrazia; James M. Alburger

(57) ABSTRACT

The description relates to MDM2 binding compounds, including bifunctional compounds comprising the same, which find utility as modulators of targeted ubiquitination, especially inhibitors of a variety of polypeptides and other proteins which are degraded and/or otherwise inhibited by bifunctional compounds according to the present invention. In particular, the description provides compounds, which contain on one end a ligand which binds to the MDM2 E3 ubiquitin ligase and on the other end a moiety which binds a target protein such that the target protein is placed in proximity to the ubiquitin ligase to effect degradation (and inhibition) of that protein. Compounds can be synthesized that exhibit a broad range of pharmacological activities consistent with the degradation/inhibition of targeted polypeptides of nearly any type.

4 Claims, 6 Drawing Sheets

(56) References Cited

U.S. PATENT DOCUMENTS

| | | | |
|---|---|---|---|
| 2014/0302523 | A1 | 10/2014 | Crews et al. |
| 2014/0356322 | A1 | 12/2014 | Crews et al. |
| 2014/0371206 | A1 | 12/2014 | Albrecht et al. |
| 2015/0119435 | A1 | 4/2015 | Crews et al. |
| 2015/0141470 | A1 | 5/2015 | Garraway et al. |
| 2015/0148342 | A1 | 5/2015 | Combs et al. |
| 2015/0225381 | A1 | 8/2015 | Lu |
| 2015/0259288 | A1 | 9/2015 | Nam et al. |
| 2015/0291562 | A1 | 10/2015 | Crew et al. |
| 2015/0344473 | A1 | 12/2015 | Du et al. |
| 2016/0022642 | A1 | 1/2016 | Crews et al. |
| 2016/0045607 | A1 | 2/2016 | Crew et al. |
| 2016/0058872 | A1 | 3/2016 | Crew et al. |
| 2016/0136230 | A1 | 5/2016 | Campos et al. |
| 2016/0176864 | A1 | 6/2016 | Norris et al. |
| 2016/0214972 | A1 | 7/2016 | Jin et al. |
| 2016/0272639 | A1 | 9/2016 | Crew et al. |
| 2016/0368911 | A1 | 12/2016 | Campos et al. |
| 2017/0008904 | A1 | 1/2017 | Crew et al. |
| 2017/0037004 | A1 | 2/2017 | Crew et al. |
| 2017/0065719 | A1 | 3/2017 | Qian et al. |
| 2017/0121321 | A1 | 5/2017 | Crews et al. |
| 2017/0281784 | A1 | 10/2017 | Wang et al. |
| 2017/0307614 | A1 | 10/2017 | Crews et al. |
| 2017/0327469 | A1 | 11/2017 | Crew et al. |
| 2018/0015087 | A1 | 1/2018 | Liu et al. |
| 2018/0072711 | A1 | 3/2018 | Crew et al. |
| 2018/0099940 | A1 | 4/2018 | Crew et al. |
| 2018/0125821 | A1 | 5/2018 | Crew et al. |
| 2018/0147202 | A1 | 5/2018 | Crew et al. |
| 2018/0155322 | A1 | 6/2018 | Crew et al. |
| 2018/0177750 | A1 | 6/2018 | Crew et al. |
| 2018/0179183 | A1 | 6/2018 | Crew et al. |
| 2018/0193470 | A1 | 7/2018 | Crew et al. |
| 2018/0215731 | A1 | 8/2018 | Crew et al. |
| 2018/0228907 | A1 | 8/2018 | Crew et al. |
| 2018/0237418 | A1 | 8/2018 | Crew et al. |
| 2018/0256586 | A1 | 9/2018 | Crew et al. |

FOREIGN PATENT DOCUMENTS

| | | |
|---|---|---|
| WO | WO 2002/066512 | 8/2002 |
| WO | WO 2006/113942 | 10/2006 |
| WO | WO 2007/115289 | 10/2007 |
| WO | WO 2010/107485 | 9/2010 |
| WO | WO 2011/008260 A2 | 1/2011 |
| WO | WO 2011/143660 | 11/2011 |
| WO | WO 2011/143669 A2 | 11/2011 |
| WO | WO 2012/003281 | 1/2012 |
| WO | WO 2012/007409 | 1/2012 |
| WO | WO 2012/040389 | 3/2012 |
| WO | WO 2012/040527 | 3/2012 |
| WO | WO 2012/078559 | 6/2012 |
| WO | WO 2012/090104 | 7/2012 |
| WO | WO 2013/106643 | 7/2013 |
| WO | WO 2013/106646 | 7/2013 |
| WO | WO 2013/170147 | 11/2013 |
| WO | WO 2013/175417 | 11/2013 |
| WO | WO 2013/178570 A1 | 12/2013 |
| WO | WO 2014/001356 | 1/2014 |
| WO | WO 2014/020502 | 2/2014 |
| WO | WO 2014/038606 | 3/2014 |
| WO | WO 2014/100065 | 6/2014 |
| WO | WO 2014/100071 | 6/2014 |
| WO | WO 2014/107713 | 7/2014 |
| WO | WO 2014/108452 | 7/2014 |
| WO | WO 2014/123418 | 8/2014 |
| WO | WO 2014/128111 | 8/2014 |
| WO | WO 2014/134201 | 9/2014 |
| WO | WO 2014/151863 | 9/2014 |
| WO | WO 2015/000868 | 1/2015 |
| WO | WO 2015/006524 | 1/2015 |
| WO | WO 2015/011084 | 1/2015 |
| WO | WO 2015/022332 | 2/2015 |
| WO | WO 2015/015318 | 5/2015 |
| WO | WO 2015/067770 | 5/2015 |
| WO | WO 2015/074064 | 5/2015 |
| WO | WO 2015/097621 | 7/2015 |
| WO | WO 2015/160845 | 10/2015 |
| WO | WO 2015/195863 | 12/2015 |
| WO | WO 2016/050821 | 4/2016 |
| WO | WO 2016/069578 | 5/2016 |
| WO | WO 2016/118666 | 7/2016 |
| WO | WO 2016/146985 | 9/2016 |
| WO | WO 2016/172134 | 10/2016 |
| WO | WO 2016/197114 | 12/2016 |
| WO | WO 2017/011590 | 1/2017 |
| WO | WO 2017/024318 A1 | 2/2017 |
| WO | WO 2017/024319 A1 | 2/2017 |
| WO | WO 2017/030814 | 2/2017 |
| WO | WO 2017 /079267 | 5/2017 |
| WO | WO 2017/176957 | 10/2017 |
| WO | WO 2017/185036 | 10/2017 |

OTHER PUBLICATIONS

Schneekloth et al., Targeted intracellular protein degradation induced by a small molecule: En route to chemical proteomics, Bioorganic & Medicinal Chemistry Letters, 2008, vol. 18, pp. 5904-5908 (Year: 2008).*

Albrecht, B., et al., "Identification of a benzoisoxazoloazepine inhibitor (CPI-0610) of the bromodomain and extra-terminal (BETA) family as a candidate for human clinical trials", Journal Med. Chem. 59, 1330-1339 (2016).

Allan, GF, et. al., "Therapeutic androgen receptor ligands", Nuclear Receptor Signaling, 2003, 1, e009 DOI:10.621.01009 9 1-4.

Asangani, I.A. et al., "Therapeutic Targeting of BET Bromodomain Proteins in Castration-Resistant Prostate Cancer", Nature, 2014, 510: 278-282.

Baratta, M.G. et al., "An in-tumor genetic screen reveals that the BET bromodomain protein, BRD4, is a potential therapeutic target in ovarian carcinonoma", PNAS, 112: 232-237 (2015).

Bargagna-Mohan, et al., "Use of Protacs as molecular probes of angiogenesis", Bioorg Med Chem Left. 15(11) 2005, 2724-2727.

Battista, M. J. & Schmidt, M. Fulvestrant for the treatment of endometrial cancer. Expert Opin Investig Drugs 25, 475-483 (2016).

Belkina, A.C. et al., "BET domain co-regulators in obesity, inflammation and cancer", Nat. Rev. Cancer, 12 (2012) 465-477.

Boi, M. et al., "The BET Bromodomain inhibitor OTX015 Affects pathogenetic Pathways in Preclinical B-cell Tumor Models and synergizes with Targeted Drugs", Clin. Cancer Res., (2015) 21(7):1628-1638.

Boitano, et al., "Aryl Hydrocarbon Receptor Antagonists Promote the Expansion of Human Hematopoietic Stem Cells", ScienceSep. 10, 2010: vol. 329, pp. 1345-1348.

Bondeson, et al., "Catalytic in vivo protein knockdown by small-molecule Protacs", National Chem Biol. 11(8) Aug. 2015, 611-617.

Bradbury, RH, et. al., "Small-molecule androgen receptor downregulators as an approach to treatment of advanced prostate cancer", Bioorganic & Medicinal Chemistry Letters, 2011, 21: 5442-5445.

Brough, et al., "4,5-Diarylisoxazole HSP90 Chaperone Inhibitors: Potential Therapeutic Agents for the Treatment of Cancer", J Med Chem. 51(2), Jan. 24, 2008, 196-218.

Buckley, DL., et al., Small Molecule Control of Intracellular Protein Levels Through Modulation of the Ubiquitin Proteasome System, Angew Chem Int Ed Engl. Feb. 24, 2014; 53(9): 2312-2330, doi: 10.1002/anie.201307761 (Year: 2014).

Buckley, et al., "HaloProtacs: use of small molecule Protacs to induce degradation of HaloTag fusion proteins", ACS Chem Biol. 10(8), 2015, 1831-1837.

Carmony, KC, et al., "Protac-Induced Proteolytic Targeting", Methods Mol. Biol., 2012, vol. 832, pp. 627-638.

CAS 155180-53-3 published 1994.

CAS 155255-73-5 published 1995.

Ceribelli, M. et al., "Blockade of oncongenic IKB kinase activity in diffuse large B-cell lymphoma by bromodomain and extraterminal domain protein inhibitors", PNAS, 111 (2014) 11365-11370.

(56) References Cited

OTHER PUBLICATIONS

Chang, et al., "Structural basis for G9a-like protein lysine methyltransferase inhibition by BIX-01294", Nat Struct Mol Biol. 16(3), Mar. 2009, 312-317.
Chapuy, B. et al., "Discovery and characterization of super-enhancer-associated dependencies in diffuse large B cell lymphoma", Cancer Cell, 24 (2013) 777-790.
Chene, P., et al., "Inhibiting the p53-MDM2 interaction: an important target for cancer therapy", Nat. Rev. Cancer (2003), 3, 102-109.
Chung, et al., "Discovery and Characterization of Small Molecule Inhibitors of the BET Family Bromodomains", J Med Chem. 54(11), Jun. 9, 2011, 3827-3838.
Corson, et al., "Design and applications of bifunctional small molecules: why two heads are better than one", ACS Chemical Biology vol. 3 No. 11, pp. 677-692; Nov. 21, 2008.
Crews, C. M., "Targeting the undruggable proteome: the small molecules of my dreams", *Chem Biol* 17, 551-555, doi:S1074-5521(10)00196-1 [pii] 10.1016/j.chembio1.2010.05.011 (2010).
Cyrus, et al., "Jostling for position: optimizing linker location in the design of estrogen receptor-targeting Protacs", Chem Med Chem. 5(7), Jul. 5, 2010, 979-985.
Cyrus, K. et al., "Impact of Linker Length on the Activity of Protacs," Mol. Biosyst., 2011, vol. 7, No. 2, pp. 359-364.
Cyrus, K. et al., "Two-Headed Protac: An Effective New Tool for Targeted Protein Degradation," Chembiochem., 2010, vol. 11, pp. 1531-1534.
Dawson, et al., "Inhibition of BET recruitment to chromatin as an effective treatment for MLL-fusion leukemia", Nature 478, Oct. 2, 2011, 529-533.
Delmore, J.E. et al., "BET Bromodomain inhibition as a therapeutic strategy to target c-Myc", Cell, 146 (2011) 904-917.
Deroo, B.J., et al., "Estrogen receptors and human disease", Journal of Clinical Investigation, (2006), vol. 116(3), pp. 561-570.
Di, J. et al. "Reactivation of p53 by inhibiting Mdm2 E3 Ligase: a novel antitumor approach", Current Cancer Drug Targets (2011), 11(8), 987-994.
Ding, Q., et al., Discovery of RG7388, a Potent and Selective p53-MDM2 Inhibitor in Clinical Development, J. Med. Chem. 2013, 56, 5979-5983, dx.doi.org/10.1021/jm400487c (Year: 2013).
Dixon, S. J. et al., "Identifying druggable disease-modifying gene products",. Curr Opin Chem Biol 13, 549-555, doi:S1367-5931(09)00107-0 [pii] 10.1016/j.cbpa.2009.08.003 (2009).
Filippakopoulos, et al., "Selective inhibition of BET bromodomains", Nature 468, Dec. 23, 2010, 1067-1073.
Finnin, et al., "Structures of a histone deacetylase homologue bound to the TSA and SAHA inhibitors", Nature 401, Sep. 9, 1999, 188-193.
Gangjee. A. et al . , "The contribution of a 2-amino group on receptor tyrosine kinase inhibition and antiangiogenic activity in 4 anilinosubstituted pyrrolo [2,3-d] pyrimidines", Bioorganic & Medicinal Chemistry Letters, 2010, vol. 20, No. 10, pp. 3177-3181.
Golub, et al., "Molecular classification of cancer: class discovery and class prediction by gene expression monitoring", Science 286, 531-537 (1991).
Gosink, M et al., "Redirecting the specificity of ubiquitination by modifying ubiquitin-conjugating enzymes", Pro. Natl. Acad Sci, vol. 92, pp. 9117-9121, 1995.
Guo C., et. al, "Design of oxobenzimidazoles and oxindoles as novel androgen receptor antagonists", Bioorganic & Medicinal Chemistry Letters, 2012, 22:2572-2578.
Gustafson, et al., "Small-Molecule-Mediated Degradation of the Androgen Receptor through Hydrophobic Tagging", Agnew Chem Int Ed., 54: 9659-9662 (2015).
Haupt, Y. et al., "Mdm2 promotes the rapid degradation of p53", Nature 387, 296-299 (1997).
Hewings, et al., "3,5-Dimethylisoxazoles Act as Acetyllysine-mimetic Bromodomain", J Med Chem. 54(19), Oct. 13, 2011, 6761-6770.
Hines, J., et al., "Posttranslational protein knockdown coupled to receptor tyrosine kinase activation with phosphoProtacs", Proc Natl Acad Sci USA 110, 8942-8947 (2013).
Hoffmann, J. et al. Characterization of New Estrogen Receptor Destabilizing Compounds: Effects on Estrogen-Sensitive and Tamoxifen-Resistant Breast Cancer. JNCI Journal of the National Cancer Institute 96, 210-218 (2004).
Huang, et al., (2016) "Drugging the undruggables: exploring the ubiquitin system for drug development." *Cell Res* 26(4):484-498.
Ishikawa, T. et al., "Design and synthesis of novel human epidermal growth factor receptor 2 (HER2)/epidermal growth factor receptor (EGFR) dual inhibitors bearing a pyrrolo[3,2-d]pyrimidine scaffold", Journal of Medicinal Chemistry 2011, 54 (23), 8030-8050.
Jang, E.R. et al., "Targeted Degradation of Proteins by Protacs," Curr. Protoc. Chem. Biol., 2010, vol. 2, No. 2, pp. 71-87.
Jung, M. E. et al "Structure-Activity Relationship for Thioydantoin Androgen Receptor Antagonists for Castration-Resistant Prostate Cancer (CRPC)", J. Med. Chem. 2010, 53, 2779-2796.
Kim, et al., "Heat shock protein as molecular targets for breast cancer therapeutics", J. Breast Cancer. 14(3), Sep. 2011, 167-174.
Knott, Edward (1955). "Compounds containing sulphur chromophores. Part I. The action of bases on heterocyclic sulphide quarternary salts", Journal of the Chemical Society (resumed). 10.1039/jr9550000916. 949-954) (USPTO summary attached).
Konecny, G.E., et al., "Activity of the Dual Kinase Inhibitor Lapatinib (GW572016) against HER-2-Overexpressing and Trastuzumab-Treated Breast Cancer Cells", Cancer Research 66, 1630-1639 (2006).
Kurimchak, A. M. et al.,"Resistance to BET Bromodomain Inhibitors Is Mediated by Kinome Reprogramming in Ovarian Cancer", Cell Reports 16, 1273-1286 (2016).
Lai, A.C., et al., "Modular Protac Design for the Degradation of Oncogenic BCR-ABL", Angew Chem Int Ed Engl 55, 807-810 (2016).
Lala, et al., "Role of nitric oxide in tumor progression: Lessons from experimental tumors", Cancer and Metastasis Reviews 17:91-106 (1998).
Lebraud, H., et al., "Protein Degradation by In-Cell Self-Assembly of Proteolysis Targeting Chimeras", ACS Central Science, 2, 927-934 (2016).
Lee, et al., "Targeted Degradation of the Aryl Hydrocarbon Receptor by the Protac Approach: A Useful Chemical Genetic Tool", ChemBioChem vol. 8, Issue 17, pp. 2058-2062, Nov. 23, 2007.
Lelais, G. et al., "Discovery of (R,E)-N-(7-Chloro-1-(1-[4-(dimethylamino)but-2-enoyl]azepan-3-yl)-1H-benzo[d]imidazol-2-yl)-2-methylisonicotinamide (EGF816), a novel, potent, and WT sparing covalent inhibitor of oncogenic (L858R, ex19del) and resistent (T790M) Egfr mutants for the treatment of EGFR mutant non-small-cell lung cancers", Journal of Medicinal Chemistry 2016, 59(14), 6671-6689.
Levine, et al., Targeting the androgen receptor with steroid conjugates, J. Med. Chem., vol. 57., No. 20. pp. 8224-8237, (2014).
Li, Yan, et al., Single Polymer-drug Conjugate Carrying Two Drugs for Fixed-dose Codelivery, Med chem vol. 4(10): 676-683 (2014)-676-683.
Liu, et al., "Discovery of a 2,4-diamino-7-aminoalkoxyquinazoline as a potent and selective inhibitor of histone lysine methyltransferase G9a", J Med Chem. 52(24), Dec. 24, 2009, 7950-7953.
Llinas-Brunet, et al., "Discovery of a potent and selective noncovalent linear inhibitor of the hepatitis C virus NS3 protease (BI 201335)", J Med Chem. 53(17), Sep. 9, 2010, 6466-6476.
Lou, KJ., Protac the protein, Lou, K.-J. Sci BX 5(20); doi:10.1038/scibx.2012.514, Published online May 17, 2012 (Year: 2012).
Lountos, et al., "Structural Characterization of Inhibitor Complexes with Checkpoint Kinase 2 (Chk2), a Drug Target for Cancer Therapy", J Struct Bio1.176(3), Dec. 2011, 292-301.
Loven, J. et al., "Selective Inhibition of Tumor Oncogenes by Disruption of Super Enhancers", Cell, 153 (2013) 320-334.
Lu, et al., "Hijacking the E3 ubiquitin ligase cereblon to efficiently target BRD4", Chem Biol 22(6), 2015, 755-763.

(56) References Cited

OTHER PUBLICATIONS

Martin-Kohler, A. et al . , "Furo [2,3-d] pyrimidines and Oxazolo [5,4-d] pyrimidines as Inhibitors of Receptor Tyrosine Kinases (RTK)", He I vet ica Chimica Act a , 2004, vol. 87, No. 4, pp. 956-975.
Medline Plus Trusted Health Information for You, www.nlm.nih.gov/medlineplus/cancer.html pp. 1-10, (2007).
Mehellou, Y., De Clercq E., "Twenty-six years of anti-HIV drug discovery: where do we stand and where do we go?", J Med Chem. Jan. 28, 2010;53(2):521-538. doi: 10.1021/jm900492g. Review. PubMed PMID: 19785437.
Mertz, J.A. et al., "Targeting MYC dependence in cancer by inhibiting BET bromodomains", PNAS, 108 (2011) 16669-16674.
Millan,—et al "Design and Synthesis of Inhaled p38 Inhibitors for the Treatment of Chronic Obstructive Pulmonary Disease", J Med Chem.54(22), Nov. 24, 2011, 7797-7814.
Miyazaki, M., et al., "Discovery of DS-5272 as a promising candidate: a potent and orally active p53-MDM2 interaction inhibitor", Bioorg. Med. Chem. Lett. (2015) 23, 2360-2367.
Mohler, M.L., et al., Androgen receptor antagonists: a patent review (2008-2011), Expert Opinion on Therapeutic Patents, vol. 22, No. 5. pp. 541-565, (2012).
Neklesa, T.K., et al., "Chemical biology: Greasy tags for protein removal", Nature 487, 308-309 (2012).
Neochoritis, et al., Chapter 12, p53-MDM2 and MDMX Antagonists, Annual Reports in Medicinal Chemistry, vol. 49, pp. 167-187 (2014).
Nicodeme, et al., "Suppression of inflammation by a synthetic histone mimic", Nature 468, Dec. 23, 2010, 1119-1123.
Noel, J. Kay, "Abstract C244: ' Development of the BET Bromodomain inhibitor OTX015", Mol Cancer Ther 2013; 12(11 Suppl); C244 1-4.
Pepe, A. et. al., "Synthesis and structure-activity relationship studies of novel dihydropyridones as androgen receptor modulators", J. Med. Chem. 2013, 56, 8280-8297.
Puissant, A. et al., "Targeting MYCN in neuroblastoma by BET bromodomain inhibition", Cancer discovery, 3 (2013) 308-323.
Puppala, D. et al., "Development of an Aryl Hydrocarbon Receptor Antagonist Using the Proteolysis-Targeting chimeric Molecules Approach: A Potential Tool for Chemoprevention," Mol. Pharmacol., 2008, vol. 73, No. 4, pp. 1064-1071.
Raina, K., et al., "Protac-induced BET protein degradation as a therapy for castration-resistant prostate cancer", Proc Natl Acad Sci USA 113, 7124-7129 (2016).
Raina, K., et al., Chemical Inducers ofTargeted Protein Degradation, The Journal of Biological Chemistry vol. 285, No. 15, pp. 11057-11060, Apr. 9, 2010 (Year: 2010).
Rew, Y, et al., "Discovery of AM-7209, a potent and selective 4-amidobenzoic acid inhibitor of the MDM2-p53 interaction", J Med Chem. Dec. 26, 2014;57(24):10499-10511. doi: 10.1021/jm501550p. Epub Dec. 4, 2014. PubMed PMID: 25384157. (J. Med. Chem. (2014) 57, 10499-10511 Rew, et al.).
Richters, A., et al., "Identification and further development of potent TBK1 inhibitors", ACS Chemical Biology, vol. 10, No. 1, Jan. 16, 2015, pp. 289-298 (2015).
Robertson, J. F. R. Fulvestrant (Faslodex)—how to make a good drug better. Oncologist 12, 774-784 (2007).
Rodriguez-Gonzalez, et al., "Targeting steroid hormone receptors for ubiquitination and degradation in breast and prostate cancer", Oncogene. 27(57), Dec. 4, 2008, 7201-7211.
Rotili, D., et al., "Photoactivable peptides for identifying enzyme-substrate and protein-protein interactions", Chem Commun (Carob) 47(5), Feb. 2011, 1488-1490.
Rusch, M., et al., "Identification of Acyl Protein Thioesterases 1 and 2 as the Cellular Targets of the Ras-Signaling Modulators Palmostatin B amd M", Angew. Chem. Int. Ed., 50: 9838-9842. doi:10.1002/anie.201102967 (Angew. Chem. Int. Ed. 2011, 50, 9838-9842) (2011).
Sakamoto, et al., "Development of Protacs to target cancer-promoting proteins for ubiquitination and degradation", Mol Cell Proteomics. 2(12), Dec. 2003, 1350-1358.
Sakamoto, et al., "Protacs: chimeric molecules that target proteins to the Skp 1-Cullin-F box complex for ubiquitination and degradation", Proc Natl Acad Sci U S A.98(15), Jul. 17, 2001, 8554-8559.
Scagliotti, G., et al., "Phase III Multinational, Randomized, Double-Blind, Placebo-Controlled Study of Tivantinib (ARQ 197) Plus Erlotinib Versus Erlotinib Alone in Previously Treated Patients With Locally Advanced or Metastatic Nonsquamous Non-Small-Cell Lung Cancer", Journal of Clinical Oncology 33, 2667-2674 (2015).
Schenkel, et al., "Discovery of Potent and Highly Selective Thienopyridine Janus Kinase 2 Inhibitors", J Med Chem.54(24), Dec. 22, 2011, 8440-8450.
Schneekloth, et al., "Chemical Genetic Control of Protein Levels: Selective in Vivo Targeted Degradation", J Am Chem Soc. 126(12), Mar. 31, 2004, 3748-3754.
Schneekloth, et al., Targeted intracellular protein degradation induced by a small molecule: En route to chemical proteomics, Bioorg. Med. Chem. Lett. 18 (2008) 5904-5908.
Sequist, L.V., et al., "Randomized Phase II Study of Erlotinib Plus Tivantinib Versus Erlotinib Plus Placebo in Previously Treated Non-Small-Cell Lung Cancer", Journal of Clinical Oncology 29, 3307-3315 (2011).
Smith, et al., "Targeted Intracellular Protein Degradation Induced by a Small Molecule: En Route to Ghemical Proteomics", Bioorg Med Chem Lett. 18(22), Nov. 15, 2008, 5904-5908.
Stuhlmiller, Timothy J., et al., "Inhibition of Lapatinib-Induced Kinome Reprogramming in ERBB2-Positive Breast Cancer by Targeting BET Family Bromodomains", Cell Reports 11, 390-404 (2015).
Suh, N. et al. Arzoxifene, a new selective estrogen receptor modulator for chemoprevention of experimental breast cancer. Cancer Res. 61, 8412-8415 (2001).
Sun, et al., Potent Bivalent Smac, Mimetics: effect of the linker on binding to inhibitor of apoptosis proteins (IAPs) and Anticancer Activity, J. Med. Chem. 2011, 54, 3306-3318.
Toure, et al., (2016) "Small-Molecule Protac: New Approaches to Protein Degradation." *Angew Chem Int Ed Engl* 55(6):1966-1973.
Vallee, et al., "Tricyclic Series of Heat Shock Protein 90 (HSP90) Inhibitors Part I: Discovery of Tricyclic Imidazo [4,5-c] Pyridines as Potent Inhibitors of the Hsp90 Molecular Chaperone", J Med Chem. 54(20), Oct. 27, 2011, 7206-7219.
Van Eis, et al., "2,6-Naphthyridines as potent and selective inhibitors of the novel protein kinase C isozymes", Bioorg Med Chem Lett.21(24), Dec. 15, 2011, 7367-7372.
Vassilev, et al., "In vivo activation of the p53 pathway by small-molecule antagonists of MDM2", Science 303, Feb. 6, 2004, 844-848.
Vazquez, A. et al., "The genetics of the p53 pathway, apoptosis and cancer therapy", Nat. Rev. Drug. Dis., 7, 979-982 (2008).
Vu, B. et al. "Discovery of RG7112: a small-molecule MDM2 inhibitor in clinical development", ACS Med. Chem. Lett. (2013) 4, 466-469.
Wang, C. et al. Estrogen induces c-myc gene expression via an upstream enhancer activated by the estrogen receptor and the AP-1 transcription factor. Mol. Endocrinol. 25, 1527-1538 (2011).
Wang, S., et al. "Small-molecule inhibitors of the MDM2-p53 protein-protein interaction (MDM2 inhibitors) in clinical trials for cancer treatment", J. Med. Chem. (2015) 58, 1038-1052.
Wang, S., et al. "Temporal activation of p53 by a specific MDM2 inhibitor is selectively toxic to tumors and leads to complete tumor growth inhabitation", PNAS USA (2008) 105, 3933-3938.
Weir, H. M. et al. AZD9496: An Oral Estrogen Receptor Inhibitor That Blocks the Growth of ER-Positive and ESR1-Mutant Breast Tumors in Preclinical Models. Cancer Res. 76, 3307-3318 (2016).
Willson, T.M. et al., "3-[4-(1,2-Diphenylbut-1-Enyl)Phenyl] Acrylic Acid: A non-steroidal estrogen with functional selectivity for bone over uterus in rats", Journal of Medicinal Chemistry, American Chemical Society, US May 25, 1994, vol. 37 No. 11, pp. 1550-1552.
Winter, et al., "Phthalimide Conjugation as a strategy for in vivo target protein degradation", Science, 2015 vol. 348 (6241), pp. 1376-1381 [Pub online: May 21, 2015].

(56) References Cited

OTHER PUBLICATIONS

Wright, et al., "Structure-Activity Relationships in Purine-Based Inhibitor Binding to HSP90 Isoforms", Chem Biol. 11 (6), Jun. 2004, 775-785.
Zengerle, et al., "Selective Small Molecule Induced Degradation of the BET Bromodomain Protein BRD4" ACS Chemical Biology, Jun. 2, 2015, vol. 10, pp. 1770-1777.
Zhang B.et al., "Small-molecule MDM2-p53 inhibitors: recent advances", Future Med. Chem. (2015) 7, 631-645.
Zhang, D. et al., "Targeted Degradation of Proteins by Small Molecules: A Novel Tool for Functional Proteomics," comb Chem. High Throughput Screen., 2004, vol. 7, No. 7, pp. 689-697.
Zillhardt, M., et al., "Foretinib (GSK1363089), an Orally Available Multikinase Inhibitor of c-Met and VEGFR-2, Blocks Proliferation, Induces Anoikis, and Impairs Ovarian Cancer Metastasis", Clinical Cancer Research 17, 4042-4051 (2011).
U.S. Appl. No. 15/206,497, filed Jul. 11, 2016, US 2017-0008904 A1.

* cited by examiner

| | A1850(RG7388) | A1851(RG7388 enantiomer) | A423 (JQ-1) | A825 (BRD4-CBL) | A1893 (BRD4-MDM2; +) | A1894(BRD4-MDM2; -) |
|---|---|---|---|---|---|---|
| IC50 | 8.677e-008 | ~2.870e-006 | 3.266e-007 | 1.020e-007 | 1.297e-007 | 1.265-e006 |

MDM2-BASED MODULATORS OF PROTEOLYSIS AND ASSOCIATED METHODS OF USE

CROSS-REFERENCE TO RELATED APPLICATIONS

This Application is a continuation of U.S. patent application Ser. No. 15/206,497, filed 11 Jul. 2016, published as U.S. Patent Application Publication No. 2017-0008904 A1 on 12 Jan. 2017, which claims the benefit of and priority to U.S. Provisional Application No. 62/191,193, filed 10 Jul. 2015, both of which are incorporated herein by reference in their entirety for all purposes.

INCORPORATION BY REFERENCE

U.S. patent application Ser. No. 14/686,640, filed Apr. 14, 2015, entitled "Imide-Based Modulators of Proteolysis and Associated Methods of Use", and PCT Patent Application Serial No. PCT/US2013/021136, filed Jan. 11, 2013 entitled "Compounds and Methods for the Enhanced Degradation of Targeted Proteins and Other Polypeptides by an E3 Ubiquitin Ligase," are incorporated herein by reference in their entirety. Furthermore, all references cited herein are incorporated by reference herein in their entirety.

FIELD OF THE INVENTION

The description provides compounds binding to MDM2, including bifunctional compounds comprising the same as mentioned and associated methods of use. The bifunctional compounds are useful as modulators of targeted ubiquitination, especially with respect to a variety of polypeptides and other proteins, which are degraded and/or otherwise inhibited by bifunctional compounds according to the present invention.

BACKGROUND

Most small molecule drugs bind enzymes or receptors in tight and well-defined pockets. On the other hand, protein-protein interactions are notoriously difficult to target using small molecules due to their large contact surfaces and the shallow grooves or flat interfaces involved. E3 ubiquitin ligases (of which hundreds are known in humans) confer substrate specificity for ubiquitination, and therefore, are more attractive therapeutic targets than general proteasome inhibitors due to their specificity for certain protein substrates. The development of ligands of E3 ligases has proven challenging, in part due to the fact that they must disrupt protein-protein interactions. However, recent developments have provided specific ligands which bind to these ligases. For example, since the discovery of Nutlins, the first small molecule E3 ligase mouse double minute 2 homolog (MDM2) inhibitors, additional compounds have been reported that target MDM2 (i.e., human double minute 2 or HDM2) E3 ligases (J. Di, et al. *Current Cancer Drug Targets* (2011), 11(8), 987-994).

Tumor suppressor gene p53 plays an important role in cell growth arrest and apoptosis in response to DNA damage or stress (A. Vazquez, et al. *Nat. Rev. Drug. Dis.* (2008), 7, 979-982), and inactivation of p53 has been suggested as one of the major pathway for tumor cell survival (A. J. Levine, et al. *Nature* (2000), 408, 307-310). In cancer patients, about 50% were found with p53 mutation (M. Hollstein, et al. *Science* (1991), 233, 49-53), while patients with wild type p53 were often found p53 down regulation by MDM2 through the protein-protein interaction of p53 and MDM2 (P. Chene, et al. *Nat. Rev. Cancer* (2003), 3, 102-109). Under normal cell condition without oncogenic stress signal, MDM2 keeps p53 at low concentration. In response to DNA damage or cellular stress, p53 level increases, and that also causes increase in MDM2 due to the feedback loop from p53/MDM2 auto regulatory system. In other words, p53 regulates MDM2 at the transcription level, and MDM2 regulates p53 at its activity level (A. J. Levine, et al. *Genes Dev.* (1993) 7, 1126-1132).

Several mechanisms can explain p53 down regulation by MDM2. First, MDM2 binds to N-terminal domain of p53 and blocks expression of p53-responsive genes (J. Momand, et al. *Cell* (1992), 69, 1237-1245). Second, MDM2 shuttles p53 from nucleus to cytoplasm to facilitate proteolytic degradation (J. Roth, et al. *EMBO J.* (1998), 17, 554-564). Lastly, MDM2 carries intrinsic E3 ligase activity of conjugating ubiquitin to p53 for degradation through ubiquitin-dependent 26s proteasome system (UPS) (Y. Haupt, et al. *Nature* (1997) 387, 296-299). Therefore, disrupting p53/MDM2 auto regulation can restore p53 activity and could bring a new approach in the treatment of cancer. Not surprisingly, since the first publication of small molecule MDM2 inhibitor Nutlins, multiple classes of MDM2 antagonists have been reported and several of them have advanced to the clinic development (B. Zhang, et al. *Future Med. Chem.* (2015) 7, 631-645)

The most studied MDM2 antagonists are imidazolines with aromatic rings decorated at the three carbons of the ring and NH group functionalized. One example is RG7112 developed by Roche, in which two adjacent phenyl rings on imidazoline core are in cis-conformation (L. T. Vassilev, et al. *Science* (2004) 57, 1454-1472; B. Vu, et al. *ACS Med. Chem. Lett.* (2013) 4, 466-469). The similar cis-bis-aryl substitution pattern is also presented in Daiichi-Sankyo's MDM2 antagonist DS-5272, although imidazoline core was replaced with thiazoloimidazoline (M. Miyazaki, et al. *Bioorg. Med. Chem. Lett.* (2015) 23, 2360-2367; WO 2014/038606). The earlier version DS-3032b advanced to clinical testing (www.clinicaltrials.gov)

The spiroindolinone compounds MI-219 and MI-888 from University of Michigan possesses a 5-membered pyrrolidine ring with two adjacent phenyl ring substituted at the core with cis- and trans-conformation (S. Wang, et al. *PNAS USA* (2008) 105, 3933-3938). Further modification in this chemical class resulted in Sanofi-Aventis' SAR405838 (S. Wang, et al. *J. Med. Chem.* (2015) 58, 1038-1052; WO 2014/107713).

Similar to spiroindolinone MDM2 antagonist, non-spiro molecules with pyrrolidine core decorated by adjacent trans-bis-aryl rings were reported by Roche, and RG7388 from this chemical series became Roche's second MDM2 inhibitor in the clinic (Q. Ding, et al. *J. Med. Chem.* (2013) 56, 5979-5983)

Piperidinone and morpholinone cores with adjacent trans-aryl substitution on the core are another chemical class of MDM2 inhibitors reported by Amgen. These compounds are structurally different from imidazoline or spiro-indolinone or pyrrolidine chemical class. AMG-232 with a piperidinone core advanced to the clinic (D. Sun, et al. *J. Med. Chem.* (2014) 57, 1454-1472). AM-7209 is a more potent molecule from Amgen reported recently (Y. Rew, et al. *J. Med. Chem.* (2014) 57, 10499-10511). A diversity of structures with 6-membered cores were reported by Amgen (WO 2014/151863, WO2014/134201, US 2014/235629, US 2014/0243372).

Pyrrolopyrimidine- and imidazolopyridine-derived carboxylic acid and acid mimetic oxadiazolone analogs are potent HDM2 inhibitors reported by Merck (WO 2014/100065; WO 2014/100071). MK-8242, also known as SCH90042, has been tested in the clinic (www.clinicaltrials.gov).

Novartis reported pyrrolopyrrolidinone chemical class where three aryl groups were attached to pyrrolopyrrolidinone core (WO 2013/175417). CMG097, also known as NVP-CMG-097 in the clinic, is a small molecule MDM2 inhibitor derived from 1,2-bis-aryl-substituted dihydro-isoquinolinone chemical class (WO 2014/020502).

All small molecule MDM2 inhibitors mentioned above showed potent activity in inhibiting p53 and MDM2 interaction, which consequently stabilizes p53. However, due to the feedback loop, antagonism mode also resulted in MDM2 up-regulation at the transcription level as shown in the literature. As such, the potential exists that degrading MDM2 could overcome issues associated with MDM2 up-regulation. Also, because MDM2 functions as E3 ligase, recruiting MDM2 to a disease causing protein and effectuating its ubiquitination and degradation is an approach of high interest for drug discovery.

An ongoing need exists in the art for effective treatments for disease, especially hyperplasias and cancers. However, non-specific effects, and the inability to target and modulate certain classes of proteins altogether, such as transcription factors, remain as obstacles to the development of effective anti-cancer agents. As such, small molecule therapeutic agents that leverage or potentiate MDM2 substrate specificity and, at the same time, are "tunable" such that a wide range of protein classes can be targeted and modulated with specificity would be very useful as a therapeutic.

SUMMARY

The present disclosure describes bifunctional compounds which function to recruit endogenous proteins to an E3 ubiquitin ligase for degradation, and methods of using the same. In particular, the present disclosure provides bifunctional or proteolysis targeting chimeric (PROTAC) compounds, which find utility as modulators of targeted ubiquitination of a variety of polypeptides and other proteins, which are then degraded and/or otherwise inhibited by the bifunctional compounds as described herein. An advantage of the compounds provided herein is that a broad range of pharmacological activities is possible, consistent with the degradation/inhibition of targeted polypeptides from virtually any protein class or family. In addition, the description provides methods of using an effective amount of the compounds as described herein for the treatment or amelioration of a disease condition, such as cancer, e.g., multiple myeloma.

As such, in one aspect the disclosure provides MDM2 ligand-based PROTAC compounds of Formula (A):

Formula (A)

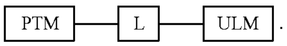

Formula (A) represents bifunctional or PROTAC compounds, which comprise an E3 ubiquitin ligase binding moiety (i.e., a ligand for an E3 ubquitin ligase or "ULM" group), coupled via linker (L) to a moiety that binds a target protein (i.e., a protein/polypeptide targeting ligand or "PTM" group) such that the target protein/polypeptide is placed in proximity to the ubiquitin ligase to effect degradation (and inhibition) of that protein. In a preferred embodiment, the ULM is a moiety that binds MDM2 E3 ubiquitin ligase (i.e., "MLM").

In Formula (A), the respective positions of the PTM and MLM moieties as well as their number as illustrated herein is provided by way of example only and is not intended to limit the compounds in any way. As would be understood by the skilled artisan, the bifunctional compounds as described herein can be synthesized such that the number and position of the respective functional moieties can be varied as desired.

In certain preferred embodiments, PTM is a protein target moiety. As such, PTM binds to a specific protein which is set to be ubiquitinated or degraded.

In certain embodiments, "L" is the linker that connects PTM and MLM. In certain embodiments, L is a bond (i.e., absent). In certain additional embodiments, L is a chemical linker as described herein. In certain preferred embodiments, the linker "L" is a connector with a linear non-hydrogen atom number in the range of 1 to 20. The connector "L" can contain, but not limited to the functional groups such as ether, amide, alkane, alkene, alkyne, ketone, hydroxyl, carboxylic acid, thioether, sulfoxide, and sulfone. The linker can contain aromatic, heteroaromatic, cyclic, bicyclic and tricyclic moieties. Substitution with halogen, such as Cl, F, Br and I can be included in the linker. In the case of fluorine substitution, single or multiple fluorines can be included.

In certain additional embodiments, the MLM of the bifunctional compound with a formula (A) comprises chemical moieties such as substituted imidazolines, substituted spiro-indolinones, substituted pyrrolidines, substituted piperidinones, substituted morpholinones, substituted pyrrolopyrimidines, substituted imidazolopyridines, substituted thiazoloimidazoline, substituted pyrrolopyrrolidinones, and substituted isoquinolinones.

In additional embodiments, the MLM comprises the core structures mentioned above with adjacent bis-aryl substitutions positioned as cis- or trans-configurations.

In still additional embodiments, the MLM comprises part of structural features as in RG7112, RG7388, SAR405838, AMG-232, AM-7209, DS-5272, MK-8242, and NVP-CGM-097, and analogs or derivatives thereof.

In certain embodiments, the compounds as described herein comprise multiple MLMs, multiple PTMs, multiple chemical linkers or a combination thereof.

In certain embodiments, PTMs can be, but not limited to, small molecules binding to kinases, enzymes, transporters, nuclear hormone receptors, non-nuclear hormone receptors, G-protein coupled receptors (GPCRs), transcription factors, and epigenetic targets.

In certain embodiments, the epigenetic targets can be bromodomain and extra terminal domain (BET) family proteins, such as, e.g., BRD1, -2, -3, or -4.

In certain embodiments, the nuclear hormone receptors can be, but not limited to, androgen receptor (AR) and estrogen receptor (ER).

In another aspect, the description provides bifunctional molecules as shows in Formula (B), wherein PTM comprises an MDM2 binding moiety (MBM) coupled via a linker (L) to ULM (ubiquitination ligase binding moiety), which comprises a moiety that binds an E3 ubiquitin ligase, e.g., Von Hippel-Lindau E3 ubiquitin ligase (VHM), Cereblon (CLM) or MDM2 (MLM).

Formula (B)

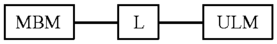

In certain embodiments, "L" is the linker that connects PTM and MLM. In certain embodiments, L is a bond (i.e., absent). In certain additional embodiments, L is a chemical linker as described herein. In certain preferred embodiments, the linker "L" is a connector with a linear non-hydrogen atom number in the range of 1 to 20. The connector "L" can contain, but not limited to the functional groups such as ether, amide, alkane, alkene, alkyne, ketone, hydroxyl, carboxylic acid, thioether, sulfoxide, and sulfone. The linker can contain aromatic, heteroaromatic, cyclic, bicyclic and tricyclic moieties. Substitution with halogen, such as Cl, F, Br and I can be included in the linker. In the case of fluorine substitution, single or multiple fluorines can be included.

In an embodiment, VLM can be hydroxyproline or a derivative thereof. Other contemplated VLMs are described in U.S. Patent Application Pub. No. 2014/03022523A1, and 2015/0291562A1, which are incorporated herein in their entirety.

In certain embodiments, MBM comprises chemical moieties such as substituted imidazolines, substituted spiroindolinones, substituted pyrrolidines, substituted piperidinones, substituted morpholinones, substituted pyrrolopyrimidines, substituted imidazolopyridines, substituted thiazoloimidazoline, substituted pyrrolopyrrolidinones, and substituted isoquinolinones.

In additional embodiments, the MBM comprises the core structures mentioned above with adjacent bis-aryl substitutions positioned as cis- or trans-configurations.

In still additional embodiments, the MBM comprises part of structural features as in RG7112, RG7388, SAR405838, AMG-232, AM-7209, DS-5272, MK-8242, and NVP-CGM-097, and analogs or derivatives thereof.

In certain embodiments, VLM is a derivative of trans-3-hydroxyproline, where both nitrogen and carboxylic acid in trans-3-hydroxyproline are functionalized as amides.

In certain embodiments, CLM is a derivative of piperidine-2,6-dione, where piperidine-2,6-dione can be substituted at the 3-position, and the 3-substitution can be bicyclic hetero-aromatics with the linkage as C—N bond or C—C bond. Examples of CLM can be, but not limited to, pomalidomide, lenalidomide and thalidomide and their derivatives In an additional aspect, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein. In certain embodiments, the therapeutic compositions as described herein may be used to effectuate the degradation of proteins of interest for the treatment or amelioration of a disease, e.g., cancer.

In yet another aspect, the description provides a method of ubiquitinating/degrading a target protein in a cell. In certain embodiments, the method comprises administering to a subject or contacting a subject, e.g., a patient or a cell, with a bifunctional compound as described herein, wherein the bifunctional compound effectuates degradation of the target protein. Degradation of the target protein will occur when the target protein is placed in proximity to the ubiquitin ligase, thus resulting in degradation/inhibition of the effects of the target protein and the control of protein levels. The control of protein levels provides treatment of a disease state or condition, which is modulated through the target protein by lowering the level of that protein in the cells of a patient.

In still another aspect, the description provides methods for treating or emeliorating a disease, disorder or symptom thereof in a subject or a patient, e.g., an animal such as a mammal or a human, comprising administering to a subject in need thereof a composition comprising an effective amount, e.g., a therapeutically effective amount, of a compound as described herein or salt form thereof, and a pharmaceutically acceptable carrier, wherein the composition is effective for treating or ameliorating the disease or disorder or symptom thereof in the subject.

In another aspect, the description provides methods for identifying the effects of the degradation of proteins of interest in a biological system using compounds according to the present invention.

The preceding general areas of utility are given by way of example only and are not intended to be limiting on the scope of the present disclosure and appended claims. Additional objects and advantages associated with the compositions, methods, and processes of the present invention will be appreciated by one of ordinary skill in the art in light of the instant claims, description, and examples. For example, the various aspects and embodiments of the invention may be utilized in numerous combinations, all of which are expressly contemplated by the present description. These additional advantages objects and embodiments are expressly included within the scope of the present invention. The publications and other materials used herein to illuminate the background of the invention, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention. Further objects, features and advantages of the invention will become apparent from the following detailed description taken in conjunction with the accompanying figures showing illustrative embodiments of the invention, in which.

DETAILED DESCRIPTION

Figure 1A:
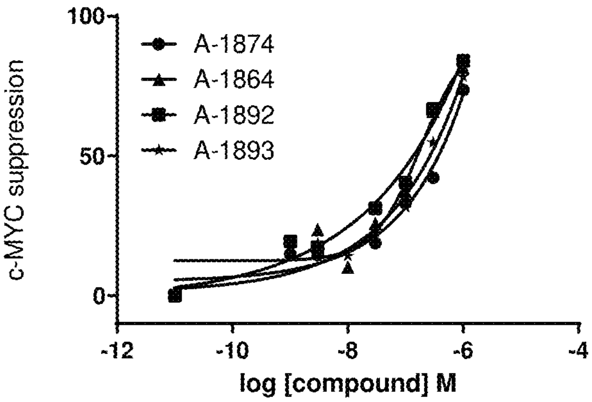
FIGS. 1A and 1B: c-Myc suppression in 22rv1 cells by chimeric molecules, where BRD4 ligand is connected through linkers to MDM2 ligands using partial structural motif in RG7388. Chimeric molecules with inactive MDM2 ligand (enantiomer of the active counterpart) demonstrated no c-Myc suppression across a range of concentrations, while chimeric molecules with active MDM2 ligand showed dose dependent c-Myc suppression, suggesting BRD4 degradation mediated by MDM2 E3 ligase ubiquitination mechanism, as c-Myc is directly regulated by the level of BRD4. Chimeric molecules with MDM2 ligand as a racemate displayed similar c-Myc suppression as observed in those containing active MDM2 ligand.

The following is a detailed description provided to aid those skilled in the art in practicing the present invention. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

The present disclosure describes bifunctional compounds which function to recruit endogenous proteins to an E3 ubiquitin ligase for degradation, and methods of using the same. In particular, the present disclosure provides bifunctional or proteolysis targeting chimeric (PROTAC) compounds, which find utility as modulators of targeted ubiquitination of a variety of polypeptides and other proteins, which are then degraded and/or otherwise inhibited by the bifunctional compounds as described herein. An advantage of the compounds provided herein is that a broad range of pharmacological activities is possible, consistent with the degradation/inhibition of targeted polypeptides from virtually any protein class or family.

As such, presently described are compositions and methods that relate to the surprising and unexpected discovery that an E3 ubiquitin ligase protein, e.g., MDM2, ubiquitinates a target protein once it and the target protein are placed in proximity by a bifunctional or chimeric construct (e.g., a PROTAC) that binds the E3 ubiquitin ligase protein and the target protein. Accordingly, the present invention provides such compounds and compositions comprising an E3 ubiquintin ligase binding moiety ("ULM") coupled to a protein target binding moiety ("PTM"), which result in the ubiquitination of a chosen target protein, which leads to degradation of the target protein by the proteasome. The present invention also provides a library of compositions and the use thereof.

In particular, the present application is directed to compounds which contain a ligand, e.g., a small molecule ligand (i.e., having a molecular weight of below 2,000, 1,000, 500, or 200 Daltons), which is capable of binding to a ubiquitin ligase, such as MDM2, and a moiety that is capable of binding to a target protein, in such a way that the target protein is placed in proximity to the ubiquitin ligase to effect degradation (and/or inhibition) of that protein.

Unless otherwise defined, all technical and scientific terms used herein have the same meaning as commonly understood by one of ordinary skill in the art to which this invention belongs. The terminology used in the description is for describing particular embodiments only and is not intended to be limiting of the invention.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The following terms are used to describe the present invention. In instances where a term is not specifically defined herein, that term is given an art-recognized meaning by those of ordinary skill applying that term in context to its use in describing the present invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising"

can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are co-administered in combination with at least one additional bioactive agent, especially including an anticancer agent. In particularly preferred aspects, the co-administration of compounds results in synergistic activity and/or therapy, including anticancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other steroisomers (diastereomers) thereof, as well as pharmaceutically acceptable salts and derivatives (including prodrug forms) thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented within the context of the compound shown.

The term "compound" or "chemical compound" as used herein can include organometallic compounds, organic compounds, metals, transitional metal complexes, and small molecules. In certain preferred embodiments, polynucleotides are excluded from the definition of compounds. In other preferred embodiments, polynucleotides and peptides are excluded from the definition of compounds. In a particularly preferred embodiment, the term compounds refers to small molecules (e.g., preferably, non-peptidic and non-oligomeric) and excludes peptides, polynucleotides, transition metal complexes, metals, and organometallic compounds.

As used herein, the term "small molecule" refers to a non-peptidic, non-oligomeric organic compound either synthesized in the laboratory or found in nature. Small molecules, as used herein, can refer to compounds that are "natural product-like", however, the term "small molecule" is not limited to "natural product-like" compounds. Rather, a small molecule is typically characterized in that it contains several carbon-carbon bonds, and has a molecular weight of less than 2000 g/mol, preferably less than 1500 g/mol, although this characterization is not intended to be limiting for the purposes of the present application. In certain other preferred embodiments, synthetic small molecules are utilized.

The term "ubiquitin ligase" refers to a family of proteins that facilitate the transfer of ubiquitin to a specific substrate protein, targeting the substrate protein for degradation. For example, MDM2 is an E3 ubiquitin ligase protein that alone or in combination with an E2 ubiquitin-conjugating enzyme causes the attachment of ubiquitin to a lysine on a target protein, and subsequently targets the specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. The most common lysine is Lys48 on the ubiquitin chain. This is the lysine used to make polyubiquitin, which is recognized by the proteasome.

The term "patient" or "subject" is used throughout the specification to describe an animal, preferably a human or a domesticated animal, to whom treatment, including prophylactic treatment, with the compositions according to the present invention is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present invention, the term patient refers to a human patient unless otherwise stated or implied from the context of the use of the term.

The term "effective" is used to describe an amount of a compound, composition or component which, when used within the context of its intended use, effects an intended result. The term effective subsumes all other effective amount or effective concentration terms, which are otherwise described or used in the present application.

DETAILED DESCRIPTION

In one aspect, the description provides compounds comprising an MDM2 E3 ubiquitin ligase binding moiety (MLM) connected to a linker (L), as shown below, wherein MLM is a ligand for MDM2 or HDM2, and L is a bond or a chemical linker group.

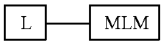

The number and/or relative positions of the moieties in the compounds illustrated herein are provided by way of example only. As would be understood by the skilled artisan, compounds as described herein can be synthesized with any desired number and/or relative position of the respective functional moieties.

In another aspect, the description provides compounds comprising an MDM2 E3 ubiquitin ligase binding moiety (MLM) coupled via a linker (L) to a protein targeting moiety (PTM), wherein L is a bond or a chemical linker group. These compounds are described herein as "MDM2 PROTAC compounds" (MDM2-mediated proteolysis targeting chimerics) and are presented as Formula (A):

Formula (A)

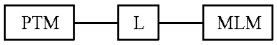

.

In Formula (A), the respective positions of the PTM and MLM moieties as well as their number as illustrated herein is provided by way of example only and is not intended to limit the compounds in any way. As would be understood by the skilled artisan, the bifunctional compounds as described herein can be synthesized such that the number and position of the respective functional moieties can be varied as desired.

In Formula (A), PTM is a protein/polypeptide targeting moiety, L is a linker, and MLM is a MDM2 E3 ubiquitin ligase binding moiety.

In another aspect, the description provides bifunctional molecules as shows in Formula (B), wherein PTM comprises an MDM2 binding moiety (MBM) coupled via a linker (L) to ULM (ubiquitination ligase binding moiety), which comprises a moiety that binds an E3 ubiquitin ligase, e.g., Von Hippel Lindau E3 Ligase (VHM), Cereblon (CLM) or MDM2 (MLM).

Formula (B)

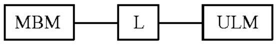

The terms ULM is used inclusively unless the context indicates otherwise to indicate an E3 ubiquitin ligase binding moiety, including those that bind MDM2 (i.e., MLMs). Further, the term MLM is inclusive of all possible MDM2 E3 ubiquitin ligase binding moieties.

In certain embodiments, the E3 ubiquitin ligase is MDM2. As such, the ULM is an MLM that binds to MDM2.

In certain preferred embodiments, PTM is a protein target moiety. As such, PTM binds to a specific protein which is set to be ubiquitinated or degraded.

In certain preferred embodiments, "L" is a linker, e.g., a bond (i.e., absent) or a chemical linker that connects PTM and MLM.

In certain additional embodiments, the MLM of the bifunctional compound as depicted in Formula (A) or (B) comprises chemical moieties such as substituted imidazolines, substituted spiro-indolinones, substituted pyrrolidines, substituted piperidinones, substituted morpholinones, substituted pyrrolopyrimidines, substituted imidazolopyridines, substituted thiazoloimidazoline, substituted pyrrolopyrrolidinones, and substituted isoquinolinones.

In additional embodiments, the MLM comprises the core structures mentioned above with adjacent bis-aryl substitutions positioned as cis- or trans-configurations.

In still additional embodiments, the MLM comprises part of structural features as in RG7112, RG7388, SAR405838, AMG-232, AM-7209, DS-5272, MK-8242, and NVP-CGM-097, and analogs or derivatives thereof.

In certain embodiments, the linker "L" is a connector with a linear non-hydrogen atom number in the range of 1 to 20. In additional embodiments, the connector "L" comprises a functional group, e.g., an ether, amide, alkane, alkene, alkyne, ketone, hydroxyl, carboxylic acid, thioether, sulfoxide, and sulfone. The linker can also comprise aromatic, heteroaromatic, cyclic, bycyclic and tricyclic moieties. Substitution with halogen, such as Cl, F, Br and I can be included in the linker. In the case of fluorine substitution, single or multiple fluorines can be included.

In certain embodiments, the compounds as described herein comprise multiple MLMs, multiple PTMs, multiple chemical linkers or a combination thereof.

In certain embodiments, PTMs can be, but not limited to, small molecules binding to kinases, enzymes, transporters, nuclear hormone receptors, non-nuclear hormone receptors, G-protein coupled receptors (GPCRs), transcription factors, and epigenetic targets.

In certain embodiments, PTM is a small molecule binding to epigenetic targets, and the epigenetic targets can be BRDs, such as BRD4.

In certain embodiments, PTM is a small molecule binding to nuclear hormone receptors, and the nuclear hormone receptor can be, but not limited to, androgen receptor (AR) and estrogen receptor (ER).

In additional embodiments, the description provides the compounds as described herein including their enantiomers, diastereomers, solvates and polymorphs, including pharmaceutically acceptable salt forms thereof, e.g., acid and base salt forms.

In certain preferred embodiments, MLM is a derivative of substituted imidazoline represented as Formula (A-1), or thiazoloimidazoline represented as Formula (A-2), or spiro indolinone represented as Formula (A-3), or pyrollidine represented as Formula (A-4), or piperidinone/morphlinone represented as Formula (A-5), or isoquinolinone represented as Formula (A-6), or pyrollopyrimidine/imidazolopyridine represented as Formula (A-7), or pyrrolopyrrolidinone/imidazolopyrrolidinone represented as Formula (A-8).

Formula (A-1)

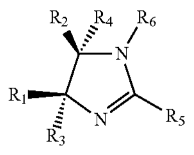

Formula (A-2)

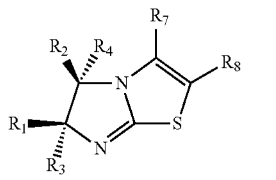

Formula (A-3)

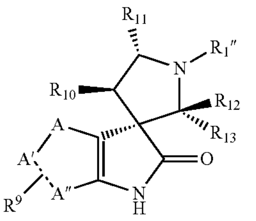

Formula (A-4)

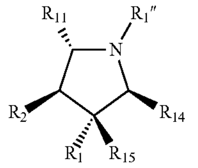

Formula (A-5)

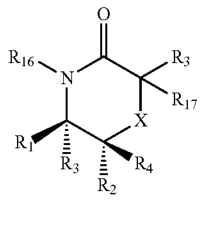

Formula (A-6)

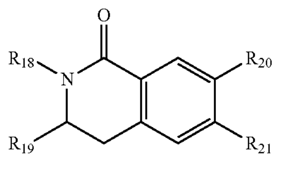

-continued

Formula (A-7)

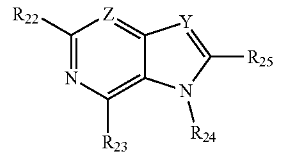

Formula (A-8)

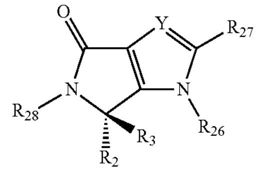

wherein above Formula (A-1) through Formula (A-8),

X is selected from the group consisting of carbon, oxygen, sulfur, sulfoxide, sulfone, and N—$R^a$;

$R^a$ is independently H or an alkyl group with carbon number 1 to 6;

Y and Z are independently carbon or nitrogen;

A, A' and A" are independently selected from C, N, O or S, can also be one or two atoms forming a fused bycyclic ring, or a 6,5- and 5,5-fused aromatic bicyclic group; $R_1$, $R_2$ are independently selected from the group consisting of an aryl or heteroaryl group, a heteroaryl group having one or two heteroatoms independently selected from sulfur or nitrogen, wherein the aryl or heteroaryl group can be mono-cyclic or bi-cyclic, or unsubstituted or substituted with one to three substituents independently selected from the group consisting of:

halogen, —CN, C1 to C6 alkyl group, C3 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons, amides with 2 to 6 carbons, and dialkyl amine with 2 to 6 carbons;

$R_3$, $R_4$ are independently selected from the group consisting of H, methyl and C1 to C6 alkyl; $R_5$ is selected from the group consisting of an aryl or heteroaryl group, a heteroaryl group having one or two heteroatoms independently selected from sulfur or nitrogen, wherein the aryl or heteroaryl group can be mono-cyclic or bi-cyclic, or unsubstituted or substituted with one to three substituents independently selected from the group consisting of:

halogen, —CN, C1 to C6 alkyl group, C3 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons, amides with 2 to 6 carbons, dialkyl amine with 2 to 6 carbons, alkyl ether (C2 to C6), alkyl ketone (C3 to C6), morpholinyl, alkyl ester (C3 to C6), alkyl cyanide (C3 to C6);

$R_6$ is H or —C(═O)$R^b$, wherein $R^b$ is selected from the group consisting of alkyl, cycloalkyl, mono-, di- or tri-substituted aryl or heteroaryl, 4-morpholinyl, 1-(3-oxopiperazunyl), 1-piperidinyl, 4-N—$R^c$-morpholinyl, 4-$R^c$-1-piperidinyl, and 3-$R^c$-1-piperidinyl, wherein $R^c$ is selected from the group consisting of alkyl, fluorine substituted alkyl, cyano alkyl, hydroxyl-substituted alkyl, cycloalkyl, alkoxyalkyl, amide alkyl, alkyl sulfone, alkyl sulfoxide, alkyl amide, aryl, heteroaryl, mono-, bis- and tri-substituted aryl or heteroaryl, CH2CH2R$^d$, and CH2CH2CH2R$^d$, wherein $R^d$ is selected from the group consisting of alkoxy, alkyl sulfone, alkyl sulfoxide, N-substituted carboxamide, —NHC(O)-alkyl, —NH—$SO_2$-alkyl, aryl, substituted aryl, heteroaryl, substituted heteroaryl;

$R_7$ is selected from the group consisting of H, C1 to C6 alkyl, cyclic alkyl, fluorine substituted alkyl, cyano substituted alkyl, 5- or 6-membered hetero aryl or aryl, substituted 5- or 6-membered hetero aryl or aryl;

$R_8$ is selected from the group consisting of —$R^e$—C(O)—$R^f$, —$R^e$-alkoxy, —$R^e$-aryl, —$R^e$-heteroaryl, and —$R^e$—C(O)—$R^f$—C(O)—$R^g$, wherein:

$R^e$ is an alkylene with 1 to 6 carbons, or a bond;

$R^f$ is a substituted 4- to 7-membered heterocycle;

$R^g$ is selected from the group consisting of aryl, hetero aryl, substituted aryl or heteroaryl, and 4- to 7-membered heterocycle;

$R_9$ is selected from the group consisting of a mono-, bis- or tri-substituent on the fused bicyclic aromatic ring in Formula (A-3), wherein the substitutents are independently selected from the group consisting of halogen, alkene, alkyne, alkyl, unsubstituted or substituted with Cl or F;

$R_{10}$ is selected from the group consisting of an aryl or heteroaryl group, wherein the heteroaryl group can contain one or two heteroatoms as sulfur or nitrogen, aryl or heteroaryl group can be mono-cyclic or bicyclic, the aryl or heteroaryl group can be unsubstituted or substituted with one to three substituents, including a halogen, F, Cl, —CN, alkene, alkyne, C1 to C6 alkyl group, C1 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons;

$R_{11}$ is —C(O)—N($R^h$)($R^i$), wherein $R^h$ and $R^i$ are selected from groups consisting of the following:

H, C1 to C6 alkyl, alkoxy substituted alkyl, sulfone substituted alkyl, aryl, heterol aryl, mono-, bis- or tri-substituted aryl or hetero aryl, alkyl carboxylic acid, heteroaryl carboxylic acid, alkyl carboxylic acid, fluorine substituted alkyl carboxylic acid, aryl substituted cycloalkyl, hetero aryl substituted cycloalkyl; wherein $R^h$ and $R^i$ are independently selected from the group consisting of H, connected to form a ring, 4-hydroxycyclohehexane; mono- and di-hydroxy substituted alkyl (C3 to C6); 3-hydroxycyclobutane; phenyl-4-carboxylic acid, and substituted phenyl-4-carboxylic acid;

$R_{12}$ and $R_{13}$ are independently selected from H, lower alkyl (C1 to C6), lower alkenyl (C2 to C6), lower alkynyl (C2 to C6), cycloalkyl (4, 5 and 6-membered ring), substituted cycloalkyl, cycloalkenyl, substituted cycloalkenyl, 5- and 6-membered aryl and heteroaryl, R12 and R13 can be connected to form a 5- and 6-membered ring with or without substitution on the ring;

$R_{14}$ is selected from the group consisting of alkyl, substituted alkyl, alkenyl, substituted alkenyl, aryl, substituted aryl, heteroaryl, substituted heteroaryl, heterocycle, substituted heterocycle, cycloalkyl, substituted cycloalkyl, cycloalkenyl and substituted cycloalkenyl;

$R_{15}$ is CN;

$R_{16}$ is selected from the group consisting of C1-6 alkyl, C1-6 cycloalkyl, C2-6 alkenyl, C1-6 alkyl or C3-6 cycloalkyl with one or multiple hydrogens replaced by fluorine, alkyl or cycloalkyl with one $CH_2$ replaced by S(═O), —S, or —S(═O)$_2$, alkyl or cycloalkyl with terminal $CH_3$ replaced by S(═O)$_2$N(alkyl)(alkyl), —C(═O)N(alkyl)(alkyl), —N(alkyl)S(═O)$_2$(alkyl), —C(═O)2(allkyl), —O(alkyl), C1-6 alkyl or alkyl-cycloalkyl with hydron replaced by hydroxyl group, a 3 to 7 membered cycloalkyl or heterocycloalkyl, optionally containing a —(C═O)— group, or a 5 to 6 membered aryl or heteroaryl group, which heterocycloalkyl or heteroaryl group can contain from one to three heteroatoms independently selected from O, N or S, and the cycloalkyl, heterocycloalkyl, aryl or heteroaryl group can be unsubstituted or substituted with from one to three substituents independently selected from halogen, C1-6 alkyl groups, hydroxylated C1-6 alkyl, C1-6 alkyl containing thioether, ether, sulfone, sulfoxide, fluorine substituted ether or cyano group;

$R_{17}$ is selected from the group consisting of ($CH_2$)nC(O)N$R^k$$R^l$, wherein $R^k$ and $R^l$ are independently selected from H, C1-6 alkyl, hydrxylated C1-6 alkyl, C1-6 alkoxy alkyl, C1-6 alkyl with one or multiple hydrogens replaced by fluorine, C1-6 alkyl with one carbon replaced by S(O), S(O)(O), C1-6 alkoxyalkyl with one or multiple hydrogens replaced by fluorine, C1-6 alkyl with hydrogen replaced by a cyano group, 5 and 6 membered aryl or heteroaryl, aklyl aryl with alkyl group containing 1-6 carbons, and alkyl heteroaryl with alkyl group containing 1-6 carbons, wherein the aryl or heteroaryl group can be further substituted;

$R_{18}$ is selected from the group consisting of substituted aryl, heteroaryl, alkyl, cycloalkyl, the substitution is preferably —N(C1-4 alkyl)(cycloalkyl), —N(C1-4 alkyl)alkyl-cycloalkyl, and —N(C1-4 alkyl)[alkyl)-(heterocycle-substituted)-cycloalkyl];

$R_{19}$ is selected from the group consisting of aryl, heteroaryl, bicyclic heteroaryl, and these aryl or heteroaryl groups can be substituted with halogen, C1-6 alkyl, C1-6 cycloalkyl, $CF_3$, F, CN, alkyne, alkyl sulfone, the halogen substitution can be mon-bis- or tri-substituted;

$R_{20}$ and $R_{21}$ are independently selected from C1-6 alkyl, C1-6 cycloalkyl, C1-6 alkoxy, hydroxylated C1-6 alkoxy, and fluorine substituted C1-6 alkoxy, wherein $R_{20}$ and $R_{21}$ can further be connected to form a 5, 6 and 7-membered cyclic or heterocyclic ring, which can further be substituted;

R22 is selected from the group consisting of H, C1-6 alkyl, C1-6 cycloalkyl, carboxylic acid, carboxylic acid ester, amide, reverse amide, sulfonamide, reverse sulfonamide, N-acyl urea, nitrogen-containing 5-membered heterocycle, the 5-membered heterocycles can be further substituted with C1-6 alkyl, alkoxy, fluorine-substituted alkyl, CN, and alkylsulfone; $R_{23}$ is selected from aryl, heteroaryl, —O-aryl, —O-heteroaryl, —O-alkyl, —O-alkyl-cycloalkyl, —NH-alkyl, —NH-alkyl-cycloalkyl, —N(H)-aryl, —N(H)-heteroaryl, —N(alkyl)-aryl, —N(alkyl)-heteroaryl, the aryl or heteroaryl groups can be substituted with halogen, C1-6 alkyl, hydroxylated C1-6 alkyl, cycloalkyl, fluorine-substituted C1-6 alkyl, CN, alkoxy, alkyl sulfone, amide and sulfonamide;

$R_{24}$ is selected from the group consisting of —CH2-(C1-6 alkyl), —CH2-cycloalkyl, —CH2-aryl, CH2-heteroaryl, where alkyl, cycloalkyl, aryl and heteroaryl can be substituted with halogen, alkoxy, hydroxylated alkyl, cyano-substituted alkyl, cycloallyl and substituted cycloalkyl;

$R_{25}$ is selected from the group consisting of C1-6 alkyl, C1-6 alkyl-cycloalkyl, alkoxy-substituted alkyl, hydroxylated alkyl, aryl, heteroaryl, substituted aryl or heteroaryl, 5,6, and 7-membered nitrogen-containing saturated heterocycles, 5,6-fused and 6,6-fused nitrogen-containing saturated heterocycles and these saturated heterocycles can be substituted with C1-6 alkyl, fluorine-substituted C1-6 alkyl, alkoxy, aryl and heteroaryl group;

$R_{26}$ is selected from the group consisting of C1-6 alkyl, C3-6 cycloalkyl, the alkyl or cycloalkyl can be substituted with —OH, alkoxy, fluorine-substituted alkoxy, fluorine-substituted alkyl, —$NH_2$, —NH-alkyl, NH—C(O)alkyl, —NH—$S(O)_2$-alkyl, and —$S(O)_2$-alkyl;

$R_{27}$ is selected from the group consisting of aryl, heteroaryl, bicyclic heteroaryl, wherein the aryl or heteroaryl groups can be substituted with C1-6 alkyl, alkoxy, NH2, NH-alkyl, halogen, or —CN, and the substitution can be independently mono-, bis- and tri-substitution;

$R_{28}$ is selected from the group consisting of aryl, 5 and 6-membered heteroaryl, bicyclic heteroaryl, cycloalkyl, saturated heterocycle such as piperidine, piperidinone, tetrahydropyran, N-acyl-piperidine, wherein the cycloalkyl, saturated heterocycle, aryl or heteroaryl can be further substituted with —OH, alkoxy, mono-, bis- or tri-substitution including halogen, —CN, alkyl sulfone, and fluorine substituted alkyl groups; and $R_1$" is selected from the group consisting of alkyl, aryl substituted alkyl, alkoxy substituted alkyl, cycloalkyl, aryl-substituted cycloalkyl, and alkoxy substituted cycloalkyl.

In certain embodiments, the heterocycles in $R^f$ and $R^g$ are substituted pyrrolidine, substituted piperidine, substituted piperizine.

Unless the context indicates otherwise, the following terms can mean:

The term "independently" is used herein to indicate that the variable, which is independently applied, varies independently from application to application.

The term "alkyl" shall mean within its context a linear, branch-chained or cyclic fully saturated hydrocarbon radical or alkyl group, preferably a $C_1$-$C_{10}$, more preferably a $C_1$-$C_6$, alternatively a $C_1$-$C_3$ alkyl group, which may be optionally substituted. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopen-tylethyl, cyclohexylethyl and cyclohexyl, among others. In certain embodiments, the alkyl group is end-capped with a halogen group (Br, Cl, F, or I).

The term "lower alkyl" refers to methyl, ethyl or propyl

The term "lower alkoxy" refers to methoxy, ethoxy or propoxy.

The term "Alkenyl" refers to linear, branch-chained or cyclic $C_2$-$C_{10}$ (preferably $C_2$-$C_6$) hydrocarbon radicals containing at least one C≡C bond.

The term "Alkynyl" refers to linear, branch-chained or cyclic $C_2$-$C_{10}$ (preferably $C_2$-$C_6$) hydrocarbon radicals containing at least one C≡C bond.

The term "alkylene" when used, refers to a —$(CH_2)_n$— group (n is an integer generally from 0-6), which may be optionally substituted. When substituted, the alkylene group preferably is substituted on one or more of the methylene groups with a $C_1$-$C_6$ alkyl group (including a cyclopropyl group or a t-butyl group), but may also be substituted with one or more halo groups, preferably from 1 to 3 halo groups or one or two hydroxyl groups, O—($C_1$-$C_6$ alkyl) groups or amino acid sidechains as otherwise disclosed herein. In certain embodiments, an alkylene group may be substituted with a urethane or alkoxy group (or other group) which is further substituted with a polyethylene glycol chain (of from 1 to 10, preferably 1 to 6, often 1 to 4 ethylene glycol units) to which is substituted (preferably, but not exclusively on the distal end of the polyethylene glycol chain) an alkyl chain substituted with a single halogen group, preferably a chlorine group. In still other embodiments, the alkylene (often, a methylene) group, may be substituted with an amino acid sidechain group such as a sidechain group of a natural or unnatural amino acid, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine.

The term "unsubstituted" shall mean substituted only with hydrogen atoms. A range of carbon atoms which includes $C_0$ means that carbon is absent and is replaced with H. Thus, a range of carbon atoms which is $C_0$-$C_6$ includes carbons atoms of 1, 2, 3, 4, 5 and 6 and for $C_0$, H stands in place of carbon.

The term "substituted" or "optionally substituted" shall mean independently (i.e., where more than substituent occurs, each substituent is independent of another substituent) one or more substituents (independently up to five substituents, preferably up to three substituents, often 1 or 2 substituents on a moiety in a compound according to the present invention and may include substituents which themselves may be further substituted) at a carbon (or nitrogen) position anywhere on a molecule within context, and includes as substituents hydroxyl, thiol, carboxyl, cyano (C≡N), nitro ($NO_2$), halogen (preferably, 1, 2 or 3 halogens, especially on an alkyl, especially a methyl group such as a trifluoromethyl), an alkyl group (preferably, $C_1$-$C_{10}$, more preferably, $C_1$-$C_6$), aryl (especially phenyl and substituted phenyl for example benzyl or benzoyl), alkoxy group (preferably, $C_1$-$C_6$ alkyl or aryl, including phenyl and substituted phenyl), thioether ($C_1$-$C_6$ alkyl or aryl), acyl (preferably, $C_1$-$C_6$ acyl), ester or thioester (preferably, $C_1$-$C_6$ alkyl or aryl) including alkylene ester (such that attachment is on the alkylene group, rather than at the ester function which is preferably substituted with a $C_1$-$C_6$ alkyl or aryl group), preferably, $C_1$-$C_6$ alkyl or aryl, halogen (preferably, F or Cl), amine (including a five- or six-membered cyclic alkylene amine, further including a $C_1$-$C_6$ alkyl amine or a $C_1$-$C_6$ dialkyl amine which alkyl groups may be substituted with one or two hydroxyl groups) or an optionally substituted —N($C_0$-$C_6$ alkyl)C(O)(O—$C_1$-$C_6$ alkyl) group (which may be optionally substituted with a polyethylene glycol chain to which is further bound an alkyl group containing a single halogen, preferably chlorine substituent), hydrazine, amido, which is preferably substituted with one or two $C_1$-$C_6$ alkyl groups (including a carboxamide which is optionally substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Substituents according to the present invention may include, for example —$SiR_1R_2R_3$ groups where each of $R_1$ and $R_2$ is as otherwise described herein and $R_3$ is H or a $C_1$-$C_6$ alkyl group, preferably $R_1$, $R_2$, $R_3$ in this context is a $C_1$-$C_3$ alkyl group (including an isopropyl or t-butyl group). Each of the above-described groups may be linked directly to the substituted moiety or alternatively, the substituent may be linked to the substituted moiety (preferably in the case of an aryl or heteraryl moiety) through an optionally substituted —$(CH_2)_m$— or alternatively an optionally substituted $-(OCH_2)_m$, $-(OCH_2CH_2)_m-$ or $-(CH_2CH_2O)_m-$ group, which may be substituted with any one or more of the above-described substituents. Alkylene groups $-(CH_2)_m-$ or $-(CH_2)_n-$ groups or other chains such as ethylene glycol chains, as identified above, may be substituted anywhere on the chain. Preferred substituents on alkylene groups include halogen or $C_1$-$C_6$ (preferably $C_1$-$C_3$) alkyl groups, which may be optionally substituted with one or two hydroxyl groups, one or two ether groups ($O-C_6$ groups), up to three halo groups (preferably F), or a side chain of an amino acid as otherwise described herein and optionally substituted amide (preferably carboxamide substituted as described above) or urethane groups (often with one or two $C_0$-$C_6$ alkyl substituents, which group(s) may be further substituted). In certain embodiments, the alkylene group (often a single methylene group) is substituted with one or two optionally substituted $C_1$-$C_6$ alkyl groups, preferably $C_1$-$C_4$ alkyl group, most often methyl or O-methyl groups or a sidechain of an amino acid as otherwise described herein. In the present invention, a moiety in a molecule may be optionally substituted with up to five substituents, preferably up to three substituents. Most often, in the present invention moieties which are substituted are substituted with one or two substituents.

The term "substituted" (each substituent being independent of any other substituent) can also mean within its context of use $C_1$-$C_6$ alkyl, $C_1$-$C_6$ alkoxy, halogen, amido, carboxamido, sulfone, including sulfonamide, keto, carboxy, $C_1$-$C_6$ ester (oxyester or carbonylester), $C_1$-$C_6$ keto, urethane $-O-C(O)-NR_1R_2$ or $-N(R_1)-C(O)-O-R_1$, nitro, cyano and amine (especially including a $C_1$-$C_6$ alkylene-$NR_1R_2$, a mono- or di-$C_1$-$C_6$ alkyl substituted amines which may be optionally substituted with one or two hydroxyl groups). In certain embodiments, the groups include for example, $-NH-$, $-NHC(O)-$, $-O-$, $=O$, $-(CH_2)_m-$ (here, m and n are in context, 1, 2, 3, 4, 5 or 6), $-S-$, $-S(O)-$, $SO_2-$ or $-NH-C(O)-NH-$, $-(CH_2)_nOH$, $-(CH_2)_nSH$, $-(CH_2)_nCOOH$, $C_1$-$C_6$ alkyl, $-(CH_2)_nO-(C_1$-$C_6$ alkyl), $-(CH_2)_nC(O)-(C_1$-$C_6$ alkyl), $-(CH_2)_nOC(O)-(C_1$-$C_6$ alkyl), $-(CH_2)_nC(O)O-(C_1$-$C_6$ alkyl), $-(CH_2)_nNHC(O)-R_1$, $-(CH_2)_nC(O)-NR_1R_2$, $-(OCH_2)_nOH$, $-(CH_2O)_nCOOH$, $C_1$-$C_6$ alkyl, $-(OCH_2)_nO-(C_1$-$C_6$ alkyl), $-(CH_2O)_nC(O)-(C_1$-$C_6$ alkyl), $-(OCH_2)_nNHC(O)-R_1$, $-(CH_2O)_nC(O)-NR_1R_2$, $-S(O)_2-R_S$, $-S(O)-R_S$ ($R_S$ is $C_1$-$C_6$ alkyl or a $-(CH_2)_m-NR_1R_2$ group), $NO_2$, CN or halogen (F, Cl, Br, I, preferably F or Cl), depending on the context of the use of the substituent. $R_1$ and $R_2$ are each, within context, H or a $C_1$-$C_6$ alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted $C_1$-$C_6$ alkyl groups (methyl, ethyl or hydroxymethyl or hydroxyethyl is preferred, thus providing a chiral center), a sidechain of an amino acid group as otherwise described herein, an amido group as described hereinabove, or a urethane group $O-C(O)-NR_1R_2$ group where $R_1$ and $R_2$ are as otherwise described herein, although numerous other groups may also be used as substituents. Various optionally substituted moieties may be substituted with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

The term "aryl" or "aromatic", in context, refers to a substituted (as otherwise described herein) or unsubstituted monovalent aromatic radical having a single ring (e.g., benzene, phenyl, benzyl) or condensed rings (e.g., naphthyl, anthracenyl, phenanthrenyl, etc.) and can be bound to the compound according to the present invention at any available stable position on the ring(s) or as otherwise indicated in the chemical structure presented. Other examples of aryl groups, in context, may include heterocyclic aromatic ring systems, "heteroaryl" groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole or fused ring systems such as indole, quinoline, indoline, azaindoline, benzofuran, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indoline, azaindoline, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, pyrimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "substituted aryl" refers to an aromatic carbocyclic group comprised of at least one aromatic ring or of multiple condensed rings at least one of which being aromatic, wherein the ring(s) are substituted with one or more substituents. For example, an aryl group can comprise a substituent(s) selected from: $-(CH_2)_nOH$, $-(CH_2)_n-O-(C_1$-$C_6)$alkyl, $-(CH_2)_n-O-(CH_2)_n-(C_1$-$C_6)$alkyl, $-(CH_2)_n-C(O)(C_0$-$C_6)$ alkyl, $-(CH_2)_n-C(O)O(C_0$-$C_6)$ alkyl, $-(CH_2)_n-OC(O)(C_0$-$C_6)$alkyl, amine, mono- or di-($C_1$-$C_6$ alkyl) amine wherein the alkyl group on the amine is optionally substituted with 1 or 2 hydroxyl groups or up to three halo (preferably F, Cl) groups, OH, COOH, $C_1$-$C_6$ alkyl, preferably $CH_3$, $CF_3$, OMe, $OCF_3$, $NO_2$, or CN group (each of which may be substituted in ortho-, meta- and/or para-positions of the phenyl ring, preferably para-), an optionally substituted phenyl group (the phenyl group itself is preferably substituted with a linker group attached to a PTM group, including a ULM group), and/or at least one of F, Cl, OH, COOH, $CH_3$, $CF_3$, OMe, $OCF_3$, $NO_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo-(preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, and combinations thereof.

"Carboxyl" denotes the group —C(O)OR, where R is hydrogen, alkyl, substituted alkyl, aryl, substituted aryl, heteroaryl or substituted heteroaryl, whereas these generic substituents have meanings which are identical with definitions of the corresponding groups defined herein.

The term "heteroaryl" or "hetaryl" can mean but is in no way limited to an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —$(CH_2)_m$—O—$C_1$-$C_6$ alkyl group or an optionally substituted —$(CH_2)_m$—C(O)—O—$C_1$-$C_6$ alkyl group), an optionally substituted pyridine (2-, 3, or 4-pyridine) or a group according to the chemical structure.

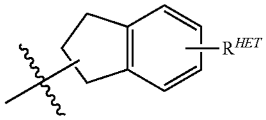

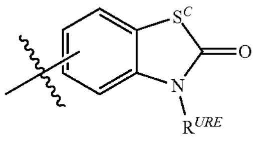

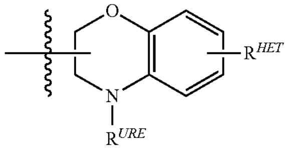

-continued

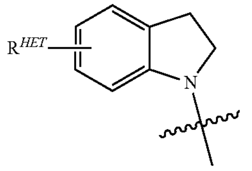

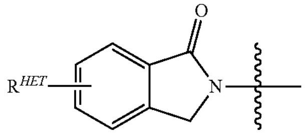

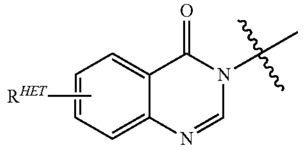

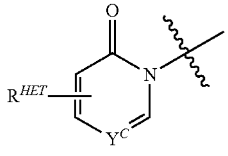

wherein $S^c$ is $CHR^{SS}$, $NR^{URE}$, or O;

$R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl).

The term "Heterocycle" refers to a cyclic group which contains at least one heteroatom, e.g., N, O or S, and may be aromatic (heteroaryl) or non-aromatic. Thus, the heteroaryl moieties are subsumed under the definition of heterocycle, depending on the context of its use. Exemplary heteroaryl groups are described hereinabove.

Exemplary heterocyclics include: azetidinyl, benzimidazolyl, 1,4-benzodioxanyl, 1,3-benzodioxolyl, benzoxazolyl, benzothiazolyl, benzothienyl, dihydroimidazolyl, dihydropyranyl, dihydrofuranyl, dioxanyl, dioxolanyl, ethyleneurea, 1,3-dioxolane, 1,3-dioxane, 1,4-dioxane, furyl, homopiperidinyl, imidazolyl, imidazolinyl, imidazolidinyl, indolinyl, indolyl, isoquinolinyl, isothiazolidinyl, isothiazolyl, isoxazolidinyl, isoxazolyl, morpholinyl, naphthyridinyl, oxazolidinyl, oxazolyl, pyridone, 2-pyrrolidone, pyridine, piperazinyl, N-methylpiperazinyl, piperidinyl, phthalimide, succinimide, pyrazinyl, pyrazolinyl, pyridyl, pyrimidinyl, pyrrolinyl, pyrrolyl, quinolinyl, tetrahydrofuranyl, tetrahydropyranyl, tetrahydroquinoline, thiazolidinyl, thiazolyl, thienyl, tetrahydrothiophene, oxane, oxetanyl, oxathiolanyl, thiane among others.

Heterocyclic groups can be optionally substituted with a member selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SOaryl, —SO-heteroaryl, —SO2-alkyl, —SO2-substituted alkyl, —SO2-aryl, oxo (═O), and —SO2-heteroaryl. Such heterocyclic groups can have a single ring or multiple condensed rings. Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles. The term "heterocyclic" also includes bicyclic groups in which any of the heterocyclic rings is fused to a benzene ring or a cyclohexane ring or another heterocyclic ring (for example, indolyl, quinolyl, isoquinolyl, tetrahydroquinolyl, and the like).

The term "cycloalkyl" can mean but is in no way limited to univalent groups derived from monocyclic or polycyclic alkyl groups or cycloalkanes, as defined herein, e.g., saturated monocyclic hydrocarbon groups having from three to twenty carbon atoms in the ring, including, but not limited to, cyclopropyl, cyclobutyl, cyclopentyl, cyclohexyl, cycloheptyl and the like. The term "substituted cycloalkyl" can mean but is in no way limited to a monocyclic or polycyclic alkyl group and being substituted by one or more substituents, for example, amino, halogen, alkyl, substituted alkyl, carbyloxy, carbylmercapto, aryl, nitro, mercapto or sulfo, whereas these generic substituent groups have meanings which are identical with definitions of the corresponding groups as defined in this legend.

"Heterocycloalkyl" refers to a monocyclic or polycyclic alkyl group in which at least one ring carbon atom of its cyclic structure being replaced with a heteroatom selected from the group consisting of N, O, S or P. "Substituted heterocycloalkyl" refers to a monocyclic or polycyclic alkyl group in which at least one ring carbon atom of its cyclic structure being replaced with a heteroatom selected from the group consisting of N, O, S or P and the group is containing one or more substituents selected from the group consisting of halogen, alkyl, substituted alkyl, carbyloxy, carbylmercapto, aryl, nitro, mercapto or sulfo, whereas these generic substituent group have meanings which are identical with definitions of the corresponding groups as defined in this legend.

More specifically, non-limiting examples of MLMs include those shown below as well as those 'hybrid' molecules that arise from the combination of 1 or more of the different features shown in the molecules below.

Using MBM or MLM in Formula A-1 through A-8, the following PROTACs can be prepared to target a particular protein for degradation, where 'L" is a connector (i.e. a linker group), and "PTM" is a ligand binding to a target protein.

In certain embodiments, the description provides a bifunctional molecule comprising a structure selected from the group consisting of:

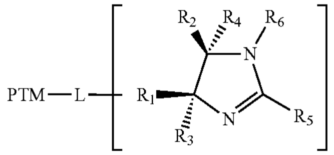
,

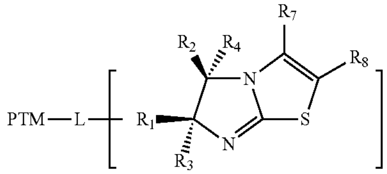
,

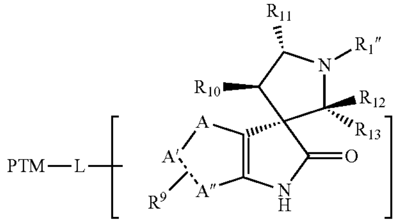
,

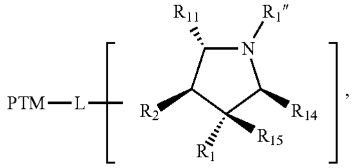
,

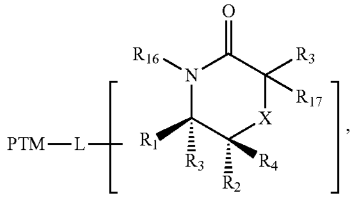
,

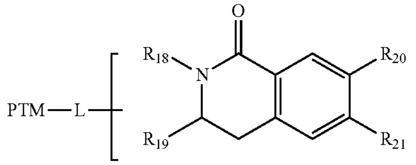
,

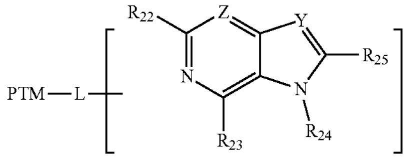
, and

-continued

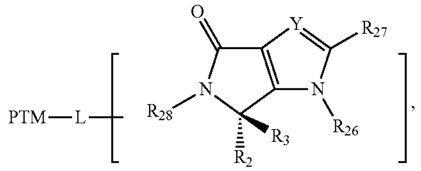

wherein

X, $R^a$, Y, Z, A, A', A", $R_1$, $R_2$, $R_3$, $R_4$, $R_5$, $R_6$, $R^b$, $R^c$, $R^d$, $R_7$, $R^e$, $R^f$, $R^g$, $R_9$, $R_{10}$, $R_{11}$, $R_{12}$, $R_{13}$, $R_{14}$, $R_{15}$, $R_{16}$, $R_{17}$, $R^k$, $R^1$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, and $R_1$" are as defined herein.

In certain embodiments, the description provides bifunctional or chimeric molecules with the structure: PTM-L-MLM, wherein PTM is a protein target binding moiety coupled to an MLM by L, wherein L is a bond (i.e., absent) or a chemical linker. In certain embodiments, the MLM has a structure selected from the group consisting of A-1-1, A-1-2, A-1-3, and A-1-4:

A-1-1

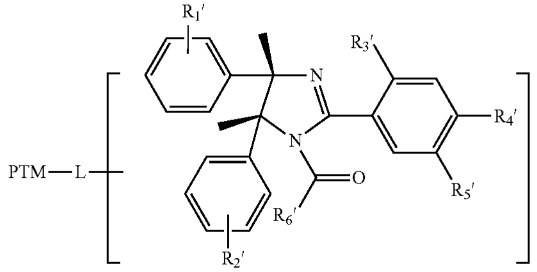

A-1-2

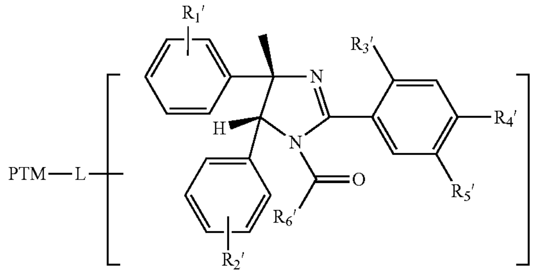

A-1-3

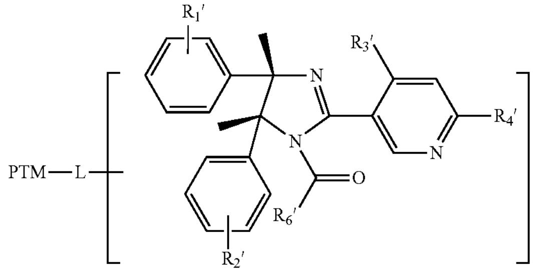

-continued

A-1-4

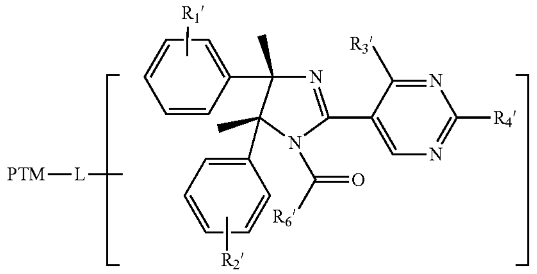

wherein R1' and R2' are independently selected from the group consisting of F, Cl, Br, I, acetylene, CN, $CF_3$ and $NO_2$;

R3' is selected from the group consisting of —$OCH_3$, —$OCH_2CH_3$, —$OCH_2CH_2F$, —$OCH_2CH_2OCH_3$, and —$OCH(CH_3)_2$;

R4' is selected from the group consisting of H, halogen, —$CH_3$, —$CF_3$, —$OCH_3$, —$C(CH_3)_3$, —$CH(CH_3)_2$, -cyclopropyl, —CN, —$C(CH_3)_2OH$, —$C(CH_3)_2OCH_2CH_3$, —$C(CH_3)_2CH_2OH$, —$C(CH_3)_2CH_2OCH_2CH_3$, —$C(CH_3)_2CH_2OCH_2CH_2OH$, —$C(CH_3)_2CH_2OCH_2CH_3$, —$C(CH_3)_2CN$, —$C(CH_3)_2C(O)CH_3$, —$C(CH_3)_2C(O)NHCH_3$, —$C(CH_3)_2C(O)N(CH_3)_2$, —$SCH_3$, —$SCH_2CH_3$, —$S(O)_2CH_3$, —$S(O_2)CH_2CH_3$, —$NHC(CH_3)_3$, —$N(CH_3)_2$, pyrrolidinyl, and 4-morpholinyl;

R5' is selected from the group consisting of halogen, -cyclopropyl, —$S(O)_2CH_3$, —$S(O)_2CH_2CH_3$, 1-pyrrolidinyl, —$NH_2$, —$N(CH_3)_2$, and —$NHC(CH_3)_3$; and R6' is selected from the structures presented below where the linker connection point is indicated as "*".

Beside R6' as the point for linker attachment, R4' can also serve as the linker attachment position. In the case that R4' is the linker connection site, linker will be connected to the terminal atom of R4' groups shown above.

In certain embodiments, the linker connection position is at least one of R4' or R6' or both.

In certain embodiments, R6' is independently selected from the group consisting of (wherein "*" indicates the point of attachment of the linker):

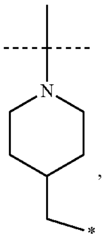 , 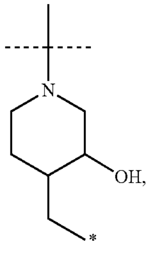 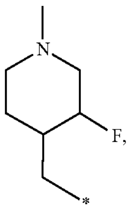

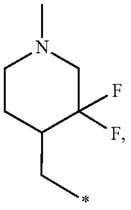 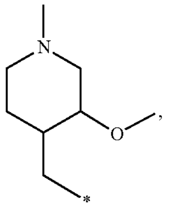 , 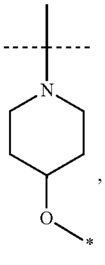 ,

-continued

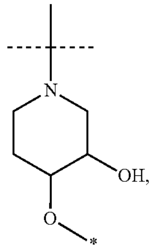
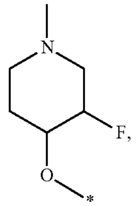
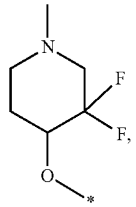
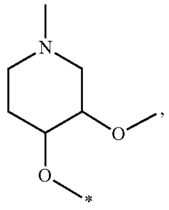
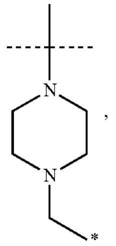
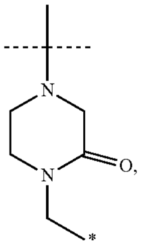
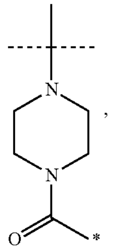
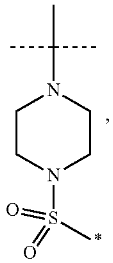
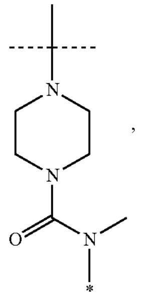
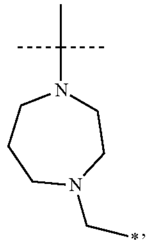
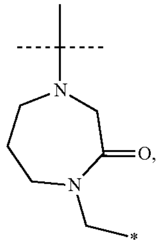
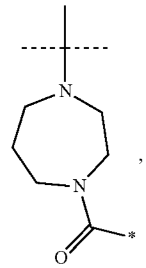
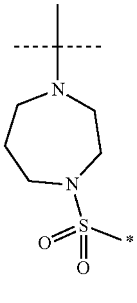
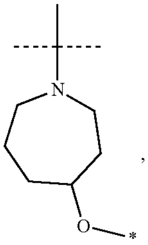
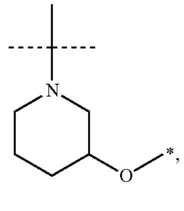

-continued

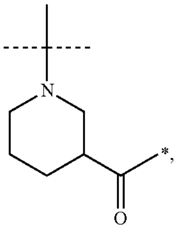
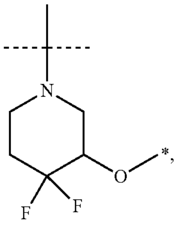
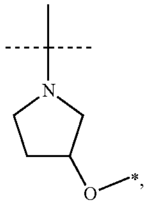
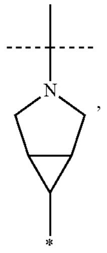
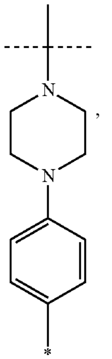
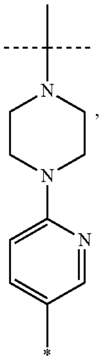
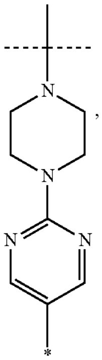
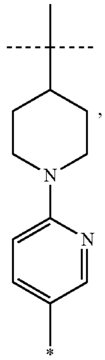
and
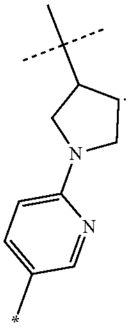

In certain embodiments, the linker is attached to at least one of R1', R2', R3', R4', R5', R6', or a combination thereof.

In certain embodiments, the description provides bifunctional or chimeric molecules with the structure: PTM-L-MLM, wherein PTM is a protein target binding moiety coupled to an MLM by L, wherein L is a bond (i.e., absent) or a chemical linker. In certain embodiments, the MLM has a structure selected from the group consisting of A-4-1, A-4-2, A-4-3, A-4-4, A-4-5, and A-4-6:

A-4-1

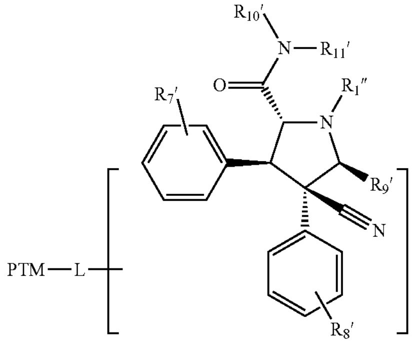

-continued

A-4-2

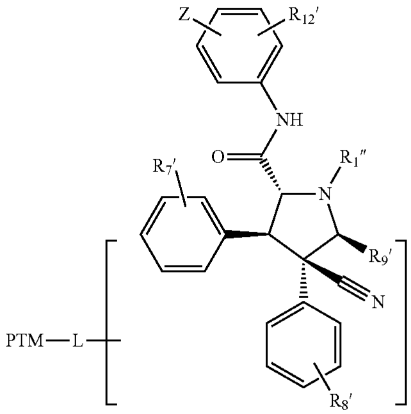

A-4-3

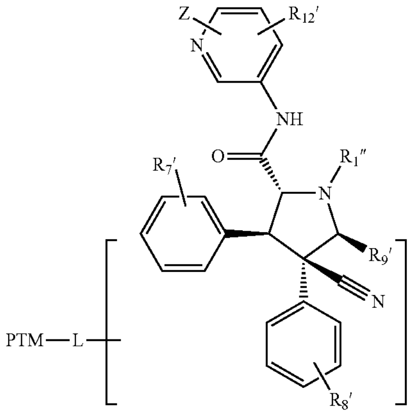

A-4-4

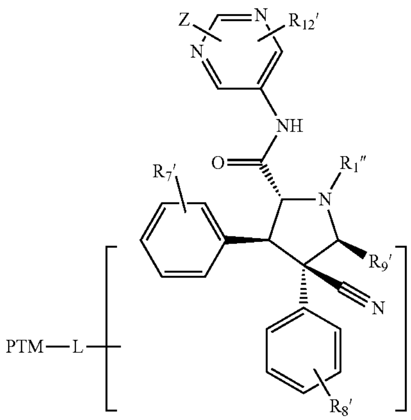

-continued

A-4-5

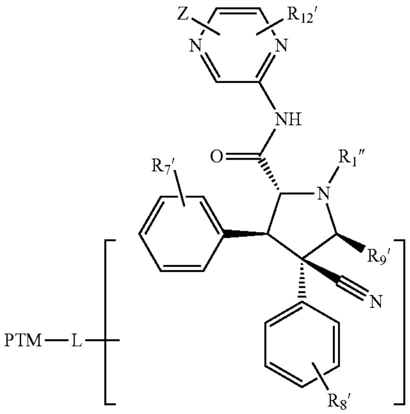

A-4-6

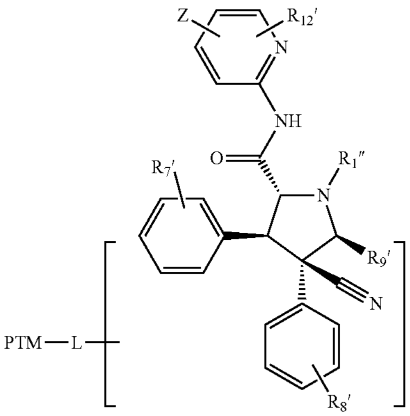

wherein:

R7' is a member selected from the group consisting of halogen, mono-, and di- or tri-substituted halogen;

R8' is selected from the group consisting of H, —F, —Cl, —Br, —I, —CN, —$NO_2$, ethylnyl, cyclopropyl, methyl, ethyl, isopropyl, vinyl, methoxy, ethoxy, isopropoxy, —OH, other C1-6 alkyl, other C1-6 alkenyl, and C1-6 alkynyl, mono-, di- or tri-substituted;

R9' is selected from the group consisting of alkyl, substituted alkyl, alkenyl, substituted alkenyl, alkynyl, substituted alkynyl, aryl, substituted aryl, hetero aryl, substituted heteroaryl, cycloalkyl, substituted cycloalkyl, alkenyl, and substituted cycloalkenyl;

Z is selected from the group consisting of H, —$OCH_3$, —$OCH_2CH_3$, and halogen;

R10' and R11' are each independently selected from the group consisting of H, $(CH_2)_n$—R', $(CH_2)_n$—NR'R", $(CH_2)_n$—NR'COR", $(CH_2)_n$—NR'$SO_2$R", $(CH_2)_n$—COOH, $(CH_2)_n$—COOR', $(CH)_n$—CONR'R", $(CH_2)_n$—OR', $(CH_2)_n$—SR', $(CH_2)_n$—SOR', $(CH_2)_n$—CH(OH)—R', $(CH_2)_n$—COR', $(CH_2)_n$—$SO_2$R', $(CH_2)_n$—SONR'R", $(CH_2)_n$—$SO_2$NR'R", $(CH_2CH_2O)_m$—$(CH_2)_n$—R', $(CH_2CH_2O)_m$—$(CH_2)_n$—OH, $(CH_2CH_2O)_m$—$(CH_2)_n$—OR', $(CH_2CH_2O)_m$—$(CH_2)_n$—NR'R", $(CH_2CH_2O)_m$—$(CH_2)_n$—NR'COR", $(CH_2CH_2O)_m(CH_2)_n$—NR'$SO_2$R", $(CH_2CH_2O)_m(CH_2)_n$—COOH, $(CH_2CH_2O)_m(CH_2)_n$—COOR', $(CH_2CH_2O)_m$—$(CH_2)_n$—CONR'R", $(CH_2CH_2O)_m$—$(CH_2)_n$—$SO_2$R', $(CH_2CH_2O)_m$—$(CH_2)_n$COR', $(CH_2CH_2O)_m$—$(CH_2)_n$—SONR'R", $(CH_2CH_2O)_m$—$(CH_2)_n$—$SO_2$NR'R", $(CH_2)_p$—$(CH_2CH_2O)_m$—$(CH_2)_n$R', $(CH_2)_p$—$(CH_2CH_2O)_m$—$(CH_2)_n$OH, $(CH_2)_p$—$(CH_2CH_2O)_m$—$(CH_2)_n$—OR', $(CH_2)_p$—$(CH_2CH_2O)_m$—$(CH_2)_n$—NR'R", $(CH_2)_p$—$(CH_2CH_2O)_m$—$(CH_2)_n$—NR'COR", $(CH_2)_p$—$(CH_2CH_2O)_m$—$(CH_2)_n$—NR'$SO_2$R", $(CH_2)_p$—$(CH_2CH_2O)_m$—$(CH_2)_n$—COOH, $(CH_2)_p$—$(CH_2CH_2O)_m$—$(CH_2)_n$—COOR', $(CH_2)_p$—$(CH_2CH_2O)_m$—$(CH_2)_n$—CONR'R", $(CH_2)$p-$(CH_2CH_2O)_m$—$(CH_2)_n$—$SO_2$R', $(CH_2)_p$—$(CH_2CH_2O)_m$—$(CH_2)_n$—COR', $(CH_2)_p$—$(CH_2CH_2O)_m$—$(CH_2)_n$—SONR'R", $(CH_2)_p$—$(CH_2CH_2O)_m$—$(CH_2)_n$—$SO_2$NR'R", Aryl-$(CH_2)_n$—COOH, and heteroaryl-alkyl-CO-alkyl-NR'R"m, wherein the alkyl may be substituted with OR', and heteroaryl-$(CH_2)_n$-heterocycle wherein the heterocycle may optionally be substituted with alkyl, hydroxyl, COOR' and COR'; wherein R' and R" are selected from H, alkyl, alkyl substituted with halogen, hydroxyl, NH2, NH(alkyl), $N(alkyl)_2$, oxo, carboxy, cycloalkyl and heteroaryl;

m, n, and p are independently 0 to 6;

R12' is selected from the group consisting of —O-(alkyl), —O-(alkyl)-alkoxy, —C(O)-(alkyl), —C(OH)-alkyl-alkoxy, —C(O)—NH-(alkyl), —C(O)—N-$(alkyl)_2$, —S(O)-(alkyl), $S(O)_2$-(alkyl), —C(O)-(cyclic amine), and —O-aryl-(alkyl), —O-aryl-(alkoxy);

R1" is selected from the group consisting of alkyl, aryl substituted alkyl, alkoxy substituted alkyl, cycloalkyl, aryl-substituted cycloalkyl, and alkoxy substituted cycloalkyl.

In any of the aspects or embodiments described herein, the alkyl, alkoxy or the like can be a lower alkyl or lower alkoxy.

In certain embodiments, the linker connection position is at least one of Z, R8', R9', R10', R11", R12", or R1".

The method used to design chimeric molecules as presented in A-1-1 through A-1-4, A-4-1 through A-4-6 can be applied to MBM or MLM with formula A-2, A-3, A-5, A-6, A-7 and A-8, wherein the solvent exposed area in the MBM or MLM can be connected to linker "L" which will be attached to target protein ligand "PTM", to construct PROTACs.

Exemplary Linkers

In certain embodiments, the compounds as described herein can be chemically linked or coupled via a chemical linker (L). In certain embodiments, the linker group L is a group comprising one or more covalently connected structural units of B (e.g., —$B_1$ . . . $B_q$—), wherein $B_1$ is a group coupled to at least one of a MBM, a PTM, or a combination thereof. In certain embodiments, $B_1$ links an MBM, a PTM, or a combination thereof. In certain embodiments $B_1$ links an MBM, a PTM or a combination thereof directly to another MBM, PTM, or combination thereof. In other embodiments, $B_1$ links a MBM, a PTM, or a combination thereof indirectly to another MBM, PTM, or combination thereof through $B_q$.

In certain embodiments, $B_1$ to $B_q$ are, each independently, a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}$═$CR^{L2}$, C≡C, $SiR^{L1}R^{L2}$, P(O)$R^{L1}$, P(O)O$R^{L1}$, $NR^{L3}$C(═NCN)$NR^{L4}$, $NR^{L3}$C(═NCN), $NR^{L3}$C(═$CNO_2$)$NR^{L4}$, $C_{3-11}$cycloalkyl optionally substituted with 0-$R^{L1}$ and/or $R^{L2}$ groups, $C_{3-11}$heteocyclyl optionally substituted with 0-6 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, where $R^{L1}$ or $R^{L2}$, each independently, can be linked to other B groups to form cycloalkyl and/or heterocyclyl moeity which can be further substituted with 0-4 $R^{L5}$ groups; wherein $R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}alkyl)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}cycloalkyl)_2$, $N(C_{1-8}$cycloalkyl)$(C_{1-8}$alkyl), OH, $NH_2$, SH, $SO_2C_{1-8}$alkyl, P(O)$(OC_{1-8}$alkyl)$(C_{1-8}$alkyl), P(O)$(OC_{1-8}alkyl)_2$, CC—$C_{1-8}$ alkyl, CCH, CH═CH($C_{1-8}$alkyl), C($C_{1-8}$alkyl)═CH($C_{1-8}$alkyl), C($C_{1-8}$alkyl)═C$(C_{1-8}alkyl)_2$, $Si(OH)_3$, $Si(C_{1-8}alkyl)_3$, Si(OH)$(C_{1-8}alkyl)_2$, $COC_{1-8}$alkyl, $CO_2$H, halogen, CN, $CF_3$, $CHF_2$, $CH_2F$, $NO_2$, $SF_5$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, N($C_{1-8}$alkyl)CONH($C_{1-8}$alkyl), N($C_{1-8}$alkyl)CON$(C_{1-8}alkyl)_2$, NHCONH($C_{1-8}$alkyl), NHCON$(C_{1-8}alkyl)_2$, $NHCONH_2$, N($C_{1-8}$alkyl)$SO_2$NH($C_{1-8}$alkyl), N($C_{1-8}$alkyl) $SO_2N(C_{1-8}alkyl)_2$, NH $SO_2$NH($C_{1-8}$alkyl), NH $SO_2N(C_{1-8}alkyl)_2$, NH $SO_2NH_2$.

In certain embodiments, q is an integer greater than or equal to 0. In certain embodiments, q is an integer greater than or equal to 1.

In certain embodiments, e.g., where q is greater than 2, $B_q$ is a group which is connected to MBM, and $B_1$ and $B_q$ are connected via structural units of B (number of such structural units of B: q-2).

In certain embodiments, e.g., where q is 2, $B_q$ is a group which is connected to $B_1$ and to a MBM.

In certain embodiments, e.g., where q is 1, the structure of the linker group L is —$B_1$—, and $B_1$ is a group which is connected to a MBM moiety and a PTM moiety.

In additional embodiments, q is an integer from 1 to 100, 1 to 90, 1 to 80, 1 to 70, 1 to 60, 1 to 50, 1 to 40, 1 to 30, 1 to 20, or 1 to 10.

In certain embodiments, the linker (L) is selected from the group consisting of: —$(CH_2)_n$-(lower alkyl)-, —$(CH_2)_n$-(lower alkoxyl)-, —$(CH_2)_n$-(lower alkoxyl)-$OCH_2$—C(O)—, —$(CH_2)_n$-(lower alkoxyl)-(lower alkyl)-$OCH_2$—C(O)—, —$(CH_2)_n$-(cycloalkyl)-(lower alkyl)-$OCH_2$—C(O)—, —$(CH_2)_n$-(hetero cycloalkyl)-, —$(CH_2CH_2O)_n$-(lower alkyl)-O—$CH_2$—C(O)—, —$(CH_2CH_2O)_n$-(hetero cycloalkyl)-O—$CH_2$—C(O)—, —$(CH_2CH_2O)_n$-Aryl-O—$CH_2$—C(O)—, —$(CH_2CH_2O)_n$-(hetero aryl)-O—$CH_2$—C(O)—, —$(CH_2CH_2O)_n$-(cyclo alkyl)-O-(hetero aryl)-O—$CH_2$—C(O)—, —$(CH_2CH_2O)_n$-(cyclo alkyl)-O-Aryl-O—$CH_2$—C(O)—, —$(CH_2CH_2O)_n$-(lower alkyl)-NH-Aryl-O—$CH_2$—C(O)—, —$(CH_2CH_2O)_n$-(lower alkyl)-O-Aryl-C(O)—, —$(CH_2CH_2O)_n$-cycloalkyl-O-Aryl-C(O)—, —$(CH_2CH_2O)_n$-cycloalkyl-O-(hetero aryl)1-C(O)—, where n can be 0 to 10;

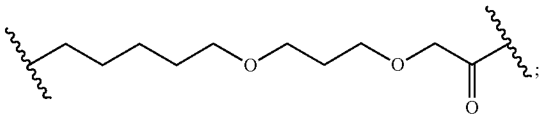;

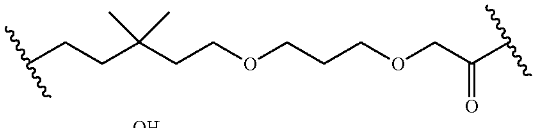;

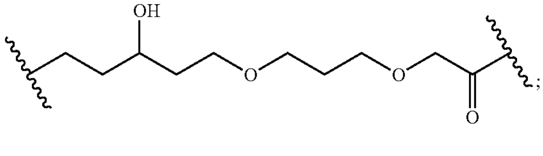;

-continued
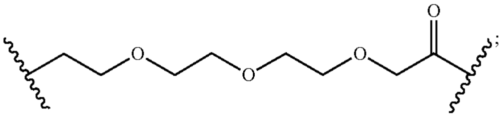
;
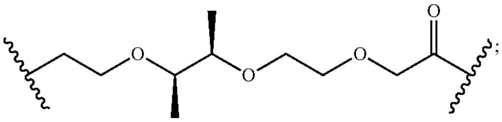
;
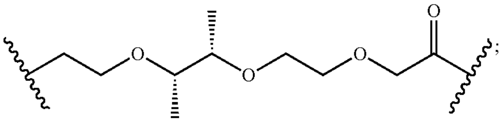
;
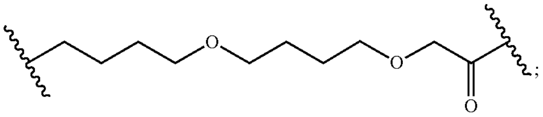
;
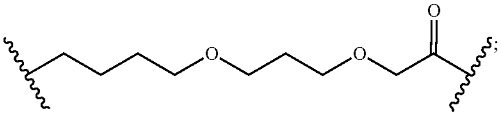
;
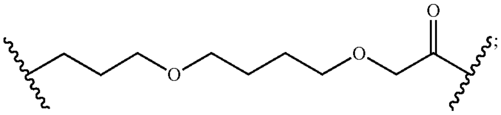
;
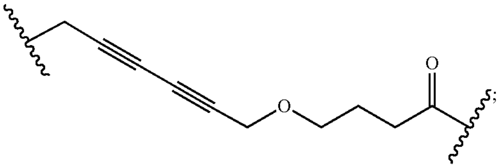
;
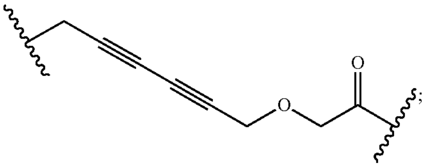
;
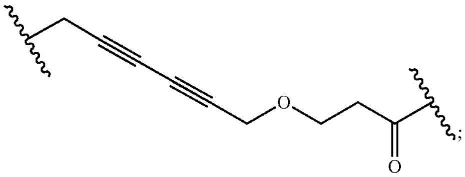
;
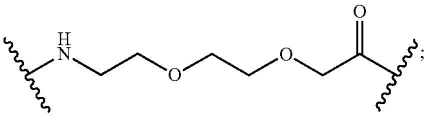
;
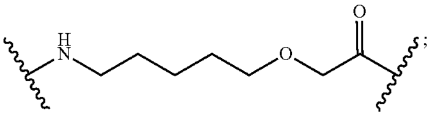
;
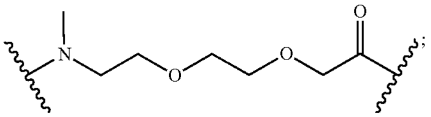
;
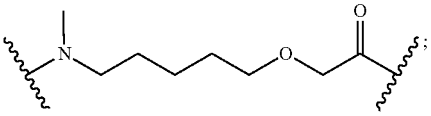
;
-continued
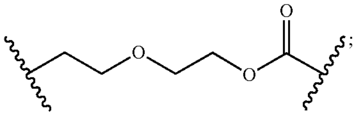
;
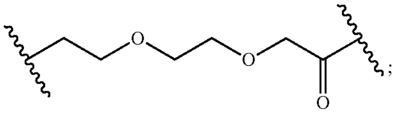
;
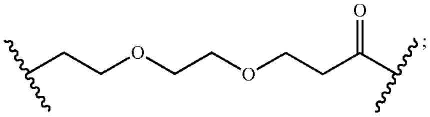
;
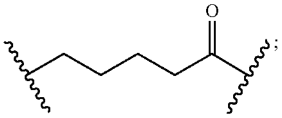
;
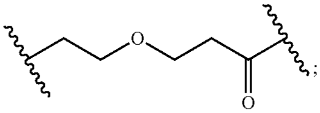
;
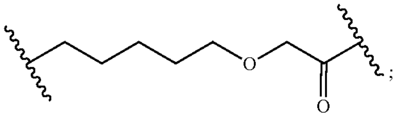
;
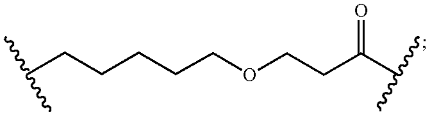
;
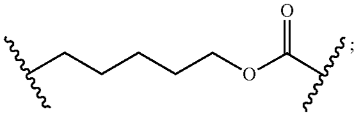
;
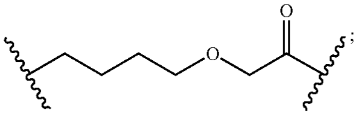
;
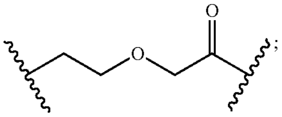
;
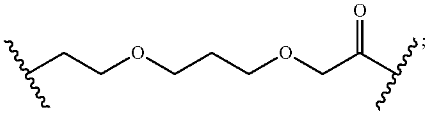
;
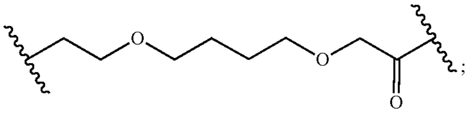
;
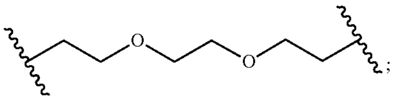
;
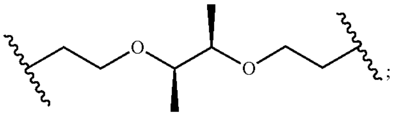
;

-continued

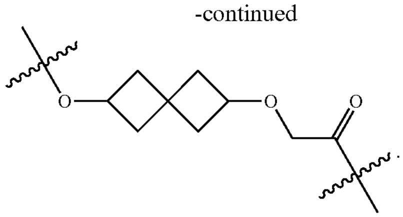

In additional embodiments, the linker group is optionally substituted (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interspersed with optionally substituted, O, N, S, P or Si atoms. In certain embodiments, the linker is substituted with an aryl, phenyl, benzyl, alkyl, alkylene, or heterocycle group. In certain embodiments, the linker may be asymmetric or symmetrical.

In any of the embodiments of the compounds described herein, the linker group may be any suitable moiety as described herein. In one embodiment, the linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

Although the MLM (or ULM) group and PTM group may be covalently linked to the linker group through any group which is appropriate and stable to the chemistry of the linker, in preferred aspects of the present invention, the linker is independently covalently bonded to the MLM group and the PTM group preferably through an amide, ester, thioester, keto group, carbamate (urethane), carbon or ether, each of which groups may be inserted anywhere on the MLM group and PTM group to provide maximum binding of the MLM group on the ubiquitin ligase and the PTM group on the target protein to be degraded. (It is noted that in certain aspects where the PTM group is a ULM group, the target protein for degradation may be the ubiquitin ligase itself). In certain preferred aspects, the linker may be linked to an optionally substituted alkyl, alkylene, alkene or alkyne group, an aryl group or a heterocyclic group on the MLM and/or PTM groups.

In certain embodiments, "L" can be linear chains with linear atoms from 4 to 24, the carbon atom in the linear chain can be substituted with oxygen, nitrogen, amide, fluorinated carbon, etc., such as the following:

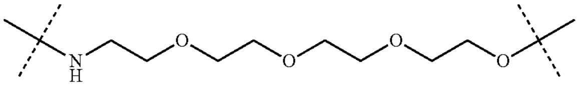

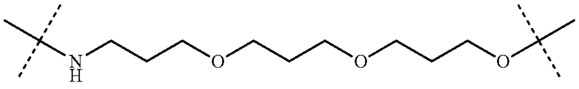

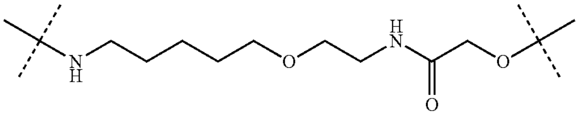

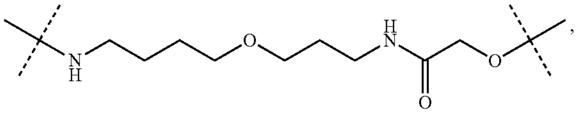
,

-continued

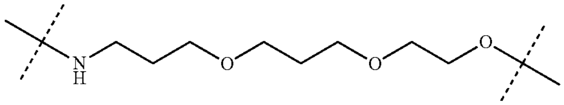

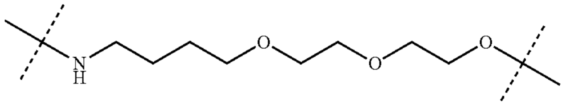

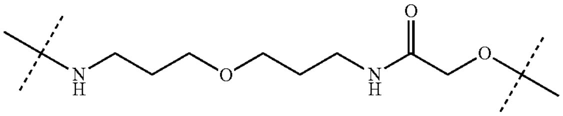
,

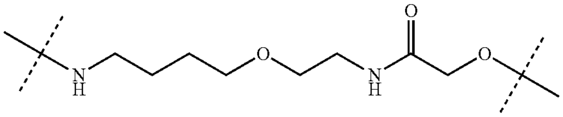
,

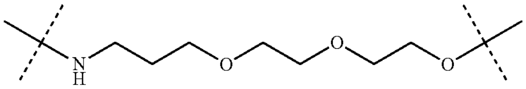

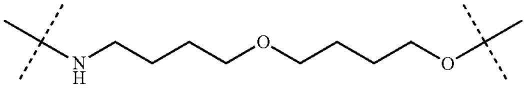

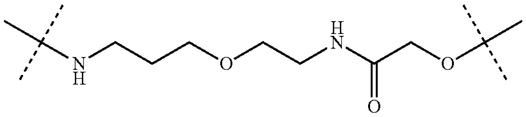

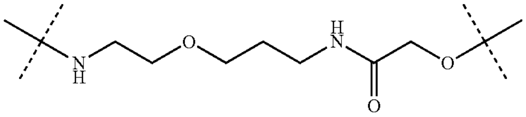
,

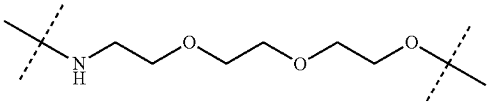

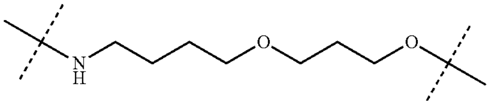

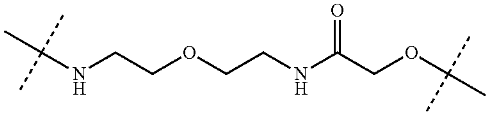

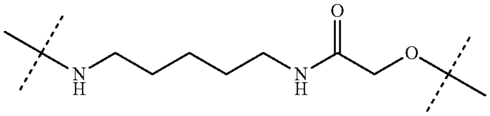
,

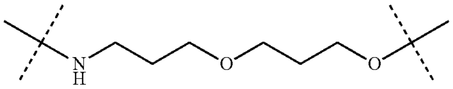

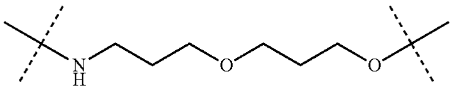

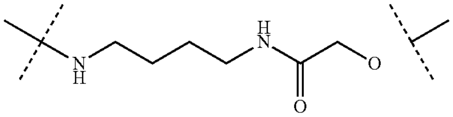

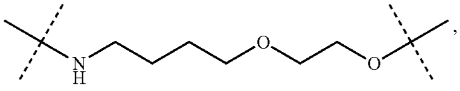
,

-continued
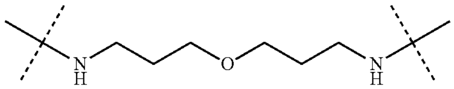
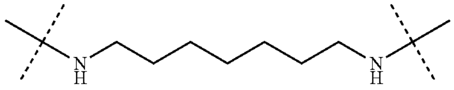
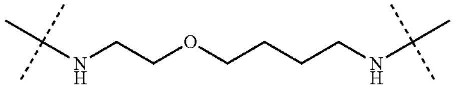
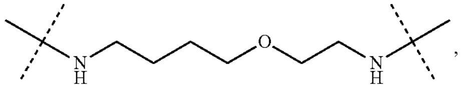
, or
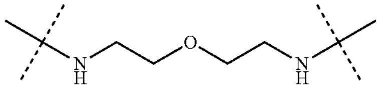
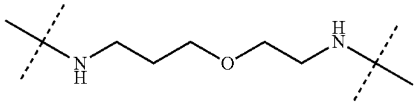
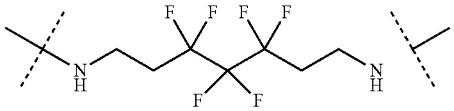
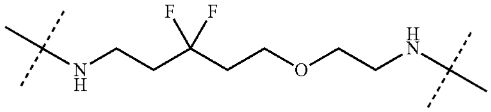
.
In certain embodiments, “L” can be nonlinear chains, and can be aliphatic or aromatic or heteroaromatic cyclic moieties, some examples of “L” include but not be limited to the following:
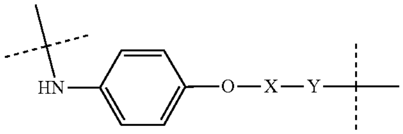
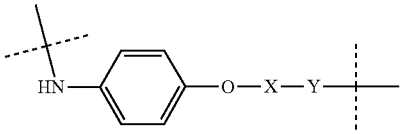
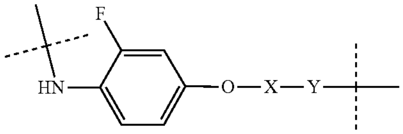
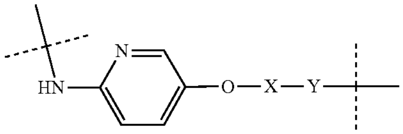
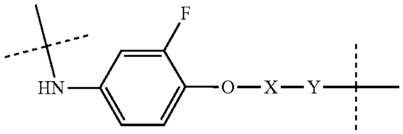
-continued
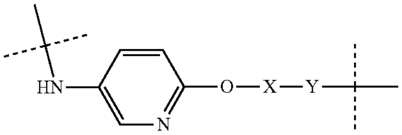
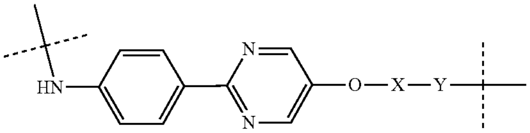
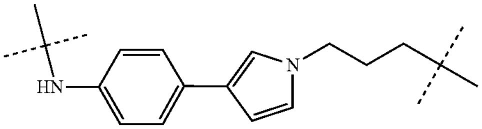
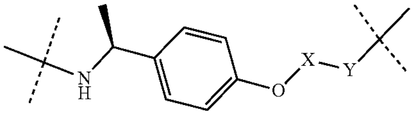
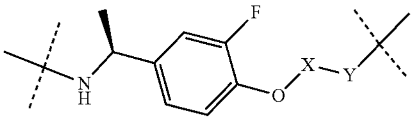
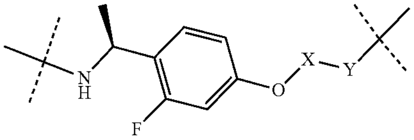
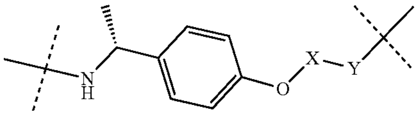
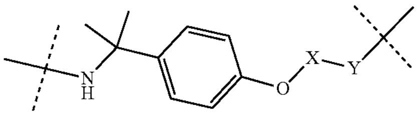
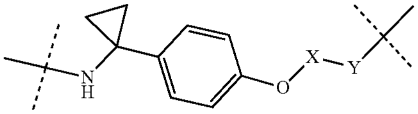
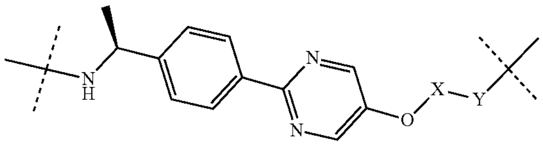
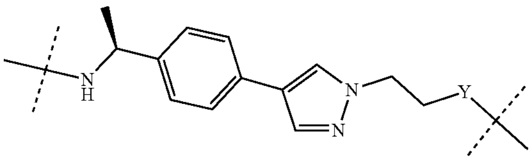
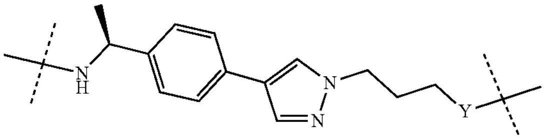
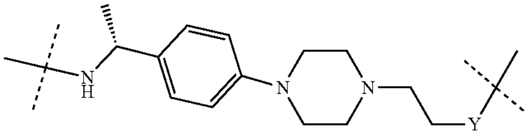

-continued

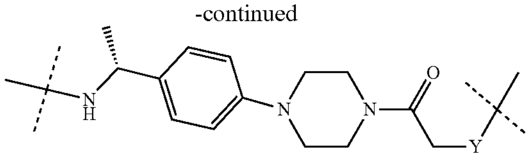

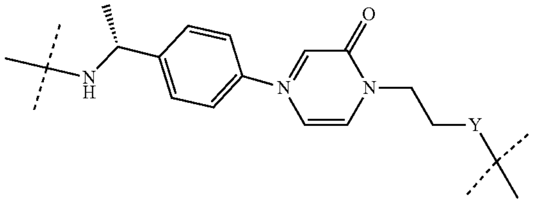

wherein:

"X" in above structures can be linear chain with atoms ranging from 2 to 14, and the mentioned chain can contain heteroatoms such as oxygen; and "Y" in above structures can be O, N, $S(O)_n$ (n=0, 1, 2).

Exemplary PTMs

In preferred aspects of the invention, the PTM group is a group, which binds to target proteins. Targets of the PTM group are numerous in kind and are selected from proteins that are expressed in a cell such that at least a portion of the sequences is found in the cell and may bind to a PTM group. The term "protein" includes oligopeptides and polypeptide sequences of sufficient length that they can bind to a PTM group according to the present invention. Any protein in a eukaryotic system or a microbial system, including a virus, bacteria or fungus, as otherwise described herein, are targets for ubiquitination mediated by the compounds according to the present invention. Preferably, the target protein is a eukaryotic protein. In certain aspects, the protein binding moiety is a haloalkane (preferably a $C_1$-$C_{10}$ alkyl group which is substituted with at least one halo group, preferably a halo group at the distal end of the alkyl group (i.e., away from the linker or CLM group), which may covalently bind to a dehalogenase enzyme in a patient or subject or in a diagnostic assay.

PTM groups according to the present invention include, for example, include any moiety which binds to a protein specifically (binds to a target protein) and includes the following non-limiting examples of small molecule target protein moieties: Hsp90 inhibitors, kinase inhibitors, compounds targeting Human BET Bromodomain-containing proteins, HDAC inhibitors, human lysine methyltransferase inhibitors, angiogenesis inhibitors, nuclear hormone receptor compounds, immunosuppressive compounds, and compounds targeting the aryl hydrocarbon receptor (AHR), among numerous others. The compositions described below exemplify some of the members of these nine types of small molecule target protein binding moieties. Such small molecule target protein binding moieties also include pharmaceutically acceptable salts, enantiomers, solvates and polymorphs of these compositions, as well as other small molecules that may target a protein of interest. These binding moieties are linked to the ubiquitin ligase binding moiety preferably through a linker in order to present a target protein (to which the protein target moiety is bound) in proximity to the ubiquitin ligase for ubiquitination and degradation.

Any protein, which can bind to a protein target moiety or PTM group and acted on or degraded by an ubiquitin ligase is a target protein according to the present invention. In general, target proteins may include, for example, structural proteins, receptors, enzymes, cell surface proteins, proteins pertinent to the integrated function of a cell, including proteins involved in catalytic activity, aromatase activity, motor activity, helicase activity, metabolic processes (anabolism and catrabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eurkaryotes and prokaryotes including humans as targets for drug therapy, other animals, including domesticated animals, microbials for the determination of targets for antibiotics and other antimicrobials and plants, and even viruses, among numerous others.

In still other embodiments, the PTM group is a haloalkyl group, wherein said alkyl group generally ranges in size from about 1 or 2 carbons to about 12 carbons in length, often about 2 to 10 carbons in length, often about 3 carbons to about 8 carbons in length, more often about 4 carbons to about 6 carbons in length. The haloalkyl groups are generally linear alkyl groups (although branched-chain alkyl groups may also be used) and are end-capped with at least one halogen group, preferably a single halogen group, often a single chloride group. Haloalkyl PT, groups for use in the present invention are preferably represented by the chemical structure $-(CH_2)_v$-Halo where v is any integer from 2 to about 12, often about 3 to about 8, more often about 4 to about 6. Halo may be any halogen, but is preferably Cl or Br, more often Cl.

In another embodiment, the present invention provides a library of compounds. The library comprises more than one compound wherein each composition has a formula of A-B, wherein A is a ubiquitin pathway protein binding moiety (preferably, an E3 ubiquitin ligase moiety as otherwise disclosed herein) and B is a protein binding member of a molecular library, wherein A is coupled (preferably, through a linker moiety) to B, and wherein the ubiquitin pathway protein binding moiety recognizes an ubiquitin pathway protein, in particular, an E3 ubiquitin ligase, such as cereblon. In a particular embodiment, the library contains a specific cereblon E3 ubiquitin ligase binding moiety bound to random target protein binding elements (e.g., a chemical compound library). As such, the target protein is not determined in advance and the method can be used to determine the activity of a putative protein binding element and its pharmacological value as a target upon degradation by ubiquitin ligase.

The present invention may be used to treat a number of disease states and/or conditions, including any disease state and/or condition in which proteins are dysregulated and where a patient would benefit from the degradation of proteins.

In an additional aspect, the description provides therapeutic compositions comprising an effective amount of a compound as described herein or salt form thereof, and a pharmaceutically acceptable carrier, additive or excipient, and optionally an additional bioactive agent. The therapeutic compositions modulate protein degradation in a patient or subject, for example, an animal such as a human, and can be used for treating or ameliorating disease states or conditions which are modulated through the degraded protein. In certain embodiments, the therapeutic compositions as described herein may be used to effectuate the degradation of proteins of interest for the treatment or amelioration of a disease, e.g., cancer. In certain additional embodiments, the disease is multiple myeloma.

In alternative aspects, the present invention relates to a method for treating a disease state or ameliorating the symptoms of a disease or condition in a subject in need thereof by degrading a protein or polypeptide through which a disease state or condition is modulated comprising administering to said patient or subject an effective amount, e.g., a therapeutically effective amount, of at least one compound as described hereinabove, optionally in combination with a pharmaceutically acceptable carrier, additive or excipient, and optionally an additional bioactive agent, wherein the composition is effective for treating or ameliorating the disease or disorder or symptom thereof in the subject. The method according to the present invention may be used to treat a large number of disease states or conditions including cancer, by virtue of the administration of effective amounts of at least one compound described herein. The disease state or condition may be a disease caused by a microbial agent or other exogenous agent such as a virus, bacteria, fungus, protozoa or other microbe or may be a disease state, which is caused by overexpression of a protein, which leads to a disease state and/or condition.

In another aspect, the description provides methods for identifying the effects of the degradation of proteins of interest in a biological system using compounds according to the present invention.

The term "target protein" is used to describe a protein or polypeptide, which is a target for binding to a compound according to the present invention and degradation by ubiquitin ligase hereunder. Such small molecule target protein binding moieties also include pharmaceutically acceptable salts, enantiomers, solvates and polymorphs of these compositions, as well as other small molecules that may target a protein of interest. These binding moieties are linked to CLM or ULM groups through linker groups L.

Target proteins which may be bound to the protein target moiety and degraded by the ligase to which the ubiquitin ligase binding moiety is bound include any protein or peptide, including fragments thereof, analogues thereof, and/or homologues thereof. Target proteins include proteins and peptides having any biological function or activity including structural, regulatory, hormonal, enzymatic, genetic, immunological, contractile, storage, transportation, and signal transduction. In certain embodiments, the target proteins include structural proteins, receptors, enzymes, cell surface proteins, proteins pertinent to the integrated function of a cell, including proteins involved in catalytic activity, aromatase activity, motor activity, helicase activity, metabolic processes (anabolism and catrabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eurkaryotes and prokaryotes, including microbes, viruses, fungi and parasites, including humans, microbes, viruses, fungi and parasites, among numerous others, as targets for drug therapy, other animals, including domesticated animals, microbials for the determination of targets for antibiotics and other antimicrobials and plants, and even viruses, among numerous others.

The term "protein target moiety" or PTM is used to describe a small molecule which binds to a target protein or other protein or polypeptide of interest and places/presents that protein or polypeptide in proximity to an ubiquitin ligase such that degradation of the protein or polypeptide by ubiquitin ligase may occur. Non-limiting examples of small molecule target protein binding moieties include Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR), among numerous others. The compositions described below exemplify some of the members of these nine types of small molecule target protein.

Exemplary protein target moieties according to the present disclosure include, haloalkane halogenase inhibitors, Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR).

Additional exemplary protein targets to which a PTM may bind and may be incorporated into compounds as described herein include, Adrenomedullin (AM), Angiopoietin (Ang), Autocrine motility factor, Bone morphogenetic proteins (BMPs), Ciliary neurotrophic factor family Ciliary neurotrophic factor (CNTF), Leukemia inhibitory factor (LIF), Interleukin-(IL-6), Colony-stimulating factors Macrophage colony-stimulating factor (m-CSF), Granulocyte colony-stimulating factor (G-CSF), Granulocyte macrophage colony-stimulating factor (GM-CSF), Epidermal growth factor (EGF), Ephrins Ephrin A1, Ephrin A2, Ephrin A3, Ephrin A4, Ephrin A5, Ephrin B1, Ephrin B2, Ephrin B3, Erythropoietin (EPO), Fibroblast growth factor (FGF), Foetal Bovine Somatotrophin (FBS), GDNF family of ligands Glial cell line-derived neurotrophic factor (GDNF), Neurturin, Persephin, Artemin, Growth differentiation factor-9 (GDF9), Hepatocyte growth factor (HGF), Hepatoma-derived growth factor (HDGF), Insulin, Insulin-like growth factors Insulin-like, growth factor-1 (IGF-1), Insulin-like growth factor-2 (IGF-2), Interleukins IL-1-Cofactor for IL-3 and IL-6, IL-2, -3, -4, -5, -6, -7, Keratinocyte growth factor (KGF), Migration-stimulating factor (MSF), Macrophage-stimulating protein (MSP), also known as hepatocyte growth factor-like protein (HGFLP), Myostatin (GDF-8), Neuregulins Neuregulin 1 (NRG1), Neuregulin 2 (NRG2), Neuregulin 3 (NRG3), Neuregulin 4 (NRG4), Neurotrophins Brain-derived neurotrophic factor (BDNF), Nerve growth factor (NGF), Neurotrophin-3 (NT-3), Neurotrophin-4 (NT-4), Placental growth factor (PGF), Platelet-derived growth factor (PDGF), Renalase (RNLS)—Anti-apoptotic survival factor, T-cell growth factor (TCGF), Thrombopoietin (TPO), Transforming growth factors Transforming growth factor alpha (TGF-α), Transforming growth factor beta (TGF-β), Tumor necrosis factor-alpha (TNF-α), Vascular endothelial growth factor (VEGF), Wnt Signaling Pathway and receptors of the same.

More specifically, a number of drug targets for human therapeutics represent protein targets to which protein target moiety may be bound and incorporated into compounds according to the present invention. These include proteins which may be used to restore function in numerous polygenic diseases, including for example B7.1 and B7, TINFR1m, TNFR2, NADPH oxidase, BclIBax and other partners in the apotosis pathway, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide (NO) synthase, cyclo-oxygenase 1, cyclo-oxygenase 2, 5HT receptors, dopamine receptors, G Proteins, i.e., Gq, histamine receptors, 5-lipoxygenase, tryptase serine protease, thymidylate synthase, purine nucleoside phosphorylase, GAPDH trypanosomal, glycogen phosphorylase, Carbonic anhydrase, chemokine receptors, JAK, STAT, RXR and similar, HIV 1 protease, HIV 1 integrase, influenza, neuramimidase, hepatitis B reverse transcriptase, sodium channel, multi drug resistance (MDR), protein P-glycoprotein (and MRP), tyrosine kinases, CD23, CD124, tyrosine kinase p56 lck, CD4, CD5, IL-2 receptor, IL-1 receptor, TNF-alphaR, ICAM1, Cat+ channels, VCAM, VLA-4 integrin, selectins, CD40/CD40L, newokinins and receptors, inosine monophosphate dehydrogenase, p38 MAP Kinase, Ras, Raf, ERK pathway, FLT-3, KSR1, SMARCA, SMARCA2, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5 alpha reductase inhibitors, angiotensin 11, glycine receptor, noradrenaline reuptake receptor, endothelin receptors, neuropeptide Y and receptor, estrogen receptors, androgen receptors, adenosine receptors, adenosine kinase and AMP deaminase, purinergic receptors (P2Y1, P2Y2, P2Y4, P2Y6, P2X1-7), farnesyltransferases, geranylgeranyl transferase, TrkA a receptor for NGF, beta-amyloid, tyrosine kinase Flk-IIKDR, vitronectin receptor, integrin receptor, Her-21 neu, telomerase inhibition, cytosolic phospholipaseA2 and EGF receptor tyrosine kinase. Additional protein targets include, for example, ecdysone 20-monooxygenase, ion channel of the GABA gated chloride channel, acetylcholinesterase, voltage-sensitive sodium channel protein, calcium release channel, and chloride channels. Still further target proteins include Acetyl-CoA carboxylase, adenylosuccinate synthetase, protoporphyrinogen oxidase, and enolpyruvylshikimate-phosphate synthase.

Haloalkane dehalogenase enzymes are another target of specific compounds according to the present invention. Compounds according to the present invention which contain chloroalkane peptide binding moieties (C1-C12 often about C2-C10 alkyl halo groups) may be used to inhibit and/or degrade haloalkane dehalogenase enzymes which are used in fusion proteins or related dioagnostic proteins as described in PCT/US2012/063401 filed Dec. 6, 2011 and published as WO 2012/078559 on Jun. 14, 2012, the contents of which is incorporated by reference herein.

These various protein targets may be used in screens that identify compound moieties which bind to the protein and by incorporation of the moiety into compounds according to the present invention, the level of activity of the protein may be altered for therapeutic end result.

The compositions described below exemplify some of the members of these types of small molecule target protein binding moieties. Such small molecule target protein binding moieties also include pharmaceutically acceptable salts, enantiomers, solvates and polymorphs of these compositions, as well as other small molecules that may target a protein of interest. References which are cited hereinbelow are incorporated by reference herein in their entirety.

I. Heat Shock Protein 90 (HSP90) Inhibitors:

HSP90 inhibitors as used herein include, but are not limited to:

1. The HSP90 inhibitors identified in Vallee, et al., "Tricyclic Series of Heat Shock Protein 90 (HSP90) Inhibitors Part I: Discovery of Tricyclic Imidazo[4,5-C] Pyridines as Potent Inhibitors of the HSP90 Molecular Chaperone (2011) *J. Med. Chem.* 54: 7206, including YKB (N-[4-(3H-imidazo[4,5-C]Pyridin-2-yl)-9H-Fluoren-9-yl]-succinamide):

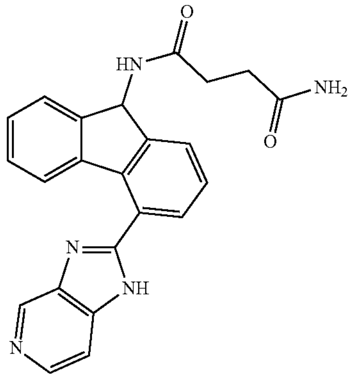 [SMILES: NC(=O)CCC(=O)NC1c2ccccc2-c2c(-c3nc4cnccc4[nH]3)cccc21]

derivatized where a linker group L or a -(L-MLM) group is attached, for example, via the terminal amide group;

2. The HSP90 inhibitor p54 (modified) (8-[(2,4-dimethylphenyl)sulfanyl]-3]pent-4-yn-1-yl-3H-purin-6-amine):

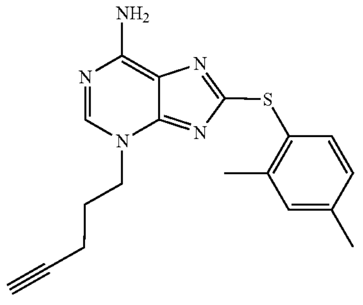 [SMILES: C#CCCCn1cnc(N)c2nc(Sc3ccc(C)cc3C)nc1-2]

derivatized where a linker group L or a -(L-MLM) group is attached, for example, via the terminal acetylene group;

3. The HSP90 inhibitors (modified) identified in Brough, et al., "4,5-Diarylisoxazole HSP90 Chaperone Inhibitors: Potential Therapeutic Agents for the Treatment of Cancer", *J. MED. CHEM. vol:* 51, page: 196 (2008), including the compound 2GJ (5-[2,4-dihydroxy-5-(1-methylethyl)phenyl]-n-ethyl-4-[4-(morpholin-4-ylm-ethyl)phenyl]isoxazole-3-carboxamide) having the structure:

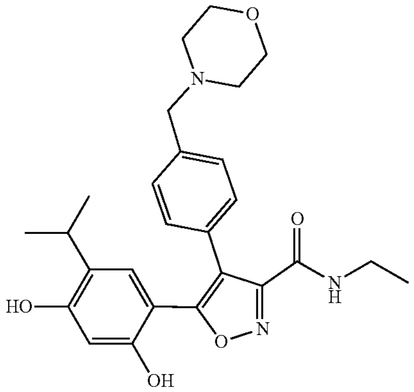 [SMILES: CCNC(=O)c1noc(-c2cc(C(C)C)c(O)cc2O)c1-c1ccc(CN2CCOCC2)cc1]

derivatized, where a linker group L or a -(L-MLM) group is attached, for example, via the amide group (at the amine or at the alkyl group on the amine);

4. The HSP90 inhibitors (modified) identified in Wright, et al., Structure-Activity Relationships in Purine-Based Inhibitor Binding to HSP90 Isoforms, *Chem Biol.* 2004 June; 11(6):775-85, including the HSP90 inhibitor PU3 having the structure:

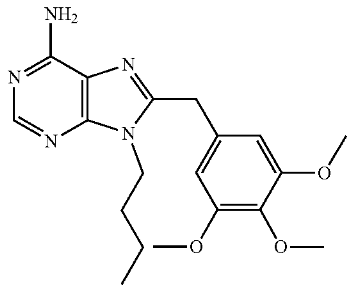 [SMILES: CCCCn1c(Cc2cc(OC)c(OC)c(OC)c2)nc2c(N)ncnc21]

derivatized where a linker group L or -(L-MLM) is attached, for example, via the butyl group; and 5. The HSP90 inhibitor geldanamycin ((4E,6Z,8S,9S,10E,12S,13R,14S,16R)-13-hydroxy-8,14,19-trimethoxy-4,10,12,16-tetramethyl-3,20,22-trioxo-2-azabicyclo[16.3.1] (derivatized) or any of its derivatives (e.g. 17-alkylamino-17-desmethoxygeldanamycin ("17-AAG") or 17-(2-dimethylaminoethyl) amino-17-desmethoxygeldanamycin ("17-DMAG")) (derivatized, where a linker group L or a-(L-MLM) group is attached, for example, via the amide group).

II. Kinase and Phosphatase Inhibitors:

Kinase inhibitors as used herein include, but are not limited to:

1. Erlotinib Derivative Tyrosine Kinase Inhibitor:

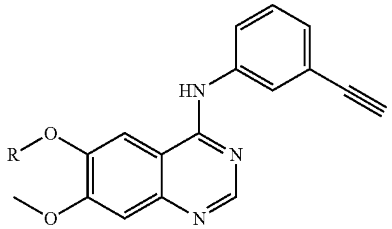

where R is a linker group L or a -(L-MLM) group attached, for example, via the ether group;

2. The kinase inhibitor sunitinib (derivatized):

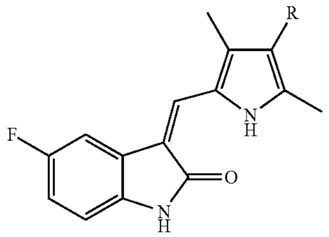

derivatized where R is a linker group L or a -(L-MLM) group attached, for example, to the pyrrole moiety;

3. Kinase Inhibitor sorafenib (derivatized):

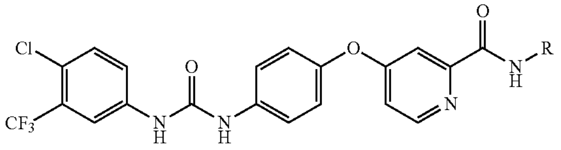

derivatized where R is a linker group L or a -(L-MLM) group attached, for example, to the amide moiety;

4. The kinase inhibitor desatinib (derivatized):

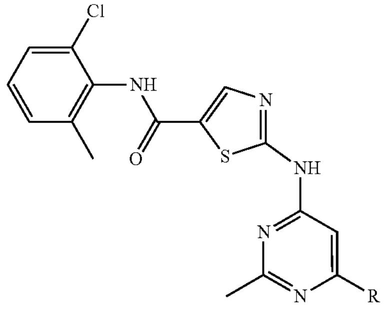

derivatized where R is a linker group Lor a-(L-MLM) attached, for example, to the pyrimidine;

5. The kinase inhibitor lapatinib (derivatized):

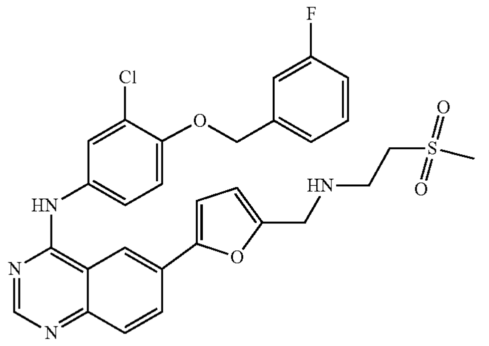 [SMILES: CS(=O)(=O)CCNCc1ccc(-c2ccc3ncnc(Nc4ccc(OCc5cccc(F)c5)c(Cl)c4)c3c2)o1]

derivatized where a linker group L or a-(L-MLM) group is attached, for example, via the terminal methyl of the sulfonyl methyl group;

6. The kinase inhibitor U09-CX-5279 (derivatized):

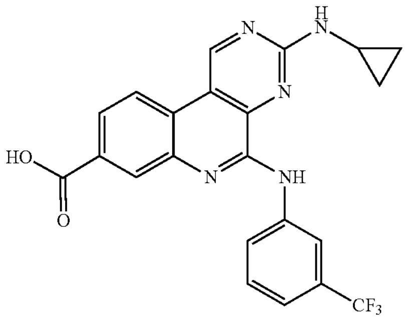 [SMILES: O=C(O)c1ccc2c(c1)nc(Nc1cccc(C(F)(F)F)c1)c1nc(NC3CC3)ncc12]

derivatized where a linker group L or a -(L-MLM) group is attached, for example, via the amine (aniline), carboxylic acid or amine alpha to cyclopropyl group, or cyclopropyl group;

7. The kinase inhibitors identified in Millan, et al., Design and Synthesis of Inhaled P38 Inhibitors for the Treatment of Chronic Obstructive Pulmonary Disease, *J. MED. CHEM. vol:* 54, page: 7797 (2011), including the kinase inhibitors Y1W and Y1X (Derivatized) having the structures:

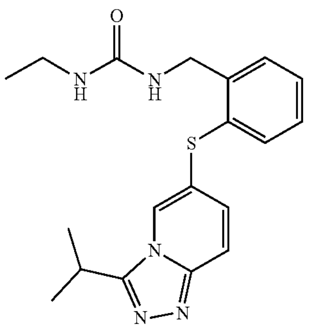 [SMILES: CCNC(=O)NCc1ccccc1Sc1ccc2nnc(C(C)C)n2c1]

YIX(1-ethyl-3-(2-{[3-(1-methylethyl)[1,2,4]triazolo[4,3-a]pyridine-6-yl]sulfanyl}benzyl)urea, derivatized where a linker group L or a-(L-MLM) group is attached, for example, via the *i*propyl group;

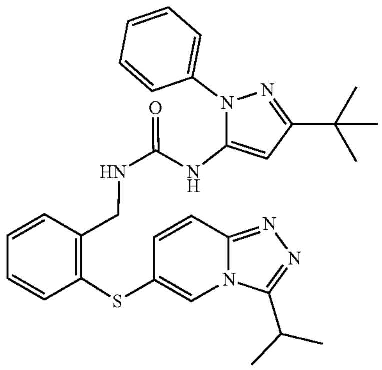 [SMILES: CC(C)c1nnc2ccc(Sc3ccccc3CNC(=O)Nc3cc(C(C)(C)C)nn3-c3ccccc3)cn12]

YIW 1-(3-tert-butyl-1-phenyl-1H-pyrazol-5-yl)-3-(2-{[3-(1-methylethyl)[1,2,4]triazolo[4,3-a]pyridin-6-yl] sulfanyl}benzyl)urea derivatized where a linker group L or a -(L-MLM) group is attached, for example, preferably via either the i-propyl group or the t-butyl group;

8. The kinase inhibitors identified in Schenkel, et al., Discovery of Potent and Highly Selective Thienopyridine Janus Kinase 2 Inhibitors *J. Med. Chem.,* 2011, 54 (24), pp 8440-8450, including the compounds 6TP and OTP (Derivatized) having the structures:

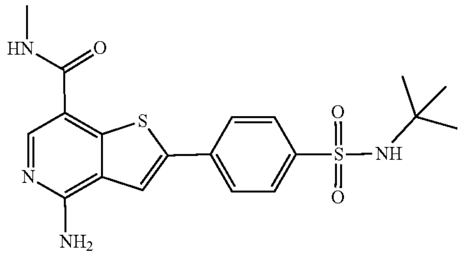 [SMILES: CNC(=O)c1cnc(N)c2cc(-c3ccc(S(=O)(=O)NC(C)(C)C)cc3)sc12]

6TP 4-amino-2-[4-(tert-butylsulfamoyl)phenyl]-N-methylthieno[3,2-c]pyridine-7-carboxamide Thienopyridine 19 derivatized where a linker group L or a -(L-MLM) group is attached, for example, via the terminal methyl group bound to amide moiety;

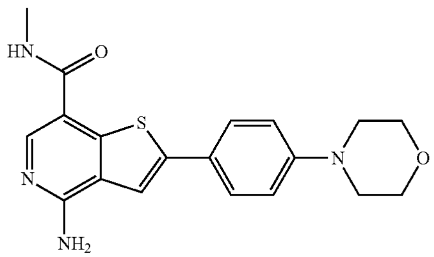 [SMILES: CNC(=O)c1cnc(N)c2cc(-c3ccc(N4CCOCC4)cc3)sc12]

0TP 4-amino-N-methyl-2-[4-(morpholin-4-yl)phenyl] thieno[3,2-c]pyridine-7-carboxamide Thienopyridine 8 derivatized where a linker group L or a -(L-MLM) group is attached, for example, via the terminal methyl group bound to the amide moiety;

9. The kinase inhibitors identified in Van Eis, et al., "2,6-Naphthyridines as potent and selective inhibitors of the novel protein kinase C isozymes", *Biorg. Med. Chem. Lett.* 2011 Dec. 15; 21(24):7367-72, including the kinase inhibitor 07U having the structure:

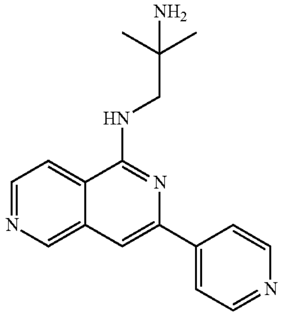 [SMILES: CC(C)(N)CNc1nc(-c2ccncc2)cc2cnccc12]

07U 2-methyl-N~1~[3-(pyridin-4-yl)-2,6-naphthyridin-1-yl]propane-1,2-diamine derivatized where a linker group L or a -(L-MLM) group is attached, for example, via the secondary amine or terminal amino group;

10. The kinase inhibitors identified in Lountos, et al., "Structural Characterization of Inhibitor Complexes with Checkpoint Kinase 2 (Chk2), a Drug Target for Cancer Therapy", *J. STRUCT. BIOL. vol:* 176, page: 292 (2011), including the kinase inhibitor YCF having the structure:

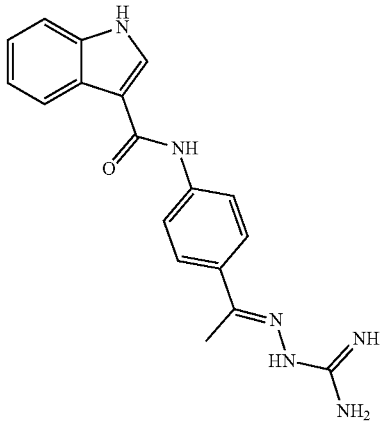

NXP

N-{4-[(1E)-N-CARBAMIMIDOYLETHANEHYDRAZONOYL]PHENYL}-1H-INDOLE-3-CARBOXAMIDE derivatized where a linker group L or a -(L-MLM) group is attached, for example, via the terminal hydroxyl group (XK9) or the hydrazone group (NXP);

12. The kinase inhibitor afatinib (derivatized) (N-[4-[(3-chloro-4-fluorophenyl)amino]-7-[[(3S)-tetrahydro-3-furanyl]oxy]-6-quinazolinyl]-4(dimethylamino)-2-

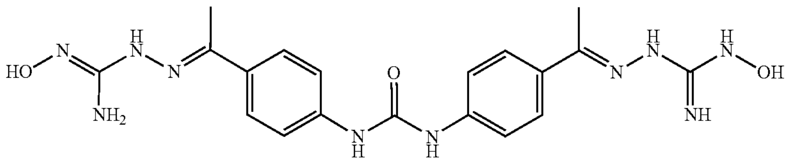 [SMILES: C/C(=N\NC(=N)NO)c1ccc(NC(=O)Nc2ccc(/C(C)=N/N/C(N)=N/O)cc2)cc1]

derivatized where a linker group L or a -(L-MLM) group is attached, for example, via either of the terminal hydroxyl groups;

11. The kinase inhibitors identified in Lountos, et al., "Structural Characterization of Inhibitor Complexes with Checkpoint Kinase 2 (Chk2), a Drug Target for Cancer Therapy", *J. STRUCT. BIOL. vol:* 176, page: 292 (2011), including the kinase inhibitors XK9 and NXP (derivatized) having the structures:

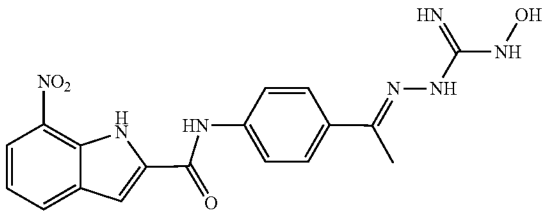 [SMILES: C/C(=N\NC(=N)NO)c1ccc(NC(=O)c2cc3cccc([N+](=O)[O-])c3[nH]2)cc1]

XK9 N-{4-[(1 E)-N—(N-hydroxycarbamimidoyl)ethanehydrazonoyl]phenyl}-7-nitro-1H-indole-2-carboxamide butenamide) (Derivatized where a linker group L or a -(L-MLM) group is attached, for example, via the aliphatic amine group);

13. The kinase inhibitor fostamatinib (derivatized) ([6-({5-fluoro-2-[(3,4,5-trimethoxyphenyl)amino]pyrimidin-4-yl}amino)-2,2-dimethyl-3-oxo-2,3-dihydro-4H-pyrido[3,2-b]-1,4-oxazin-4-yl]methyl disodium phosphate hexahydrate) (Derivatized where a linker group L or a -(L-MLM) group is attached, for example, via a methoxy group);

14. The kinase inhibitor gefitinib (derivatized) (N-(3-chloro-4-fluoro-phenyl)-7-methoxy-6-(3-morpholin-4-ylpropoxy)quinazolin-4-amine):

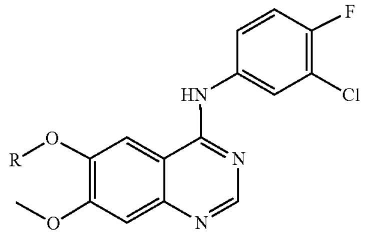

derivatized where a linker group L or a -(L-MLM) group is attached, for example, via a methoxy or ether group;

15. The kinase inhibitor lenvatinib (derivatized) (4-[3-chloro-4-(cyclopropylcarbamoylamino)phenoxy]-7- methoxy-quinoline-6-carboxamide) (derivatized where a linker group L or a -(L-MLM) group is attached, for example, via the cyclopropyl group);

16. The kinase inhibitor vandetanib (derivatized) (N-(4-bromo-2-fluorophenyl)-6-methoxy-7-[(1-methylpiperidin-4-yl)methoxy]quinazolin-4-amine) (derivatized where a linker group L or a -(L-MLM) group is attached, for example, via the methoxy or hydroxyl group);

17. The kinase inhibitor vemurafenib (derivatized) (propane-1-sulfonic acid {3-[5-(4-chlorophenyl)-1H-pyrrolo[2,3-b]pyridine-3-carbonyl]-2,4-difluoro-phenyl}-amide), derivatized where a linker group L or a -(L-MLM) group is attached, for example, via the sulfonyl propyl group;

18. The kinase inhibitor Gleevec (derivatized):

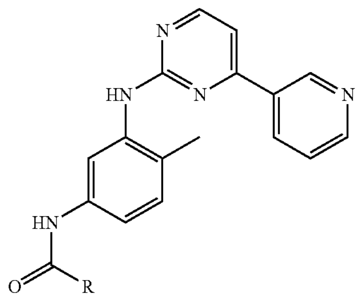

derivatized where R as a linker group L or a-(L-MLM) group is attached, for example, via the amide group or via the aniline amine group;

19. The kinase inhibitor pazopanib (derivatized) (VEGFR3 inhibitor):

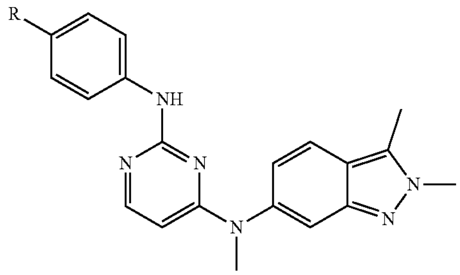

derivatized where R is a linker group L or a-(L-MLM) group attached, for example, to the phenyl moiety or via the aniline amine group;

20. The kinase inhibitor AT-9283 (Derivatized) Aurora Kinase Inhibitor

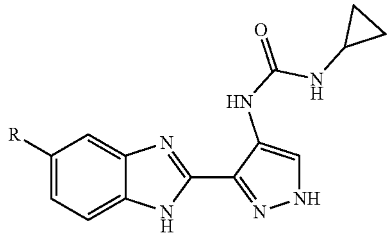

where R is a linker group L or a -(L-MLM) group attached, for example, to the phenyl moiety);

21. The kinase inhibitor TAE684 (derivatized) ALK inhibitor

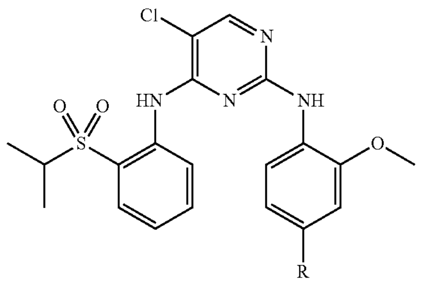

where R is a linker group L or a -(L-MLM) group attached, for example, to the phenyl moiety);

22. The kinase inhibitor nilotanib (derivatized) Abl inhibitor:

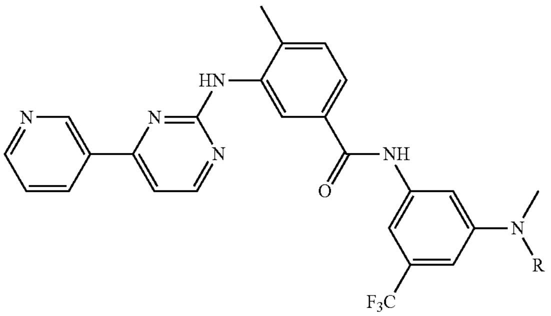

derivatized where R is a linker group L or a -(L-MLM) group attached, for example, to the phenyl moiety or the aniline amine group;

23. Kinase Inhibitor NVP-BSK805 (derivatized) JAK2 Inhibitor

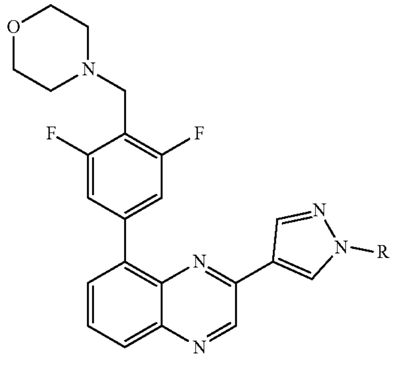

derivatized where R is a linker group L or a -(L-MLM) group attached, for example, to the phenyl moiety or the diazole group;

24. Kinase Inhibitor crizotinib Derivatized Alk Inhibitor

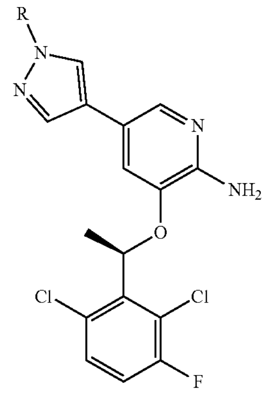

derivatized where R is a linker group L or a -(L-MLM) group attached, for example, to the phenyl moiety or the diazole group;

25. Kinase Inhibitor JNJ FMS (derivatized) Inhibitor

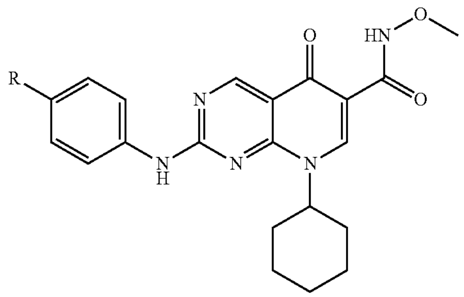

derivatized where R is a linker group L or a -(L-MLM) group attached, for example, to the phenyl moiety;

26. The kinase inhibitor foretinib (derivatized) Met Inhibitor

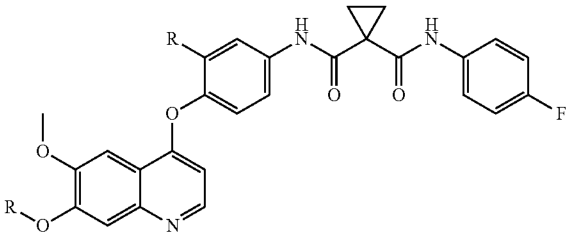

derivatized where R is a linker group L or a -(L-MLM) group attached, for example, to the phenyl moiety or a hydroxyl or ether group on the quinoline moiety;

27. The allosteric Protein Tyrosine Phosphatase Inhibitor PTP1B (derivatized):

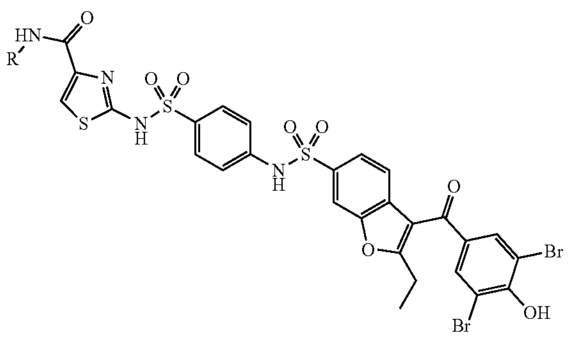

derivatized where a linker group L or a -(L-MLM) group is attached, for example, at R, as indicated;

28. The inhibitor of SHP-2 Domain of Tyrosine Phosphatase (derivatized):

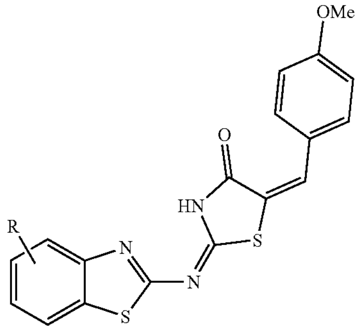

derivatized where a linker group L or a -(L-MLM) group is attached, for example, at R;

29. The inhibitor (derivatized) of BRAF ($BRAF^{V600E}$)/MEK:

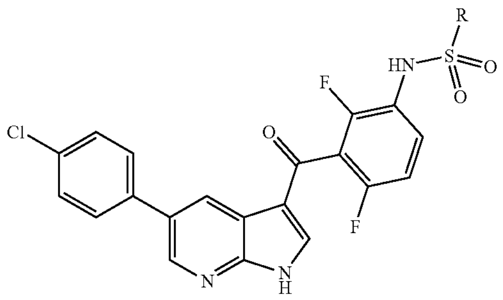

derivatized where a linker group L or a-(L-MLM) group is attached, for example, at R;

30. Inhibitor (derivatized) of Tyrosine Kinase ABL

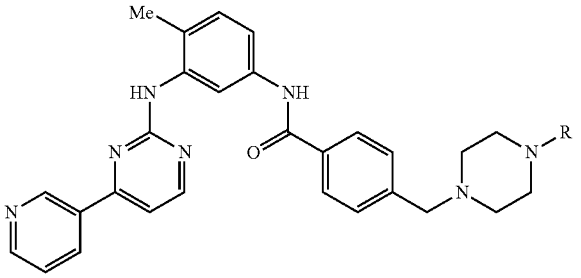

derivatized where a linker group L or a-(L-MLM) group is attached, for example, at R;

31. The kinase inhibitor OSI-027 (derivatized) mTORC1/2 inhibitor

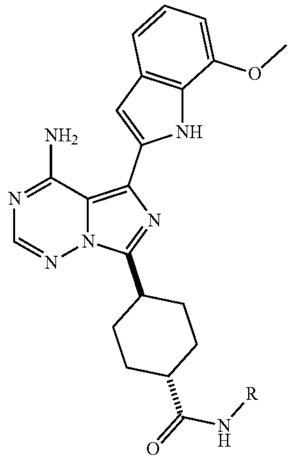

derivatized where a linker group L or a-(L-MLM) group is attached, for example, at R;

32. The kinase inhibitor OSI-930 (derivatized) c-Kit/KDR inhibitor

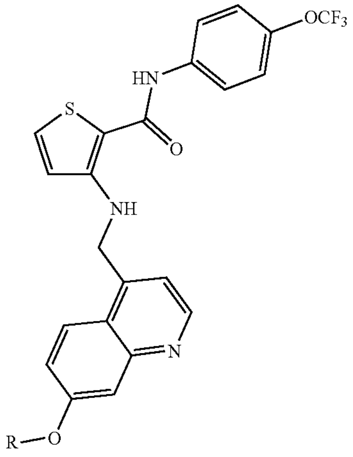

derivatized where a linker group L or a-(L-MLM) group is attached, for example, at R; and 33. The kinase inhibitor OSI-906 (derivatized) IGF1R/IR inhibitor

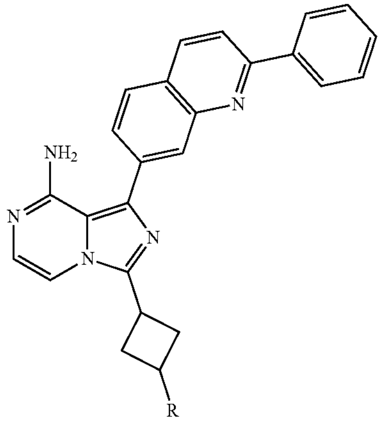

derivatized where a linker group L or a-(L-MLM) group is attached, for example, at R.

Wherein, in any of the embodiments described in sections I-XVII, "R" designates a site for attachment of a linker group L or a -(L-MLM) group on the piperazine moiety.

III. HDM2/1VIDM2 Inhibitors:

HDM2/MDM2 inhibitors as used herein include, but are not limited to:

1. The HDM2/MDM2 inhibitors identified in Vassilev, et al., In vivo activation of the p53 pathway by small-molecule antagonists of MDM2, *SCIENCE vol:* 303, page: 844-848 (2004), and Schneekloth, et al., Targeted intracellular protein degradation induced by a small molecule: En route to chemical proteomics, *Bioorg. Med. Chem. Lett.* 18 (2008) 5904-5908, including (or additionally) the compounds nutlin-3, nutlin-2, and nutlin-1 (derivatized) as described below, as well as all derivatives and analogs thereof:

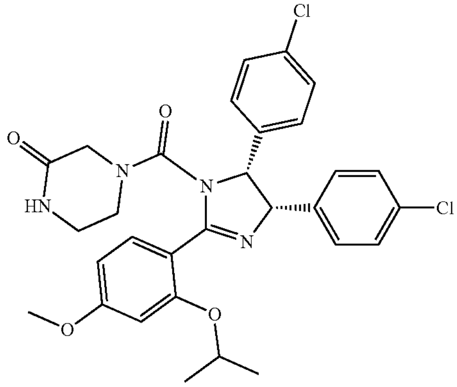 [SMILES: COc1ccc(C2=N[C@@H](c3ccc(Cl)cc3)[C@@H](c3ccc(Cl)cc3)N2C(=O)N2CCNC(=O)C2)c(OC(C)C)c1]

(derivatized where a linker group L or a -(L-MLM) group is attached, for example, at the methoxy group or as a hydroxyl group);

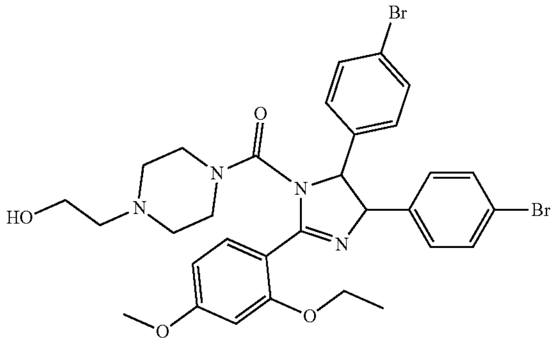 [SMILES: CCOc1cc(OC)ccc1C1=NC(c2ccc(Br)cc2)C(c2ccc(Br)cc2)N1C(=O)N1CCN(CCO)CC1]

(derivatized where a linker group L or a -(L-MLM) group is attached, for example, at the methoxy group or hydroxyl group);

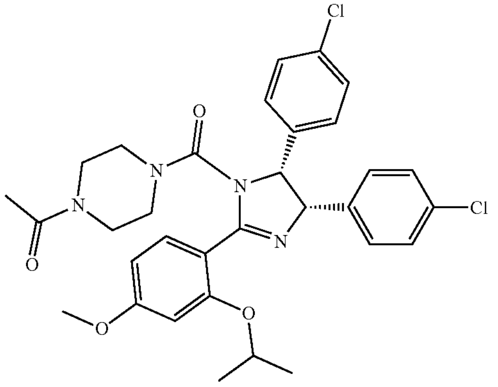 [SMILES: COc1ccc(C2=N[C@@H](c3ccc(Cl)cc3)[C@@H](c3ccc(Cl)cc3)N2C(=O)N2CCN(C(C)=O)CC2)c(OC(C)C)c1]

(derivatized where a linker group L or a -(L-MLM) group is attached, for example, via the methoxy group or as a hydroxyl group); and 2. Trans-4-Iodo-4'-Boranyl-Chalcone

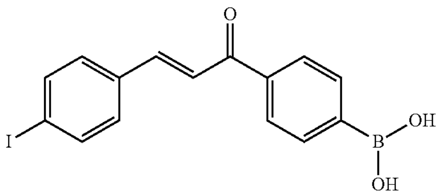 [SMILES: O=C(/C=C/c1ccc(I)cc1)c1ccc(B(O)O)cc1]

(derivatized where a linker group L or a a linker group L or a-(L-MLM) group is attached, for example, via a hydroxy group).

IV. Compounds Targeting Human BET Bromodomain-Containing Proteins:

In certain embodiments, "PTM" can be ligands binding to Bromo- and Extra-terminal (BET) proteins BRD2, BRD3 and BRD4. Compounds targeting Human BET Bromodomain-containing proteins include, but are not limited to the compounds associated with the targets as described below, where "R" or "linker" designates a site for linker group L or a-(L-MLM) group attachment, for example:

1. JQ1, Filippakopoulos et al. Selective inhibition of BET bromodomains. *Nature* (2010):

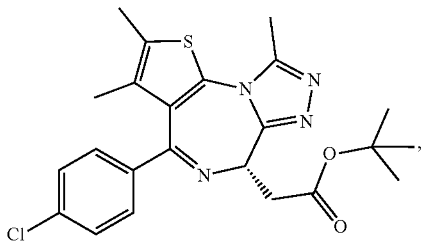

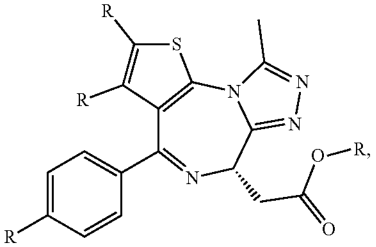

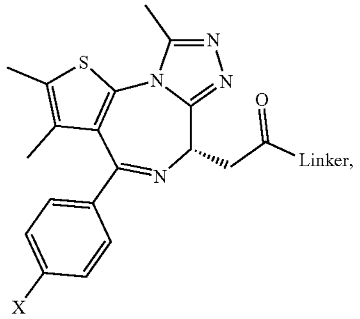

X = Cl, Br, F, H

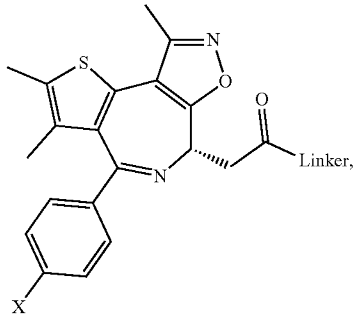

X = Cl, Br, F, H

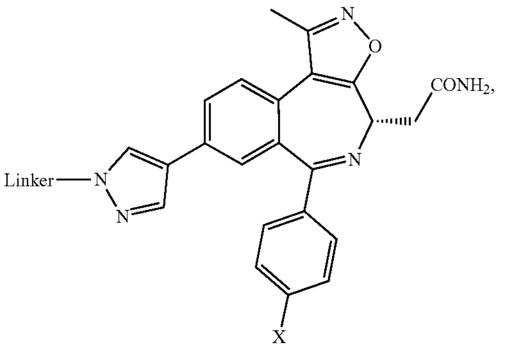

X = Cl, Br, F, H

-continued

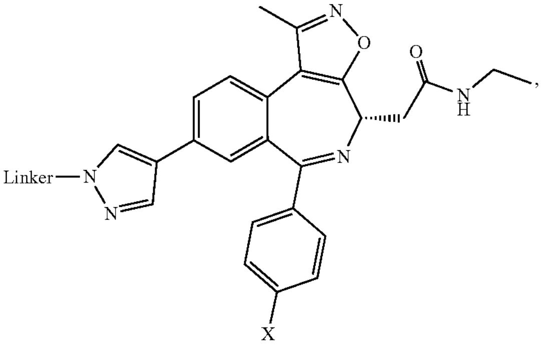

X = Cl, Br, F, H

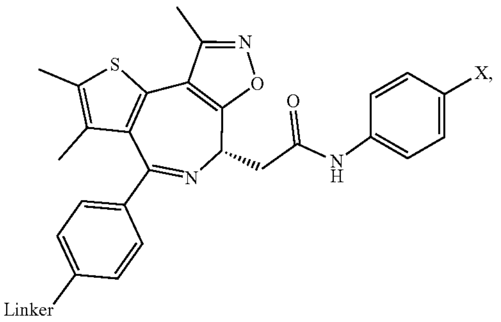

or

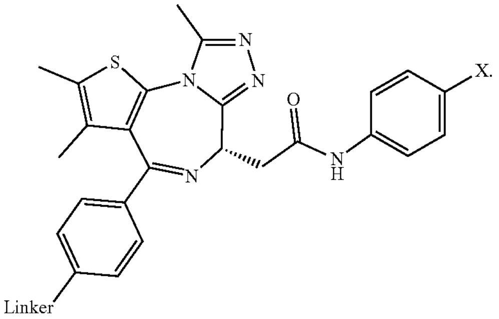

X = H, F

2. I-BET, Nicodeme et al. Supression of Inflammation by a Synthetic Histone Mimic. *Nature* (2010). Chung et al. Discovery and Characterization of Small Molecule Inhibitors of the BET Family Bromodomains. J. Med Chem. (2011):

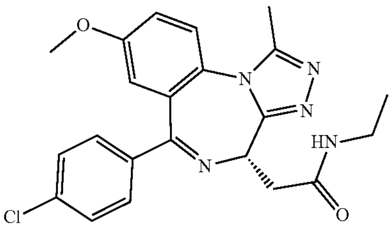

-continued

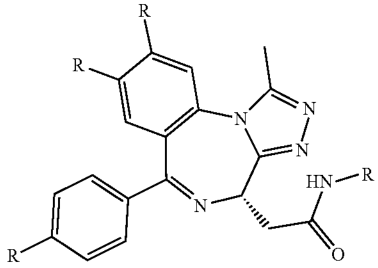

3. Compounds described in Hewings et al. 3,5-Dimethylisoxazoles Act as Acetyl-lysine Bromodomain Ligands. J. Med. Chem. (2011) 54 6761-6770.

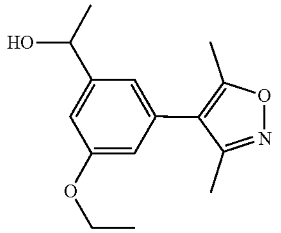

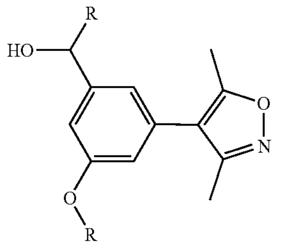

4. I-BET151, Dawson et al. Inhibition of BET Recruitment to Chromatin as an Efective Treatment for MLL-fusion Leukemia. Nature (2011):

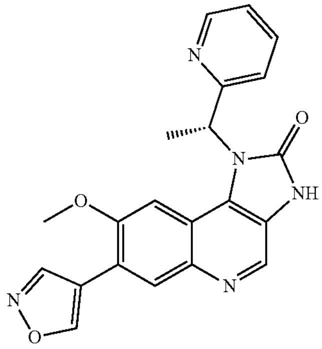

-continued
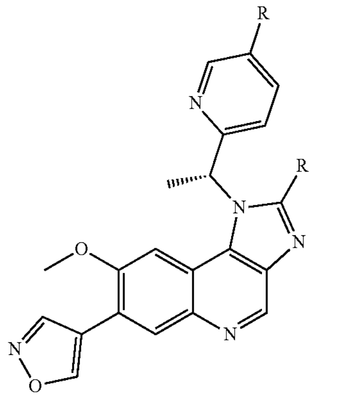
5. Carbazole type (US 2015/0256700)
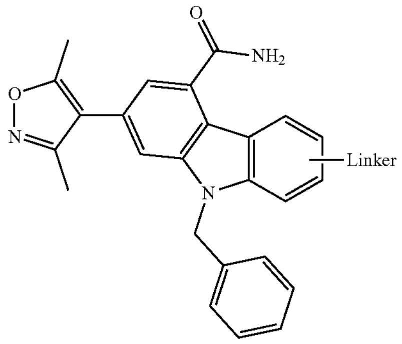
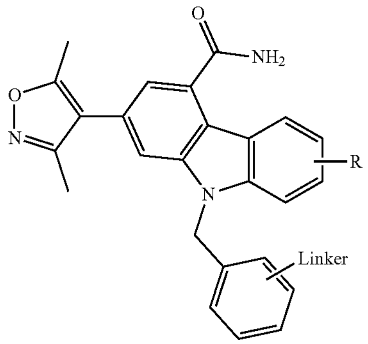
6. Pyrrolopyridone type (US 2015/0148342)
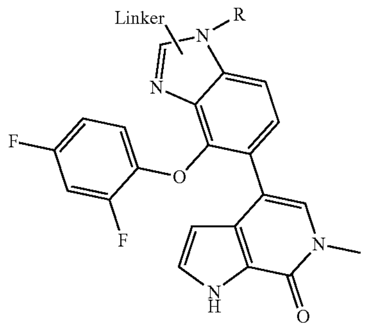
-continued
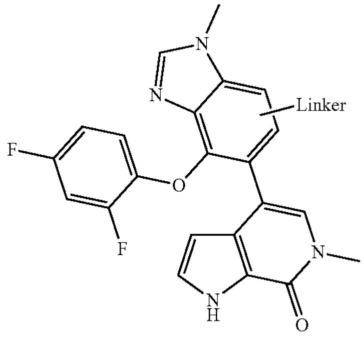
7. Tetrahydroquinoline type (WO 2015/074064)
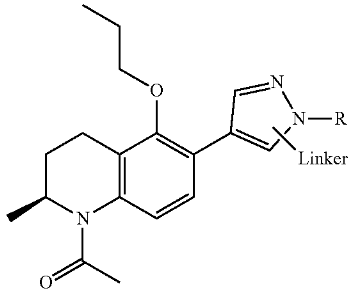
8. Triazolopyrazine type (WO 2015/067770)
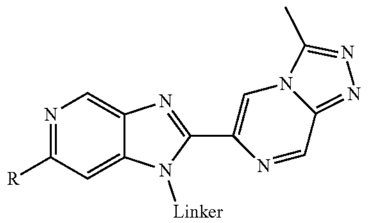
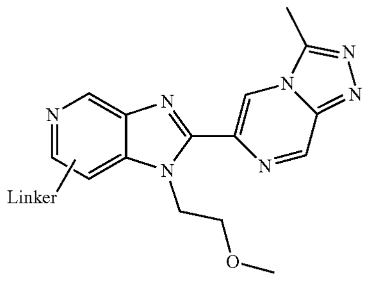

9. Pyridone type (WO 2015/022332)

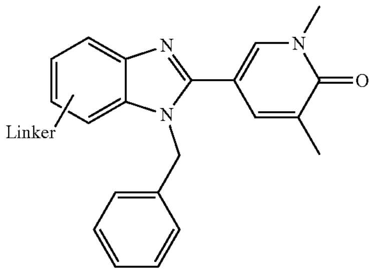

10. Quinazolinone type (WO 2015/015318)

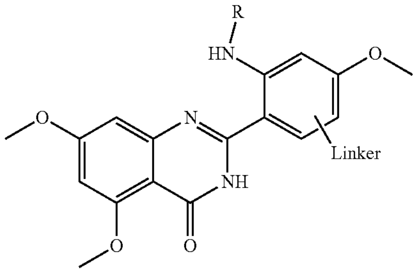

11. Dihydropyridopyrazinone type (WO 2015/011084)

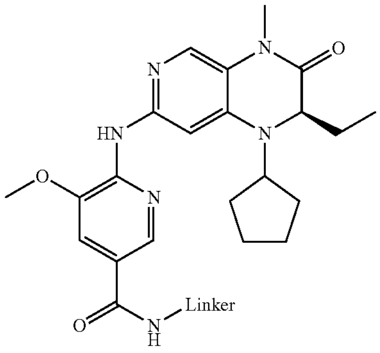

V. HDAC Inhibitors:

HDAC Inhibitors (derivatized) include, but are not limited to:

1. Finnin, M. S. et al. Structures of Histone Deacetylase Homologue Bound to the TSA and SAHA Inhibitors. Nature 40, 188-193 (1999).

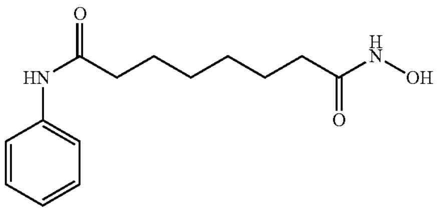

-continued

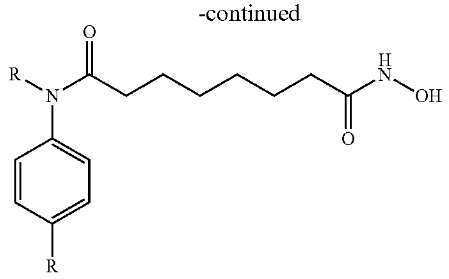

(Derivatized where "R" designates a site for attachment, for example, of a linker group L or a-(L-MLM) group); and 2. Compounds as defined by formula (I) of PCT WO0222577 ("DEACETYLASE INHIBITORS") (Derivatized where a linker group L or a -(L-MLM) group is attached, for example, via the hydroxyl group);

VI. Human Lysine Methyltransferase Inhibitors:

Human Lysine Methyltransferase inhibitors include, but are not limited to:

1. Chang et al. Structural Basis for G9a-Like protein Lysine Methyltransferase

Inhibition by BIX-1294. Nat. Struct. Biol. (2009) 16(3) 312.

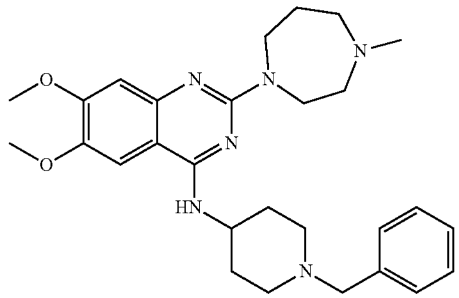

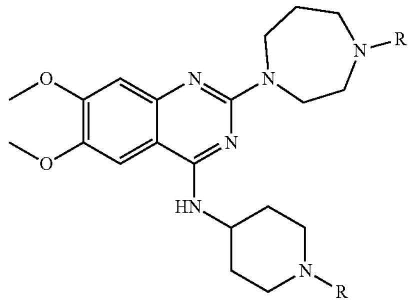

(Derivatized where "R" designates a site for attachment, for example, of a linker group L or a -(L-MLM) group);

2. Liu, F. et al Discovery of a 2,4-Diamino-7-aminoalkoxyquinazoline as a Potent and Selective Inhibitor of Histone Methyltransferase G9a. J. Med. Chem. (2009) 52(24) 7950.

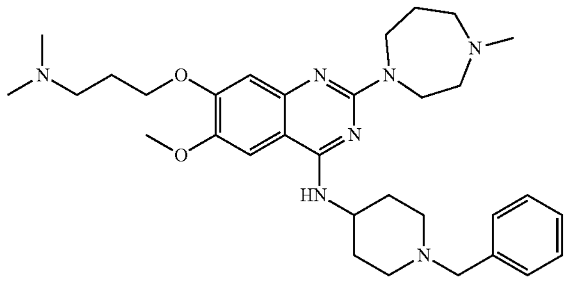

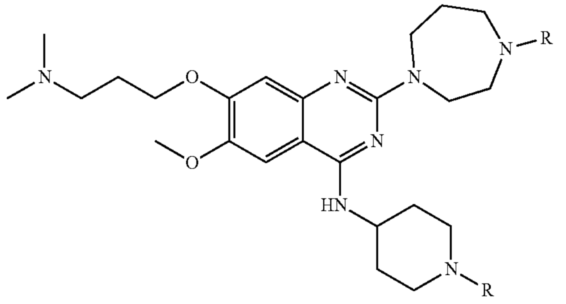

(Derivatized where "R" designates a potential site for attachment, for example, of a linker group L or a -(L-MLM) group);

3. Azacitidine (derivatized) (4-amino-1-β-D-ribofuranosyl-1,3,5-triazin-2(1H)-one) (Derivatized where a linker group L or a -(L-MLM) group is attached, for example, via the hydroxy or amino groups); and
4. Decitabine (derivatized) (4-amino-1-(2-deoxy-b-D-erythro-pentofuranosyl)-1,3,5-triazin-2(1H)-one) (Derivatized where a linker group L or a -(L-MLM) group is attached, for example, via either of the hydroxy groups or at the amino group).

VII. Angiogenesis Inhibitors:

Angiogenesis inhibitors include, but are not limited to:

1. GA-1 (derivatized) and derivatives and analogs thereof, having the structure(s) and binding to linkers as described in Sakamoto, et al., Development of Protacs to target cancer-promoting proteins for ubiquitination and degradation, *Mol Cell Proteomics* 2003 December; 2(12):1350-8;
2. Estradiol (derivatized), which may be bound to a linker group L or a -(L-MLM) group as is generally described in Rodriguez-Gonzalez, et al., Targeting steroid hormone receptors for ubiquitination and degradation in breast and prostate cancer, *Oncogene* (2008) 27, 7201-7211;
3. Estradiol, testosterone (derivatized) and related derivatives, including but not limited to DHT and derivatives and analogs thereof, having the structure(s) and binding to a linker group L or a -(L-MLM) group as generally described in Sakamoto, et al., Development of Protacs to target cancer-promoting proteins for ubiquitination and degradation, *Mol Cell Proteomics* 2003 December; 2(12):1350-8; and
4. Ovalicin, fumagillin (derivatized), and derivatives and analogs thereof, having the structure(s) and binding to a linker group L or a -(L-MLM) group as is generally described in Sakamoto, et al., Protacs: chimeric molecules that target proteins to the Skp1-Cullin-F box complex for ubiquitination and degradation *Proc Natl Acad Sci USA*. 2001 Jul. 17; 98(15):8554-9 and U.S. Pat. No. 7,208,157.

VIII. Immunosuppressive Compounds:

Immunosuppressive compounds include, but are not limited to:

1. AP21998 (derivatized), having the structure(s) and binding to a linker group L or a -(L-MLM) group as is generally described in Schneekloth, et al., Chemical Genetic Control of Protein Levels: Selective in Vivo Targeted Degradation, *J. AM. CHEM. SOC.* 2004, 126, 3748-3754;
2. Glucocorticoids (e.g., hydrocortisone, prednisone, prednisolone, and methylprednisolone) (Derivatized where a linker group L or a -(L-MLM) group is to bound, e.g. to any of the hydroxyls) and beclometasone dipropionate (Derivatized where a linker group or a -(L-MLM) is bound, e.g. to a proprionate);
3. Methotrexate (Derivatized where a linker group or a -(L-MLM) group can be bound, e.g. to either of the terminal hydroxyls);
4. Ciclosporin (Derivatized where a linker group or a -(L-MLM) group can be bound, e.g. at any of the butyl groups);
5. Tacrolimus (FK-506) and rapamycin (Derivatized where a linker group L or a -(L-MLM) group can be bound, e.g. at one of the methoxy groups); and
6. Actinomycins (Derivatized where a linker group L or a -(L-MLM) group can be bound, e.g. at one of the isopropyl groups).

IX. Compounds Targeting the Aryl Hydrocarbon Receptor (AHR):

Compounds targeting the aryl hydrocarbon receptor (AHR) include, but are not limited to:

1. Apigenin (Derivatized in a way which binds to a linker group L or a -(L-MLM) group as is generally illustrated in Lee, et al., Targeted Degradation of the Aryl Hydrocarbon Receptor by the PROTAC Approach: A Useful Chemical Genetic Tool, ChemBioChem Volume 8, Issue 17, pages 2058-2062, Nov. 23, 2007); and
2. SR1 and LGC006 (derivatized such that a linker group L or a -(L-MLM) is bound), as described in Boitano, et al., Aryl Hydrocarbon Receptor Antagonists Promote the Expansion of Human Hematopoietic Stem Cells, *Science* 10 Sep. 2010: Vol. 329 no. 5997 pp. 1345-1348.

X. Compounds Targeting RAF Receptor (Kinase):

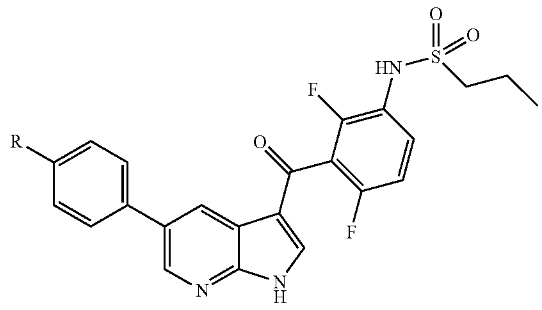

PLX4032

(Derivatized where "R" designates a site for linker group L or -(L-MLM) group attachment, for example).

XI. Compounds Targeting FKBP:

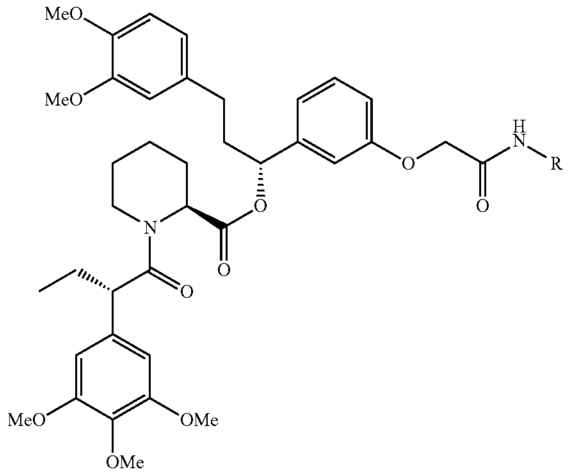

(Derivatized where "R" designates a site for a linker group L or a -(L-MLM) group attachment, for example).

XII. Compounds Targeting Androgen Receptor (AR)

1. RU59063 Ligand (derivatized) of Androgen Rceptor

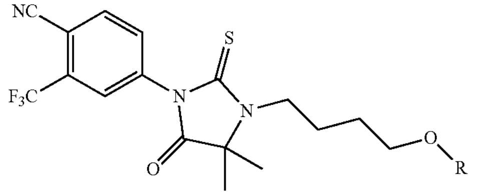

(Derivatized where "R" designates a site for a linker group L or a -(L-MLM) group attachment, for example).

2. SARM Ligand (derivatized) of Androgen Receptor

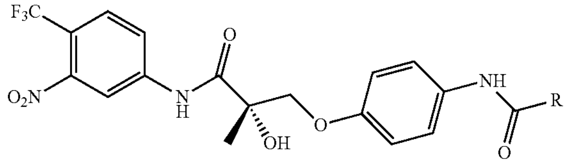

(Derivatized where "R" designates a site for a linker group L or a-(L-MLM) group attachment, for example).

3. Androgen Receptor Ligand DHT (derivatized)

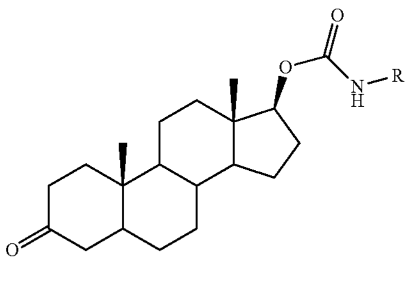

(Derivatized where "R" designates a site for a linker group L or -(L-MLM) group attachment, for example).

4. MDV3100 Ligand (derivatized)

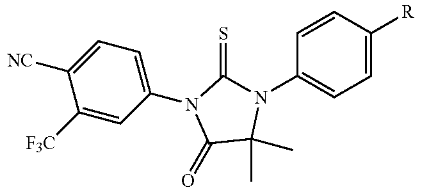

5. ARN-509 Ligand (derivatized)

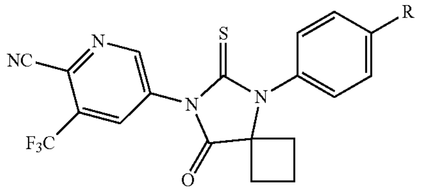

6. Hexahydrobenzisoxazoles

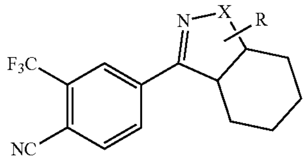

7. Tetramethylcyclobutanes

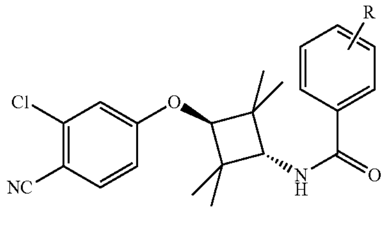

XIII. Compounds Targeting Estrogen Receptor (ER) ICI-182780

1. Estrogen Receptor Ligand

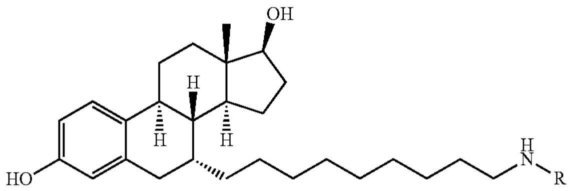

(Derivatized where "R" designates a site for linker group L or -(L-MLM) group attachment).

XIV. Compounds Targeting Thyroid Hormone Receptor (TR)

1. Thyroid Hormone Receptor Ligand (derivatized)

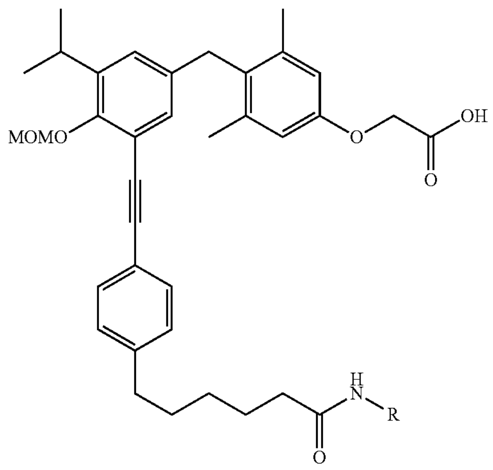

(Derivatized where "R" designates a site for linker group L or -(L-MLM) group attachment and MOMO indicates a methoxymethoxy group).

XV. Compounds targeting HIV Protease

1. Inhibitor of HIV Protease (derivatized)

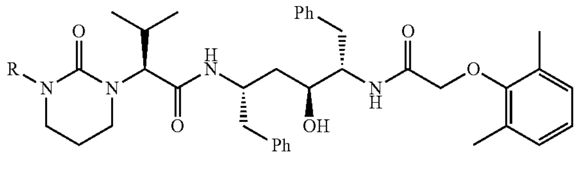

(Derivatized where "R" designates a site for linker group L or -(L-MLM) group attachment). See, *J. Med. Chem.* 2010, 53, 521-538.

2. Inhibitor of HIV Protease

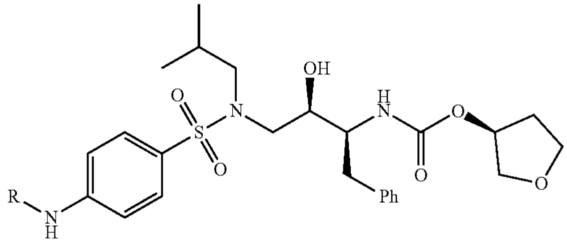

(Derivatized where "R" designates a potential site for linker group L or -(L-MLM) group attachment). See, *J. Med. Chem.* 2010, 53, 521-538.

XVI. Compounds Targeting HIV Integrase

1. Inhibitor of HIV Integrase (derivatized)

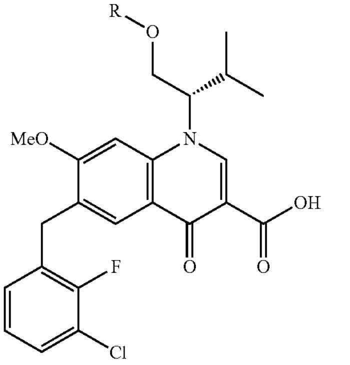

(Derivatized where "R" designates a site for linker group L or -(L-MLM) group attachment). See, *J. Med. Chem.* 2010, 53, 6466.

2. Inhibitor of HIV Integrase (derivatized)

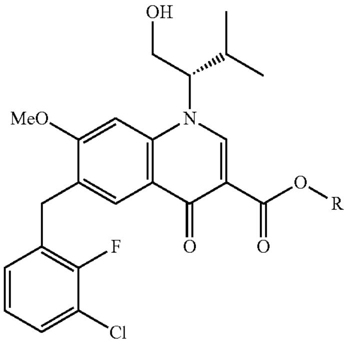

3. Inhibitor of HIV integrase Isetntress (derivatized)

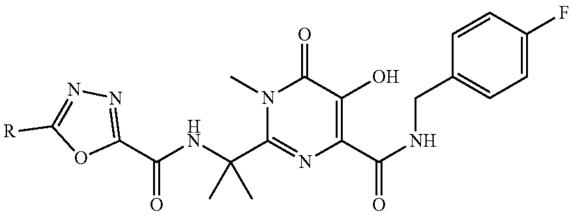

(Derivatized where "R" designates a site for linker group L or -(L-MLM) group attachment). See, *J. Med. Chem.* 2010, 53, 6466.

XVII. Compounds Targeting HCV Protease

1. Inhibitors of HCV Protease (derivatized)

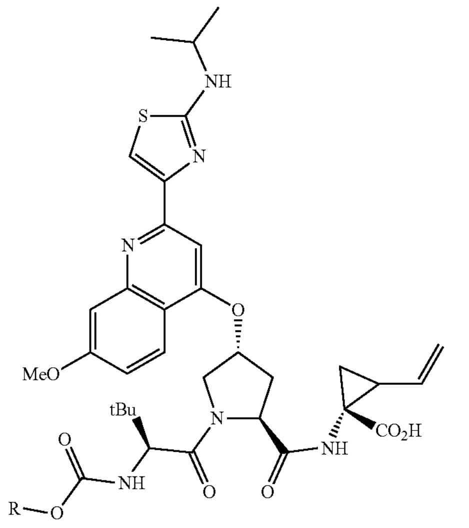

(Derivatized where "R" designates a site for linker group L or -(L-MLM) group attachment).

XVIII. Compounds targeting Acyl-protein Thioesterase-1 and -2 (APT1 and APT2)

1. Inhibitor of APT1 and APT2 (derivatized)

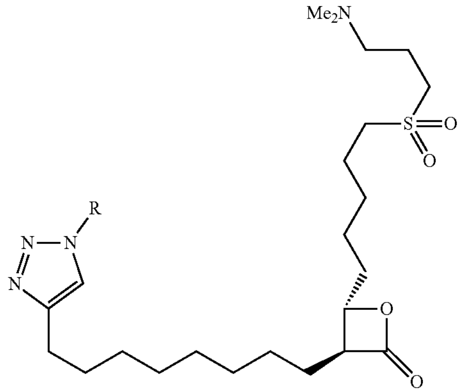

(Derivatized where "R" designates a site for linker group L or -(L-MLM) group attachment). See, *Angew. Chem. Int. Ed.* 2011, 50, 9838-9842, where L is a linker group as otherwise described herein and said MLM group is as otherwise described herein such that -(L-MLM) binds the MLM group to a PTMgroup as otherwise described herein.

Therapeutic Compositions

Pharmaceutical compositions comprising combinations of an effective amount of at least one bifunctional compound as described herein, and one or more of the compounds otherwise described herein, all in effective amounts, in combination with a pharmaceutically effective amount of a carrier, additive or excipient, represents a further aspect of the present disclosure.

The present disclosure includes, where applicable, the compositions comprising the pharmaceutically acceptable salts, in particular, acid or base addition salts of compounds as described herein. The acids which are used to prepare the pharmaceutically acceptable acid addition salts of the aforementioned base compounds useful according to this aspect are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds or derivatives according to the present disclosure. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (eg, calcium, zinc and magnesium), ammonium or water-soluble amine addition salts such as N-methylglucamine-(meglumine), and the lower alkanolammonium and other base salts of pharmaceutically acceptable organic amines, among others.

The compounds as described herein may, in accordance with the disclosure, be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present disclosure as sprays, mists, or aerosols for intra-nasal, intra-tracheal or pulmonary administration may also be used. The present disclosure therefore also is directed to pharmaceutical compositions comprising an effective amount of compound as described herein, optionally in combination with a pharmaceutically acceptable carrier, additive or excipient. Compounds according to the present disclosureion may be administered in immediate release, intermediate release or sustained or controlled release forms. Sustained or controlled release forms are preferably administered orally, but also in suppository and transdermal or other topical forms. Intramuscular injections in liposomal form may also be used to control or sustain the release of compound at an injection site.

The compositions as described herein may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions as described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Hely or similar alcohol.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions as described herein may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. In certain preferred aspects of the invention, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions as described herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition as described herein that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other compound according to the present invention.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the methods described herein can be treated by administering to the patient (subject) an effective amount of the compound according to the present invention including pharmaceutically acceptable salts, solvates or polymorphs, thereof optionally in a pharmaceutically acceptable carrier or diluent, either alone, or in combination with other known erythopoiesis stimulating agents as otherwise identified herein.

These compounds can be administered by any appropriate route, for example, orally, parenterally, intravenously, intradermally, subcutaneously, or topically, including transdermally, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 μM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as erythropoietin stimulating agents, including EPO and darbapoietin alfa, among others. In certain preferred aspects of the invention, one or more compounds according to the present invention are coadministered with another bioactive agent, such as an erythropoietin stimulating agent or a would healing agent, including an antibiotic, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Therapeutic Methods

In an additional aspect, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein.

The terms "treat", "treating", and "treatment", etc., as used herein, refer to any action providing a benefit to a patient for which the present compounds may be administered, including the treatment of any disease state or condition which is modulated through the protein to which the present compounds bind. Disease states or conditions, including cancer, which may be treated using compounds according to the present invention are set forth hereinabove.

The description provides therapeutic compositions as described herein for effectuating the degradation of proteins of interest for the treatment or amelioration of a disease, e.g., cancer. In certain additional embodiments, the disease is multiple myeloma. As such, in another aspect, the description provides a method of ubiquitinating/degrading a target protein in a cell. In certain embodiments, the method comprises administering a bifunctional compound as described herein comprising, e.g., a MLM and a PTM, preferably linked through a linker moiety, as otherwise described herein, wherein the MLM is coupled to the PTM and wherein the MLM recognizes a ubiquitin pathway protein (e.g., an ubiquitin ligase, preferably an E3 ubiquitin ligase such as, e.g., cereblon) and the PTM recognizes the target protein such that degradation of the target protein will occur when the target protein is placed in proximity to the ubiquitin ligase, thus resulting in degradation/inhibition of the effects of the target protein and the control of protein levels. The control of protein levels afforded by the present invention provides treatment of a disease state or condition, which is modulated through the target protein by lowering the level of that protein in the cell, e.g., cell of a patient. In certain embodiments, the method comprises administering an effective amount of a compound as described herein, optionally including a pharmaceutically acceptable excipient, carrier, adjuvant, another bioactive agent or combination thereof.

In additional embodiments, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable excipient, carrier, adjuvant, another bioactive agent or combination thereof, wherein the composition is effective for treating or ameliorating the disease or disorder or symptom thereof in the subject.

In another aspect, the description provides methods for identifying the effects of the degradation of proteins of interest in a biological system using compounds according to the present invention.

In another embodiment, the present invention is directed to a method of treating a human patient in need for a disease state or condition modulated through a protein where the degradation of that protein will produce a therapeutic effect in that patient, the method comprising administering to a patient in need an effective amount of a compound according to the present invention, optionally in combination with another bioactive agent. The disease state or condition may be a disease caused by a microbial agent or other exogenous agent such as a virus, bacteria, fungus, protozoa or other microbe or may be a disease state, which is caused by overexpression of a protein, which leads to a disease state and/or condition The term "disease state or condition" is used to describe any disease state or condition wherein protein dysregulation (i.e., the amount of protein expressed in a patient is elevated) occurs and where degradation of one or more proteins in a patient may provide beneficial therapy or relief of symptoms to a patient in need thereof. In certain instances, the disease state or condition may be cured.

Disease states of conditions which may be treated using compounds according to the present invention include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome.

Further disease states or conditions which may be treated by compounds according to the present invention include Alzheimer's disease, Amyotrophic lateral sclerosis (Lou Gehrig's disease), Anorexia nervosa, Anxiety disorder, Atherosclerosis, Attention deficit hyperactivity disorder, Autism, Bipolar disorder, Chronic fatigue syndrome, Chronic obstructive pulmonary disease, Crohn's disease, Coronary heart disease, Dementia, Depression, Diabetes mellitus type 1, Diabetes mellitus type 2, Epilepsy, Guillain-Barr-syndrome, Irritable bowel syndrome, Lupus, Metabolic syndrome, Multiple sclerosis, Myocardial infarction, Obesity, Obsessive-compulsive disorder, Panic disorder, Parkinson's disease, Psoriasis, Rheumatoid arthritis, Sarcoidosis, Schizophrenia, Stroke, Thromboangiitis obliterans, Tourette syndrome, Vasculitis.

Still additional disease states or conditions which can be treated by compounds according to the present invention include aceruloplasminemia, Achondrogenesis type II, achondroplasia, Acrocephaly, Gaucher disease type 2, acute intermittent porphyria, Canavan disease, Adenomatous Polyposis Coli, ALA dehydratase deficiency, adenylosuccinate lyase deficiency, Adrenogenital syndrome, Adrenoleukodystrophy, ALA-D porphyria, ALA dehydratase deficiency, Alkaptonuria, Alexander disease, Alkaptonuric ochronosis, alpha 1-antitrypsin deficiency, alpha-1 proteinase inhibitor, emphysema, amyotrophic lateral sclerosis Alström syndrome, Alexander disease, Amelogenesis imperfecta, ALA dehydratase deficiency, Anderson-Fabry disease, androgen insensitivity syndrome, Anemia Angiokeratoma Corporis Diffusum, Angiomatosis retinae (von Hippel-Lindau disease) Apert syndrome, Arachnodactyly (Marfan syndrome), Stickler syndrome, Arthrochalasis multiplex congenital (Ehlers-Danlos syndrome#arthrochalasia type) ataxia telangiectasia, Rett syndrome, primary pulmonary hypertension, Sandhoff disease, neurofibromatosis type II, Beare-Stevenson cutis gyrata syndrome, Mediterranean fever, familial, Benjamin syndrome, beta-thalassemia, Bilateral Acoustic Neurofibromatosis (neurofibromatosis type II), factor V Leiden thrombophilia, Bloch-Sulzberger syndrome (incontinentia pigmenti), Bloom syndrome, X-linked sideroblastic anemia, Bonnevie-Ullrich syndrome (Turner syndrome), Bourneville disease (tuberous sclerosis), prion disease, Birt-Hogg-Dubé syndrome, Brittle bone disease (osteogenesis imperfecta), Broad Thumb-Hallux syndrome (Rubinstein-Taybi syndrome), Bronze Diabetes/Bronzed Cirrhosis (hemochromatosis), Bulbospinal muscular atrophy (Kennedy's disease), Burger-Grutz syndrome (lipoprotein lipase deficiency), CGD Chronic granulomatous disorder, Campomelic dysplasia, biotinidase deficiency, Cardiomyopathy (Noonan syndrome), Cri du chat, CAVD (congenital absence of the vas deferens), Caylor cardiofacial syndrome (CBAVD), CEP (congenital erythropoietic porphyria), cystic fibrosis, congenital hypothyroidism, Chondrodystrophy syndrome (achondroplasia), otospondylomegaepiphyseal dysplasia, Lesch-Nyhan syndrome, galactosemia, Ehlers-Danlos syndrome, Thanatophoric dysplasia, Coffin-Lowry syndrome, Cockayne syndrome, (familial adenomatous polyposis), Congenital erythropoietic porphyria, Congenital heart disease, Methemoglobinemia/ Congenital methaemoglobinaemia, achondroplasia, X-linked sideroblastic anemia, Connective tissue disease, Conotruncal anomaly face syndrome, Cooley's Anemia (beta-thalassemia), Copper storage disease (Wilson's disease), Copper transport disease (Menkes disease), hereditary coproporphyria, Cowden syndrome, Craniofacial dysarthrosis (Crouzon syndrome), Creutzfeldt-Jakob disease (prion disease), Cockayne syndrome, Cowden syndrome, Curschmann-Batten-Steinert syndrome (myotonic dystrophy), Beare-Stevenson cutis gyrata syndrome, primary hyperoxaluria, spondyloepimetaphyseal dysplasia (Strudwick type), muscular dystrophy, Duchenne and Becker types (DBMD), Usher syndrome, Degenerative nerve diseases including de Grouchy syndrome and Dejerine-Sottas syndrome, developmental disabilities, distal spinal muscular atrophy, type V, androgen insensitivity syndrome, Diffuse Globoid Body Sclerosis (Krabbe disease), Di George's syndrome, Dihydrotestosterone receptor deficiency, androgen insensitivity syndrome, Down syndrome, Dwarfism, erythropoietic protoporphyria Erythroid 5-aminolevulinate synthetase deficiency, Erythropoietic porphyria, erythropoietic protoporphyria, erythropoietic uroporphyria, Friedreich's ataxia, familial paroxysmal polyserositis, porphyria cutanea tarda, familial pressure sensitive neuropathy, primary pulmonary hypertension (PPH), Fibrocystic disease of the pancreas, fragile X syndrome, galactosemia, genetic brain disorders, Giant cell hepatitis (Neonatal hemochromatosis), Gronblad-Strandberg syndrome (pseudoxanthoma elasticum), Gunther disease (congenital erythropoietic porphyria), haemochromatosis, Hallgren syndrome, sickle cell anemia, hemophilia, hepatoerythropoietic porphyria (HEP), Hippel-Lindau disease (von Hippel-Lindau disease), Huntington's disease, Hutchinson-Gilford progeria syndrome (progeria), Hyperandrogenism, Hypochondroplasia, Hypochromic anemia, Immune system disorders, including X-linked severe combined immunodeficiency, Insley-Astley syndrome, Jackson-Weiss syndrome, Joubert syndrome, Lesch-Nyhan syndrome, Jackson-Weiss syndrome, Kidney diseases, including hyperoxaluria, Klinefelter's syndrome, Kniest dysplasia, Lacunar dementia, Langer-Saldino achondrogenesis, ataxia telangiectasia, Lynch syndrome, Lysyl-hydroxylase deficiency, Machado-Joseph disease, Metabolic disorders, including Kniest dysplasia, Marfan syndrome, Movement disorders, Mowat-Wilson syndrome, cystic fibrosis, Muenke syndrome, Multiple neurofibromatosis, Nance-Insley syndrome, Nance-Sweeney chondrodysplasia, Niemann-Pick disease, Noack syndrome (Pfeiffer syndrome), Osler-Weber-Rendu disease, Peutz-Jeghers syndrome, Polycystic kidney disease, polyostotic fibrous dysplasia (McCune-Albright syndrome), Peutz-Jeghers syndrome, Prader-Labhart-Willi syndrome, hemochromatosis, primary hyperuricemia syndrome (Lesch-Nyhan syndrome), primary pulmonary hypertension, primary senile degenerative dementia, prion disease, progeria (Hutchinson Gilford Progeria Syndrome), progressive chorea, chronic hereditary (Huntington) (Huntington's disease), progressive muscular atrophy, spinal muscular atrophy, propionic acidemia, protoporphyria, proximal myotonic dystrophy, pulmonary arterial hypertension, PXE (pseudoxanthoma elasticum), Rb (retinoblastoma), Recklinghausen disease (neurofibromatosis type I), Recurrent polyserositis, Retinal disorders, Retinoblastoma, Rett syndrome, RFALS type 3, Ricker syndrome, Riley-Day syndrome, Roussy-Levy syndrome, severe achondroplasia with developmental delay and acanthosis nigricans (SADDAN), Li-Fraumeni syndrome, sarcoma, breast, leukemia, and adrenal gland (SBLA) syndrome, sclerosis tuberose (tuberous sclerosis), SDAT, SED congenital (spondyloepiphyseal dysplasia congenita), SED Strudwick (spondyloepimetaphyseal dysplasia, Strudwick type), SEDc (spondyloepiphyseal dysplasia congenita) SEMD, Strudwick type (spondyloepimetaphyseal dysplasia, Strudwick type), Shprintzen syndrome, Skin pigmentation disorders, Smith-Lemli-Opitz syndrome, South-African genetic porphyria (variegate porphyria), infantile-onset ascending hereditary spastic paralysis, Speech and communication disorders, sphingolipidosis, Tay-Sachs disease, spinocerebellar ataxia, Stickler syndrome, stroke, androgen insensitivity syndrome, tetrahydrobiopterin deficiency, beta-thalassemia, Thyroid disease, Tomaculous neuropathy (hereditary neuropathy with liability to pressure palsies), Treacher Collins syndrome, Triplo X syndrome (triple X syndrome), Trisomy 21 (Down syndrome), Trisomy X, VHL syndrome (von Hippel-Lindau disease), Vision impairment and blindness (Alström syndrome), Vrolik disease, Waardenburg syndrome, Warburg Sjo Fledelius Syndrome, Weissenbacher-Zweymüller syndrome, Wolf-Hirschhorn syndrome, Wolff Periodic disease, Weis senbacher-Zweymüller syndrome and Xeroderma pigmentosum, among others.

The term "neoplasia" or "cancer" is used throughout the specification to refer to the pathological process that results in the formation and growth of neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present invention include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

The term "bioactive agent" is used to describe an agent, other than a compound according to the present invention, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents and anti-HCV agents, antimicrobial agents, antifungal agents, etc.

The term "anti-cancer agent" is used to describe an anti-cancer agent, which may be incorporated into the bifunctional compounds according to the present invention or incombination with the same to treat cancer. These agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitor, an AKT inhibitor, an mTORC1/2 inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdRi KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo [2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, lonafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

The term "anti-HIV agent" includes, for example, nucleoside reverse transcriptase inhibitors (NRTI), other non-nucleoeside reverse transcriptase inhibitors (i.e., those which are not representative of the present invention), protease inhibitors, fusion inhibitors, among others, exemplary compounds of which may include, for example, 3TC (Lamivudine), AZT (Zidovudine), (−)-FTC, ddl (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development.

Other anti-HIV agents which may be used in coadministration with compounds according to the present invention include, for example, other NNRTI's (i.e., other than the NNRTI's according to the present invention) may be selected from the group consisting of nevirapine (BI-R6-587), delavirdine (U-90152S/T), efavirenz (DMP-266), UC-781 (N-[4-chloro-3-(3-methyl-2-butenyloxy)phenyl]-2methyl3-furancarbothiamide), etravirine (TMC 125), Trovirdine (Ly300046.HCl), MKC-442 (emivirine, coactinon), HI-236, HI-240, HI-280, HI-281, rilpivirine (TMC-278), MSC-127, HBY 097, DMP266, Baicalin (TJN-151) ADAM-II (Methyl 3',3'-dichloro-4',4"-dimethoxy-5',5"-bis (methoxycarbonyl)-6,6-diphenylhexenoate), Methyl 3-Bromo-5-(1-5-bromo-4-methoxy-3-(methoxycarbonyl) phenyl)hept-1-enyl)-2-methoxybenzoate (Alkenyldiarylmethane analog, Adam analog), (5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-cyano-2-indolyl)carbonyl]-4-[3-(isopropylamino)-2-pyridinyl]piperazine, 1-[5-[[N-(methyl)methylsulfonylamino]-2-indolylcarbonyl-4-[3-(isopropylamino)-2-pyridinyl] piperazine, 1-[3-(Ethylamino)-2-[pyridinyl]-4-[(5-hydroxy-2-indolyl)carbonyl]piperazine, 1-[(6-Formyl-2-indolyl) carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S (1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea {PETT derivative), N-{2-(2,6-Difluorophenethyl]-N'-[2-(5-methylpyridyl)]thiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 3-[2-(4,7-Difluorobenzoxazol-2-yl)ethyl}-5-ethyl-6-methyl (pypridin-2(1H)-thione (2-Pyridinone Derivative), 3-[[(2-Methoxy-5,6-dimethyl-3-pyridyl)methyl]amine]-5-ethyl-6-methyl(pypridin-2(1H)-thione, R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a]isoindol-5(9bH)-one, Tivirapine (R86183), UC-38 and UC-84, among others.

The term "pharmaceutically acceptable salt" is used throughout the specification to describe, where applicable, a salt form of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present invention.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

EXAMPLES

The following structures are ligands for BET (bromodomain and extra terminal domain). These ligands are used as an example only to demonstrate the current invention of using MDM2 E3 ligase to degrade a target protein and in no way limit the present invention. In the exampled structures below, the target protein is BRD2 (BRD2, BRD3 and BRD4). In a certain embodiment, the PTM is selected from the group consisting of:

BRD-PTM-1

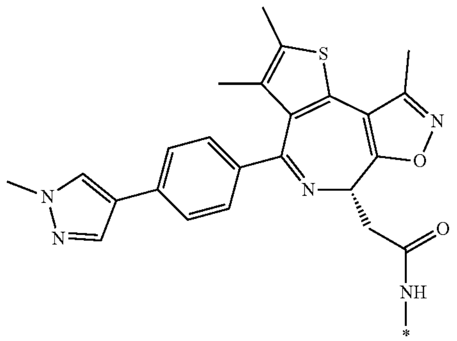

BRD-PTM-2

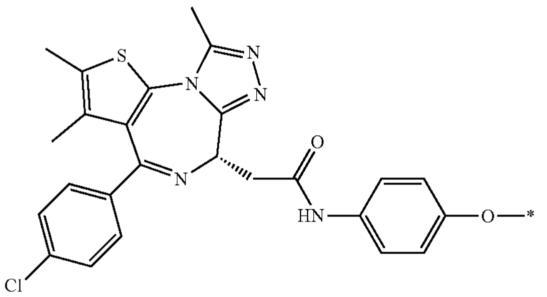

BRD-PTM-3

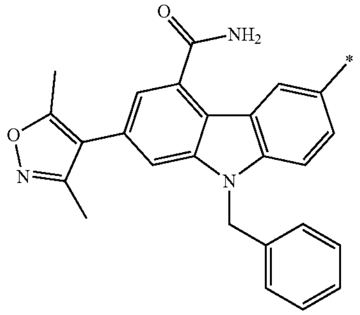

BRD-PTM-4

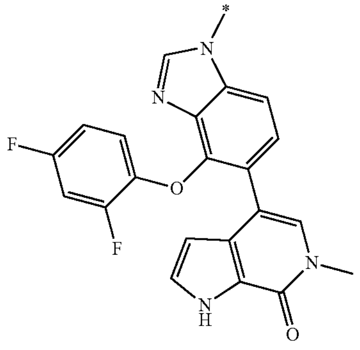

-continued

BRD-PTM-5

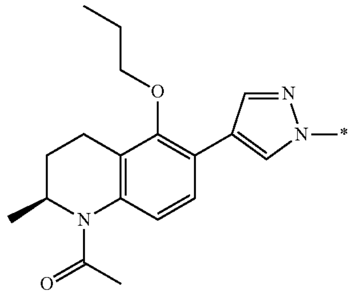

BRD-PTM-6

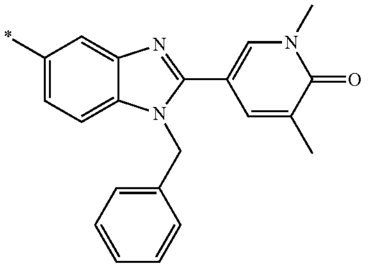

wherein "*" indicates one of the positions to connect linker.

The following are examples of androgen receptor ligands. These ligands are used as examples only to demonstrate the current invention of using MDM2 E3 ligase to degrade a target protein and in no way limited the present invention. In a particular embodiment, the PTM is selected from the group consisting of:

AR-PTM-1

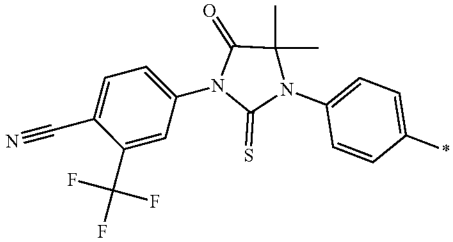

AR-PTM-2

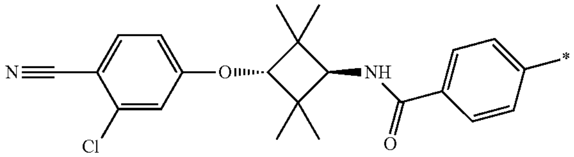

wherein "*" indicates one of the positions to connect linker.

The following is an example of EZH2 ligand. The ligands is used as an example only to demonstrate the current invention of using MDM2 E3 ligase to degrade a target protein and in no way limited the present invention. In a particular embodiment, the PTM is selected from the group consisting of:

EZH2-PTM

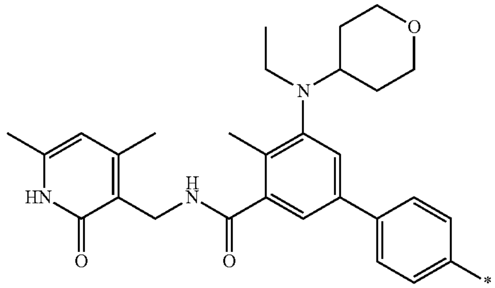

wherein "*" indicates one of the positions to connect linker.

The following is an example of JNK ligand. The ligands is used as an example only to demonstrate the current invention of using MDM2 E3 ligase to degrade a target protein and in no way limited the present invention. In a particular embodiment, the PTM is selected from the group consisting of:

JNK-PTM

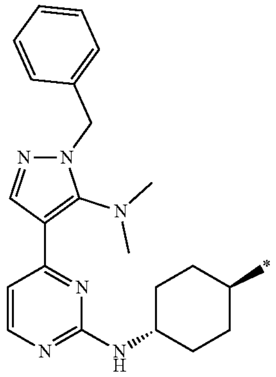

wherein "*" indicates one of the positions to connect linker.

The following are examples of MDM2 ligand derived chimeric molecules using MDM2 E3 ligase to degrade BRDs and androgen receptor and in no way limit the present invention. In an embodiment, the chimeric molecule is selected from the group consisting of:

A1283
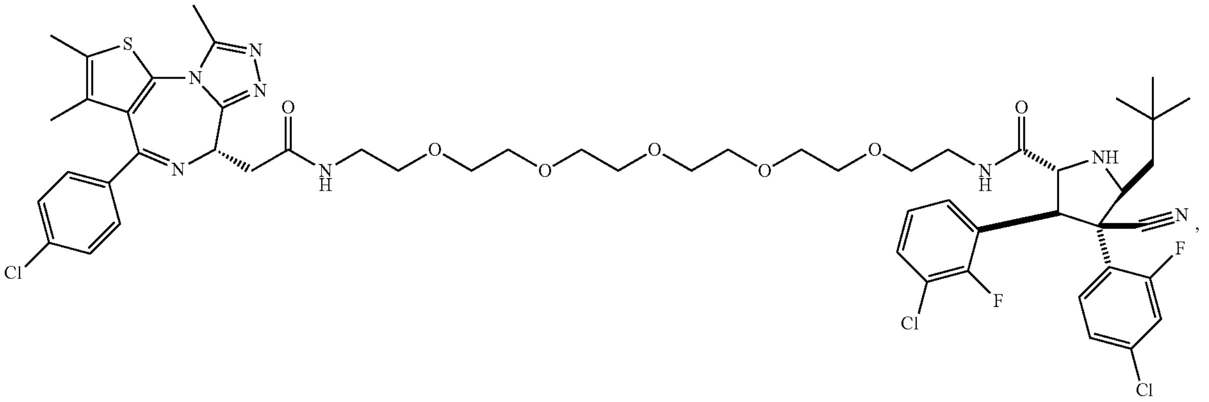
A1306
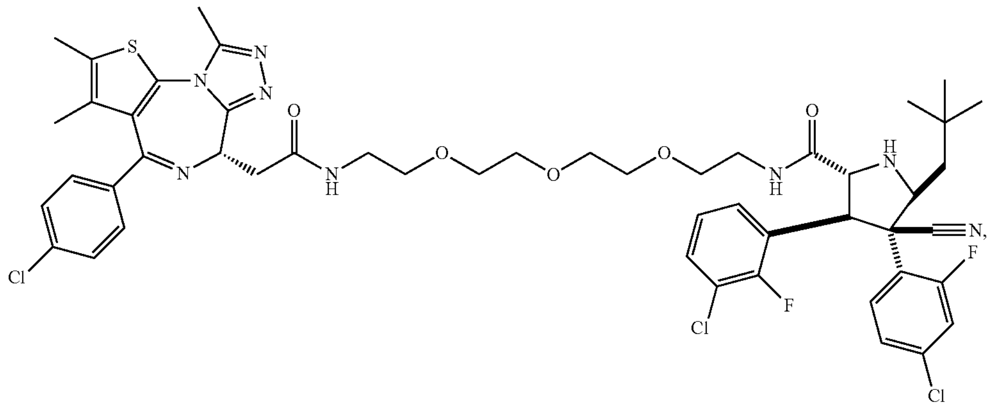
A1307
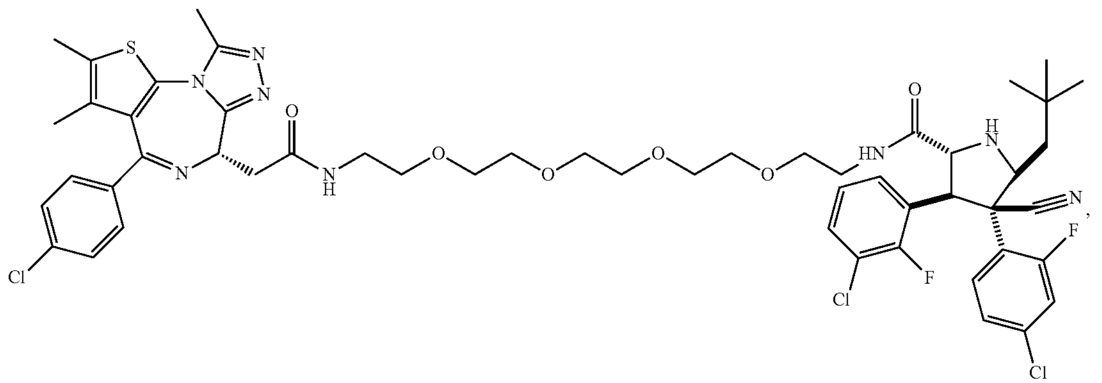
A1863
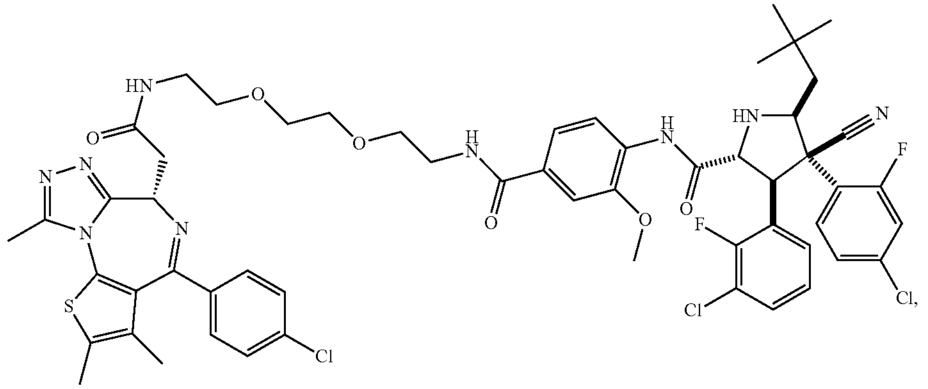

-continued
A1864
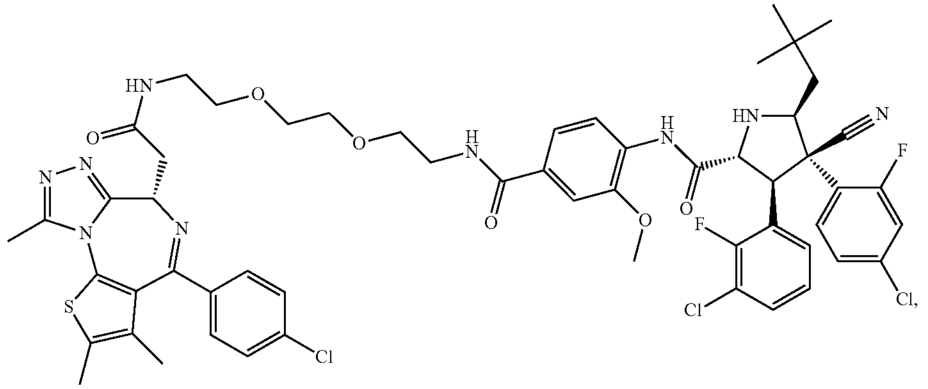
A1865
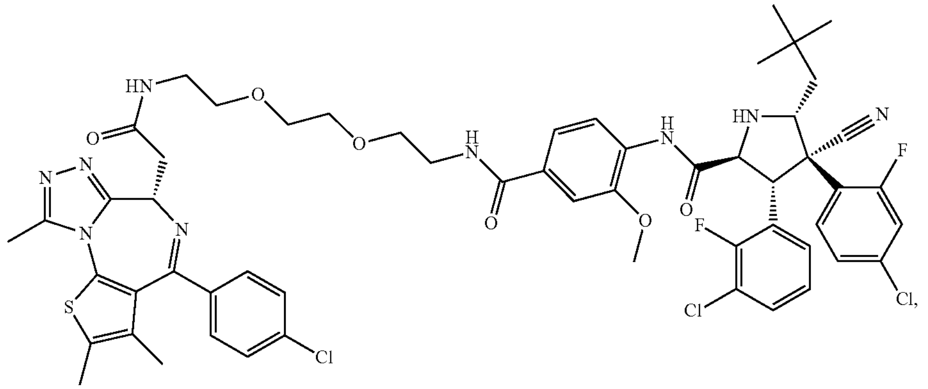
A1829
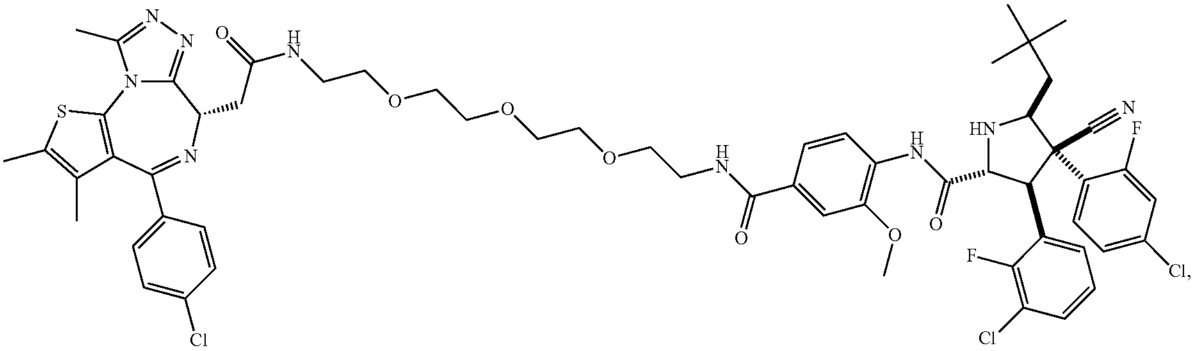
A1874
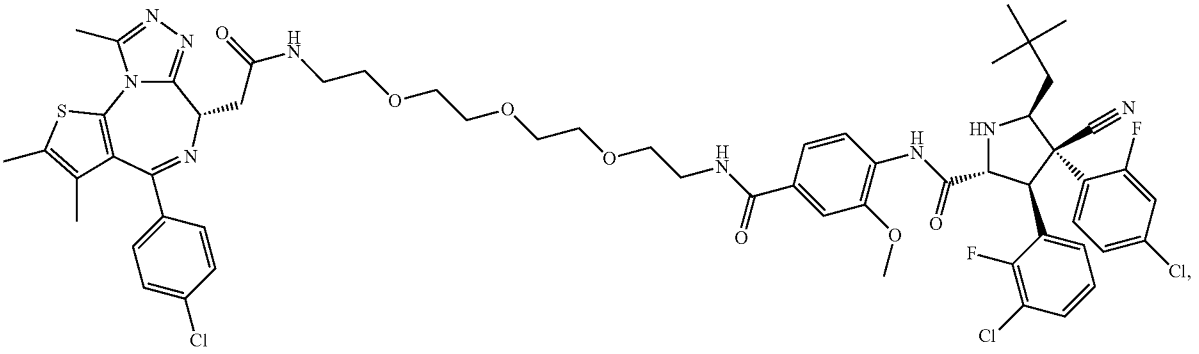

-continued
A1875
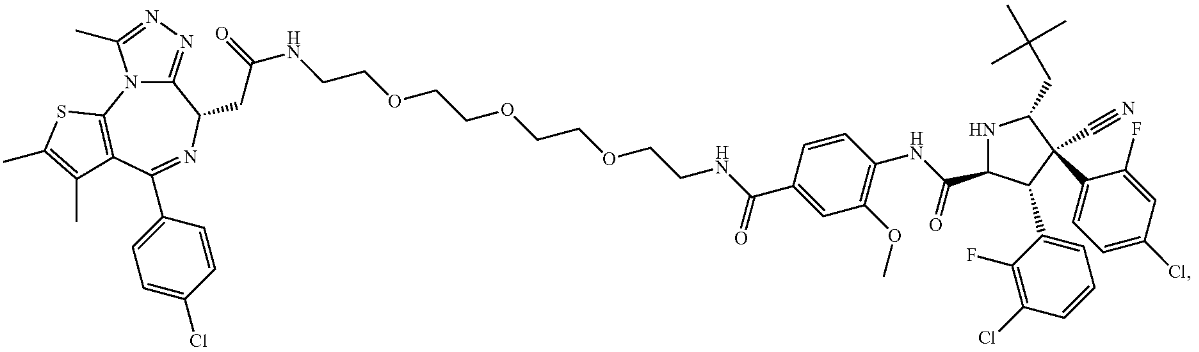
A1876
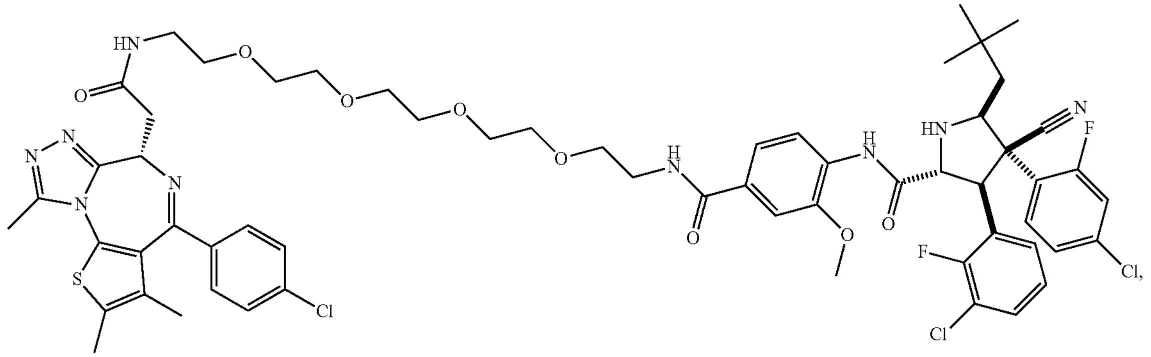
A1893
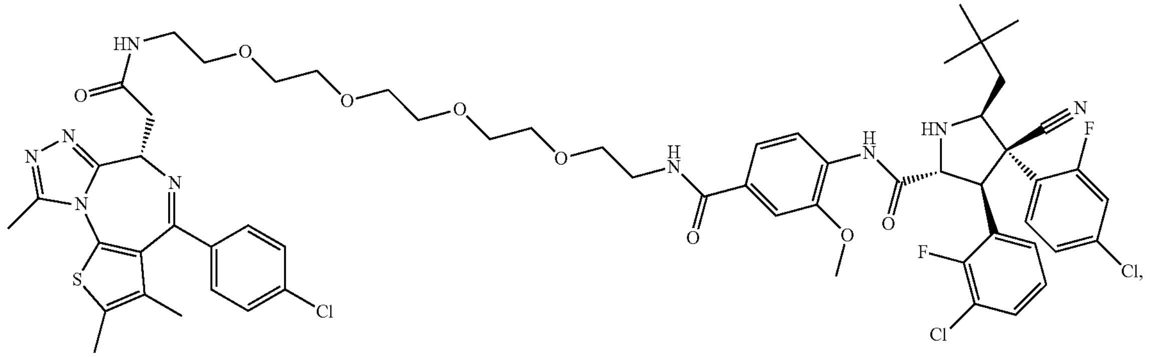
A1894
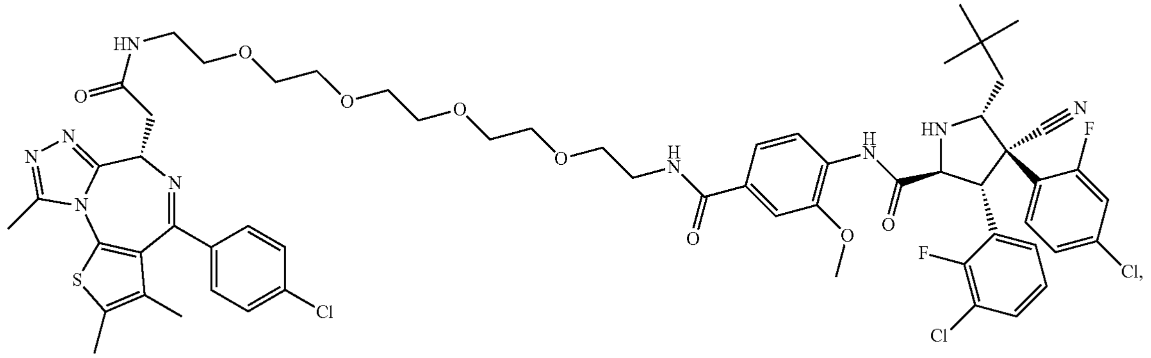

-continued
A1890
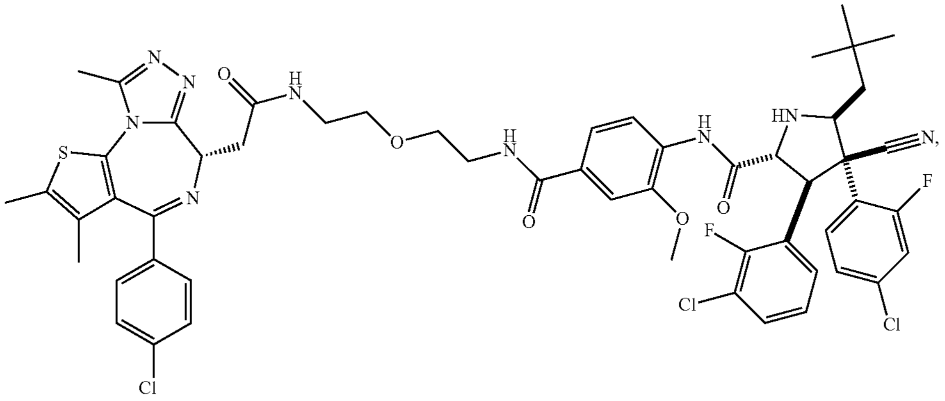
A1891
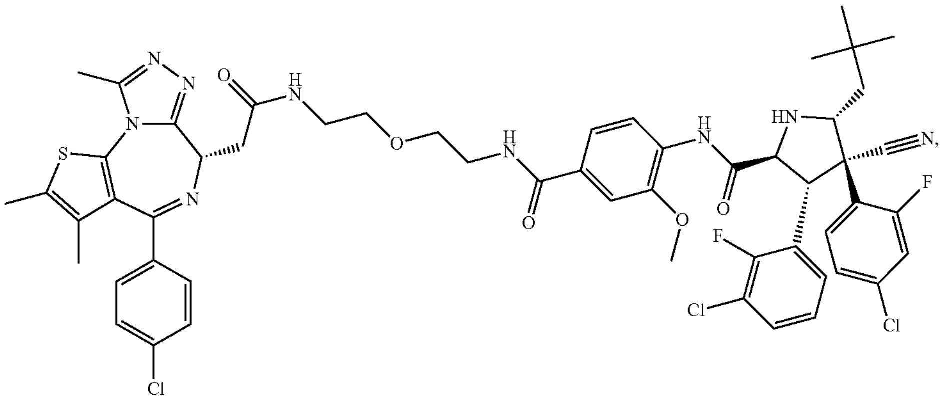
and
A1892
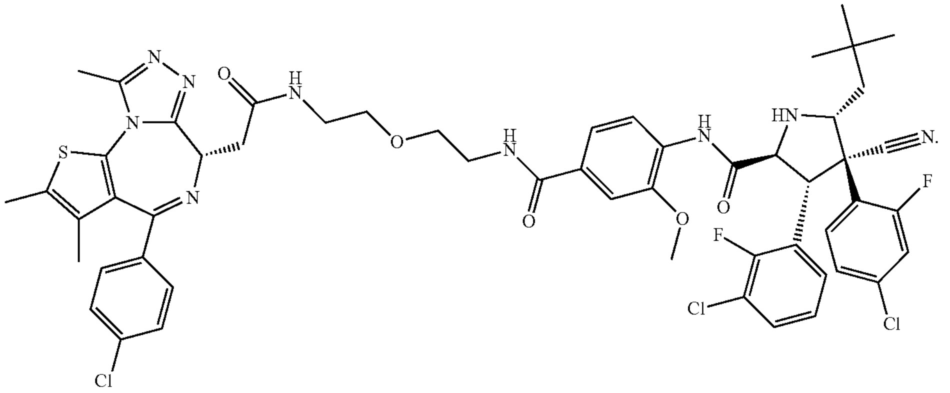
The following are examples of MDM2 ligand derived chimeric molecules using VHL E3 ligase to degrade MDM2, which provides examples for Formula (B) as described herein. Thus, in certain embodiments, the description provides a bifunctional molecules selected from the group consisting of:

A1895
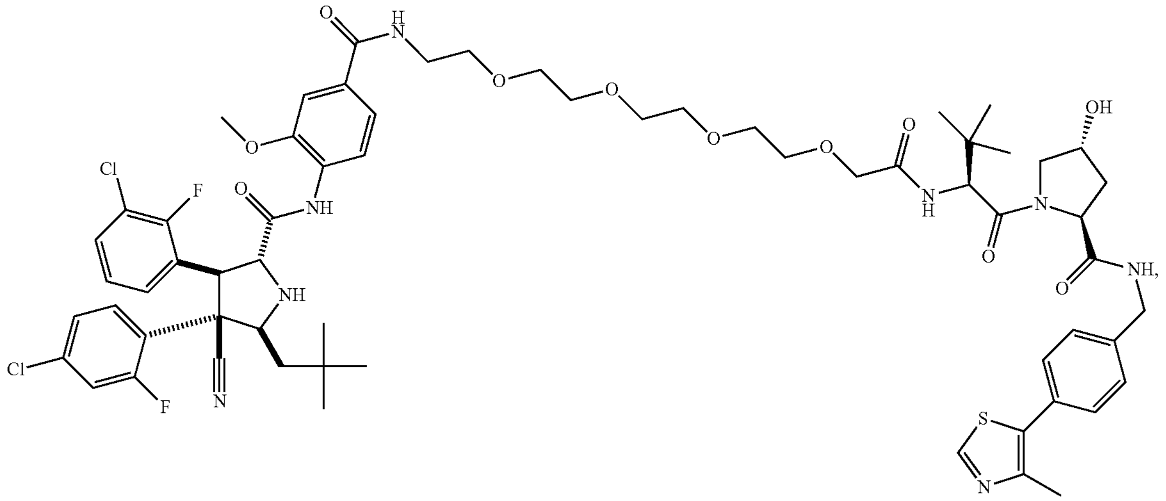
A1896
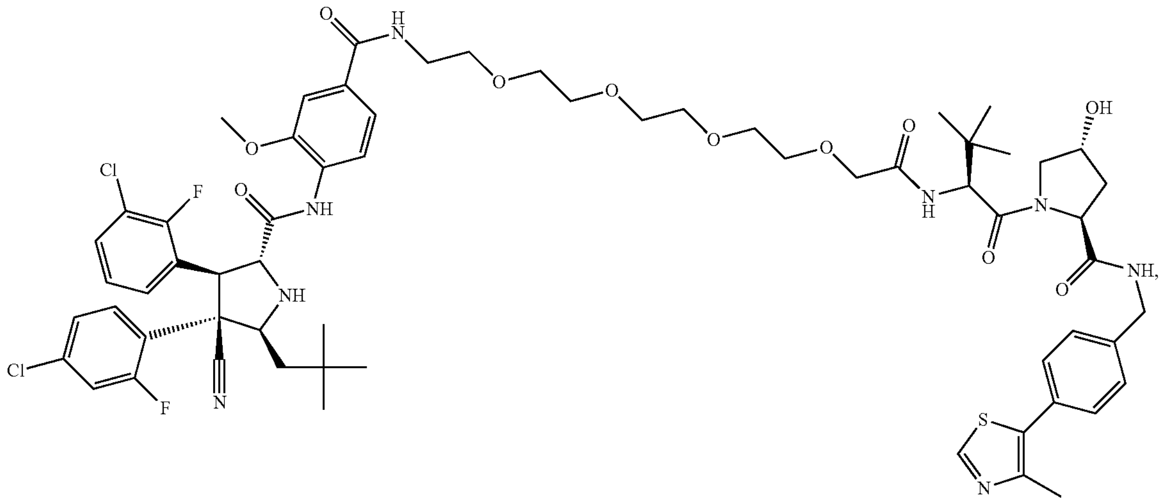
A1897
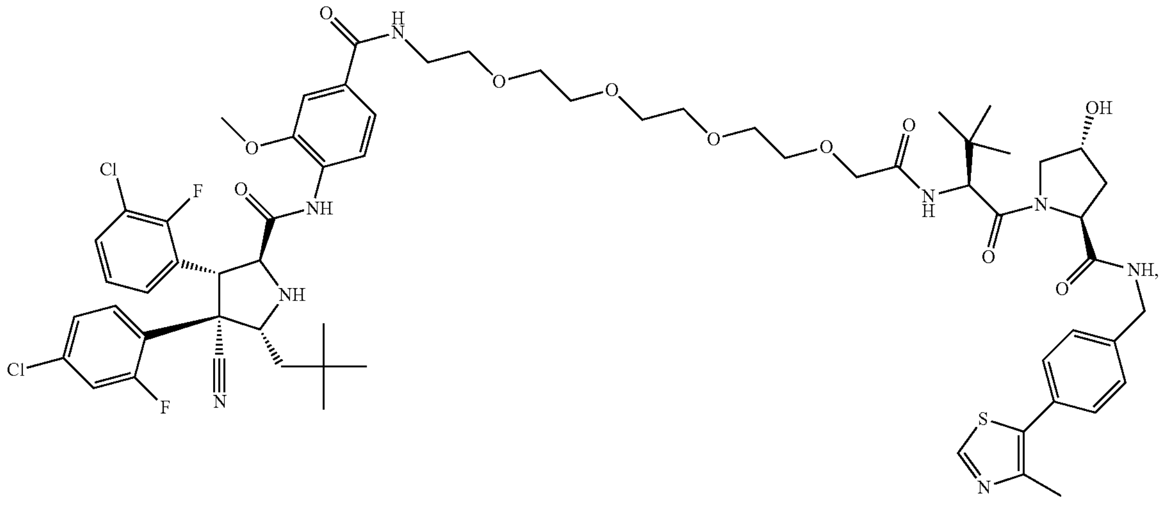

-continued
A1877
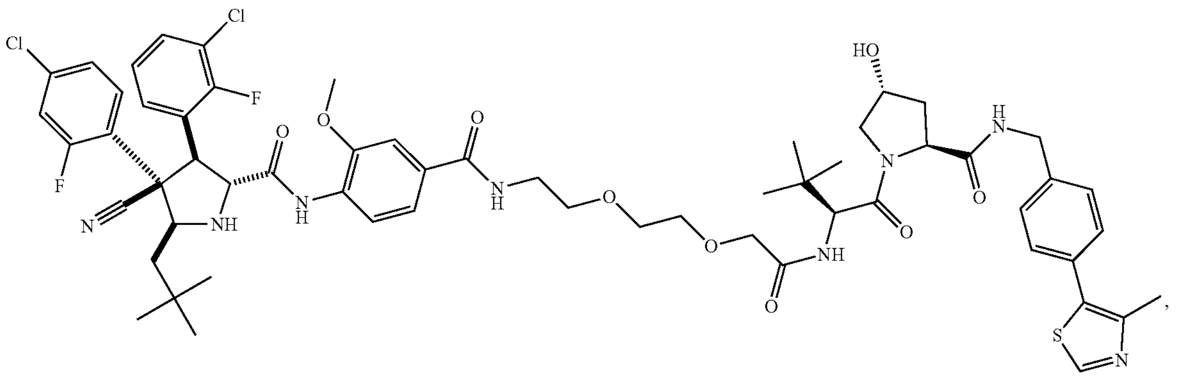
A1907
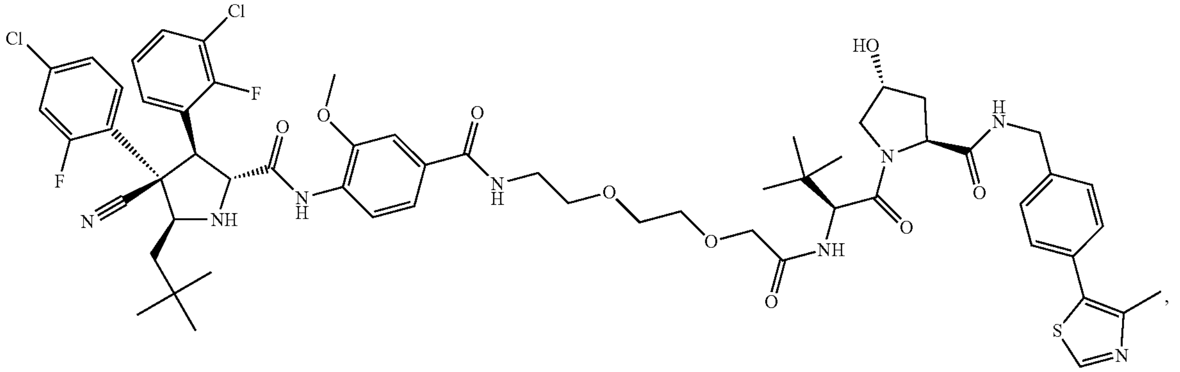
A1908
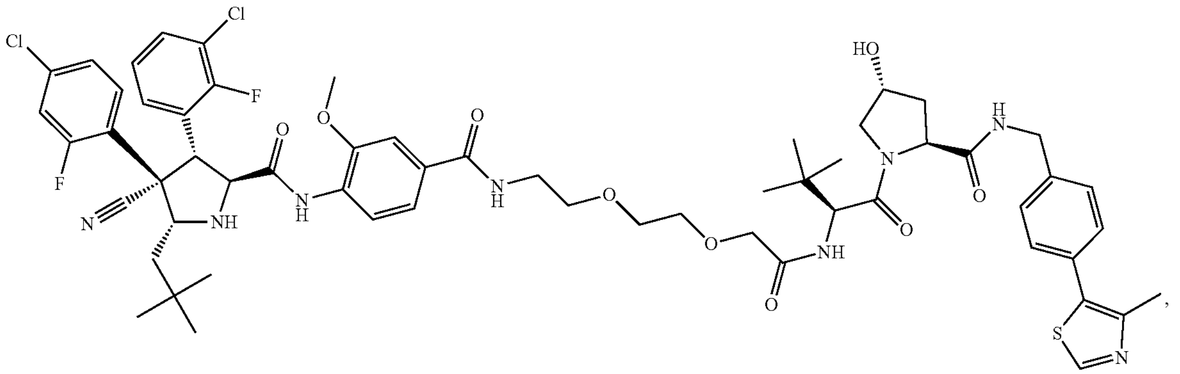
A1909
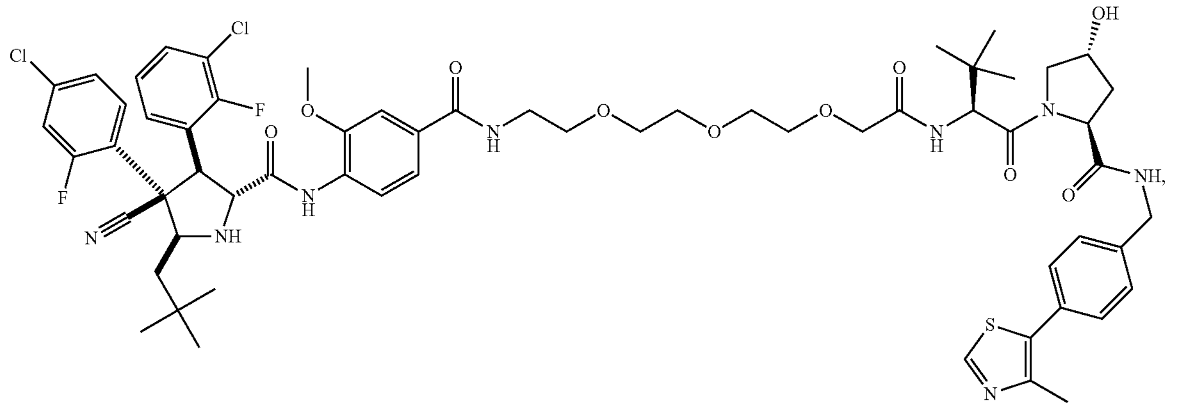

-continued
A1910
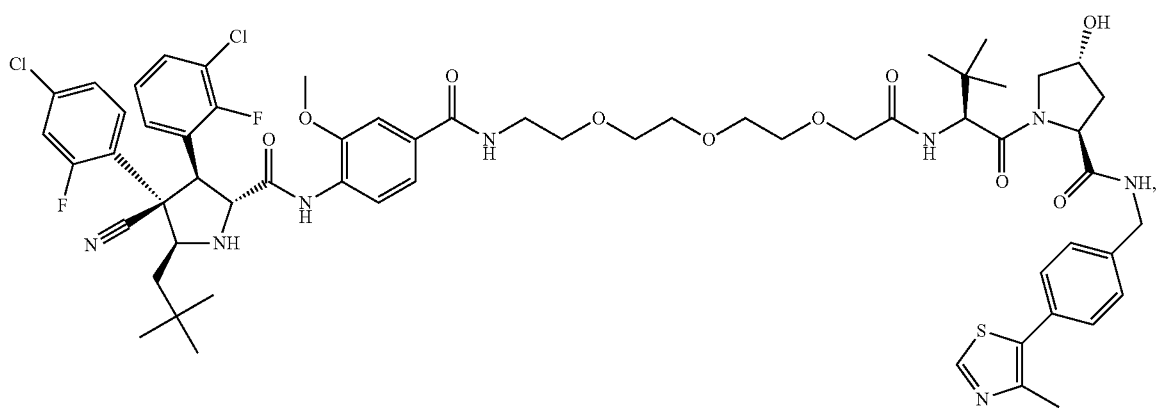
and
A1911
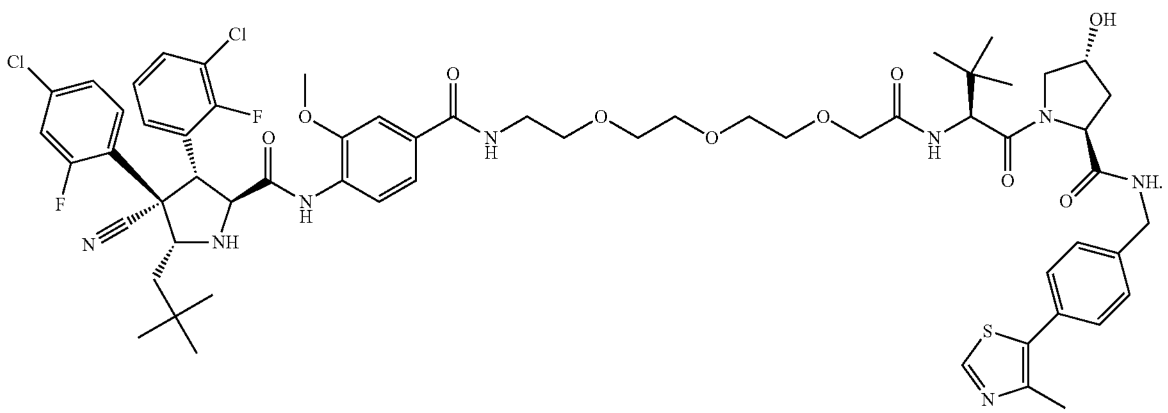
The following are examples of MDM2 ligand derived chimeric molecules using MDM2 E3 ligase to degrade androgen receptor. In an embodiment, the chimeric molecule is selected from the group consisting of:
A679
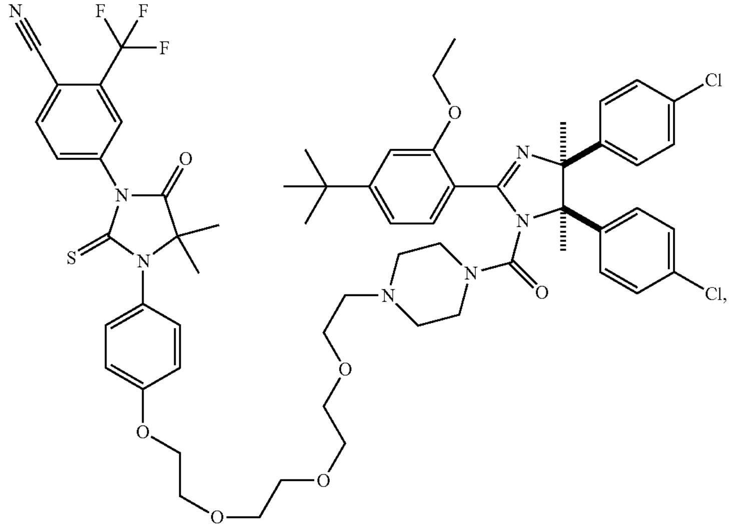
, -continued
A680
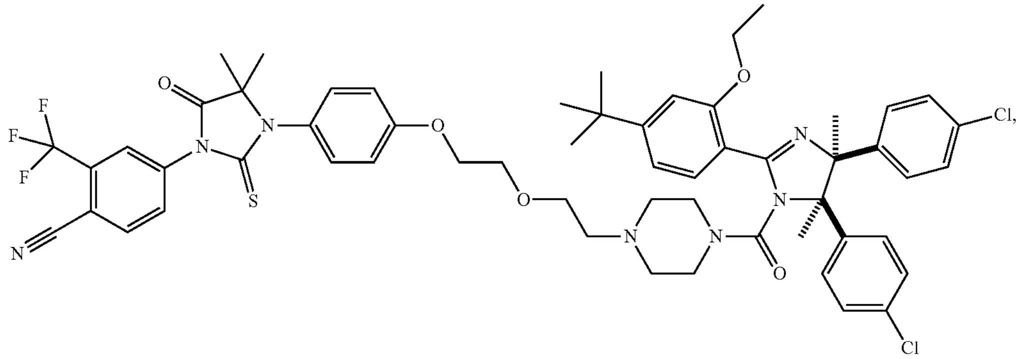
A702
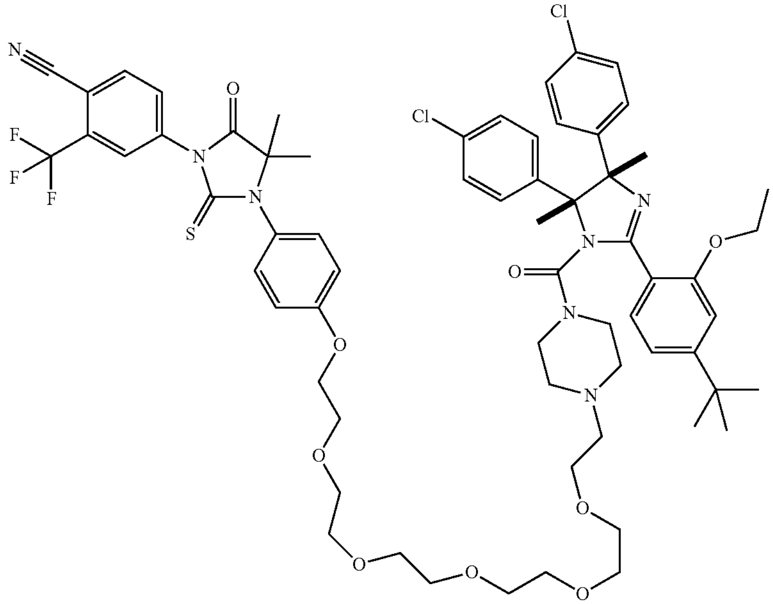
,
A1717
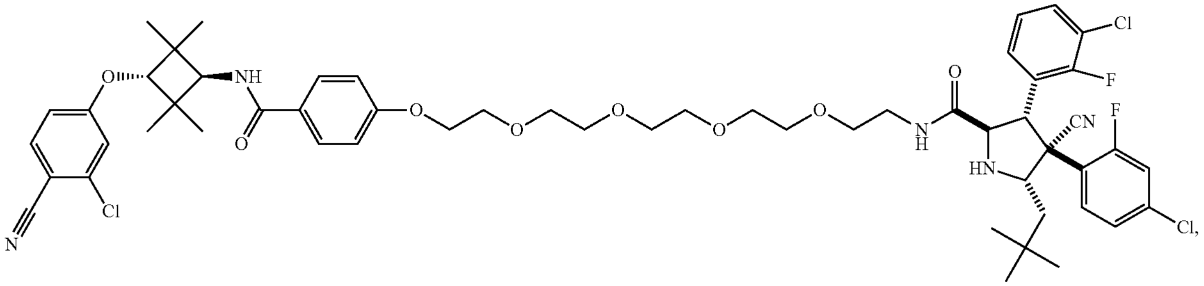
A1720
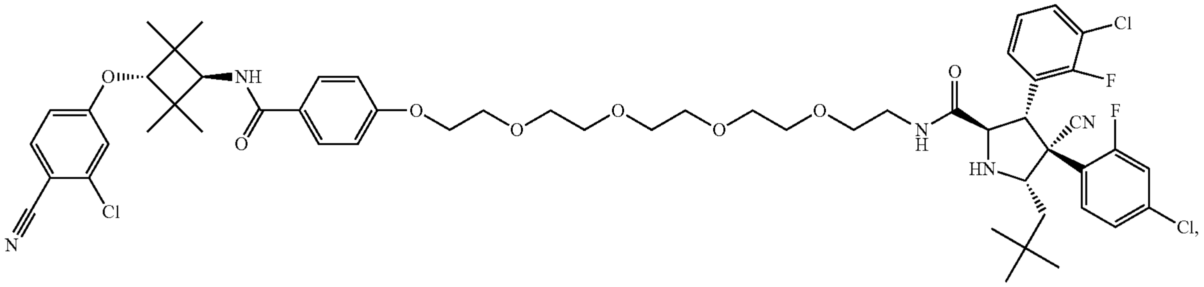

-continued
A1735
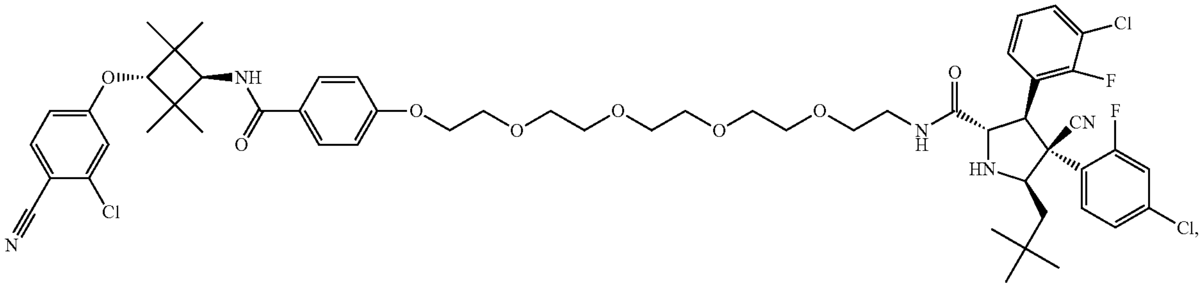
A1571
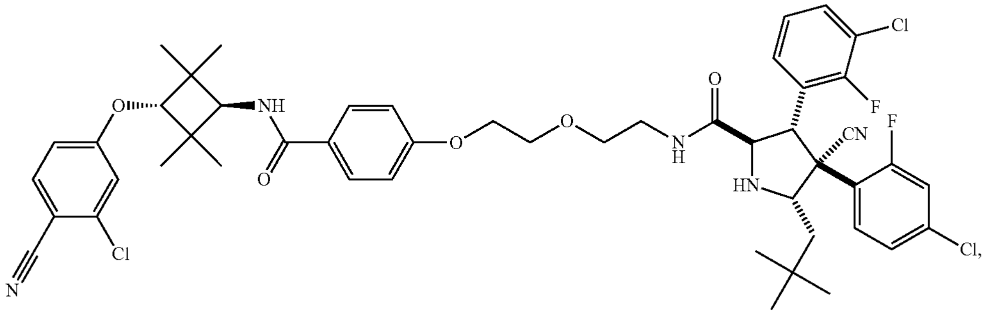
A1603
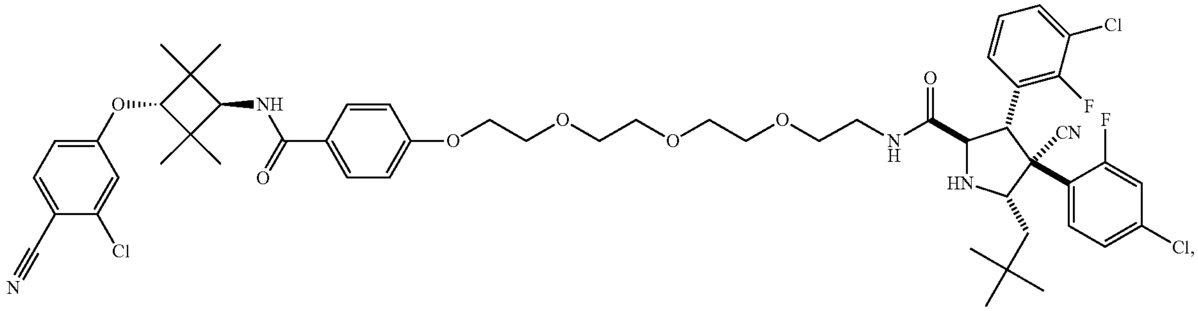
A1621
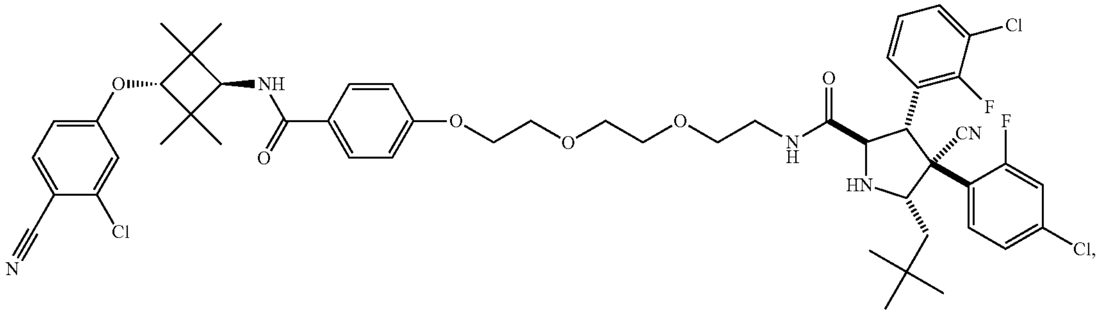
A1688
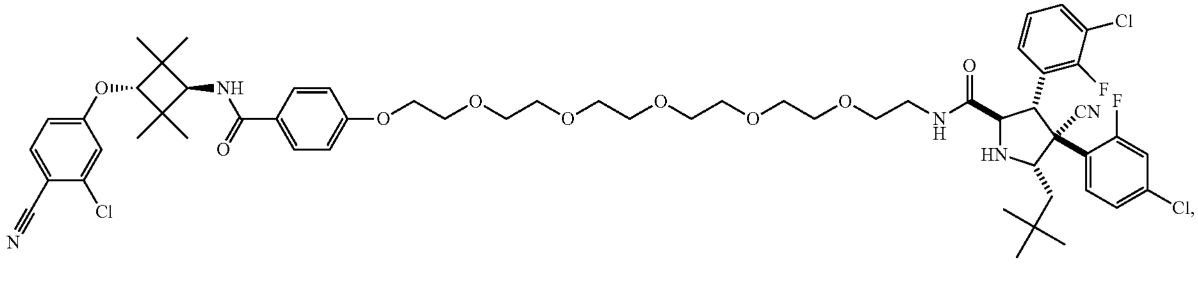

-continued

A2434

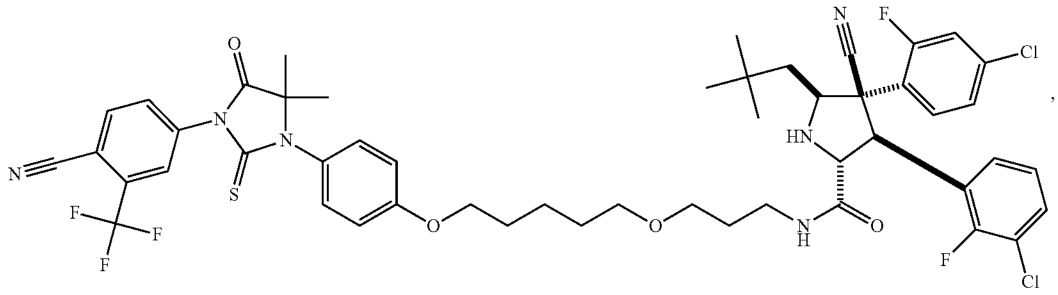

, and

A2435

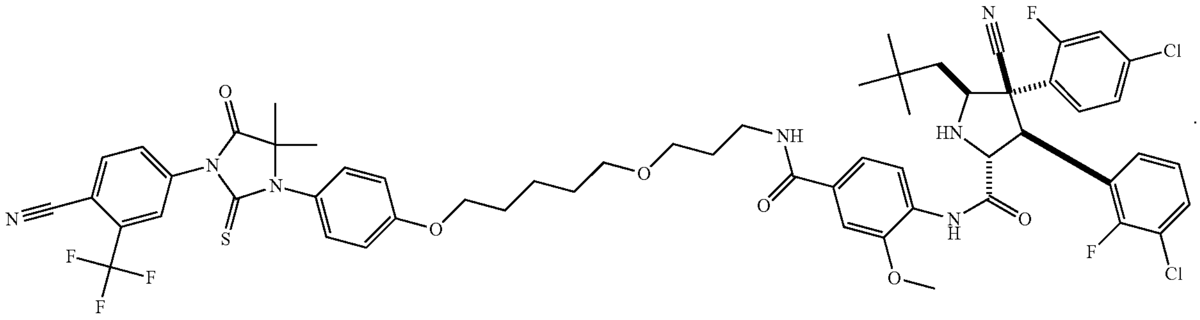

.

The following are examples of MDM2 ligand derived chimeric molecules using MDM2 E3 ligase to degrade EZH2. Thus, in certain additional embodiments, the description provides a bifunctional compound selected from the group consisting of:

The following are examples of MDM2 ligand derived chimeric molecules using MDM2 E3 ligase to degrade JNK. Thus, in certain additional embodiments, the description provides a bifunctional compound selected from the group consisting of:

A2790

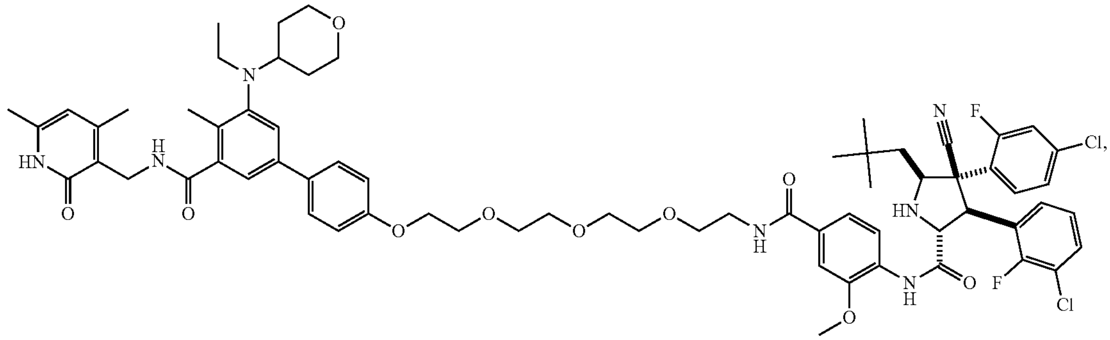

, and

A2844

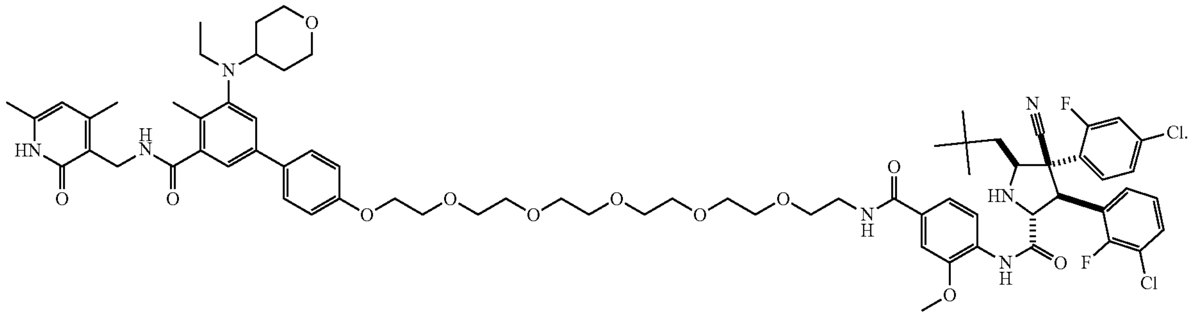

.

A2720
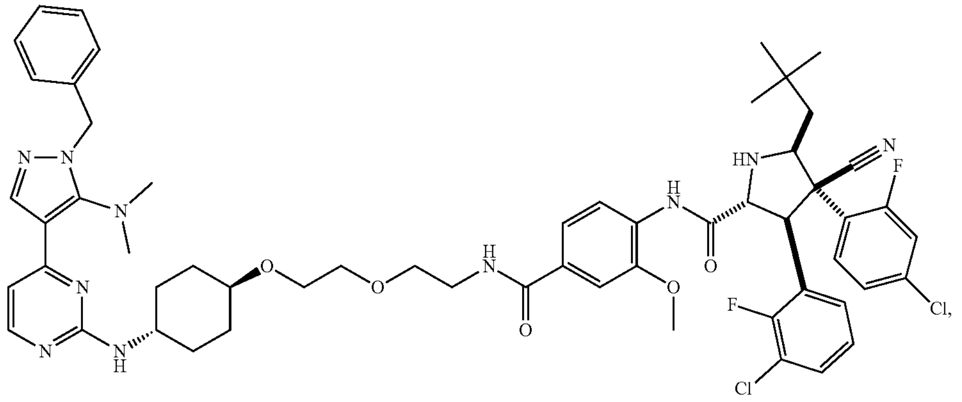
A2766
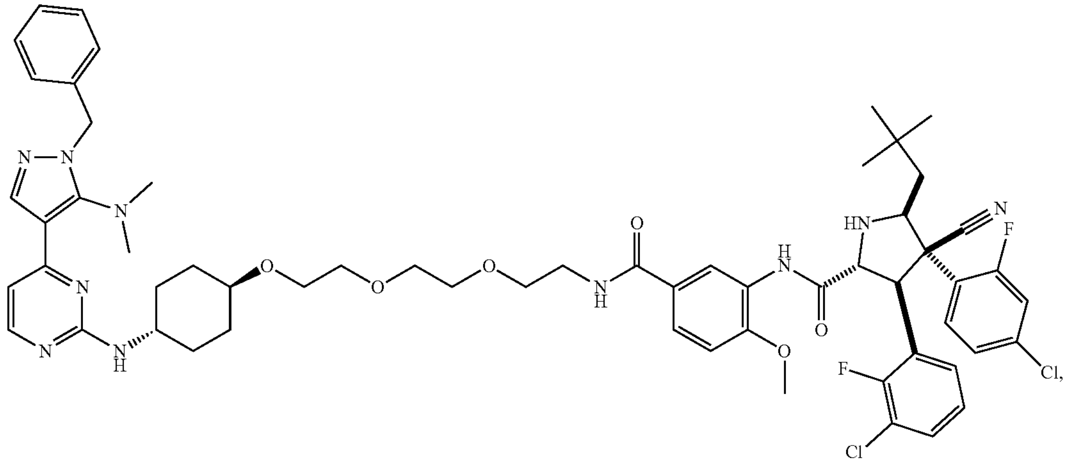
A2791
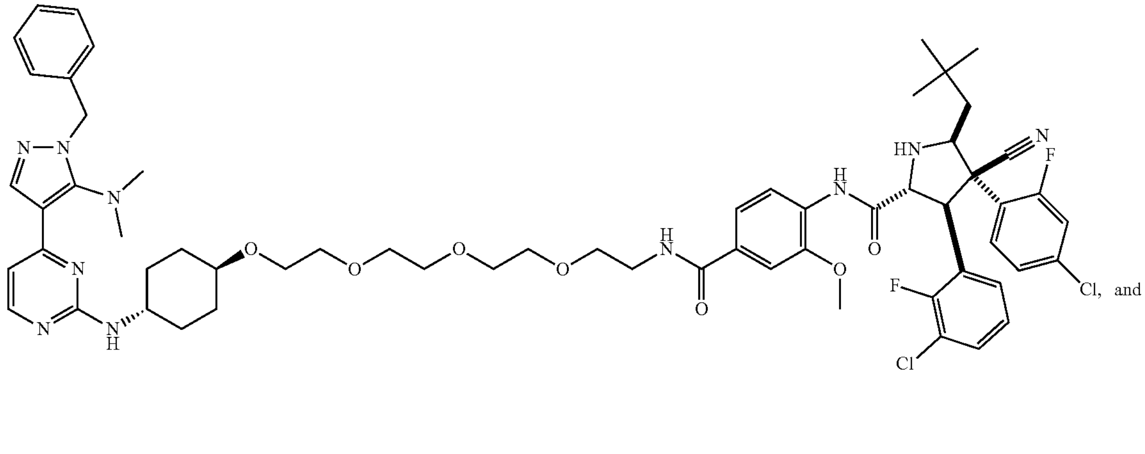
and

-continued

A2792

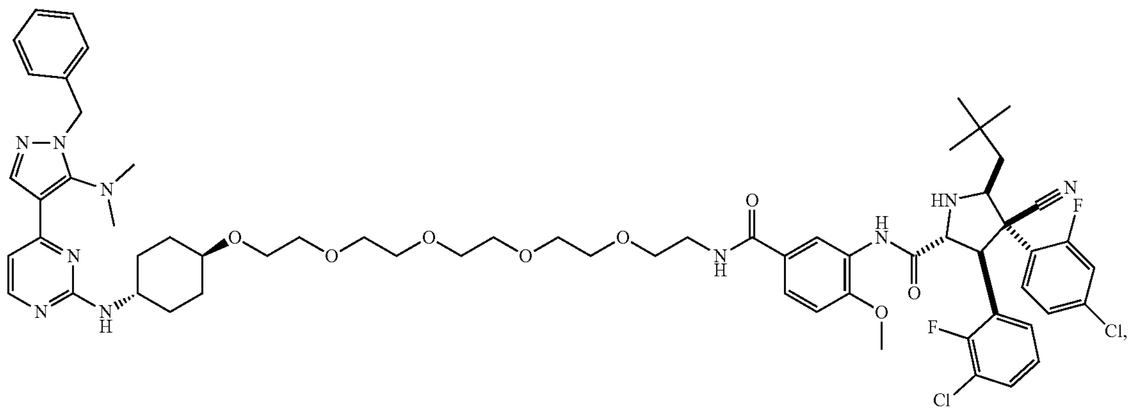

In certain aspects, the description provides a composition, e.g., a pharmaceutical composition or therapeutic composition comprising an effective amount of at least one compound as described or exemplified herein, and a pharmaceutically acceptable excipient.

Synthetic Procedures

Compounds claimed in this document can be synthesized using synthetic methods known in the art of organic chemistry. The following examples are representatives of claimed compounds. All MDM2 ligand-derived PROTACs disclosed in this document were analyzed for purity by LC/MS and all final compounds had purity larger than 95%.

Example 1

Synthesis of A1876

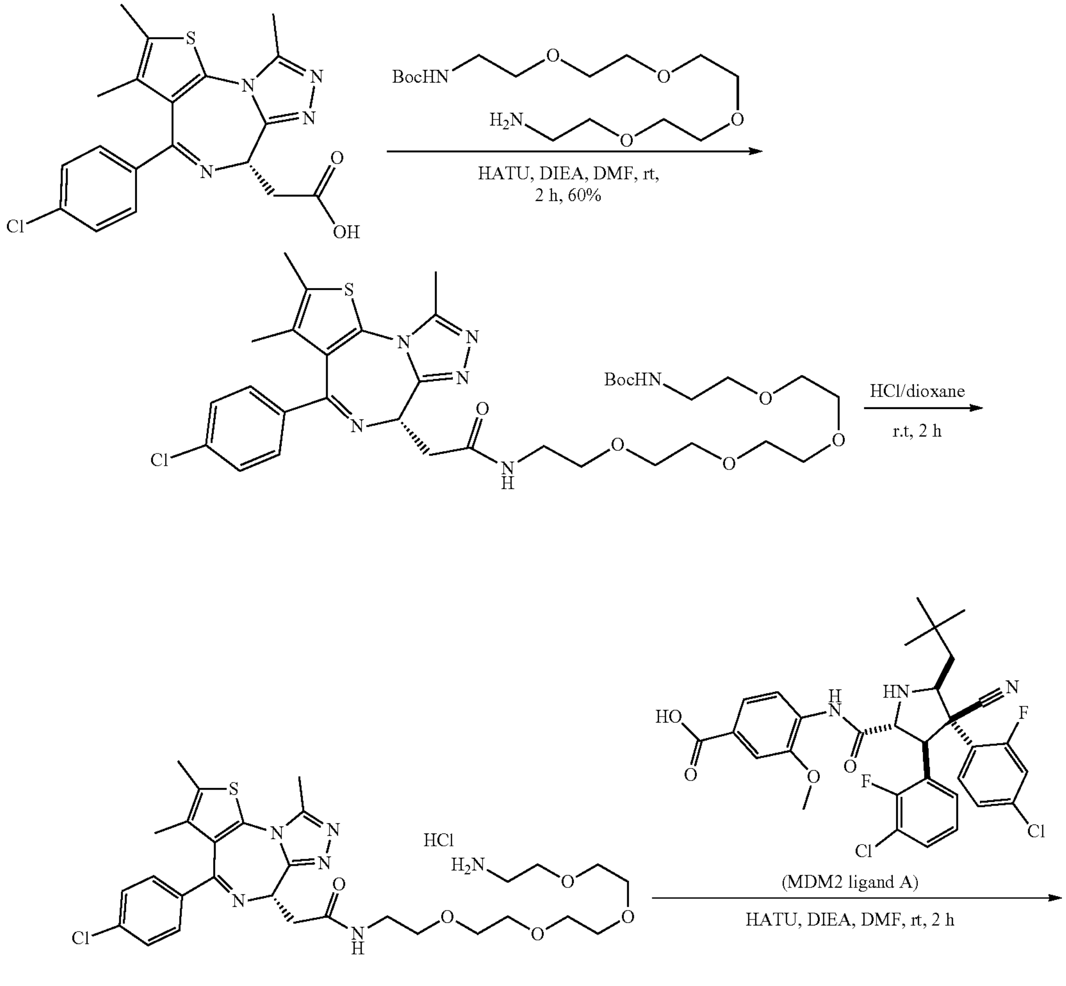

-continued

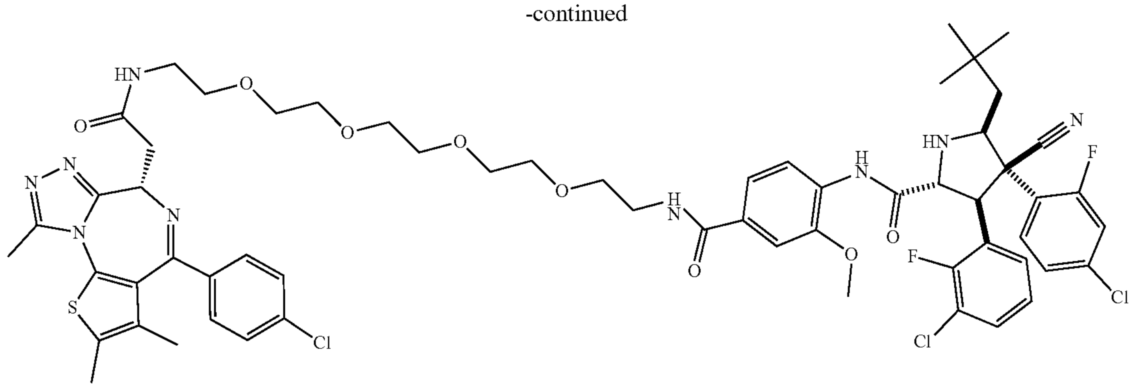

A1876

Step 1: Synthesis of tert-butyl N-(14-[2-[(9S)-7-(4-chlorophenyl)-4,5,13-trimethyl-3-thia-1,8,11,12-tetraazatricyclo[8.3.0.0^[2,6]]trideca-2(6),4,7,10,12-pentaen-9-yl]acetamido]-3,6,9,12-tetraoxatetradecan-1-yl)carbamate Into a 100-mL round-bottom flask, was placed 2-[9S)-7-(4-chlorophenyl)-4,5,13-trimethyl-3-thia-1,8,11,12-tetraazatricyclo[8.3.0.0^[2,6]]trideca-2(6),4,7,10,12-pentaen-9-yl]acetic acid (70.0 mg, 0.17 mmol, 1.00 equiv, prepared from the corresponding carboxylic acid tert-butyl ester as described in the literature: *Chem. & Bio.* 2015, 22, 755-763; *PNAS* 2016, Jun. 6), tert-butyl N-(14-amino-3,6,9,12-tetraoxatetradecan-1-yl)carbamate (59.0 mg, 0.18 mmol, 1.00 equiv), O-(7-azabenzotriazol-1-yl)-N,N,N,N-tetramethyluronium hexafluorophosphate (80.0 mg, 0.21 mmol, 1.20 equiv), N,N-Diisopropylethylamine (0.1 mL, 3.00 equiv), N,N-dimethylformamide (1.0 mL). The resulting solution was stirred for 1.0 h at room temperature and diluted with water (20 mL). The mixture was extracted with ethyl acetate (3×10 mL) and the organic layers were combined. The residue was applied onto a silica gel column and eluted with dichloromethane/methanol (10/1). This resulted in 160 mg (crude) of tert-butyl N-14-[2-[(9S)-7-(4-chlorophenyl)-4,5,13-trimethyl-3-thia-1,8,11,12-tetraazatricyclo[8.3.0.0^[2,6]trideca-2(6),4,7,10,12-pentaen-9-yl]acetamido]-3,6,9,12-tetraoxatetradecan-1-yl)carbamate as a colorless oil.

Step 2: Synthesis of N-(14-amino-3,6,9,12-tetraoxatetradecan-1-yl)-2-[(9S)-7-(4-chlorophenyl)-4,5,13-trimethyl-3-thia-1,8,11,12-tetraazatricyclo[8.3.0.0^[2,6]]trideca-2(6),4,7,10,12-pentaen-9-yl]acetamide Into a 100-mL round-bottom flask purged and maintained with an inert atmosphere of nitrogen, was placed tert-butyl N-(14-[2-[(9S)-7-(4-chlorophenyl)-4,5,13-trimethyl-3-thia-1,8,11,12-tetraazatricyclo[8.3.0.0^[2,6]]trideca-2(6),4,7,10,12-pentaen-9-yl]acetamido]-3,6,9,12-tetraoxatetradecan-1-yl)carbamate (160 mg, 0.22 mmol, 1.00 equiv), hydrogen chloride/dioxane (10.0 mL). The resulting solution was stirred for 1 h at room temperature. The resulting mixture was concentrated under vacuum. This resulted in 150.0 mg (crude) of N-(14-amino-3,6,9,12-tetraoxatetradecan-1-yl)-2-[(9S)-7-(4-chlorophenyl)-4,5,13-trimethyl-3-thia-1,8,11,12-tetraazatricyclo[8.3.0.0^[2,6]]trideca-2(6),4,7,10,12-pentaen-9-yl]acetamide as a white solid.

Step 3: 3-(3-Chloro-2-fluorophenyl)-4-(4-chloro-2-fluorophenyl)-N-{4-[(14-{2-[(9S)-7-(4-chlorophenyl)-4,5,13-trimethyl-3-thia-1,8,11,12-tetraazatricyclo[8.3.0.0$^{2}$,$^{6}$]trideca-2(6),4,7,10,12-pentaen-9-yl]acetamido}-3,6,9,12-tetraoxatetradecan-1-yl)carbamoyl]-2-methoxyphenyl}-4-cyano -5-(2,2-dimethylpropyl)pyrrolidine-2-carboxamide (A1876)

Into a 100-mL round-bottom flask purged and maintained with an inert atmosphere of nitrogen, was placed N-(14-amino-3,6,9,12-tetraoxatetradecan-1-yl)-2-[(9S)-7-(4-chlorophenyl)-4,5,13-trimethyl-3-thia-1,8,11,12-tetraazatricyclo[8.3.0.0^[2,6]]trideca-2(6),4,7,10,12-pentaen-9-yl]acetamide (93.0 mg, 0.15 mmol, 1.00 equiv), racemate of 4-[(2S,3R,4S,5R)-3-(3-chloro-2-fluorophenyl)-4-(4-chloro-2-fluorophenyl)-4-cyano-5-(2,2-dimethylpropyl)pyrrolidine-2-amido]-3-methoxybenzoic acid (80.0 mg, 0.13 mmol, 1.00 equiv, prepared according to literature procedure, *J. Med. Chem.* 2013, 56, 5979), O-(7-azabenzotriazol-1-yl)-N,N,N,N-tetramethyluronium hexafluorophosphate (60.0 mg, 0.16 mmol, 1.20 equiv), N,N-Diisopropylethylamine (0.5 mL, 3.00 equiv), N,N-dimethylformamide (3.0 mL). The resulting solution was stirred for 1.0 h at room temperature and diluted with water (20 mL). The mixture was extracted with ethyl acetate (3×10 mL) and the organic layers were combined. The crude product was purified by Prep-HPLC (mobile phase: water (10 mmol/L $NH_4HCO_3$) and $CH_3CN$, 6 min, UV detector at 220 nm), which resulted in 10.7 mg (6%) of A1876 as a white solid.

$^1$H NMR (300 MHz, $CD_3OD$): δ8.35-8.20 (m, 1H), 7.80-7.70 (m, 1H), 7.55-7.30 (m, 9H), 7.29-7.12 (m, 2H), 4.80-4.70 (m, 1H), 4.68-4.58 (m, 2H), 4.18-3.99 (m, 1H), 3.88 (s, 3H), 3.71-3.54 (m, 18H), 3.52-3.40 (m, 3H), 2.73 (s, 3H), 2.45 (s, 3H), 1.62-1.50 (m, 4H), 1.30-1.25 (m, 2H), 0.98 (s, 9H); LC-MS calculated for $C_{60}H_{66}C_{13}F_2N_9O_8S$ (m/z) 1216.38, obsd 1216, 1218 [$MH^+$, $Cl^{35}$ and $Cl^{37}$], $t_R$=2.49 (3.5 minute run).

Example 2
Preparation of A1893 and A1894
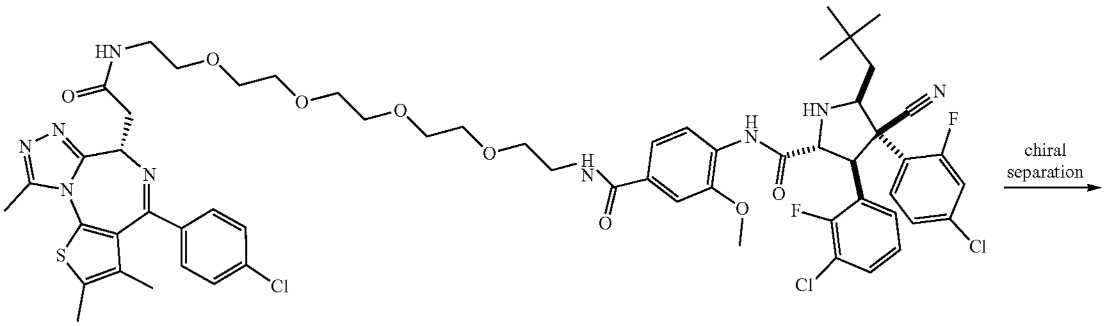
A1876
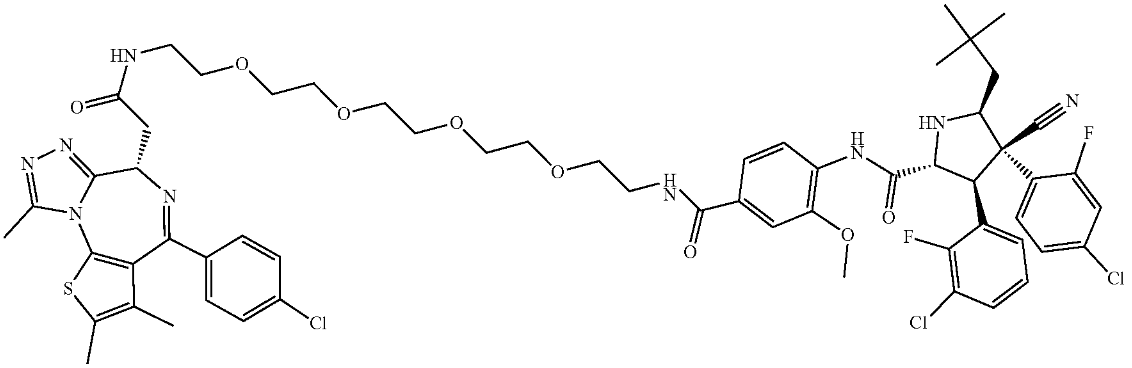
A1873
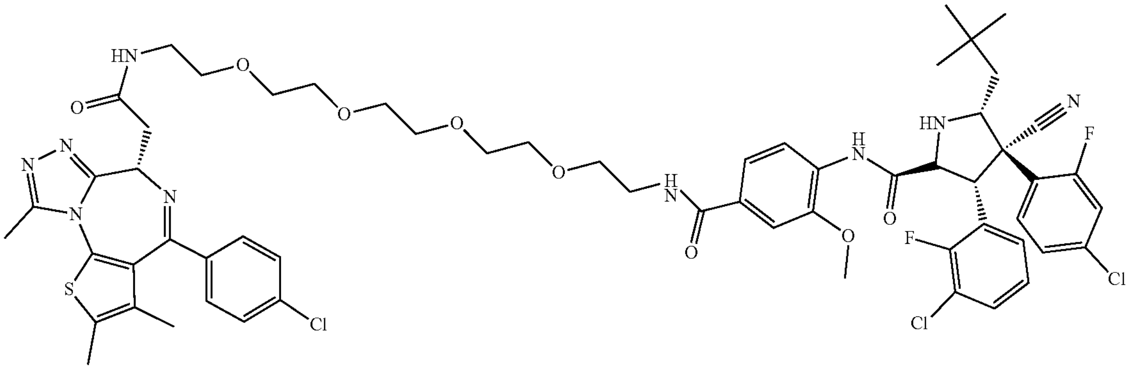
A1874

Preparation of (2R*,3S*,4R*,5S*)-3-(3-chloro-2-fluorophenyl)-4-(4-chloro -2-fluorophenyl)-N-{4-[(14-{2-[(9S)-7-(4-chlorophenyl)-4,5,13-trimethyl-3-thia-1,8,11,12-tetraazatricyclo[8.3.0.0$^{2}$,$^{6}$]trideca-2(6),4,7,10,12-pentaen-9-yl]acetamido}-3,6,9,12-tetraoxatetradecan-1-yl)carbamoyl]-2-methoxyphenyl}-4-cyano -5-(2,2-dimethylpropyl) pyrrolidine-2-carboxamide (A1893) and (2S*,3R*,4S*,5R*)-3-(3-chloro -2-fluorophenyl)-4-(4-chloro-2-fluorophenyl)-N-{4-[(14-{2-[(9S)-7-(4-chlorophenyl)-4,5,13-trimethyl-3-thia-1,8,11,12-tetraazatricyclo[8.3.0.0$^{2}$,$^{6}$]trideca-2(6),4,7,10,12-pentaen-9-yl]acetamido}-3,6,9,12-tetraoxatetradecan-1-yl)carbamoyl]-2-methoxyphenyl}-4-cyano -5-(2,2-dimethylpropyl) pyrrolidine-2-carboxamide (A1894)

A1876 was separated by preparative LC with a chiral column to provide two fractions as A1893 and A1894.

Fraction 1: $^{1}$H NMR (300 MHz, $CD_3OD$): δ8.35-8.27 (m, 1H), 7.80-7.70 (m, 1H), 7.55-7.30 (m, 9H), 7.29-7.12 (m, 2H), 4.80-4.70 (m, 1H), 4.68-4.58 (m, 2H), 4.18-3.99 (m, 1H), 3.88 (s, 3H), 3.71-3.54 (m, 18H), 3.52-3.40 (m, 3H), 3.30-3.25 (m, 1H), 2.73 (s, 3H), 2.45 (s, 3H), 1.62-1.50 (m, 4H), 1.30-1.25 (m, 1H), 0.98 (s, 9H); LC-calculated for $C_{60}H_{66}C_{13}F_2N_9O_8S$ (m/z) 1216.38, obsd 1216, 1218 [$MH^+$, $Cl^{35}$ and $Cl^{37}$], $t_R$=1.96 min (2.9 minute run).

Fraction 2: $^{1}$H NMR (300 MHz, $CD_3OD$): δ8.35-8.27 (m, 1H), 7.80-7.70 (m, 1H), 7.55-7.30 (m, 9H), 7.29-7.12 (m, 2H), 4.80-4.70 (m, 1H), 4.68-4.58 (m, 2H), 4.18-3.99 (m, 1H), 3.88 (s, 3H), 3.71-3.54 (m, 18H), 3.52-3.40 (m, 3H), 2.73-2.60 (m, 4H), 2.45 (s, 3H), 1.62-1.50 (m, 4H), 1.30-1.25 (m, 1H), 0.98 (s, 9H); LC-MS calculated for $C_{60}H_{66}C_{13}F_2N_9O_8S$ (m/z) 1216.38, obsd 1216, 1218 [$MH^+$, $Cl^{35}$ and $Cl^{37}$], $t_R$=1.96 min (2.9 minute run).

Using the same synthetic method as described for A1876, A1893 and A1894, the following molecules were prepared: A1283, A1306, A1307, A1863, A1864, A1865, A1829, A1874, A1875, A1890, A1891 and a1892. The MDM2 ligand for A1283, A1306 and A1306 was synthesized according to literature procedure (*J. Med. Chem.* 2013, 56, 5979)

Example 3

Preparation of A1895

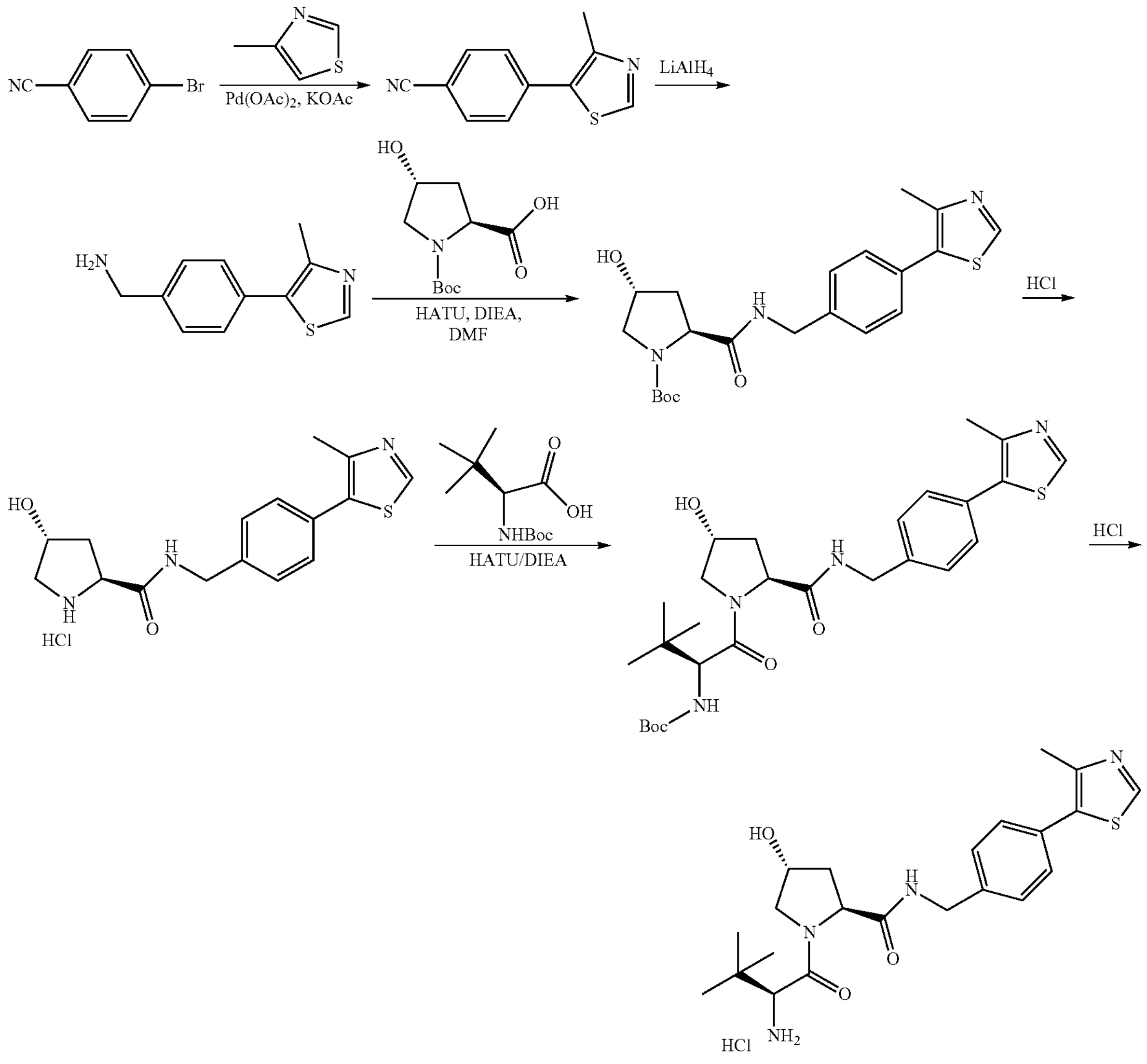

-continued
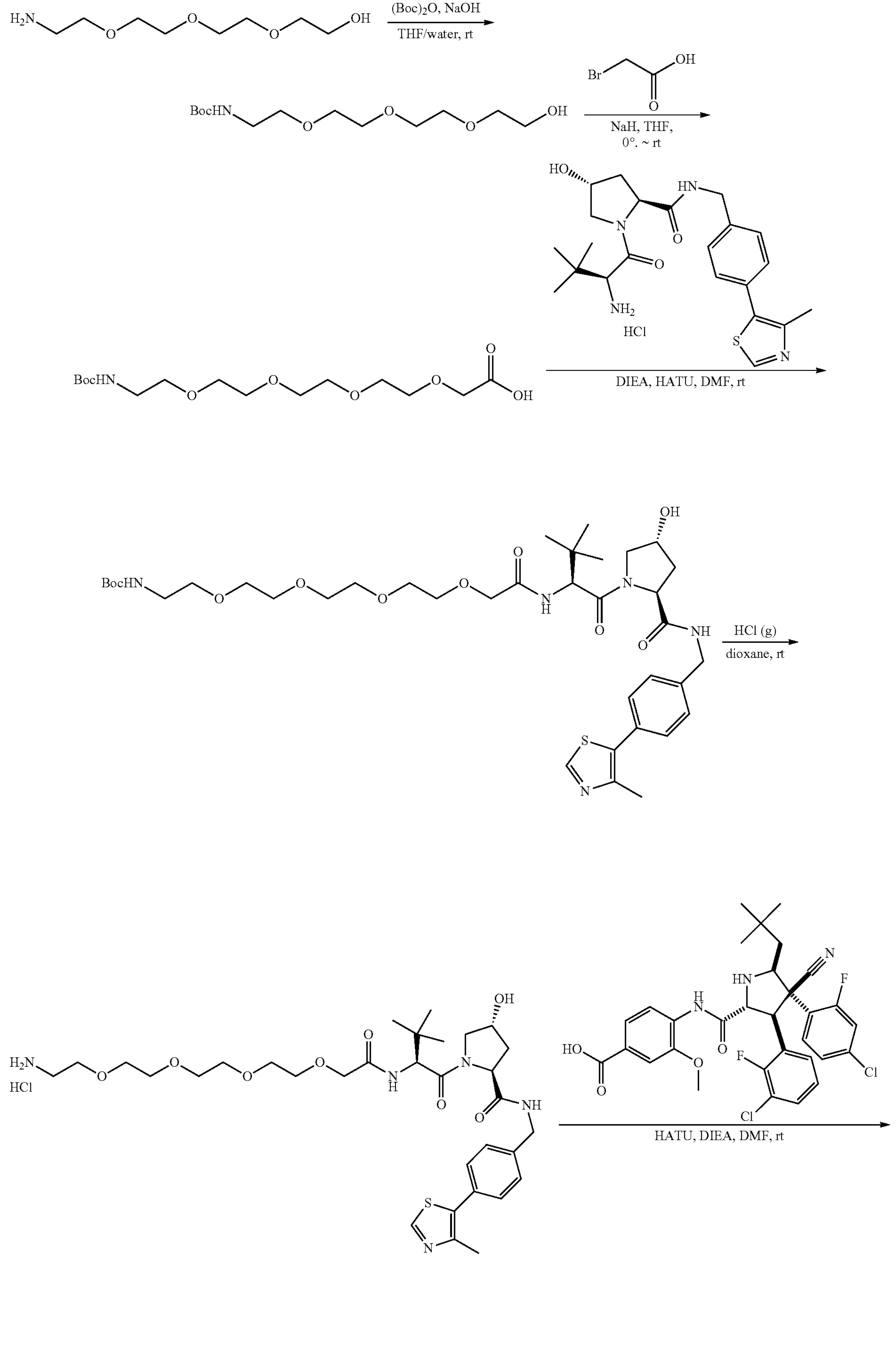

-continued

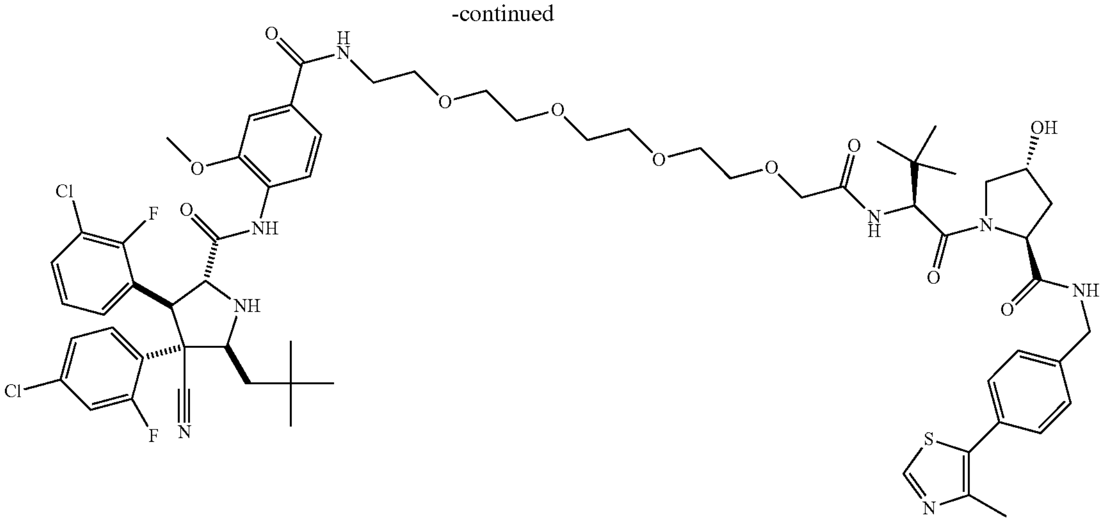

A1895

Step 1: Synthesis of 4-(4-methyl-1,3-thiazol-5-yl)benzonitrile

To a stirred solution of 4-bromobenzonitrile (20 g, 109.88 mmol) in DMA (250 mL) under a nitrogen atmosphere was added 4-methyl-1,3-thiazole (21.88 g, 220.67 mmol), palladium (II) acetate (743 mg, 3.31 mmol) and potassium acetate (21.66 g, 220.71 mmol) at rt. The resulting solution was heated to 150° C. and stirred at this temperature for 5 h, at which time LC-MS indicated completion of reaction. The reaction was cooled to rt, diluted with 1 L of water and extracted with ethyl acetate (300 mL×3). The organic layers were combined, washed with saturated aqueous solution of sodium chloride (200 mL), dried over anhydrous sodium sulfate and then concentrated under reduced pressure to give a crude residue, which was purified by flash silica gel chromatography (eluent: ethyl acetate/petroleum ether, v:v=1:5) to give the titled compound (yield: 91%) as a white solid.

Step 2: Synthesis of [4-(4-methyl-1,3-thiazol-5-yl) phenyl]methanamine

To a stirred solution of 4-(4-methyl-1,3-thiazol-5-yl)benzonitrile (35 g, 174.77 mmol) in tetrahydrofuran (1000 mL) was added $LiAlH_4$ (20 g, 526.32 mmol) in portions at 0° C. in 10 min under a nitrogen atmosphere. The resulting solution was then stirred at 60° C. for 3 h, at which time LC-MS indicated completion of reaction. The reaction was cooled to 0° C., then quenched by the addition water (20 mL, added slowly), aq. solution of NaOH (15%, 20 mL) and water (60 mL). The resulting mixture was then extracted with ethyl acetate (300 mL×2). The organic layers were combined, washed with saturated aqueous solution of sodium chloride (100 mL), dried over anhydrous sodium sulfate and then concentrated under reduced pressure to give a crude residue, which was purified by flash silica gel chromatography (eluent: dichloromethane/methanol (v:v=10:1)) to give the titled compound (yield: 56%) as a yellow oil.

Step 3: Synthesis of tert-butyl (2S,4R)-4-hydroxy-2-([[4-(4-methyl-1,3-thiazol-5-yl)phenyl]methyl] carbamoyl)pyrrolidine-1-carboxylate To a stirred solution of (2S,4R)-1-[(tert-butoxy)carbonyl]-4-hydroxypyrrolidine-2-carboxylic acid (2.7 g, 11.68 mmol) in N,N-dimethylformamide (20 mL) was added DIEA (2.52 g, 19.50 mmol), HATU (4.47 g, 11.76 mmol) and [4-(4-methyl-1,3-thiazol-5-yl)phenyl]methanamine (2 g, 9.79 mmol) at rt. The resulting mixture was stirred at rt overnight, at which time LC-MS indicated completion of reaction. The reaction mixture was diluted by 20 mL of water and extracted with ethyl acetate (50 mL×3). The organic layers were combined, washed with saturated aqueous solution of sodium chloride (50 mL), dried over anhydrous sodium sulfate and then concentrated under reduced pressure to give a crude residue, which was purified by flash silica gel chromatography (eluent: dichloromethane/methanol (v:v=20:1)) to give the titled compound (yield: 56%) as a yellow solid.

Step 4: Synthesis of (25,4R)-4-hydroxy-N-[[4-(4-methyl-1,3-thiazol-5-yl)phenyl]methyl]pyrrolidine-2-carboxamide hydrochloride To a solution of tert-butyl (2S,4R)-4-hydroxy-2-([[4-(4-methyl-1,3-thiazol-5-yl)phenyl]methyl]carbamoyl)pyrrolidine-1-carboxylate (45 g, 107.78 mmol) in dioxane was added a solution of hydrogen chloride (13.44 L) in dioxane (300 mL). The resulting solution was stirred for 2 h at 20° C. The solids were collected by filtration to give the titled product (yield: 98%) as a yellow solid.

Step 5: Synthesis of tert-butyl N-[(2S)-1-[(2S,4R)-4-hydroxy-2-([[4-(4-methyl-1,3-thiazol-5-yl)phenyl] methyl]carbamoyl)pyrrolidin-1-yl]-3,3-dimethyl-1-oxobutan-2-yl]carbamate To a stirred solution of (2S)-2-[[(tert-butoxy)carbonyl] amino]-3,3-dimethylbutanoic acid (15.73 g, 68.01 mmol) in N,N-dimethylformamide (500 mL) was added DIEA (29.2 g, 225.94 mmol), HATU (25.9 g, 68.12 mmol, 1.20 equiv) and (2S,4R)-2-amino-5-chloro-4-hydroxy-N-[[4-(4-methyl- 1,3-thiazol-5-yl)phenyl]methyl]pentanamide (20 g, 56.52 mmol) at rt. The resulting solution was stirred at rt for 16 h, at which time LC-MS indicated completion of reaction. The reaction mixture was diluted by water (200 mL) and extracted with ethyl acetate (200 mL×3). The organic layers were combined, washed with saturated aqueous solution of sodium chloride (50 mL×2), dried over anhydrous sodium sulfate and then concentrated under reduced pressure to give a crude residue, which was purified by flash silica gel chromatography (eluent: ethyl acetate/petroleum ether (v:v=2:1)) to give the titled compound (yield: 51%) as a yellow solid.

Step 6: Synthesis of (2S, 4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide hydrochloride To a stirred solution of tert-butyl N-[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamate (12 g, 22.61 mmol) in dioxane (20 mL) was added a solution of hydrogen chloride (3.584 L) in dioxane (80 mL) at rt. The resulting solution was stirred at rt for 2 h, at which time LC-MS indicated completion of reaction. Precipitated solids were collected by filtration to give the titled product (yield: 48%) as a yellow solid. $^1$HNMR (400 MHz, $CD_3OD$): δ9.84-9.82 (s, 1H), 7.58-7.54 (m, 4H), 4.71-4.41 (m, 4H), 4.13-4.08 (m, 1H), 3.86-3.71 (m, 2H), 3.36 (s, 1H), 2.60-2.58 (s, 3H), 2.35-2.07 (m, 2H), 1.19-1.12 (m, 9H). LC-MS ($ES^+$): m/z 431.11 [$MH^+$], $t_R$=0.73 min.

Step 7: Synthesis of tert-butyl N-(2-[2-[2-(2-hydroxyethoxy)ethoxy]ethoxy]ethyl)carbamate Into a 100-mL round-bottom flask, was placed a solution of 2-[2-[2-(2-aminoethoxy)ethoxy]ethoxy]ethan-1-ol (3.0 g, 15.52 mmol, 1.00 equiv) in tetrahydrofuran/water (30/30 mL), di-tert-butyl dicarbonate (3.6 g, 16.49 mmol, 1.05 equiv), sodium hydroxide (2.5 g, 62.50 mmol, 4.00 equiv). The resulting solution was stirred for 16 h at room temperature. The resulting solution was diluted with water (20 mL) and extracted with ethyl acetate (20 mL×3). The combined organic layers were washed with brine (20 mL×1), dried over anhydrous sodium sulfate and concentrated under vacuum. The residue was applied onto a silica gel column and eluted with ethyl acetate/petroleum ether (1:1). This resulted in 2.0 g (44%) of tert-butyl N-(2-[2-[2-(2-hydroxyethoxy)ethoxy]ethoxy]ethyl)carbamate as light yellow oil. LC-MS ($ES^+$): m/z 294.05 [$MH^+$], $t_R$=0.93 min, (1.9 minute run).

Step 8: Synthesis of 14-[[(tert-butoxy)carbonyl]amino]-3,6,9,12-tetraoxatetradecanoic acid Into a 50-mL round-bottom flask, was placed a solution of tert-butyl N-(2-[2-[2-(2-hydroxyethoxy)ethoxy]ethoxy]ethyl)carbamate (300.0 mg, 1.02 mmol, 1.00 equiv) in tetrahydrofuran (10 mL), sodium hydride (50.0 mg, 2.08 mmol, 1.20 equiv), 2-bromoacetic acid (141.0 mg, 1.01 mmol, 1.00 equiv). The resulting solution was stirred for 4 h at room temperature. The reaction was then quenched by the addition of water (20 mL). The resulting solution was extracted with ethyl acetate (20 mL×3). The combined organic layers were washed with brine (20 mL×1). The resulting mixture was concentrated under vacuum. This resulted in 310.0 mg (86%) of 14-[[(tert-butoxy)carbonyl]amino]-3,6,9,12-tetraoxatetradecanoic acid as light yellow oil.

Step 9: Synthesis of tert-butyl N-(1-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]-2,5,8,11-tetraoxatridecan-13-yl)carbamate Into a 25-mL round-bottom flask, was placed a solution of 14-[[(tert-butoxy)carbonyl]amino]-3,6,9,12-tetraoxatetradecanoic acid (175.0 mg, 0.50 mmol, 1.00 equiv) in N,N-dimethylformamide (10 mL), (2S,4R)-1-((S)-2-amino-3,3-dimethylbutanoyl)-4-hydroxy-N-(4-(4-methylthiazol-5-yl)benzyl) pyrrolidine-2-carboxamide hydrochloride (250.0 mg, 0.54 mmol, 1.10 equiv, from Step 6), O-(7-azabenzotriazol-1-yl)-N,N,N,N-tetramethyluronium hexafluorophosphate (277.0 mg, 0.73 mmol, 1.20 equiv), N,N-diisopropylethylamine (0.5 mL, 5.00 equiv). The resulting solution was stirred for 2 h at room temperature. The reaction was then quenched by the addition of water (20 mL). The resulting solution was extracted with ethyl acetate (20 mL×3). The combined organic layers were washed with brine (20 mL×1). The mixture was dried over anhydrous sodium sulfate and concentrated under vacuum. The residue was applied onto a silica gel column eluted with dichloromethane/methanol (10:1). This resulted in 227.0 mg (60%) of tert-butyl N-(1-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]-2,5,8,11-tetraoxatridecan-13-yl)carbamate as yellow oil. LC-MS ($ES^+$): m/z 764.35 [$MH^+$], $t_R$=1.08 min, (1.9 minute run).

Step 10: Synthesis of (2S,4R)-1-[(2S)-2-(14-amino-3,6,9,12-tetraoxatetradecanamido)-3,3-dimethylbutanoyl]-4-hydroxy-N-[[4-(4-methyl-1,3-thiazol-5-yl)phenyl]methyl]pyrrolidine-2-carboxamide Into a 25-mL round-bottom flask, was placed a solution of tert-butyl N-(1-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]-2,5,8,11-tetraoxatridecan-13-yl)carbamate (227.0 mg, 0.30 mmol, 1.00 equiv) in dioxane (10 mL), then HCl (g) was introduced in. The resulting solution was stirred for 2 h at room temperature. The resulting mixture was concentrated under vacuum. This resulted in 190.0 mg (96%) of (2S,4R)-1-[(2S)-2-(14-amino-3,6,9,12-tetraoxatetradecanamido)-3,3-dimethylbutanoyl]-4-hydroxy-N-[[4-(4-methyl-1,3-thiazol-5-yl)phenyl]methyl]pyrrolidine-2-carboxamide as yellow oil.

Step 11: Synthesis of 3-(3-chloro-2-fluorophenyl)-4-(4-chloro-2-fluorophenyl)-4-cyano-5-(2,2-dimethylpropyl)-N-[4-[(1-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]-2,5,8,11-tetraoxatridecan-13-yl)carbamoyl]-2-methoxyphenyl]pyrrolidine-2-carboxamide (A1895)

Into a 50-mL round-bottom flask, was placed a solution of racemate of 4-[(2R, 3S, 4R, 5S)-3-(3-chloro-2-fluorophenyl)-4-(4-chloro-2-fluorophenyl)-4-cyano-5-(2,2-dimethylpropyl)pyrrolidine-2-amido]-3-methoxybenzoic acid (80 mg, 0.13 mmol, 1.00 equiv) in N,N-dimethylformamide (10 mL), (2S,4R)-1-[(2S)-2-(14-amino-3,6,9,12-tetraoxatetradecanamido)-3,3-dimethylbutanoyl]-4-hydroxy-N-[[4-(4-methyl-1,3-thiazol-5-yl)phenyl]methyl]pyrrolidine-2-carboxamide (320.0 mg, 0.48 mmol, 1.10 equiv), O-(7-azabenzotriazol-1-yl)-N,N,N,N-tetramethyluronium hexafluorophosphate (64.0 mg, 0.17 mmol, 1.20 equiv), N,N-diisopropylethylamine(0.4 mL, 5.00 equiv). The resulting solution was stirred for 2 h at room temperature. The reaction was then quenched by the addition of water (20 mL). The resulting solution was extracted with ethyl acetate (20 mL×3) and the combined organic layers were washed with brine (20 mL×1). The mixture was dried over anhydrous sodium sulfate and concentrated under vacuum. The crude material was purified by prep-HPLC (column: XBridge Shield RP18 OBD Column, 5 um, 19*150 mm; Mobile Phase A: water (10 mmol/L bicarbonate amine), Mobile Phase B: acetonitrile; Flow rate: 20 mL/min; Gradient: 50% B to 60% B in 9 min; 254 nm). This resulted in 40.0 mg (24%) of (2R/2S, 3S/3R, 4R/4S, 55/5R)-3-(3-chloro-2-fluorophenyl)-4-(4-chloro-2-fluorophenyl)-4-cyano-5-(2,2-dimethylpropyl)-N-[4-[(1-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]-2,5,8,11-tetraoxatridecan-13-yl)carbamoyl]-2-methoxyphenyl]pyrrolidine-2-carboxamide as a white solid.

$^1$H NMR (300 MHz, $CD_3OD$) δ 8.84 (s, 1H), 8.34-8.31 (m, 1H), 7.62-7.64 (m, 1H), 7.51 (s, 1H), 7.40-7.29 (m, 8H), 7.24-7.19 (m, 2H), 4.80-4.75 (m, 1H), 4.70-4.55 (m, 3H), 4.55-4.45 (m, 1H), 4.27-4.25 (m, 1H), 4.10-4.00 (m, 1H), 3.99-3.77 (m, 5H), 3.70-3.66 (m, 2H), 3.66-3.61 (m, 15H), 3.59-3.55 (m, 2H), 2.48 (s, 3H), 2.25-2.19 (m, 1H), 2.19-1.92 (m, 1H), 1.66-1.63 (m, 1H), 1.40-1.35 (m, 1H), 0.99 (s, 18H). LC-MS calcd for $C_{63}H_{76}Cl_2F_2N_8O_{11}S$ (m/z) 1260.47, obsd 1284.05/1286.05 [M+Na$^+$], $t_R$=2.27 min, (3.6 minute run).

Example 4

Preparation of A1896 and a1897

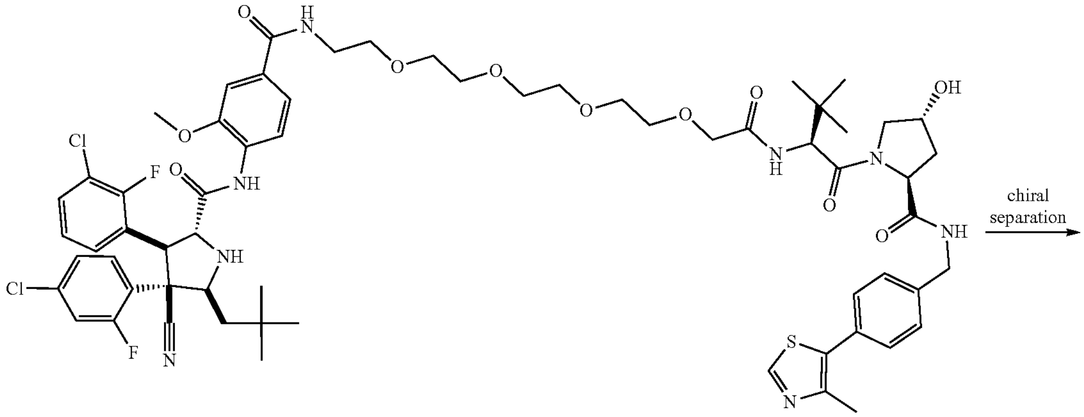

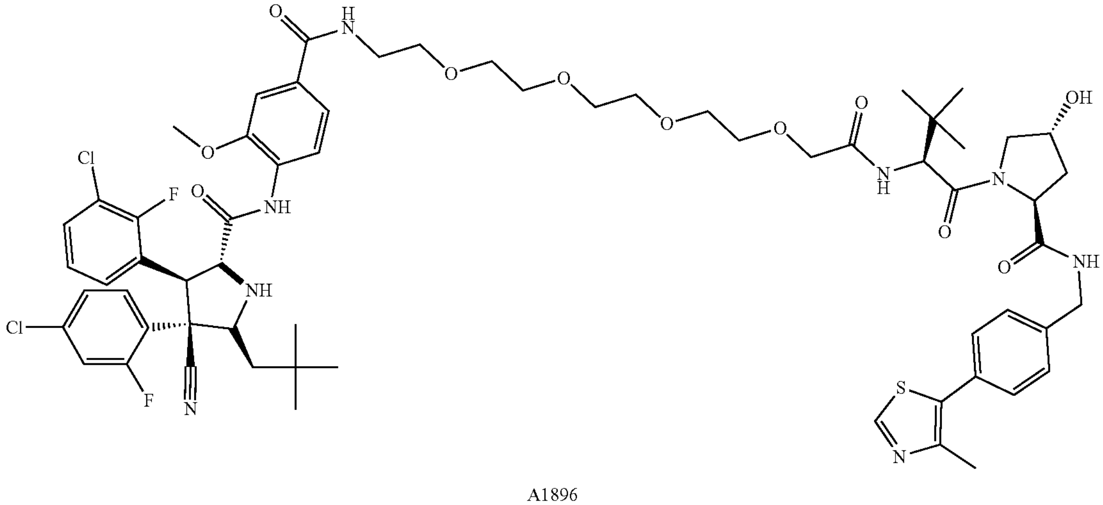

A1896

-continued

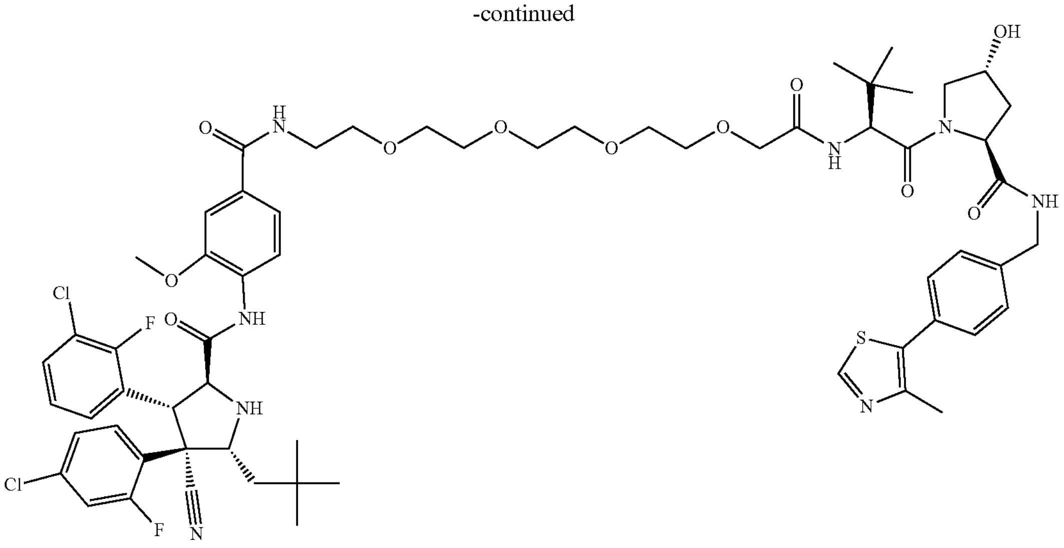

A1897

Preparation of (2R*,3 S*,4R*,5S*)-3-(3-chloro-2-fluorophenyl)-4-(4-chloro -2-fluorophenyl)-4-cyano-5-(2,2-dimethylpropyl)-N-{4-[(1-{[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}-2,5,8,11-tetraoxatridecan-13-yl)carbamoyl]-2-methoxyphenyl}pyrrolidine-2-carboxamide (A1896) and (2S*,3R*,4S*,5R*)-3-(3-chloro-2-fluorophenyl)-4-(4-chloro-2-fluorophenyl)-4-cyano-5-(2,2-dimethylpropyl)-N-{4-[(1-{[2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}-2,5,8,11-tetraoxatridecan-13-yl)carbamoyl]-2-methoxyphenyl}pyrrolidine-2-carboxamide (A1897)

A1895 was separated by Prep-chiral-HPLC (column: Phenomenex Lux 5u Cellulose-4, AXIA Packed 250*21.2 mm, 5 um; Mobile Phase: methanol in water, Flow rate: 20 mL/min; run time: 24 min; 254/220 nm). Two fractions were collected. Fraction A (RT1: 11.68 min) gave A1896 (15 mg) as a white solid.

$^1$H NMR (300 MHz, $CD_3OD$) δ 8.83 (s, 1H), 8.34-8.31 (m, 1H), 7.62-7.64 (m, 1H), 7.51 (s, 1H), 7.40-7.29 (m, 8H), 7.24-7.19 (m, 2H), 4.80-4.74 (m, 3H), 4.70-4.55 (m, 3H), 4.33-4.28 (m, 1H), 4.06-4.03 (m, 1H), 3.98-3.94 (m, 5H), 3.81-3.77 (m, 2H), 3.66-3.61 (m, 16H), 2.48 (s, 3H), 2.25-2.19 (m, 1H), 2.19-1.92 (m, 1H), 1.66-1.63 (m, 1H), 1.40-1.35 (m, 1H), 0.99 (s, 18H). LC-MS calcd for $C_{63}H_{76}Cl_2F_2N_8O_{11}S$ (m/z) 1260.47, obsd 1284.05/1286.05 [M+Na$^+$], $t_R$=2.27 min, (3.6 minute run).

Fraction B (RT2: 20.22 min) gave A1897 also as a white solid (15 mg).

$^1$H NMR (300 MHz, $CD_3OD$) δ 8.83 (s, 1H), 8.34-8.31 (m, 1H), 7.62-7.64 (m, 1H), 7.51 (s, 1H), 7.40-7.29 (m, 8H), 7.24-7.19 (m, 2H), 4.80-4.55 (m, 6H), 4.33-4.28 (m, 1H), 4.06-4.03 (m, 1H), 3.98-3.94 (m, 5H), 3.81-3.77 (m, 2H), 3.66-3.61 (m, 16H), 2.48 (s, 3H), 2.25-2.19 (m, 1H), 2.19-1.92 (m, 1H), 1.72-1.63 (m, 1H), 1.40-1.25 (m, 1H), 1.02 (s, 18H). LC-MS calcd for $C_{63}H_{76}Cl_2F_2N_8O_{11}S$ (m/z) 1260.47, obsd 1284.05/1286.05 [M+Na$^+$], $t_R$=2.42 min, (3.6 minute run).

Using the same synthetic method as described for A1895, A1896 and A1897, the following molecules were prepared: A1877, A1907, A1908, A1909, A1910, and A1911.

Example 5
Preparation of A1717
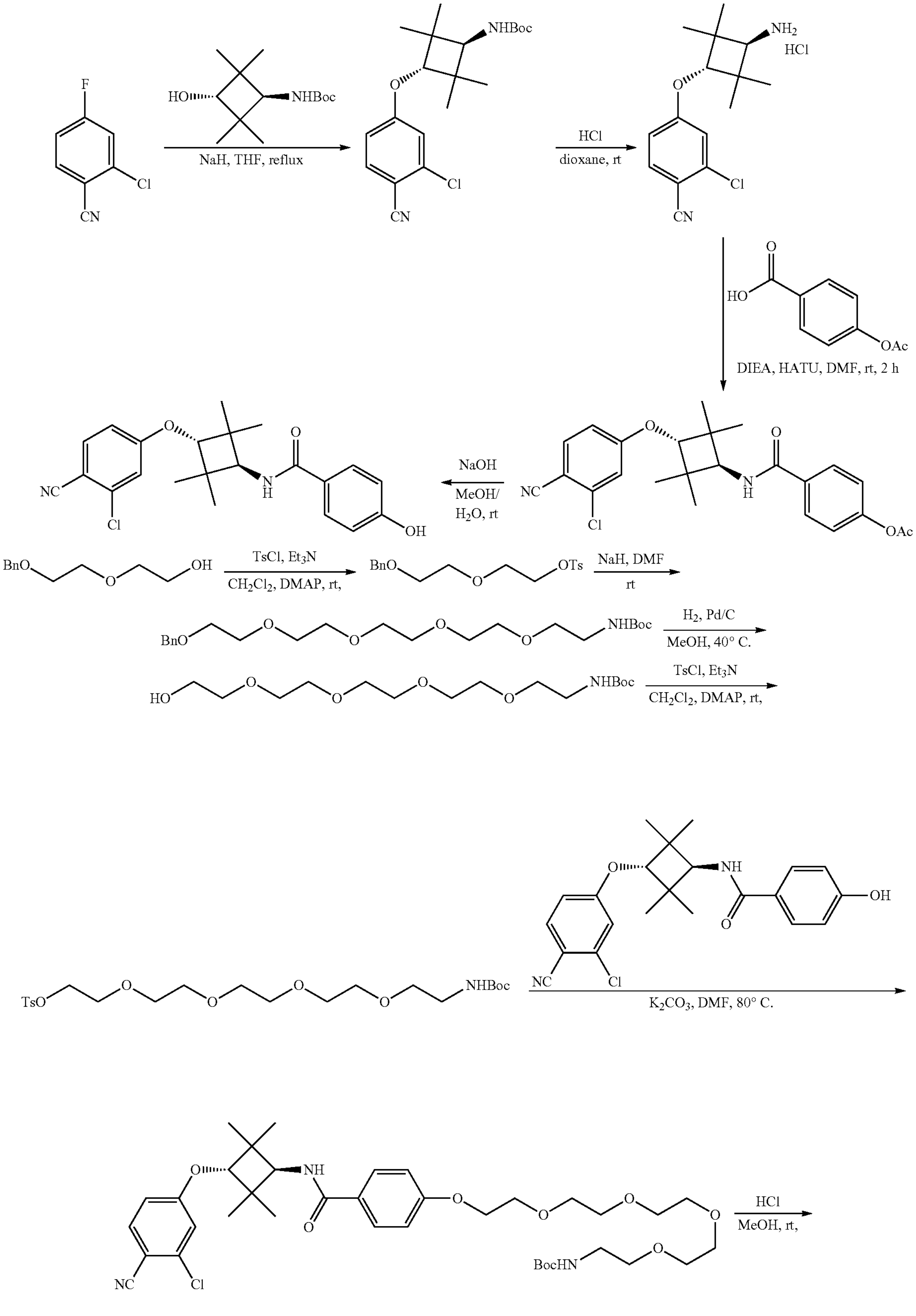

-continued

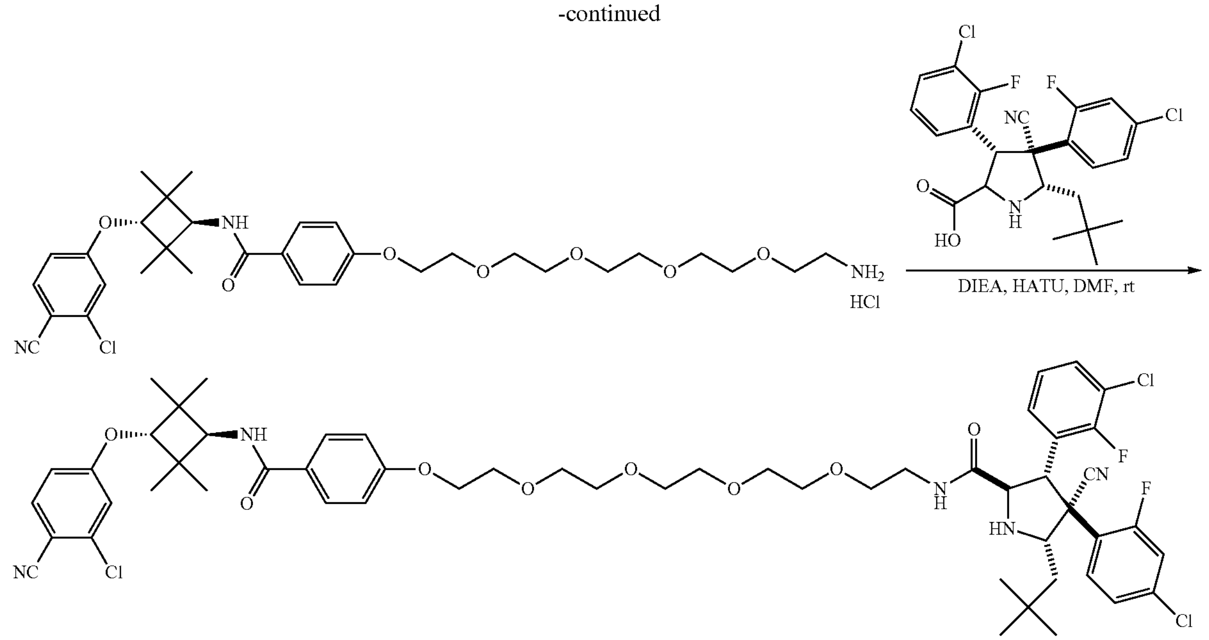

A1717

Step 1: Synthesis of tert-butyl N-[(1,3-trans)-3-(3-chloro-4-cyanophenoxy)-2,2,4,4-tetramethylcyclobutyl]carbamate Into a 100-mL 3-necked round-bottom flask purged and maintained with an inert atmosphere of nitrogen, was placed a solution of tert-butyl N-[(1,3-trans)-3-hydroxy-2,2,4,4-tetramethylcyclobutyl]carbamate (600.0 mg, 2.47 mmol, 1.00 equiv) in N,N-dimethylformamide (10.0 mL). This was followed by the addition of sodium hydride (198.0 mg, 8.25 mmol, 2.00 equiv), in portions at 0° C. After 30 min, to this was added 2-chloro-4-fluorobenzonitrile (459.0 mg, 2.95 mmol, 1.20 equiv). The resulting solution was stirred for 1 h at 70° C. The reaction mixture was cooled to room temperature with a water bath. The reaction was then quenched by the addition of water (20 mL). The resulting solution was extracted with ethyl acetate (20 mL×3) and the organic layers were combined. The resulting solution was washed with brine and concentrated. The residue was applied onto a silica gel column eluted with ethyl acetate/petroleum ether (1/5). This resulted in 100.0 mg (11%) of tert-butylN-[(1,3-trans)-3-(3-chloro-4-cyanophenoxy)-2,2,4,4-tetramethylcyclobutyl]carbamate as colorless oil. LC-MS ($ES^+$): m/z 279.10 $[MH-100]^+$, $t_R$=1.20 min (2.5 minute run).

Step 2: Synthesis of 2-chloro-4-[(1,3-trans)-3-amino-2,2,4,4-tetramethylcyclobutoxy]-benzonitrile Into a 100-mL round-bottom flask purged and maintained with an inert atmosphere of nitrogen, was placed tert-butyl N-[(1,3-trans)-3-(3-chloro-4-cyanophenoxy)-2,2,4,4-tetramethylcyclobutyl]carbamate (500.0 mg, 1.32 mmol, 1.00 equiv), hydrogen chloride/dioxane (3 mL, 4M), 1,4-dioxane (3 mL). The resulting solution was stirred for 1 h at room temperature. The resulting mixture was concentrated under vacuum. This resulted in 447 mg (87%) of 2-chloro-4-[(1,3-trans)-3-amino-2,2,4,4-tetramethylcyclobutoxy]benzonitrile as a white solid.

Step 3: Synthesis of 4-[[(1,3-trans)-3-(3-chloro-4-cyanophenoxy)-2,2,4,4-tetramethylcyclobutyl]carbamoyl]phenyl acetate Into a 25-mL round-bottom flask, was placed a solution of 4-(acetyloxy)benzoic acid (100.0 mg, 0.56 mmol, 1.00equiv) in N,N-dimethylformamide (10 mL), 2-chloro-4-[(1,3-trans)-3-amino-2,2,4,4-tetramethylcyclobutoxy] benzonitrile (190.0 mg, 0.68 mmol, 1.10 equiv), HATU (253.0 g, 665.39 mmol, 1.20 equiv), DIEA (0.5 mL, 5.00 equiv). The resulting solution was stirred for 2 h at room temperature. The reaction was then quenched by the addition of water (10 mL). The resulting solution was extracted with ethyl acetate (10 mL×3) and the organic layers were combined. The resulting mixture was washed with brine (10 mL×1). The mixture was dried over anhydrous sodium sulfate and concentrated under vacuum. This resulted in 230.0 mg (94%) of 4-[[(1,3-trans)-3-(3-chloro-4-cyanophenoxy)-2,2,4,4-tetramethylcyclobutyl]carbamoyl]phenyl acetate as a light brown solid. LC-MS ($ES^+$): m/z 441.00 $[M+H^+]$, $t_R$=1.09 min Step 4: Synthesis of 4-hydroxy-N-[(1,3-trans)-3-(3-chloro-4-cyanophenoxy)-2,2,4,4-tetramethylcyclobutyl]benzamide Into a 50-mL round-bottom flask, was placed 4-[[(1,3-trans)-3-(3-chloro-4-cyanophenoxy)-2,2,4,4-tetramethylcyclobutyl]carbamoyl]phenyl acetate (230.0 mg, 0.52 mmol, 1.00 equiv), sodium hydroxide (100.0 mg, 2.50 mmol, 3.00 equiv) and methanol (10 mL). The resulting solution was stirred at room temperature. The resulting mixture was concentrated under vacuum and diluted with water (10 mL). The pH value of the solution was adjusted to 4-5 with hydrogen chloride (1 mol/L). The resulting solution was extracted with ethyl acetate (10 mL×3) and the organic layers were combined. The solution was washed with brine (10 mL×1) and concentrated under vacuum. The residue was applied onto a silica gel column eluted with ethyl acetate/ petroleum ether (1:1). This resulted in 200.0 mg (96%) of 4-hydroxy-N-[(1,3-trans)-3-(3-chloro-4-cyanophenoxy)-2,2,4,4-tetramethylcyclobutyl]-benzamide as light yellow oil.

Step 5: Synthesis of 2-[2-(benzyloxy)ethoxy]ethyl 4-methylbenzene-1-sulfonate

Into a 250-mL round-bottom flask, 2-[2-(benzyloxy)ethoxy]ethan-1-ol (3.0 g, 15.29 mmol, 1.00 equiv), 4-methylbenzene-1-sulfonyl chloride (4.36 g, 22.87 mmol, 1.50 equiv), triethylamine (3.09 g, 30.54 mmol, 2.00 equiv), 4-dimethylaminopyridine (933.0 mg, 7.64 mmol, 0.50 equiv) were mixed in dichloromethane (20 mL). The resulting solution was stirred for 3 h at room temperature. The mixture was applied onto a silica gel column eluted with ethyl acetate/petroleum ether (⅓). This resulted in 4.9 g (91%) of 2-[2-(benzyloxy)ethoxy]ethyl 4-methylbenzene-1-sulfonate as light yellow oil.

Step 6: Synthesis of tert-butyl N-(1-phenyl-2,5,8,11,14-pentaoxahexadecan-16-yl)carbamate Into a 25-mL round-bottom flask, sodium hydride (67 mg, 2.79 mmol, 1.20 equiv, 60% in oil) was added to a solution of tert-butyl N-2-[2-(2-hydroxyethoxy)ethoxy]ethylcarbamate (320.0 mg, 1.28 mmol, 1.00 equiv) in N,N-dimethylformamide (10 mL) at 0° C. The mixture was stirred for 15 min at that temperature. Then 2-[2-(benzyloxy)ethoxy]ethyl 4-methylbenzene-1-sulfonate (536 mg, 1.53 mmol, 1.20 equiv) was added and the reaction was warmed to room temperature and stirred for 4 h. After quenched by addition of water, the resulting solution was extracted with ethyl acetate (50 mL×3) and the organic layers were combined. The resulting mixture was washed with brine (50 mL×3) and dried over anhydrous sodium sulfate. The filtered solution was concentrated and the residue was applied onto a silica gel column eluted with ethyl acetate/petroleum ether (4/1). This resulted in 290 mg (53%) of tert-butyl N-(1-phenyl-2,5,8,11,14-pentaoxahexadecan-16-yl)carbamate as light yellow oil. LC-MS ($ES^+$): m/z 428.95 [$M+H^+$], $t_R$=0.92 min, (1.9 minute run).

Step 7: Synthesis of tert-butyl 14-hydroxy-3,6,9,12-tetraoxatetradecylcarbamate

Into a 50-mL round-bottom flask, palladium on carbon (200.0 mg) was added to a solution of tert-butyl N-(1-phenyl-2,5,8,11,14-pentaoxahexadecan-16-yl)carbamate (290.0 mg, 0.68 mmol, 1.00 equiv) in methanol (10 mL) at room temperature under nitrogen atmosphere. The reaction flask was vacuumed and charged with a hydrogen balloon. The resulting solution was stirred for 8 h at 40° C. in an oil bath. The reaction mixture was then filtered through a Celite pad and the filtrate was concentrated under reduced pressure. This resulted in 220 mg (crude) of tert-butyl 14-hydroxy-3,6,9,12-tetraoxatetradecylcarbamate as yellow oil Step 8: Synthesis of tert-butyl N-(14-[[(4-methylbenzene)sulfonyl]oxy]-3,6,9,12-tetraoxatetradecan-1-yl)carbamate Into a 25-mL round-bottom flask, tert-butyl N-(14-hydroxy-3,6,9,12-tetraoxatetradecan-1-yl)carbamate (228.0 mg, 0.68 mmol, 1.00 equiv), 4-methylbenzene-1-sulfonyl chloride (192.0 mg, 1.01 mmol, 1.50 equiv), triethylamine (136.2 mg, 1.35 mmol, 2.00 equiv), 4-dimethylaminopyridine (16.4 mg, 0.13 mmol, 0.20 equiv) were mixed in dichloromethane (10 mL). The resulting solution was stirred for 8 h at room temperature. The residue was applied onto a silica gel column eluted with ethyl acetate/petroleum ether (3/2). This resulted in 110.0 mg (33%) of tert-butyl N-(14-[[(4-methylbenzene)sulfonyl]oxy]-3,6,9,12-tetraoxatetradecan-1-yl)carbamate as light yellow oil. LC-MS ($ES^+$): m/z 492.00 [$M+H^+$], $t_R$=0.93 min, (1.9 minute run).

Step 9: Synthesis of tert-butyl N-[1-(4-[[(1,3-trans)-3-(3-chloro-4-cyanophenoxy)-2,2,4,4-tetramethylcyclobutyl]carbamoyl]phenyl)-1,4,7,10,13-pentaoxapentadecan-15-yl]carbamate Into a 25-mL round-bottom flask, was placed 4-hydroxy-N-[(1,3-trans)-3-(3-chloro-4-cyanophenoxy)-2,2,4,4-tetramethylcyclobutyl]benzamide (50.0 mg, 0.13 mmol, 1.00 equiv), potassium carbonate (34.7 mg, 0.25 mmol, 2.00 equiv), tert-butyl N-(14-[(4-methylbenzene)sulfonyl]oxy-3,6,9,12-tetraoxatetradecan-1-yl)carbamate (74.0 mg, 0.15 mmol, 1.20 equiv) in N,N-dimethylformamide (5.0 mL). The resulting solution was stirred for 5 h at 80° C. in an oil bath. The reaction was quenched with 50 mL of water. The resulting solution was extracted with ethyl acetate (50 mL×3) and the organic layers were combined. The resulting mixture was washed with brine (50 mL×3) and dried over anhydrous sodium sulfate. After the evaporation of solvents, the crude product was purified by prep-TLC with ethyl acetate/petroleum ether (4/1). This resulted in 110.0 mg of tert-butyl N-[1-(4-[[(1,3-trans)-3-(3-chloro-4-cyanophenoxy)-2,2,4,4-tetramethylcyclobutyl]carbamoyl]phenyl)-1,4,7,10,13-pentaoxapentadecan-15-yl]carbamate as light yellow oil. LC-MS ($ES^+$): m/z 740.10/742.10 [$M+Na^+$], $t_R$=1.14 min, (1.9 minute run).

Step 10: Synthesis of 4-[(14-amino-3,6,9,12-tetraoxatetradecan-1-yl)oxy]-N-[(1,3-trans)-3-(3-chloro-4-cyanophenoxy)-2,2,4,4-tetramethylcyclobutyl]benzamide hydrochloride Into a 25-mL round-bottom flask, hydrogen chloride (2 mL, 2N in dioxane) was added to a solution of tert-butyl N-[1-(4-[[(1,3-trans)-3-(3-chloro-4-cyanophenoxy)-2,2,4,4-tetramethylcyclobutyl]carbamoyl]phenyl)-1,4,7,10,13-pentaoxapentadecan-15-yl]carbamate (110.0 mg, 0.15 mmol, 1.00 equiv) in methanol (15 mL). The resulting solution was stirred for 3 h at room temperature and concentrated under vacuum. This resulted in 100.0 mg (crude) of 4-[(14-amino-3,6,9,12-tetraoxatetradecan-1-yl)oxy]-N-[(1,3-trans)-3-(3-chloro-4-cyanophenoxy)-2,2,4,4-tetramethylcyclobutyl]benzamide hydrochloride as light yellow oil.

Step 11: Synthesis of 3-(3-chloro-2-fluorophenyl)-4-(4-chloro-2-fluorophenyl)-4-cyano-5-(2,2-dimethylpropyl)-N-[1-(4-[[(1,3-trans)-3-(3-chloro-4-cyanophenoxy)-2,2,4,4-tetramethylcyclobutyl]carbamoyl]phenyl)-1,4,7,10,13-pentaoxapentadecan-15-yl]pyrrolidine-2-carboxamide (A1717)

Into a 25-mL round-bottom flask, was placed (2R/2S,3S/3R,4R/4S,5S/5R)-3-(3-chloro-2-fluorophenyl)-4-(4-chloro-2-fluorophenyl)-4-cyano-5-(2,2-dimethylpropyl)pyrrolidine-2-carboxylic acid (59.4 mg, 0.13 mmol, 1.00 equiv, prepared according to literature procedure: *J. Med. Chem.* 2013, 56, 5979), 4-[(14-amino-3,6,9,12-tetraoxatetradecan-1-yl)oxy]-N-[(1,3-trans)-3-(3-chloro-4-cyanophenoxy)-2,2,4,4-tetramethylcyclobutyl]benzamide hydrochloride (100.0 mg, 0.15 mmol, 1.20 equiv), N,N,N',N'-tetramethyl-O-(7- azabenzotriazol-1-yl)uronium hexafluorophospate (58.0 mg, 0.15 mmol, 1.20 equiv), N,N-dimethylformamide (5.0 mL). N,N-Diisopropylethylamine (82.3 mg, 0.64 mmol, 5.00 equiv) was added and the reaction was stirred for 2 h at room temperature. The reaction mixture was quenched by addition of 20 mL of water. The resulting solution was extracted with ethyl acetate (50 mL×3) and the organic layers were combined. The resulting mixture was washed with brine (50 mL×3) and dried over anhydrous sodium sulfate. After the evaporation of solvents, the crude product was purified by Prep-HPLC with the following conditions: Column, XBridge Shield RP18 OBD Column, 5 um, 19*150 mm; mobile phase: water with 10 mmol/L ammonium bicarbonate and acetonitrile (hold 74.0% acetonitrile in 10 min); Detector, UV 254 nm. This resulted in 45 mg (33%) of 3-(3-chloro-2-fluorophenyl)-4-(4-chloro-2-fluorophenyl)-4-cyano-5-(2,2-dimethylpropyl)-N-[1-(4-[[(1,3-trans)-3-(3-chloro-4-cyanophenoxy)-2,2,4,4-tetramethylcyclobutyl]carbamoyl]phenyl)-1,4,7,10,13-pentaoxapentadecan-15-yl]pyrrolidine-2-carboxamide (A1717) as a white solid.

$^1$H NMR (400 MHz, $CD_3OD$): δ7.82-7.80 (d, J=8.0 Hz, 2H), 7.74-7.65 (m, 2H), 7.39-7.31 (m, 3H), 7.26-7.22 (m, 2H), 7.14 (d, J=2.8 Hz, 1H), 7.05-6.98 (m, 3H), 4.73-4.71 (d, J=7.2 Hz, 1H), 4.44-4.42 (d, J=8.4 Hz, 1H), 4.29 (s, 1H), 4.23-4.20 (d, J=9.2 Hz, 2H), 4.16 (s, 1H), 4.00 (m, 1H), 3.90-3.88 (d, J=9.2 Hz, 2H), 3.74-3.57 (m, 13H), 3.50-3.40 (m, 1H), 3.36-3.32 (m, 1H), 1.65-1.55 (m, 1H), 1.31-1.29 (m, 1H), 1.28 (s, 6H), 1.24 (s, 6H), 0.95 (s, 9H); LC-MS calcd for $C_{55}H_{64}Cl_3F_2N_5O_8$ (m/z) 1067.48, obsd 1068.50 [M+H$^+$], $t_R$=2.76 min, (3.6 minute run).

Example 6

Preparation of A1720 and A1735

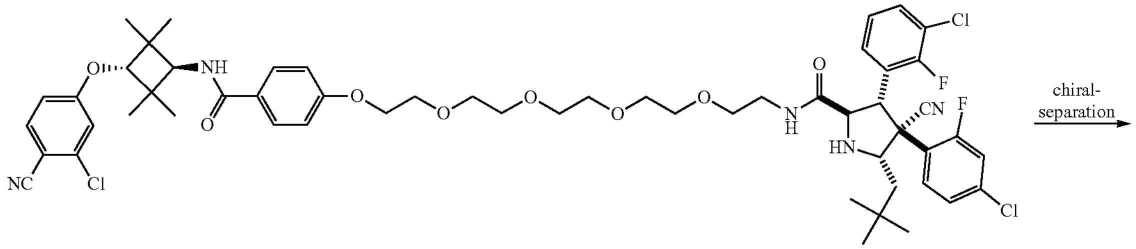

A1717

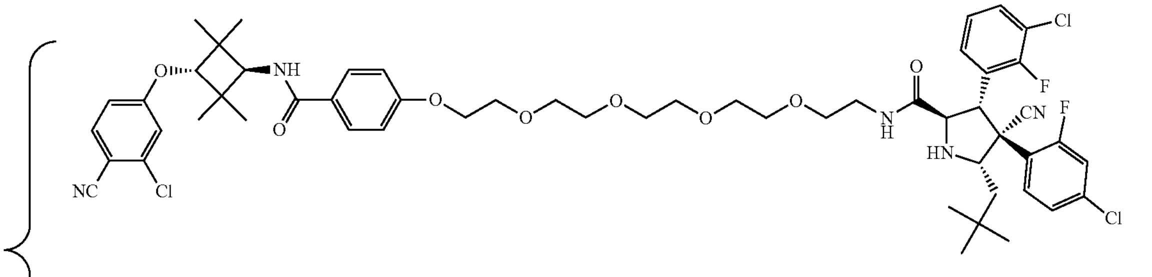

A1720

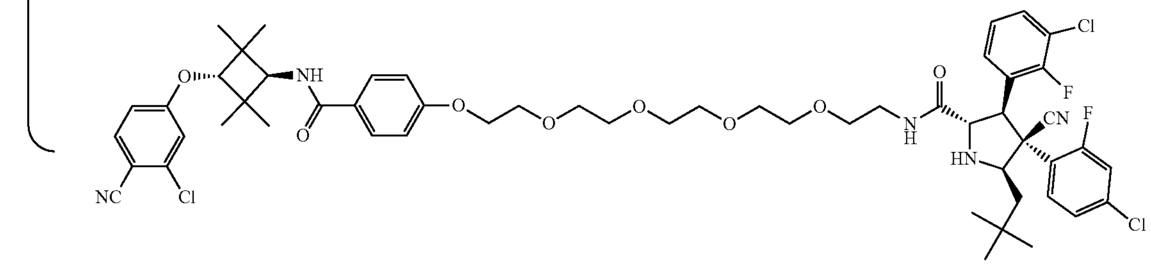

A1735

Preparation of (2R,3S,4R,5S)-3-(3-chloro-2-fluorophenyl)-4-(4-chloro-2-fluorophenyl)-4-cyano-5-(2,2-dimethylpropyl)-N-[1-(4-{[(1,3-trans)-3-(3-chloro-4-cyanophenoxy)-2,2,4,4-tetramethylcyclobutyl]carbamoyl}phenyl)-1,4,7,10,13-pentaoxapentadecan-15-yl]pyrrolidine-2-carboxamide (A1720) and (2S,3R,4S,5R)-3-(3-chloro-2-fluorophenyl)-4-(4-chloro-2-fluorophenyl)-4-cyano-5-(2,2-dimethylpropyl)-N-[1-(4-{[(1,3-trans)-3-(3-chloro-4-cyanophenoxy)-2,2,4,4-tetramethylcyclobutyl]carbamoyl}phenyl)-1,4,7,10,13-pentaoxapentadecan-15-yl]pyrrolidine-2-carboxamide (A1735)

A1717 was separated by preparative chiral HPLC (Column: Chiralpak IA 2*25 cm, 5 um; Mobile Phase A: hexane; Mobile Phase B: ethanol; Flow rate: 15 mL/min; Gradient: 50 B to 50 B in 35 min; 254/220 nm). The chiral separation resulted in two fractions. Fraction A (RT1: 16.962 min) gave 10.0 mg (29%) of (2R,3S,4R,5S)-3-(3-chloro-2-fluorophenyl)-4-(4-chloro-2-fluorophenyl)-4-cyano-5-(2,2-dimethylpropyl)-N-[1-(4-[[(1,3-tran)-3-(3-chloro-4-cyanophenoxy)-

2,2,4,4-tetramethylcyclobutyl]carbamoyl]phenyl)-1,4,7,10,13-pentaoxapentadecan-15-yl]pyrrolidine-2-carboxamide as a white solid.

$^1$H NMR (400 MHz, $CD_3OD$): δ 7.82-7.80 (d, J=8.0 Hz, 2H), 7.74-7.65 (m, 2H), 7.39-7.31 (m, 3H), 7.26-7.22 (m, 2H), 7.14 (d, J=2.8 Hz, 1H), 7.05-6.98 (m, 3H), 4.73-4.71 (d, J=7.2 Hz, 1H), 4.44-4.42 (d, J=8.4 Hz, 1H), 4.29 (s, 1H), 4.23-4.20 (d, J=9.2 Hz, 2H), 4.16 (s, 1H), 4.00 (m, 1H), 3.90-3.88 (d, J=9.2 Hz, 2H), 3.74-3.57 (m, 13H), 3.50-3.40 (m, 1H), 3.36-3.32 (m, 1H), 1.65-1.55 (m, 1H), 1.31-1.29 (m, 1H), 1.28 (s, 6H), 1.24 (s, 6H), 0.95 (s, 9H); LC-MS calcd for $C_{55}H_{64}Cl_3F_2N_5O_8$ (m/z) 1067.48, obsd 1068.10/1070.10 [M+H$^+$], $t_R$=2.62 min, (3.6 minute run).

The second fraction (RT2: 28.90 min) gave 10.0 mg (29%) of (2S,3R,4S,5R)-3-(3-chloro-2-fluorophenyl)-4-(4-chloro-2-fluorophenyl)-4-cyano-5-(2,2-dimethylpropyl)-N-4.23-4.20 (d, J=9.2 Hz, 2H), 4.16 (s, 1H), 4.00 (m, 1H), 3.90-3.88 (d, J=9.2 Hz, 2H), 3.74-3.57 (m, 13H), 3.50-3.40 (m, 1H), 3.36-3.32 (m, 1H), 1.65-1.55 (m, 1H), 1.31-1.29 (m, 1H), 1.28 (s, 6H), 1.24 (s, 6H), 0.95 (s, 9H); LC-MS calcd for $C_{55}H_{64}Cl_3F_2N_5O_8$ (m/z) 1067.48, obsd 1068.10/1070.10 [M+H$^+$], $t_R$=2.62 min, (3.6 minute run).

Compounds A1751, A1603, A1621 and A1688 were prepared using the same method as described for the preparation of A1717, A1720 and A1735

Example 7

Preparation of A2434

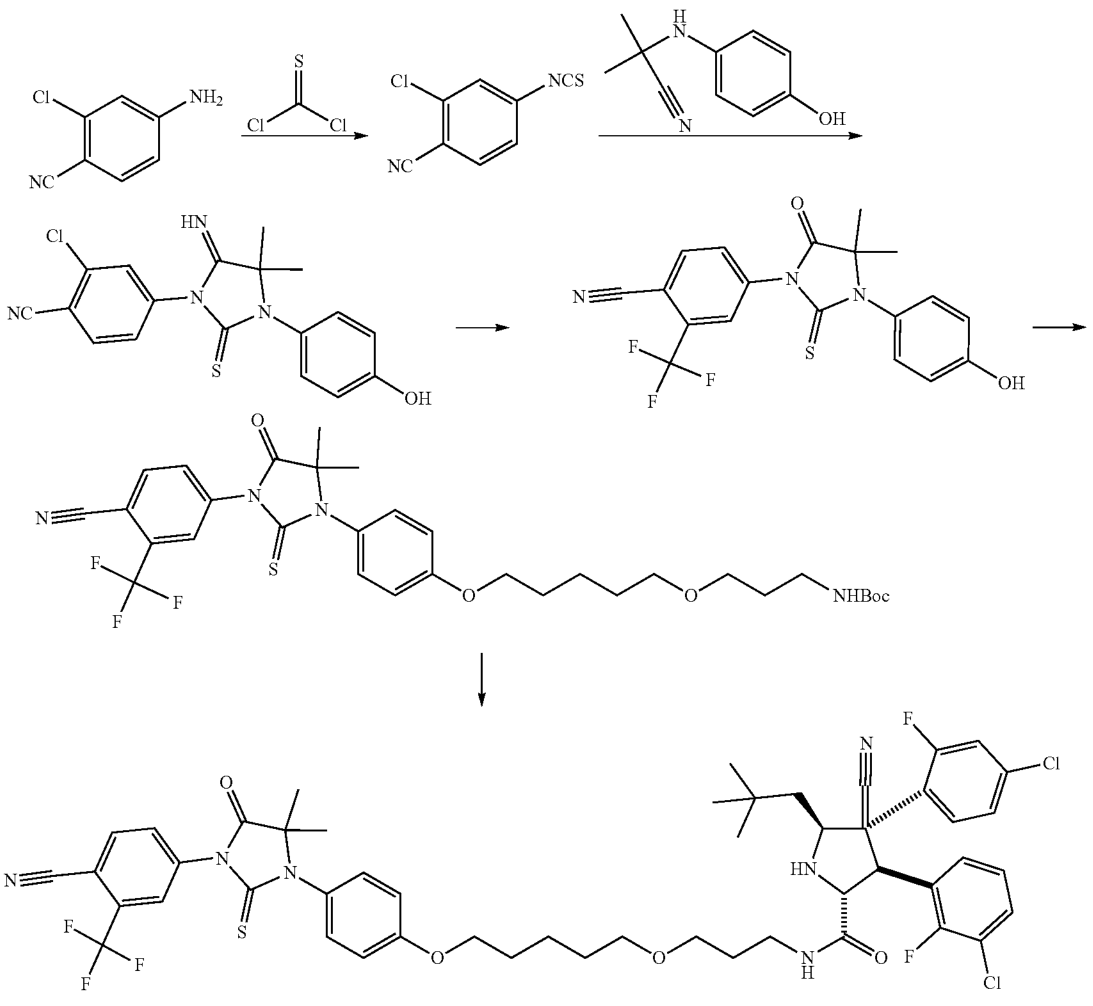

A2435

[1-(4-[[(1r,3r-3-(3-chloro-4-cyanophenoxy)-2,2,4,4-tetramethylcyclobutyl]carbamoyl]phenyl)-1,4,7,10,13-pentaoxapentadecan-15-yl]pyrrolidine-2-carboxamide as a white solid.

$^1$H NMR (400 MHz, $CD_3OD$): δ 7.82-7.80 (d, J=8.0 Hz, 2H), 7.74-7.65 (m, 2H), 7.39-7.31 (m, 3H), 7.26-7.22 (m, 2H), 7.14 (d, J=2.8 Hz, 1H), 7.05-6.98 (m, 3H), 4.73-4.71 (d, J=7.2 Hz, 1H), 4.44-4.42 (d, J=8.4 Hz, 1H), 4.29 (s, 1H),

Step 1: Synthesis of 2-chloro-4-isothiocyanatobenzonitrile

To a stirred solution of 4-amino-2-chlorobenzonitrile (1 g, 6.55 mmol) in dichloromethane (9 mL) was added sodium bicarbonate (2.21 g, 26.31 mmol) and water (9 mL), followed by addition of thiophosgene (817 mg, 7.11 mmol) drop wise in 30 min at 0° C. The resulting mixture was stirred for 1 h at room temperature. The reaction mixture was diluted with dichloromethane (200 mL), washed with brine (50 mL×2), dried over anhydrous sodium sulfate and then concentrated under reduced pressure to give a crude residue. The residue was purified by flash silica gel chromatography (eluent: ethyl acetate/petroleum ether (v:v=1: 30)) to give the desired product (yield: 71%) $^1$HNMR (400 MHz, $CDCl_3$): δ 7.69 (d, J=8.0 Hz, 1H), 7.38 (s, 1H), 7.28 (m, 1H).

Step 2: Synthesis of 2-chloro-4-[3-(4-hydroxyphenyl)-5-imino-4, 4-dimethyl-2-sulfanylideneimidazolidin-1-yl]benzonitrile To a stirred solution of 2-chloro-4-isothiocyanatobenzonitrile (399 mg, 2.05 mmol) in toluene (5 mL) was added 2-[(4-hydroxyphenyl)amino]-2-methylpropanenitrile (300 mg, 1.70 mmol) and 4-dimethylaminopyridine (312 mg, 2.55 mmol). The resulting solution was then heated in an oil bath to 100° C. and stirred at the same temperature for 16h. The resulting mixture was concentrated under vacuum. The residue was purified by flash silica gel chromatography (eluent: ethyl acetate/petroleum ether, v:v=1:1) to give the desired product (yield: 48%) as a brown solid. LC-MS ($ES^+$): m/z 370.95 [$M+H^+$], $t_R$=0.74 min.

Step 3: Synthesis of 2-chloro -4-[3-(4-hydroxyphenyl)-4, 4-dimethyl-5-oxo-2-sulfanylideneimidazolidin-1-yl]benzonitrile To a stirred solution of 2-chloro-4-[3-(4-hydroxyphenyl)-5-imino-4, 4-dimethyl-2-sulfanylideneimidazolidin-1-yl]benzonitrile (300 mg, 0.81 mmol) in methanol (6 mL) was added aqeuous hydrogen chloride (2N, 3.0 mL). The resulting solution was then heated in an oil bath to 100° C. and stirred at the same temperature for 2 h. The reaction mixture was diluted with water (30 mL), extracted with ethyl acetate (60 mL×3), washed with water (50 mL), dried over anhydrous sodium sulfate and concentrated under vacuum to give titled product (yield: 93%) as a yellow solid, which was used for next step without any further purifications. LC-MS ($ES^+$): m/z 372.00 [$M+H^{30}$], $t_R$=0.97 min.

Step 4 and Step 5: Preparation of (2R,3S,4R,5S)-3-(3-chloro-2-fluorophenyl)-4-(4-chloro -2-fluorophenyl)-4-cyano-N-(3-{[5-(4-{3-[4-cyano-3-(trifluoromethyl)phenyl]-5,5-dimethyl-4-oxo-2-sulfanylideneimidazolidin-1-yl}phenoxy)pentyl]oxy}propyl)-5-(2,2-dimethylpropyl)pyrrolidine-2-carboxamide (A2434)

Step 4 and step 5 were carried out using the method as described for the synthesis of A1717. Compound A2434 was isolated as a solid. LC-MS calcd for $C_{50}H_{51}Cl_2F_5N_6O_4S$ (m/z) 997.94, obsd 997/999.

Compound A2435 was prepared with the same method as described for the preparation of A2434.

In the case of the preparation of compound A679, A680 and A702, the similar synthetic route was used. The MDM2 ligand of imidazoline chemotype was synthesized according to literature procedure (*ACS Med. Chem. Lett.* 2103, 4, 466).

Example 8

Preparation of A2844

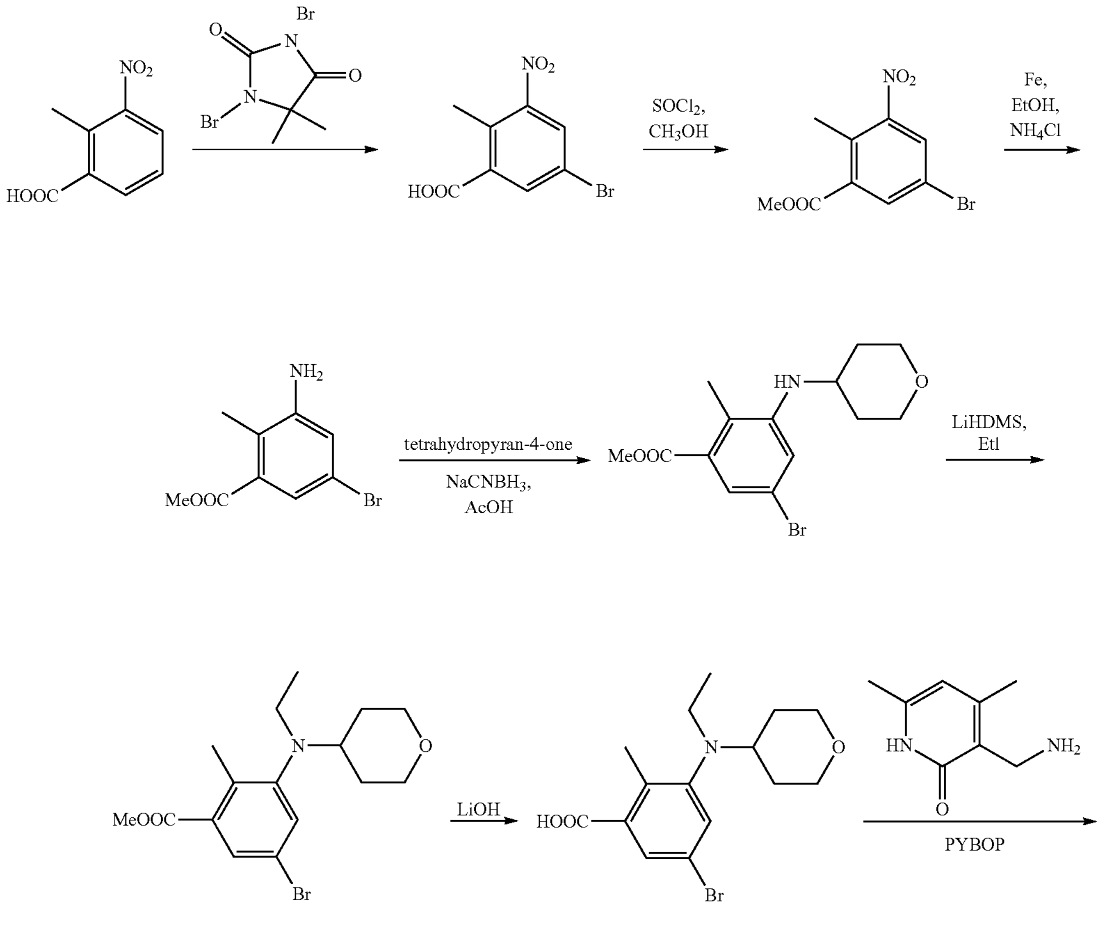

-continued
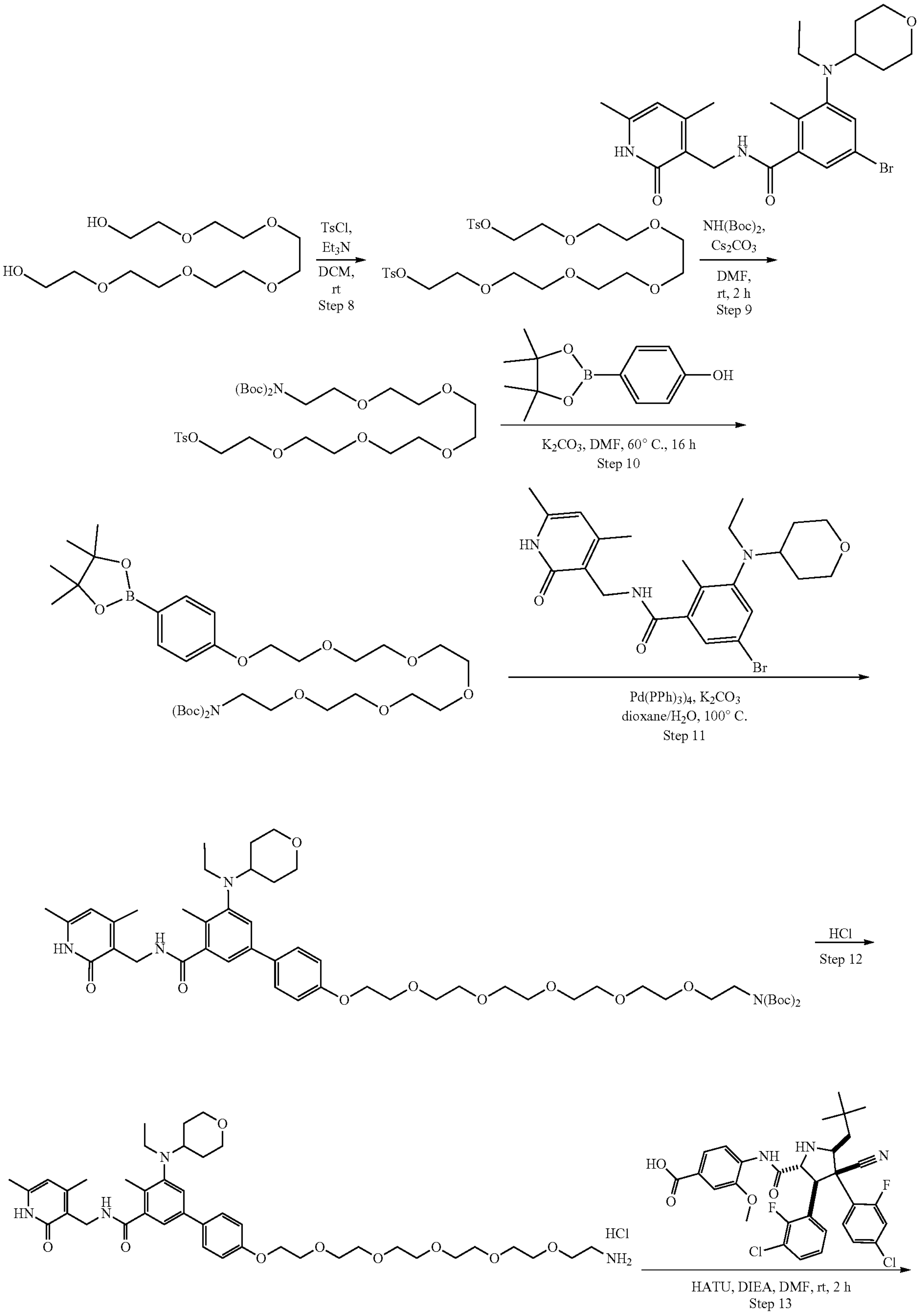

-continued

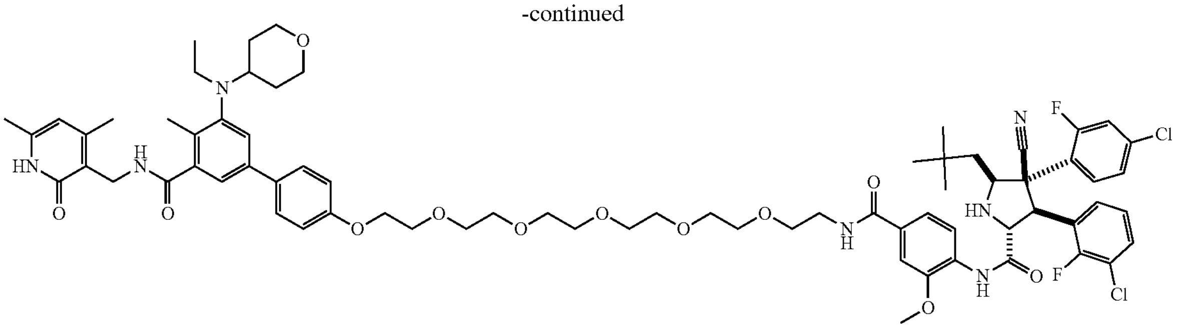

A2844

Step 1: Synthesis of 5-bromo-2-methyl-3-nitrobenzoic acid

To a stirred solution of 2-methyl-3-nitrobenzoic acid (10 g, 55 mmol) in conc. $H_2SO_4$ (40 mL), 1,3-dibromo-5,5-dimethyl-2,4-imidazolidinedione (9 g, 32 mmol) was added portion wise at room temperature and reaction was stirred at room temperature for 5 h. Then the reaction mass was poured on an ice cold water. Solid was filtered, and the resulting residue was washed with water and dried under vacuum to afford 5-bromo-2-methyl-3-nitrobenzoic acid (12 g, 84%) as a light yellow solid. $^1H$ NMR (400 MHz, DMSO-$d_6$): δ 8.28 (d, J=2.0 Hz, 1H), 8.13 (d, J=2.0 Hz, 1H), 2.51 (s, 3H)

Step 2: Synthesis of methyl 5-bromo-2-methyl-3-nitrobenzoate

A mixture of 5-bromo-2-methyl-3-nitrobenzoic acid (12 g, 41 mmol) in $SOCl_2$/MeOH (v:v=1:10) (250 mL) was heated to reflux overnight. The reaction mixture was cooled and concentrated. The residue was dissolved in 300 mL of ethyl acetate. The organic layer was washed sequentially with sat. aq. $NaHCO_3$ and brine, dried over $Na_2SO_4$, and concentrated. The residue was purified by chromatography (silica gel, petroleum ether/ethyl acetate (20:1, v:v)) to afford the desired compound (11 g, yield: 87%). $^1H$ NMR (400 MHz, $CDCl_3$): δ 8.12 (d, J=2.0 Hz, 1H), 7.97 (d, J=2.0 Hz, 1H), 3.95 (s, 3H), 2.57 (s, 3H)

Step 3: Synthesis of methyl 3-amino-5-bromo-2-methylbenzoate

To a stirred solution of methyl 5-bromo-2-methyl-3-nitrobenzoate (11 g, 40 mmol) in ethanol (100 mL), was added $NH_4Cl$ solution (13 g in 50 mL water, 240 mmol) followed by Fe powder (20 g, 360 mmol). The resulting reaction was stirred at 80° C. for 2-3 h. Then the reaction mixture was filtered and the filtrate was concentrated till dryness to give a solid which was dissolved in sat. sodium bicarbonate solution. Aqueous layer was extracted with ethyl acetate (3×100 mL). The combined organic layers were dried over sodium sulfate and concentrated to afford the desired compound (8.1 g, 83%).

$^1H$ NMR (400 MHz, $CDCl_3$): δ 7.33 (s, 1H), 6.94 (s, 1H), 3.87 (s, 3H), 3.79 (br, 2H), 2.28 (s, 3H)

Step 4: Synthesis of methyl 5-bromo-2-methyl-3-((tetrahydro-2H-pyran-4-yl) amino) benzoate To a solution of methyl 3-amino-5-bromo-2-methylbenzoate (2 g, 8.2 mmol) in dichloromethane (20 mL) and acetic acid (2.5 g, 40 mol) was added tetrahydropyran-4-one (1.2 g, mol 12 mmol) at 25° C. After 2.5 h, $NaCNBH_3$ was added into the reaction in portions and the mixture was stirred overnight. The reaction was quenched with a solution of sodium hydroxide (1.6 g, 40 mmol) in water (50 mL). After stirring for 10 minutes at ambient temperature, the organic layer was washed with water (2×50 mL), dried ($Na_2SO_4$) and concentrated. The crude product was purified by silica gel chromatography eluting with 5-20% ethyl acetate in petroleum to afford the desired compound (1.3 g, 50%) as a light yellow oil. $^1H$ NMR 400 MHz, DMSO-$d_6$): δ 6.97 (s, 1H), 6.93 (s, 1H), 4.99 (d, J=8.0 Hz, 1H), 3.87 (d, d, J=10.80 Hz, 2H), 3.80 (s, 3H), 3.60 (br, 1H), 3.44 (t, J=11.6 Hz, 3H), 2.15 (s, 3H), 1.84 (d, J=12.4 Hz, 2H), 1348-1.57 (m, 2H)

Step 5: Synthesis of methyl 5-bromo-3-[ethyl(oxan-4-yl)amino]-2-methylbenzoate

To a stirred solution of methyl 5-bromo-2-methyl-3-[(oxan-4-yl)amino]benzoate (1 g, 119 mmol) in THF (20 mL) was added LiHDMS (1.0M, 2.0 eq, THF) at 0° C. After 30 min, EtI (4.0 eq) was added into the mixture at 0° C. Then reaction mixture was stirred at rt for 3h. Saturated $NaHCO_3$ was added and the mixture was separated. The aqueous layer was extracted with $CH_2Cl_2$ and the combined organic layers were concentrated in vacuo to afford the desired product (1.2 g crude) which was used into next step without further purification.

Step 6: Synthesis of 5-bromo-3-(ethyl(tetrahydro-2H-pyran-4-yl)amino)-2-methylbenzoic acid To a stirred solution of 5-bromo-3-(ethyl(tetrahydro-2H-pyran-4-yl)amino)-2-methylbenzoate (1.2 g, crude) in ethanol (15 mL) was added LiOH (0.3 g, 10 mmol) and the resulting mixture was stirred at 60° C. for 1 h. Upon the completion of the reaction as determined by TLC, the solvent was removed under reduced pressure and the residue was acidified with 1N HCl until pH~5, and it was concentrated. The crude product was purified by silica gel chromatography eluting with 5-10% ($CH_3OH$/DCM) to afford the desired product (0.7 g, 70%) as a light yellow oil. $^1H$ NMR (400 MHz, $CDCl_3$): δ 7.88 (s, 1H), 7.42 (s, 1H), 3.98 (d, J=11.2 Hz, 2H), 3.34 (t, J=11.2 Hz, 2H), 3.03-3.09 (m, 2H), 2.95-3.00 (m, 1H), 2.52 (s, 3H), 1.64-1.73 (m, 4H), 0.88 (t, J=6.8 Hz, 3H)

Step 7: Synthesis of 5-bromo-N-((4,6-dimethyl-2-oxo-1,2-dihydropyridin-3-yl)methyl)-3-(ethyl(tetrahydro-2H-pyran-4-yl)amino)-2-methylbenzamide The acid from step 6 (0.5 g, 1.5 mmol) was dissolved in DMF (5 mL), and 3-(amino methyl)-4,6-dimethylpyridin-2

(1H)-one (0.45 g, 2.9 mmol) and DIEA (0.84 g, 5.8 mmol) were added. The reaction mixture was stirred at room temperature for 15 minutes, and then PYBOP (1.6 g, 3.0 mmol) was added. The mixture was stirred at room temperature for 3h. Upon the completion of the reaction as determined by TLC, the reaction mixture was poured onto ice-cold water (150 mL). The mixture was stirred for another 10 minutes and the solid was collected by filtration. The solid was washed with water (50 mL) and dried by air. Then the solid was slurried in 5% MeOH in DCM solution to afford desired product as a solid (200 mg, 30%). $^1$H NMR (DMSO-$d_6$, 400 MHz) δ 11.46 (s, 1H), 8.21 (s, 1H), 7.31 (s, 1H), 7.09 (s, 1H), 5.86 (s, 1H), 4.26 (d, J=4.4 Hz, 2H), 3.83 (d, J=9.60 Hz, 2H), 3.20-3.27 (m, 2H), 3.00-3.02 (m, 3H), 2.19 (s, 3H), 2.15 (s, 3H), 2.11 (s, 3H), 1.48-1.62 (m, 4H), 0.78 (t, J=6.8 Hz, 3H).

Step 8 to step 13: Synthesis of 3-(3-chloro-2-fluorophenyl)-4-(4-chloro-2-fluorophenyl)-4-cyano-N-[4-({1-[4-(3-{[(4,6-dimethyl-2-oxo -1,2-dihydropyridin-3-yl)methyl]carbamoyl}-5-[ethyl(oxan-4-yl) amino]-4-methylphenyl)phenyl]-1,4,7,10,13,16-hexaoxaoctadecan-18-yl}carbamoyl)-2-methoxyphenyl]-5-(2,2-dimethylpropyl)pyrrolidine-2-carboxamide (A2844)

Reactions in step 8 through step 10 were carried out using the standard procedure of tosylation on hydroxyl group, tosyl group displacement by bis-Boc-amine under potassium carbonate condition and tosyl group displacement by phenol. The Suzuki coupling in Step 11 was carried out using palladium tetrakis(triphenylphosphine) under the stand Suzuki coupling condition. The final two steps in forming A2844 were followed the same procedure as described for the synthesis of A1717. Compound A2844 was isolated as a solid.

$^1$H NMR (400 MHz, $CD_3OD$, ppm) δ 8.41-8.36 (m, 1H), 7.78-7.69 (m, 1H), 7.59-7.46 (m, 4H), 7.45-7.33 (m, 4H), 7.32-7.22 (m, 3H), 7.02-6.97 (m, 2H), 6.11 (s, 1H), 4.79-4.76 (m, 1H), 4.65-4.61 (m, 1H), 4.51 (s, 2H), 4.18-4.13 (m, 2H), 4.11-4.05 (m, 1H), 3.99 (s, 3H), 3.98-3.88 (m, 2H), 3.85-3.3.79 (m, 2H), 3.71-3.53 (m, 20H), 3.42-3.31 (m, 2H), 3.18-3.03 (m, 3H), 2.40 (s, 3H), 2.32 (s, 3H), 2.25 (s, 3H), 1.79-1.62 (m, 5H), 1.41-1.32 (m, 1H), 1.05 (s, 9H), 0.92-0.88 (t, J=6.8 Hz, 3H).

LC-MS calcd for $C_{72}H_{87}Cl_2F_2N_7O_{12}$ (m/z) 1351.40, obsd 1352.70 (M+H$^+$); $t_R$=2.15 min (3.0 minute run).

Compound A2790 was prepared using the same method as described for the preparation of A2844.

Example 9

Preparation of A2766

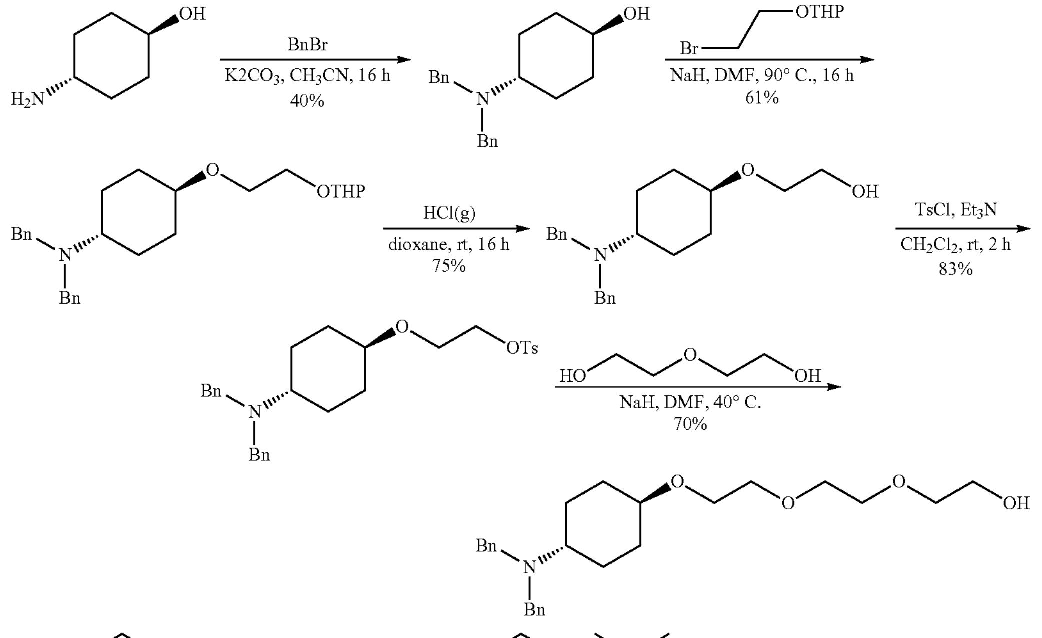

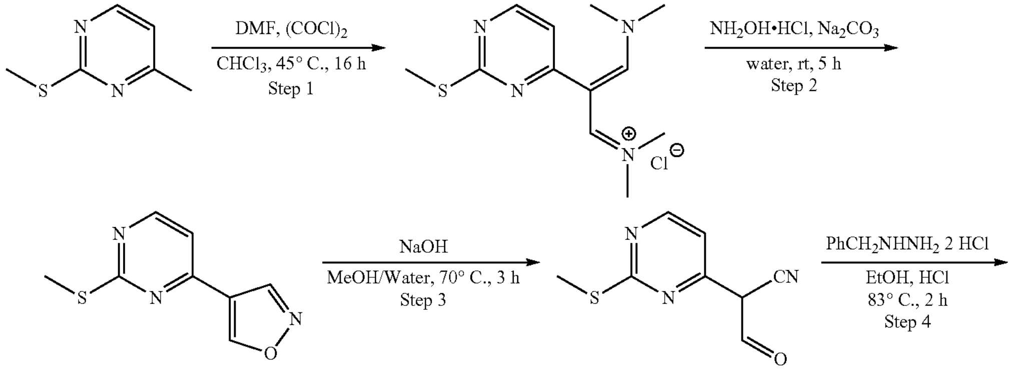

-continued
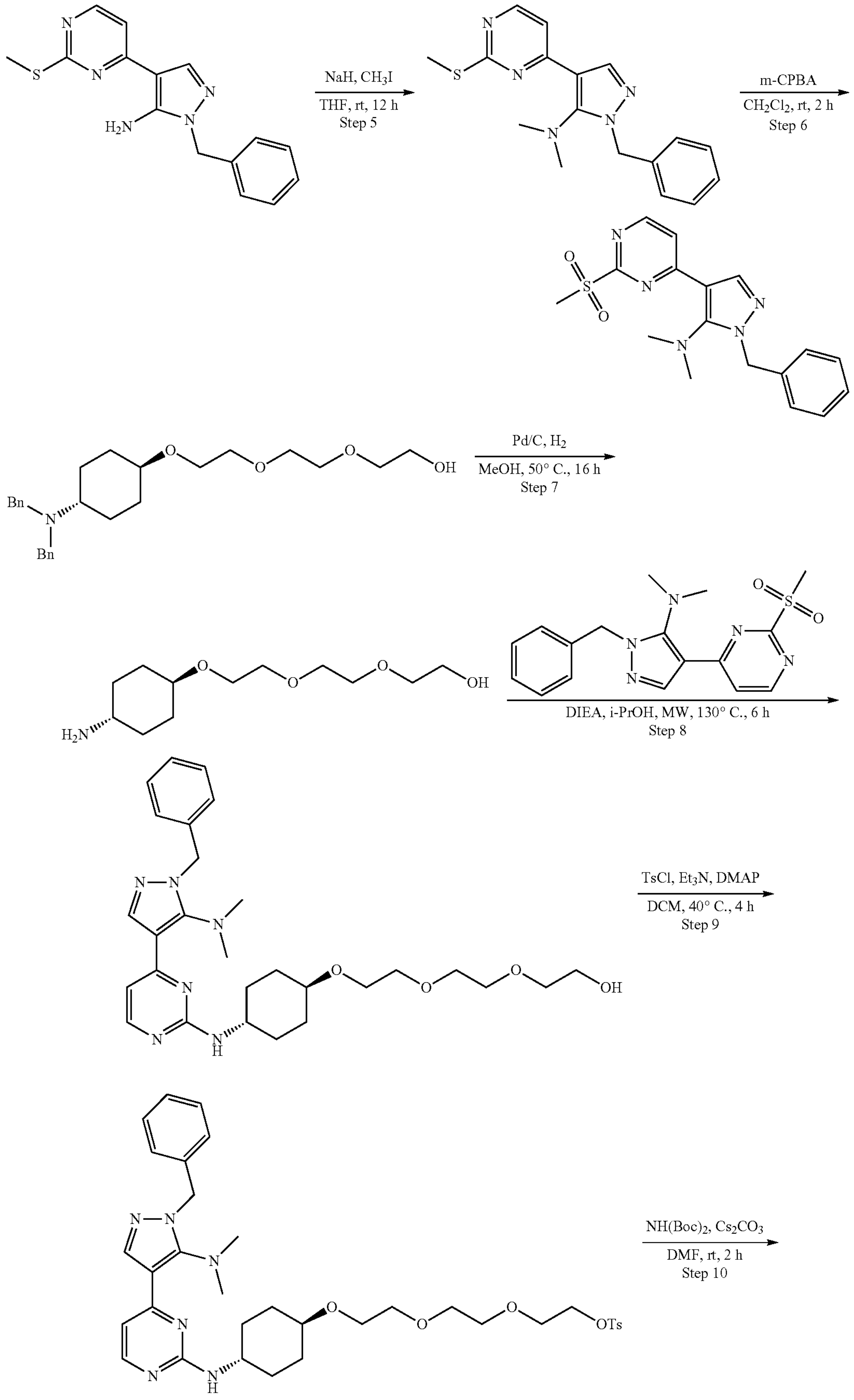

-continued

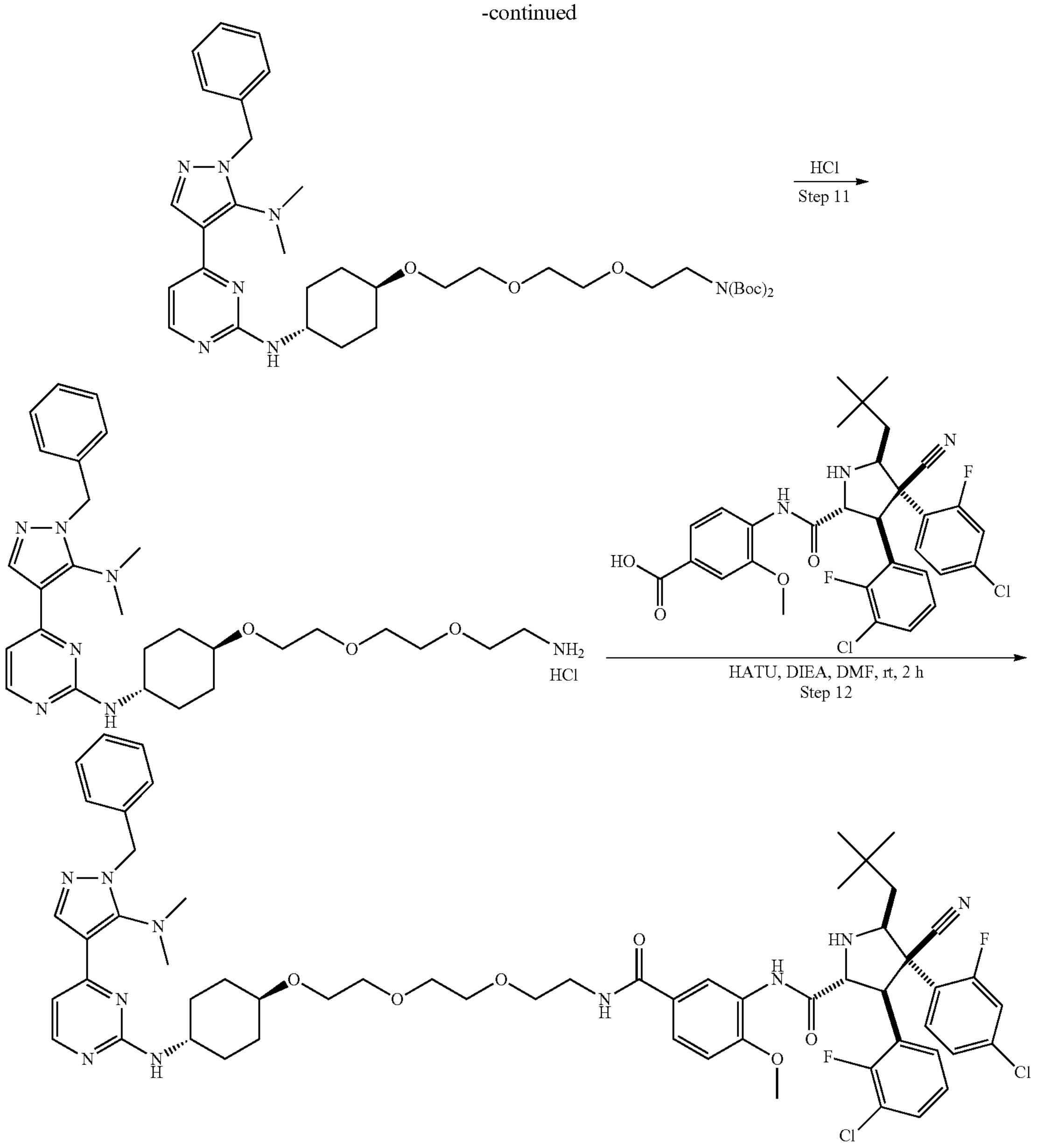

A2766

Step 1: Synthesis of [(2E)-3-(dimethylamino)-2-[2-(methylsulfanyl)pyrimidin-4-yl]prop-2-en-1-ylidene] dimethylazanium Into a 100 mL 3-necked round-bottom flask, was placed a solution of oxalyl dichloride (6.6 mL, 2.00 equiv) in chloroform/N,N-dimethylformamide (45/6 mL) at 0° C. The above mixture was stirred for 30 min at 45° C. The reaction was cooled to 0° C. 4-methyl-2-(methylsulfanyl)pyrimidine (5.0 g, 142.65 mmol, 1.00 equiv) was added to the solution separately at 0° C. The resulting solution was stirred for 16 h at 45° C. in an oil bath. The solids were collected by filtration. This resulted in 8.5 g (90%) of [(2E)-3-(dimethylamino)-2-[2-(methylsulfanyl)pyrimidin-4-yl]prop-2-en-1-ylidene]-dimethylazanium as a yellow solid. LC-MS ($ES^+$): m/z 250.95 [$M+H^+$], $t_R$=0.38 min, (1.9 minute run).

Step 2: Synthesis of 2-(methylsulfanyl)-4-(1,2-oxazol-4-yl)pyrimidine

Into a 1000 mL 3-necked round-bottom flask, was placed a solution of hydroxylamine hydrogen chloride (6.4 g, 92.75 mmol, 3.00 equiv) in water (300 mL), sodium carbonate (14.3 g, 134.92 mmol, 4.40 equiv), [(2E)-3-(dimethylamino)-2-[2-(methylsulfanyl)pyrimidin-4-yl]prop-2-en-1-ylidene]dimethylazanium (7.7 g, 30.63 mmol, 1.00 equiv). The resulting solution was stirred for 5 h at room temperature. The solids were collected by filtration, concentrated under vacuum. This resulted in 2.9 g (49%) of 2-(methylsulfanyl)-4-(1,2-oxazol-4-yl)pyrimidine as a brown solid.

LC-MS ($ES^+$): m/z 193.95[$MH^+$], $t_R$=1.22 min, (2.6 minute run).

Step 3: Synthesis of 2-[2-(methylsulfanyl)pyrimidin-4-yl]-3-oxopropanenitrile

Into a 25-mL round-bottom flask, was placed a solution of 2-(methylsulfanyl)-4-(1,2-oxazol-4-yl)pyrimidine (1.0 g, 5.18 mmol, 1.00 equiv) in methanol/water (5/5 mL). Sodium hydroxide (210.0 mg, 5.25 mmol, 1.00 equiv) was added. The resulting solution was stirred overnight at 70° C. in an oil bath. The resulting mixture was concentrated under vacuum. The pH value of the solution was adjusted to 3-4 with hydrogen chloride. The solids were collected by filtration, concentrated under vacuum. This resulted in 1.0 g (100%) of 2-[2-(methylsulfanyl)pyrimidin-4-yl]-3-oxopropanenitrile as a brown solid.

LC-MS ($ES^+$): m/z 193.85[$MH^+$], $t_R$=0.48 min, (1.9 minute run).

Step 4: Synthesis of 1-benzyl-4-[2-(methylsulfanyl)pyrimidin-4-yl]-1H-pyrazol-5-amine Into a 100-mL round-bottom flask, was placed a solution of 2-[2-(methylsulfanyl)pyrimidin-4-yl]-3-oxopropanenitrile (1.0 g, 5.18 mmol, 1.00 equiv) in ethanol/3M hydrogen chloride (10/6 mL). Benzylhydrazine hydrogen chloride (1.5 g, 7.73 mmol, 1.50 equiv) was added. The resulting solution was stirred for 2 h at 83° C. in an oil bath. The resulting mixture was concentrated under vacuum. The pH value of the solution was adjusted to 9 with sodium carbonate. The resulting solution was extracted with dichloromethane (20 mL×3) and the organic layers were combined and concentrated under vacuum. The residue was applied onto a silica gel column with ethyl acetate/petroleum ether (1:1). This resulted in 900.0 mg (58%) of 1-benzyl-4-[2-(methylsulfanyl)pyrimidin-4-yl]-1H-pyrazol-5-amine as a golden solid.

LC-MS ($ES^+$): m/z 297.90[$MH^+$], $t_R$=0.83 min, (1.9 minute run).

Step 5: Synthesis of 1-benzyl-N,N-dimethyl-4-[2-(methylsulfanyl)pyrimidin-4-yl]-1H-pyrazol-5-amine Into a 25-mL round-bottom flask, was placed a solution of 1-benzyl-4-[2-(methylsulfanyl)pyrimidin-4-yl]-1H-pyrazol-5-amine (150.0 mg, 0.50 mmol, 1.00 equiv) in tetrahydrofuran (10 mL), sodium hydride (61.0 mg, 2.54 mmol, 3.00 equiv) was added to the solution separately at 0° C., 30 min later. To this mixture iodomethane (0.4 mL, 10.00 equiv) was added. The resulting solution was stirred for 12 h at room temperature. The reaction was then quenched by the addition of water (20 mL). The resulting solution was extracted with ethyl acetate (20 mL×3) and the organic layers were combined and concentrated under vacuum. The residue was applied onto a silica gel column with ethyl acetate/petroleum ether (1:2). This resulted in 76.0 mg (46%) of 1-benzyl-N,N-dimethyl-4-[2-(methylsulfanyl)pyrimidin-4-yl]-1H-pyrazol-5-amine as light yellow oil. LC-MS ($ES^+$): m/z 325.95 [$M+H^+$], $t_R$=1.07 min, (1.9 minute run).

Step 6: Synthesis of 1-benzyl-4-(2-methanesulfonylpyrimidin-4-yl)-N,N-dimethyl-1H-pyrazol-5-amine Into a 25-mL round-bottom flask, was placed a solution of 1-benzyl-N,N-dimethyl-4-[2-(methylsulfanyl)pyrimidin-4-yl]-1H-pyrazol-5-amine (76.0 mg, 0.23 mmol, 1.00 equiv) in dichloromethane (10 mL). To this solution was added 3-chlorobenzoperoxoic acid (172.0 g, 996.70 mmol). The resulting solution was stirred for 2 h at room temperature. The reaction was then quenched by the addition of water (20 mL). The resulting solution was extracted with dichloromethane (20 mL×3) and the organic layers were combined and concentrated under vacuum. This resulted in 76.0 mg (91%) of 1-benzyl-4-(2-methanesulfonylpyrimidin-4-yl)-N,N-dimethyl-1H-pyrazol-5-amine as a light yellow solid. LC-MS ($ES^+$): m/z 358.00[$MH^+$], $t_R$=0.86 min, (1.9 minute run).

Step 7: Synthesis of 2-(2-(2-(1,4-trans)-4-aminocyclohexyloxy)-ethoxy)ethoxy)ethanol To a solution of 2-(2-(2-((1,4-trans)-4-(dibenzylamino) cyclohexyloxy)-ethoxy)-ethoxy)-ethanol (512.0 mg, 1.2 mol, 1.0 equiv) in 20 mL MeOH was added Pd/C (10%, 500 mg) under nitrogen atmosphere in a 100 mL round bottom flask. The reaction flask was vacuumed and charged with a hydrogen balloon. The reaction mixture was stirred for 16 h at 50° C. under hydrogen atmosphere. After the reaction was done, the reaction mixture was filtered through a Celite pad and the filtrate was concentrated under reduced pressure. This resulted in 247 mg of 2-[2-(2-[[(1,4-trans)-4-aminocyclohexyl]oxy]ethoxy)ethoxy]ethan-1-ol as colorless oil. LC-MS ($ES^+$): m/z 248.10 [$M+H^+$], $t_R$=0.55 min, (2.6 minute run).

Step 8: Synthesis of 2-(2-(2-((1,4-trans)-4-(4-(1-benzyl-5-(dimethylamino)-1H-pyrazol-4-yl)pyrimidin-2-ylamino)cyclohexyloxy)ethoxy)ethoxy)ethanol Into a 20 mL microwave vial, was placed a solution of 2-[2-(2-[[(1,4-trans)-4-aminocyclohexyl]oxy]ethoxy) ethoxy]ethan-1-ol (247.0 mg, 1.0 mmol, 1.0 equiv) in isopropanol (3.0 mL), 1-benzyl-4-(2-methanesulfonylpyrimidin-4-yl)-N,N-dimethyl-1H-pyrazol-5-amine (357.0 mg, 1.0 mmol, 1.0 equiv), N,N-Diisopropylethylamine (516.0 mg, 4.0 mmol, 4.0 equiv). The vial was irradiated in a microwave at 130° C. for 6 h. The resulting mixture was concentrated under vacuum. The residue was applied onto a silica gel column eluting with ethyl acetate/petroleum ether (1:1). This resulted in 230.0 mg (44%) of 2-[2-(2-[[(1,4-trans)-4-([4-[1-benzyl-5-(dimethylamino)-1H-pyrazol-4-yl]pyrimidin-2-yl]amino)cyclohexyl]-oxy]ethoxy)ethoxy]ethan-1-ol as colorless oil. LC-MS ($ES^+$): m/z 525.10 [$M+H^+$], $t_R$=0.75 min, (2.0 minute run).

Step 9: Synthesis of 2-[2-(2-[[(1,4-trans)-4-([4-[1-benzyl-5-(dimethylamino)-1H-pyrazol-4-yl]pyrimidin-2-yl]amino)cyclohexyl]oxy]ethoxy)ethoxy]ethyl 4-methylbenzene-1-sulfonate Into a 100-mL round-bottom flask, was placed a solution of 2-[2-(2-[[(1,4-trans)-4-([4-[1-benzyl-5-(dimethylamino)-1H-pyrazol-4-yl]pyrimidin-2-yl]amino)cyclohexyl]oxy] ethoxy)ethoxy]ethan-1-ol (105.0 mg, 0.2 mmol, 1.0 equiv) in dichloromethane (20.0 mL), triethylamine (40.0 mg, 0.4 mmol, 2.0 equiv), 4-dimethylaminopyridine (12.0 mg, 0.10 mmol, 0.1 equiv), 4-toluene sulfonyl chloride (57.0 mg, 0.3 mmol, 1.5 equiv). The resulting solution was stirred for 4 h at 40° C. in an oil bath. The resulting solution was quenched with 15 ml of water and extracted with dichloromethane (20 mL×2). The combined organic layers was dried over anhydrous sodium sulfate and concentrated under vacuum. The residue was applied onto a silica gel column eluting with ethyl acetate/petroleum ether (1:1). This resulted in 110 mg (81%) of 2-[2-(2-[[(1,4-trans)-4-([4-[1-benzyl-5-(dimethylamino)-1H-pyrazol-4-yl]pyrimidin-2-yl]amino)cyclohexyl]oxy]-ethoxy)ethoxy]ethyl 4-methylbenzene-1-sulfonate as colorless oil. LC-MS ($ES^+$): m/z 679.35 [$M+H^+$], $t_R$=1.34 min, (2.0 minute run).

Step 10 through Step 12: Preparation of 3-(3-chloro-2-fluorophenyl)-4-(4-chloro-2-fluorophenyl)-4-cyano-5-(2,2-dimethylpropyl)-N-[2-methoxy-5-({2-[2-(2-{[(1r,4r)-4-({4-[1-benzyl-5-(dimethylamino)-1H-pyrazol-4-yl]pyrimidin-2-yl}amino)cyclohexyl]oxy}-ethoxy)ethoxy]ethyl}carbamoyl)phenyl]pyrrolidine-2-carboxamide (A2766)

The preparation of A2766 from the intermediate prepared in step 9 was carried out using the same method descried for the preparation of A1717, namely, the conversion of the tosyl group to amine and followed by amide formation with MDM2 ligand.

$^1$H NMR (400 MHz, $CD_3OD$, ppm) δ 8.43-8.38 (m, 1H), 8.21-8.15 (m, 1H), 7.95 (s, 1H), 7.75-7.65 (m, 1H), 7.58 (s, 1H), 7.51-7.45 (m, 1H), 7.41-7.28 (m, 10H), 6.88-6.83 (m, 1H), 5.33 (s, 2H), 4.78-4.73 (m, 1H), 4.65-4.56 (m, 1H), 4.11-4.05 (m, 1H), 3.99 (s, 3H), 3.98-3.85 (m, 1H), 3.72-3.3.67 (m, 6H), 3.66-3.58 (m, 6H), 2.79 (s, 6H), 2.11-2.01 (m, 4H), 1.74-1.65 (m, 1H), 1.41-1.23 (m, 6H), 1.03 (s, 9H).

LC-MS calcd for $C_{59}H_{68}Cl_2F_2N_{10}O_6$ (m/z) 1120.47, obsd 1121.50 ($M+H^+$); $t_R$=3.40 min (5.0 minute run).

Compound A2720, A2791 and A2792 were prepared with the same method as described for the preparation of A2766.

In one aspect, the description provides compounds having a chemical structure comprising of:

PTM-L-MLM wherein MLM is a MDM2 E3 ubiquitin ligase binding moiety, PTM is a protein targeting moiety, and L is a linker coupling the MLM to the PTM, and wherein the PTM binds to a targeted protein having a function or activity selected from the group consisting of: structural protein, regulatory, growth factor, receptor, cytoskeletal, hormonal, enzymatic, nucleic acid binding, immunological, contractile, storage, transportation, signal transduction, catalytic activity, protein binding, aromatase activity, lipase, protease, nuclease, motor activity, helicase activity, metabolism, antioxidant activity, proteolysis, biosynthesis, kinase, oxidoreductase, transferase, hydrolase, lyase, isomerase, ligase, enzyme regulator, signal transducer, protein or lipid binding, cell motility, membrane fusion, cell communication, cell growth or differentiation, cell division, response to stimulus, cell adhesion, apoptosis, transport, secretion, electron transport, ion channel, chaperone or chaperone regulator, nucleic acid binding activity, transcription regulator, extracellular organization and biogenesis, and translation regulator, or a pharmaceutically acceptable salt, enantiomer, stereoisomer, solvate, polymorph or prodrug thereof.

In any of the aspects or embodiments described herein, PTM binds to a protein selected from the group consisting of B7.1, B7, TINFR1m, TNFR2, NADPH oxidase, Bcl, Bax, apotosis pathway proteins, C5a receptor, HMG-CoA reductase, PDE V phosphodiesterase, PDE IV phosphodiesterase, PDEI, PDEII, PDEIII, squalene cyclase inhibitor, CXCR1, CXCR2, nitric oxide (NO) synthase, cyclo-oxygenase 1, cyclo-oxygenase 2, 5HT receptor, dopamine receptor, G Protein, Gq, histamine receptor, 5-lipoxygenase, tryptase serine protease, thymidylate synthase, purine nucleoside phosphorylase, GAPDH trypanosomal, glycogen phosphorylase, carbonic anhydrase, chemokine receptor, JAK, STAT, RXR, HIV 1 protease, HIV 1 integrase, influenza, neuramimidase, hepatitis B reverse transcriptase, sodium channel, multi drug resistance (MDR), protein P-glycoprotein (and MRP), tyrosine kinase, CD23, CD124, tyrosine kinase p56 lck, CD4, CD5, IL-2 receptor, IL-1 receptor, TNF-alphaR, ICAM1, Cat+ channel, VCAM, VLA-4 integrin, selectin, CD40/CD40L, receptor, inosine monophosphate dehydrogenase, p38 MAP Kinase, JNK, Ras, Raf, ERK, FLT-3, KSR1, SMARCA, SMARCA2, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I), protease, cytomegalovirus (CMV) protease, poly (ADP-ribose) polymerase, cyclin dependent kinase, growth factor, growth factor receptor, receptor tyrosine kinase, cytokine, GPCR, vascular endothelial growth factor, EGF, EGFR, HGF, HGFR, VEGF, VEGFR, Wnt, TNF-α, TPO, TCGF, PGF, NT-3, NT-4, TGF, TGF-β, oxytocin receptor, microsomal transfer protein inhibitor, bile acid transport inhibitor, 5 alpha reductase, angiotensin 11, glycine receptor, noradrenaline reuptake receptor, endothelin receptor, neuropeptide Y and receptor, estrogen receptor, androgen receptor, adenosine receptor, adenosine kinase and AMP deaminase, purinergic receptor, P2Y1, P2Y2, P2Y4, P2Y6, P2X1-7, an E1, E2 or E3 ubiquitin ligase, VHL, cereblon, p53, farnesyltransferase, geranylgeranyl transferase, TrkA a receptor for NGF, beta-amyloid, tyrosine kinase Flk-IIKDR, vitronectin receptor, integrin receptor, Her-21 neu, telomerase, cytosolic phospholipaseA2 and EGF receptor tyrosine kinase, ecdysone 20-monooxygenase, GABA gated chloride channel, acetylcholinesterase, voltage-sensitive sodium channel protein, calcium release channel, chloride channel, Acetyl-CoA carboxylase, adenylosuccinate synthetase, protoporphyrinogen oxidase, enolpyruvylshikimate-phosphate synthase, haloalkane halogenase inhibitors, Hsp90, kinase, MDM2, human BET Bromodomain-containing protein, HDAC, EZH2, human lysine methyltransferase, and aryl hydrocarbon receptor (AHR).

In any of the aspects or embodiments described herein, PTM binds to a protein selected from the group consisting of a kinases, enzymes, transporters, nuclear hormone receptors, non-nuclear hormone receptors, G-protein coupled receptors (GPCRs), transcription factors, and epigenetic targets particularly, a human BET Bromodomain-containing protein (BRD), Brd4, Ras, Raf, MDM2, androgen receptor (AR) and estrogen receptor (ER), EZH2 and JNK.

In any of the aspects or embodiments described herein, the description provides bifunctional molecules comprising a structure selected from the group consisting of:

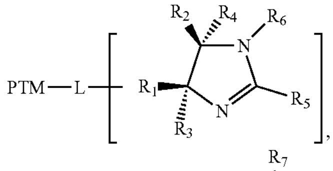
,

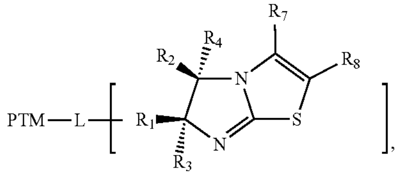
,

-continued

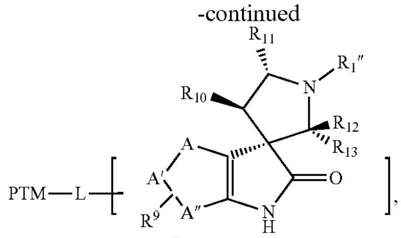

,

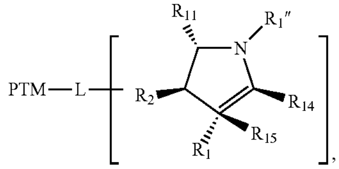

,

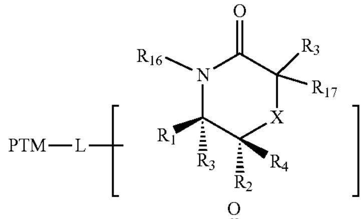

,

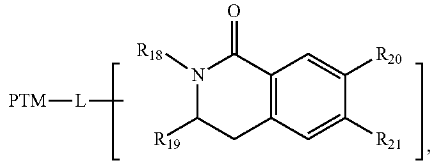

,

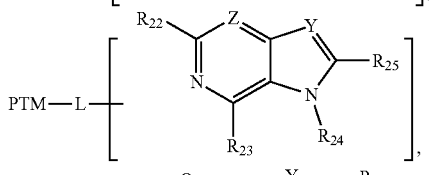

, and

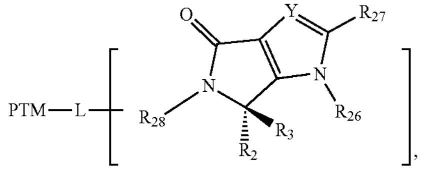

, wherein,

PTM is a protein targeting moiety that binds a target protein, and L is a linker coupling the PTM to the molecule shown;

X is selected from the group consisting of carbon, oxygen, sulfur, sulfoxide, sulfone, and N—$R^a$;

$R^a$ is independently H or an alkyl group with carbon number 1 to 6;

Y and Z are independently carbon or nitrogen;

A, A' and A" are independently selected from C, N, O or S, can also be one or two atoms forming a fused bycyclic ring, or a 6,5- and 5,5-fused aromatic bicyclic group;

$R_1$, $R_2$ are independently selected from the group consisting of an aryl or heteroaryl group, a heteroaryl group having one or two heteroatoms independently selected from sulfur or nitrogen, wherein the aryl or heteroaryl group can be mono-cyclic or bi-cyclic, or unsubstituted or substituted with one to three substituents independently selected from the group consisting of: halogen, —CN, C1 to C6 alkyl group, C3 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons, amides with 2 to 6 carbons, and dialkyl amine with 2 to 6 carbons;

$R_3$, $R_4$ are independently selected from the group consisting of H, methyl and C1 to C6 alkyl;

$R_5$ is selected from the group consisting of an aryl or heteroaryl group, a heteroaryl group having one or two heteroatoms independently selected from sulfur or nitrogen, wherein the aryl or heteroaryl group can be mono-cyclic or bi-cyclic, or unsubstituted or substituted with one to three substituents independently selected from the group consisting of: halogen, —CN, C1 to C6 alkyl group, C3 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons, amides with 2 to 6 carbons, dialkyl amine with 2 to 6 carbons, alkyl ether (C2 to C6), alkyl ketone (C3 to C6), morpholinyl, alkyl ester (C3 to C6), alkyl cyanide (C3 to C6);

$R_6$ is H or —C(═O)$R^b$, wherein $R^b$ is selected from the group consisting of alkyl, cycloalkyl, mono-, di- or tri-substituted aryl or heteroaryl, 4-morpholinyl, 1-(3-oxopiperazunyl), 1-piperidinyl, 4-N—$R^c$-morpholinyl, 4-$R^c$-1-piperidinyl, and 3-$R^c$-1-piperidinyl, wherein $R^c$ is selected from the group consisting of alkyl, fluorine substituted alkyl, cyano alkyl, hydroxyl-substituted alkyl, cycloalkyl, alkoxyalkyl, amide alkyl, alkyl sulfone, alkyl sulfoxide, alkyl amide, aryl, heteroaryl, mono-, bis- and tri-substituted aryl or heteroaryl, CH2CH2$R^d$, and CH2CH2CH2$R^d$, wherein $R^d$ is selected from the group consisting of alkoxy, alkyl sulfone, alkyl sulfoxide, N-substituted carboxamide, —NHC(O)-alkyl, —NH—$SO_2$-alkyl, aryl, substituted aryl, heteroaryl, substituted heteroaryl;

$R_7$ is selected from the group consisting of H, C1 to C6 alkyl, cyclic alkyl, fluorine substituted alkyl, cyano substituted alkyl, 5- or 6-membered hetero aryl or aryl, substituted 5- or 6-membered hetero aryl or aryl;

$R_8$ is selected from the group consisting of —$R^e$—C(O)—$R^f$, —$R^e$-alkoxy, —$R^e$-aryl, —$R^e$-heteroaryl, and —$R^e$—C(O)—$R^f$—C(O)—$R^g$, wherein:

$R^e$ is an alkylene with 1 to 6 carbons, or a bond;

$R^f$ is a substituted 4- to 7-membered heterocycle;

$R^g$ is selected from the group consisting of aryl, hetero aryl, substituted aryl or heteroaryl, and 4- to 7-membered heterocycle;

$R_9$ is selected from the group consisting of a mono-, bis- or tri-substituent on the fused bicyclic aromatic ring in Formula (A-3), wherein the substitutents are independently selected from the group consisting of halogen, alkene, alkyne, alkyl, unsubstituted or substituted with Cl or F; $R_{10}$ is selected from the group consisting of an aryl or heteroaryl group, wherein the heteroaryl group can contain one or two heteroatoms as sulfur or nitrogen, aryl or heteroaryl group can be mono-cyclic or bi-cyclic, the aryl or heteroaryl group can be unsubstituted or substituted with one to three substituents, including a halogen, F, Cl, —CN, alkene, alkyne, C1 to C6 alkyl group, C1 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons; $R_{11}$ is —C(O)—N($R^h$)($R^i$), wherein $R^h$ and $R^i$ are selected from groups consisting of the following: H, C1 to C6 alkyl, alkoxy substituted alkyl, sulfone substituted alkyl, aryl, heterol aryl, mono-, bis- or tri-substituted aryl or hetero aryl, alkyl carboxylic acid, heteroaryl carboxylic acid, alkyl carboxylic acid, fluorine substituted alkyl carboxylic acid, aryl substituted cycloalkyl, hetero aryl substituted cycloalkyl; wherein $R^h$ and $R^i$ are independently selected from the group consisting of H, connected to form a ring, 4-hydroxy-cyclohehexane; mono- and di-hydroxy substituted alkyl (C3 to C6); 3-hydroxycyclobutane; phenyl-4-carboxylic acid, and substituted phenyl-4-carboxylic acid;

$R_{12}$ and $R_{13}$ are independently selected from H, lower alkyl (C1 to C6), lower alkenyl (C2 to C6), lower alkynyl (C2 to C6), cycloalkyl (4, 5 and 6-membered ring), substituted cycloalkyl, cycloalkenyl, substituted cycloalkenyl, 5- and 6-membered aryl and heteroaryl, R12 and R13 can be connected to form a 5- and 6-membered ring with or without substitution on the ring;

$R_{14}$ is selected from the group consisting of alkyl, substituted alkyl, alkenyl, substituted alkenyl, aryl, substituted aryl, heteroaryl, substituted heteroaryl, heterocycle, substituted heterocycle, cycloalkyl, substituted cycloalkyl, cycloalkenyl and substituted cycloalkenyl;

$R_{15}$ is CN;

$R_{16}$ is selected from the group consisting of C1-6 alkyl, C1-6 cycloalkyl, C2-6 alkenyl, C1-6 alkyl or C3-6 cycloalkyl with one or multiple hydrogens replaced by fluorine, alkyl or cycloalkyl with one $CH_2$ replaced by S(═O), —S, or —$S(═O)_2$, alkyl or cycloalkyl with terminal $CH_3$ replaced by $S(═O)_2N$(alkyl)(alkyl), —C(═O)N(alkyl)(alkyl), —N(alkyl)$S(═O)_2$(alkyl), —$C(═O)_2$(allkyl), —O(alkyl), C1-6 alkyl or alkyl-cycloalkyl with hydron replaced by hydroxyl group, a 3 to 7 membered cycloalkyl or heterocycloalkyl, optionally containing a —(C═O)— group, or a 5 to 6 membered aryl or heteroaryl group, which heterocycloalkyl or heteroaryl group can contain from one to three heteroatoms independently selected from O, N or S, and the cycloalkyl, heterocycloalkyl, aryl or heteroaryl group can be unsubstituted or substituted with from one to three substituents independently selected from halogen, C1-6 alkyl groups, hydroxylated C1-6 alkyl, C1-6 alkyl containing thioether, ether, sulfone, sulfoxide, fluorine substituted ether or cyano group;

$R_{17}$ is selected from the group consisting of $(CH_2)nC(O)NR^kR^l$, wherein $R^k$ and $R^l$ are independently selected from H, C1-6 alkyl, hydrxylated C1-6 alkyl, C1-6 alkoxy alkyl, C1-6 alkyl with one or multiple hydrogens replaced by fluorine, C1-6 alkyl with one carbon replaced by S(O), S(O)(O), C1-6 alkoxyalkyl with one or multiple hydrogens replaced by fluorine, C1-6 alkyl with hydrogen replaced by a cyano group, 5 and 6 membered aryl or heteroaryl, alkyl aryl with alkyl group containing 1-6 carbons, and alkyl heteroaryl with alkyl group containing 1-6 carbons, wherein the aryl or heteroaryl group can be further substituted;

$R_{18}$ is selected from the group consisting of substituted aryl, heteroaryl, alkyl, cycloalkyl, the substitution is preferably —N(C1-4 alkyl)(cycloalkyl), —N(C1-4 alkyl)alkyl-cycloalkyl, and —N(C1-4 alkyl)[(alkyl)-(heterocycle-substituted)-cycloalkyl];

$R_{19}$ is selected from the group consisting of aryl, heteroaryl, bicyclic heteroaryl, and these aryl or heteroaryl groups can be substituted with halogen, C1-6 alkyl, C1-6 cycloalkyl, $CF_3$, F, CN, alkyne, alkyl sulfone, the halogen substitution can be mon- bis- or tri-substituted;

$R_{20}$ and $R_{21}$ are independently selected from C1-6 alkyl, C1-6 cycloalkyl, C1-6 alkoxy, hydroxylated C1-6 alkoxy, and fluorine substituted C1-6 alkoxy, wherein $R_{20}$ and $R_{21}$ can further be connected to form a 5, 6 and 7-membered cyclic or heterocyclic ring, which can further be substituted;

$R_{22}$ is selected from the group consisting of H, C1-6 alkyl, C1-6 cycloalkyl, carboxylic acid, carboxylic acid ester, amide, reverse amide, sulfonamide, reverse sulfonamide, N-acyl urea, nitrogen-containing 5-membered heterocycle, the 5-membered heterocycles can be further substituted with C1-6 alkyl, alkoxy, fluorine-substituted alkyl, CN, and alkylsulfone;

$R_{23}$ is selected from aryl, heteroaryl, —O-aryl, —O-heteroaryl, —O-alkyl, —O-alkyl-cycloalkyl, —NH-alkyl, —NH-alkyl-cycloalkyl, —N(H)-aryl, —N(H)-heteroaryl, —N(alkyl)-aryl, —N(alkyl)-heteroaryl, the aryl or heteroaryl groups can be substituted with halogen, C1-6 alkyl, hydroxylated C1-6 alkyl, cycloalkyl, fluorine-substituted C1-6 alkyl, CN, alkoxy, alkyl sulfone, amide and sulfonamide;

$R_{24}$ is selected from the group consisting of —CH2-(C1-6 alkyl), —CH2-cycloalkyl, —CH2-aryl, CH2-heteroaryl, where alkyl, cycloalkyl, aryl and heteroaryl can be substituted with halogen, alkoxy, hydroxylated alkyl, cyano-substituted alkyl, cycloallyl and substituted cycloalkyl;

$R_{25}$ is selected from the group consisting of C1-6 alkyl, C1-6 alkyl-cycloalkyl, alkoxy-substituted alkyl, hydroxylated alkyl, aryl, heteroaryl, substituted aryl or heteroaryl, 5,6, and 7-membered nitrogen-containing saturated heterocycles, 5,6-fused and 6,6-fused nitrogen-containing saturated heterocycles and these saturated heterocycles can be substituted with C1-6 alkyl, fluorine-substituted C1-6 alkyl, alkoxy, aryl and heteroaryl group;

$R_{26}$ is selected from the group consisting of C1-6 alkyl, C3-6 cycloalkyl, the alkyl or cycloalkyl can be substituted with —OH, alkoxy, fluorine-substituted alkoxy, fluorine-substituted alkyl, —$NH_2$, —NH-alkyl, NH—C(O)alkyl, —NH—$S(O)_2$-alkyl, and —$S(O)_2$-alkyl;

$R_{27}$ is selected from the group consisting of aryl, heteroaryl, bicyclic heteroaryl, wherein the aryl or heteroaryl groups can be substituted with C1-6 alkyl, alkoxy, NH2, NH-alkyl, halogen, or —CN, and the substitution can be independently mono-, bis- and tri-substitution; R28 is selected from the group consisting of aryl, 5 and 6-membered heteroaryl, bicyclic heteroaryl, cycloalkyl, saturated heterocycle such as piperidine, piperidinone, tetrahydropyran, N-acyl-piperidine, wherein the cycloalkyl, saturated heterocycle, aryl or heteroaryl can be further substituted with —OH, alkoxy, mono-, bis- or tri-substitution including halogen, —CN, alkyl sulfone, and fluorine substituted alkyl groups; and $R_1$" is selected from the group consisting of alkyl, aryl substituted alkyl, alkoxy substituted alkyl, cycloalkyl, aryl-substituted cycloalkyl, and alkoxy substituted cycloalkyl, or a pharmaceutically acceptable salt, enantiomer, stereoisomer, solvate, polymorph or prodrug thereof.

In any of the aspects or embodiments described herein, the heterocycles in $R^f$ and $R^g$ are independently selected from the group consisting of substituted pyrrolidine, substituted piperidine, and substituted piperizine.

In any of the aspects or embodiments described herein, $R_9$ substituents are selected from Cl and F.

In any of the aspects or embodiments described herein, $R_{10}$ substituents are selected from H, F and Cl.

In any of the aspects or embodiments described herein, $R^h$ and $R^i$ are selected from the group consisting of:

(i) $R^h$ is H, and $R^i$ is 4-hydroxycyclohehexane;

(ii) $R^h$ is H, and $R^i$ is mono- and di-hydroxy substituted lower alkyl (C3 to C6);

(iii) $R^h$ is H, and $R^i$ is 3-hydroxycyclobutane; and (iv) $R^h$ is H, and $R^i$ is phenyl-4-carboxylic acid, substituted phenyl-4-carboxylic acid.

In any of the aspects or embodiments described herein, $R_{18}$ substitution is selected from the group consisting of —N(C1-4 alkyl)(cycloalkyl), —N(C1-4 alkyl)alkyl-cycloalkyl, and —N(C1-4 alkyl)[(alkyl)-(heterocycle-substituted)-cycloalkyl].

In any of the aspects or embodiments described herein, $R_{28}$ saturated heterocycle is selected from piperidine, piperidinone, tetrahydropyran, and N-acyl-piperidine.

In any of the aspects or embodiments, the description provides compounds with structures selected from the group consisting of:

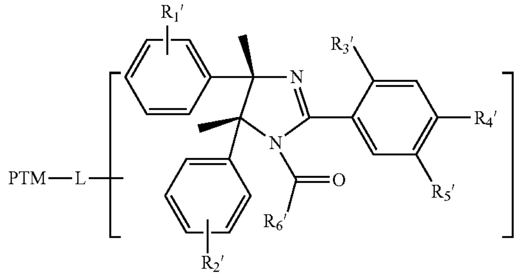

,

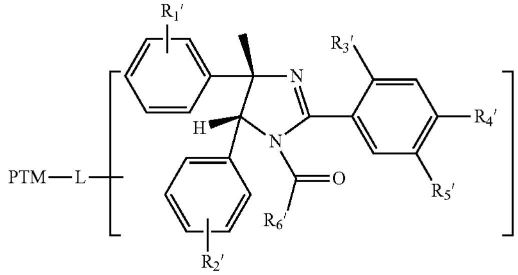

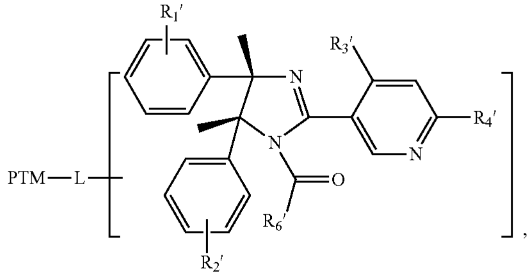

, and

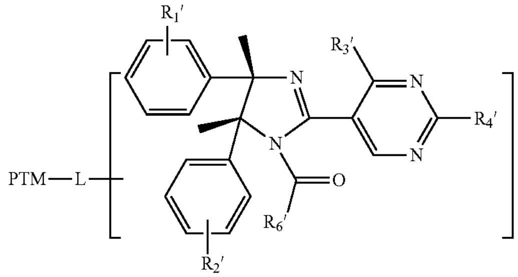

wherein R1' and R2' are independently selected from the group consisting of F, Cl, Br, I, acetylene, CN, $CF_3$ and $NO_2$;

R3' is selected from the group consisting of $—OCH_3$, $—OCH_2CH_3$, $—OCH_2CH_2F$, $—OCH_2CH_2OCH_3$, and $—OCH(CH_3)_2$;

R4' and R6' are independently selected from the group consisting of H, halogen, $—CH_3$, $—CF_3$, $—OCH_3$, $—C(CH_3)_3$, $—CH(CH_3)_2$, -cyclopropyl, —CN, $—C(CH_3)_2OH$, $—C(CH_3)_2OCH_2CH_3$, $—C(CH_3)_2CH_2OH$, $—C(CH_3)_2CH_2OCH_2CH_3$, $—C(CH_3)_2CH_2OCH_2CH_2OH$, $—C(CH_3)_2CH_2OCH_2CH_3$, $—C(CH_3)_2CN$, $—C(CH_3)_2C(O)CH_3$, $—C(CH_3)_2C(O)NHCH_3$, $—C(CH_3)_2C(O)N(CH_3)_2$, $—SCH_3$, $—SCH_2CH_3$, $—S(O)_2CH_3$, $—S(O_2)CH_2CH_3$, $—NHC(CH_3)_3$, $—N(CH_3)_2$, pyrrolidinyl, and 4-morpholinyl; and R5' is selected from the group consisting of halogen, -cyclopropyl, $—S(O)_2CH_3$, $—S(O)_2CH_2CH_3$, 1-pyrrolidinyl, $—NH_2$, $—N(CH_3)_2$, and $—NHC(CH_3)_3$, or a pharmaceutically acceptable salt, enantiomer, stereoisomer, solvate, polymorph or prodrug thereof.

In any of the aspects or embodiments described herein, the linker is attached to at least one of R1', R2', R3', R4', R5', R6', or a combination thereof.

In any of the aspects or embodiments described herein, R6' is independently selected from the group consisting of H,

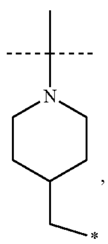
,
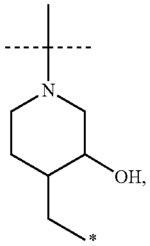
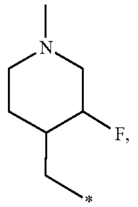
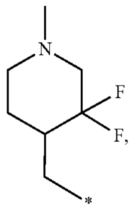
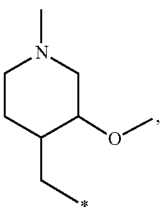
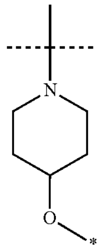
,
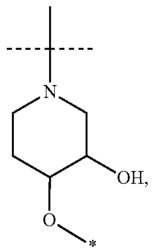
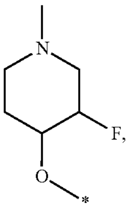
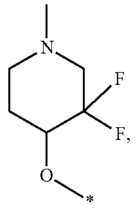

-continued
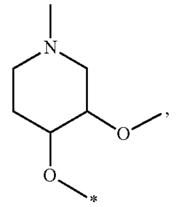 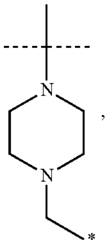 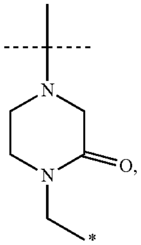
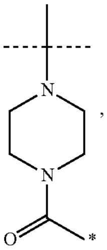 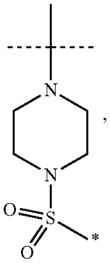 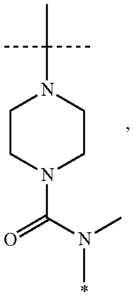
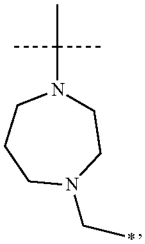 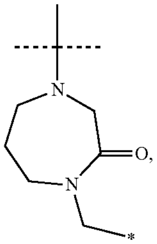 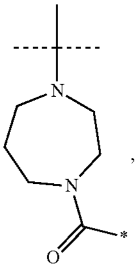
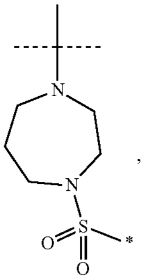 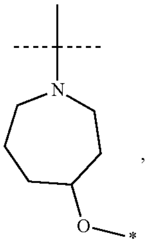 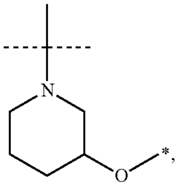
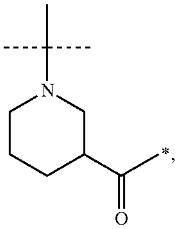 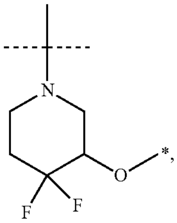 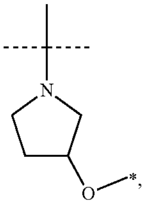
-continued
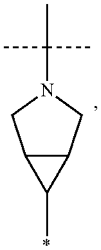 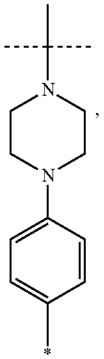 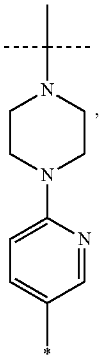 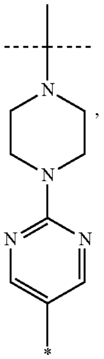
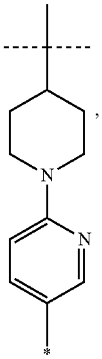 and 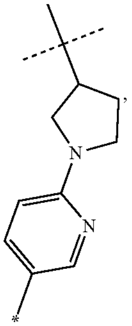
wherein * indicates the point of attachment of the linker.
In any of the aspects or embodiments described herein, the compound has a structure selected from the group consisting of:
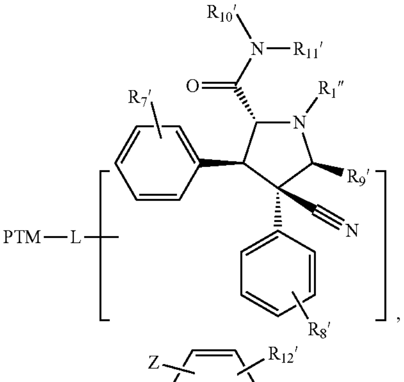
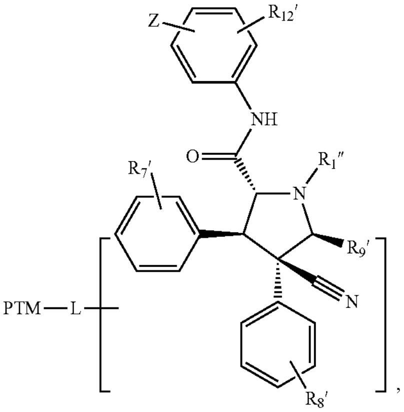

-continued

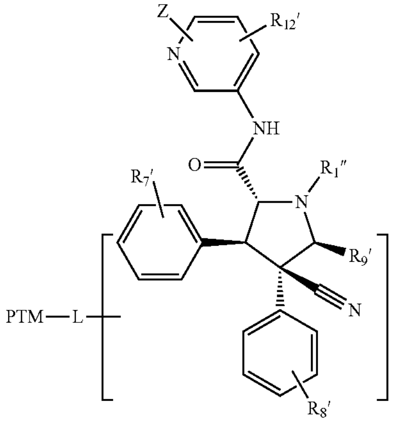

,

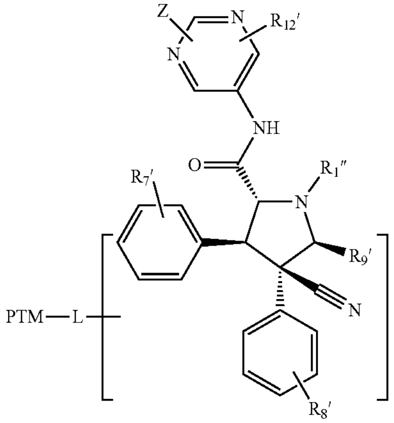

,

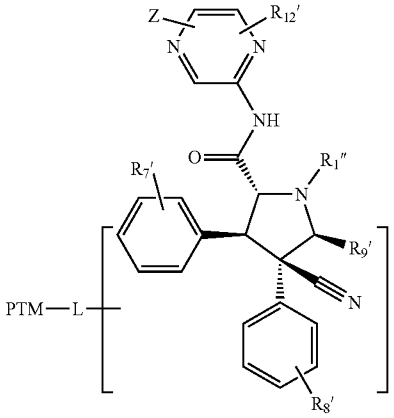

, and

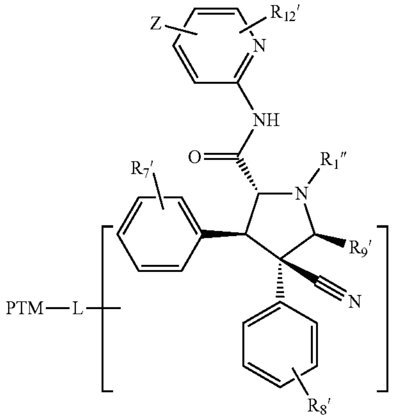

, wherein $R_7'$ is a member selected from the group consisting of halogen, mono-, and di- or tri-substituted halogen;

$R_8'$ is selected from the group consisting of H, —F, —Cl, —Br, —I, —CN, —$NO_2$, ethylnyl, cyclopropyl, methyl, ethyl, isopropyl, vinyl, methoxy, ethoxy, isopropoxy, —OH, other C1-6 alkyl, other C1-6 alkenyl, and C1-6 alkynyl, mono-, di- or tri-substituted;

$R_9'$ is selected from the group consisting of alkyl, substituted alkyl, alkenyl, substituted alkenyl, alkynyl, substituted alkynyl, aryl, substituted aryl, hetero aryl, substituted heteroaryl, cycloalkyl, substituted cycloalkyl, alkenyl, and substituted cycloalkenyl;

Z is selected from the group consisting of H, —$OCH_3$, —$OCH_2CH_3$, and halogen;

$R_{10}'$ and $R_{11}'$ are each independently selected from the group consisting of H, $(CH_2)_n$—R', $(CH_2)_n$—NR'R", $(CH_2)_n$—NR'COR", $(CH_2)_n$—NR'$SO_2$R", $(CH_2)_n$—COOH, $(CH_2)_n$—COOR', $(CH)_n$—CONR'R", $(CH_2)_n$—OR', $(CH_2)_n$—SR', $(CH_2)_n$—SOR', $(CH_2)_n$—CH(OH)—R', $(CH_2)_n$—COR', $(CH_2)_n$—$SO_2$R', $(CH_2)_n$—SONR'R", $(CH_2)_n$—$SO_2$NR'R", $(CH_2CH_2O)_m$—$(CH_2)_n$—R', $(CH_2CH_2O)_m$—$(CH_2)_n$—OH, $(CH_2CH_2O)_m$—$(CH_2)_n$OR', $(CH_2CH_2O)_m$—$(CH_2)_n$—NR'R", $(CH_2CH_2O)_m$—$(CH_2)_n$—NR'COR", $(CH_2CH_2O)_m(CH_2)_n$—NR'$SO_2$R", $(CH_2CH_2O)_m(CH_2)_n$—COOH, $(CH_2CH_2O)_m(CH_2)_n$—COOR', $(CH_2CH_2O)_m$—$(CH_2)_n$—CONR'R", $(CH_2CH_2O)_m$—$(CH_2)_n$—$SO_2$R', $(CH_2CH_2O)_m$—$(CH_2)_n$—COR', $(CH_2CH_2O)_m$—$(CH_2)_n$—SONR'R", $(CH_2CH_2O)_m$—$(CH_2)_n$—$SO_2$NR'R", $(CH_2)_p$—$(CH_2CH_2O)_m$—$(CH_2)_n$R', $(CH_2)$p-$(CH_2CH_2O)_m$—$(CH_2)_n$—OH, $(CH_2)_p$—$(CH_2CH_2O)_m$—$(CH_2)$n-OR', $(CH_2)_p$—$(CH_2CH_2O)_m$—$(CH_2)_n$NR'R", $(CH_2)_p$—$(CH_2CH_2O)_m$—$(CH_2)_n$—NR'COR", $(CH_2)_p$—$(CH_2CH_2O)$m-$(CH_2)_n$—NR'$SO_2$R", $(CH_2)_p$—$(CH_2CH_2O)_m$—$(CH_2)_n$—COOH, $(CH_2)_p$—$(CH_2CH_2O)_m$—$(CH_2)_n$—COOR', $(CH_2)_p$—$(CH_2CH_2O)_m$—$(CH_2)_n$—CONR'R", $(CH_2)$p-$(CH_2CH_2O)_m$—$(CH_2)_n$—$SO_2$R', $(CH_2)_p$—$(CH_2CH_2O)_m$—$(CH_2)_n$—COR', $(CH_2)_p$—$(CH_2CH_2O)_m$—$(CH_2)_n$—SONR'R", $(CH_2)_p$—$(CH_2CH_2O)_m$—$(CH_2)_n$$SO_2$NR'R", Aryl-$(CH_2)_n$—COOH, and heteroaryl-alkyl-CO-alkyl-NR'R"m, wherein the alkyl may be substituted with OR', and heteroaryl-$(CH_2)_n$-heterocycle wherein the heterocycle may optionally be substituted with alkyl, hydroxyl, COOR' and COR'; wherein R' and R" are selected from H, alkyl, alkyl substituted with halogen, hydroxyl, NH2, NH(alkyl), $N(alkyl)_2$, oxo, carboxy, cycloalkyl and heteroaryl;

m, n, and p are independently 0 to 6;

$R_{12}'$ is selected from the group consisting of —O—(alkyl), —O—(alkyl)-alkoxy, —C(O)-(alkyl), —C(OH)-alkyl-alkoxy, —C(O)—NH-(alkyl), —C(O)—N-$(alkyl)_2$, —S(O)-(alkyl), $S(O)_2$-(alkyl), —C(O)-(cyclic amine), and —O-aryl-(alkyl), —O-aryl-(alkoxy); and $R_1''$ is selected from the group consisting of alkyl, aryl substituted alkyl, alkoxy substituted alkyl, cycloalkyl, aryl-substituted cycloalkyl, and alkoxy substituted cycloalkyl, or a pharmaceutically acceptable salt, enantiomer, stereoisomer, solvate, polymorph or prodrug thereof.

In any of the aspects or embodiments described herein, the linker is attached to at least one of Z, $R_8'$, $R_9'$, $R_{10}'$, $R_{11}'$, $R_{12}'$, $R_1''$, or a combination thereof.

In any of the aspects or embodiments described herein, the linker group (L) comprises a chemical structural unit represented by the formula:

-Aqwherein:

q is an integer greater than 1; and

A is independently selected from the group consisting of a bond, CRL1RL2, O, S, SO, SO2, NRL3, SO2NRL3, SONRL3, CONRL3, NRL3CONRL4, NRL3SO2NRL4, CO, CRL1=CRL2, C≡C, SiRL1RL2, P(O)RL1, P(O)ORL1, NRL3C(=NCN)NRL4, NRL3C(=NCN), NRL3C(=CNO2)NRL4, C3-1 lcycloalkyl optionally substituted with 0-6 RL1 and/or RL2 groups, C3-1 lheteocyclyl optionally substituted with 0-6 RL1 and/or RL2 groups, aryl optionally substituted with 0-6 RL1 and/or RL2 groups, heteroaryl optionally substituted with 0-6 RL1 and/or RL2 groups; wherein RL1, RL2, RL3, RL4 and RL5 are each, independently, selected from the group consisting of H, halo, C1-8alkyl, OC1-8alkyl, SC1-8alkyl, NHC1-8a1kyl, N(C1-8alkyl)2, C3-11cycloalkyl, aryl, heteroaryl, C3-11heterocyclyl, OC1-8cycloalkyl, SC1-8cycloalkyl, NHC1-8cycloalkyl, N(C1-8cycloalkyl)2, N(C1-8cycloalkyl)(C1-8alkyl), OH, NH2, SH, SO2C1-8alkyl, P(O)(OC1-8alkyl)(C1-8alkyl), P(O)(OC1-8alkyl)2, CC-C1-8alkyl, CCH, CH=CH(C1-8alkyl), C(C1-8alkyl)=CH(C1-8alkyl), C(C1-8alkyl)=C(C1-8alkyl)2, Si(OH)3, Si(C1-8alkyl)3, Si(OH)(C1-8alkyl)2, COC1-8alkyl, CO2H, halogen, CN, CF3, CHF2, CH2F, NO2, SFS, SO2NHC1-8alkyl, SO2N(C1-8alkyl)2, SONHC1-8alkyl, SON(C1-8alkyl)2, CONHC1-8alkyl, CON(C1-8alkyl)2, N(C1-8alkyl)CONH(C1-8alkyl), N(C1-8alkyl)CON(C1-8alkyl)2, NHCONH(C1-8alkyl), NHCON(C1-8alkyl)2, NHCONH2, N(C1-8alkyl) SO2NH(C1-8alkyl), N(C1-8alkyl) SO2N(C1-8alkyl)2, NH SO2NH(C1-8alkyl), NH SO2N(C1-8alkyl)2, and NH SO2NH2; and wherein:

when q is greater than 1, RL1 or RL2 each, independently, can be linked to another A group to form cycloalkyl and/or heterocyclyl moeity that can be further substituted with 0-4 RL5 groups.

In any of the aspects or embodiments described herein, the linker group (L) is selected from the structure consisting of:

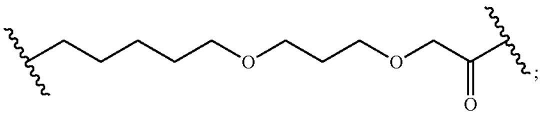
;

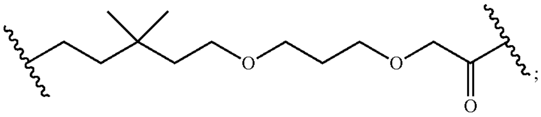
;

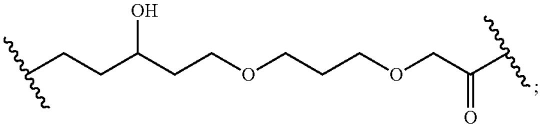
;

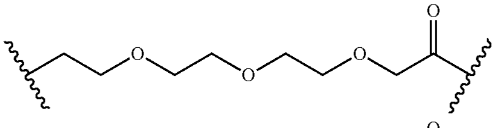
;

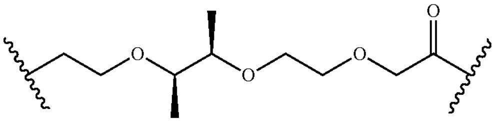
;

-continued

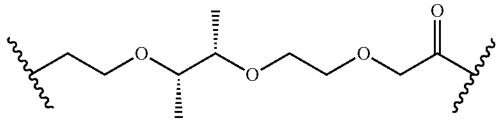
;

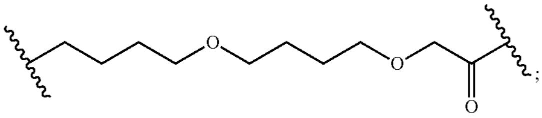
;

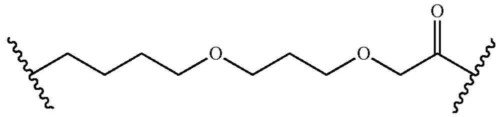
;

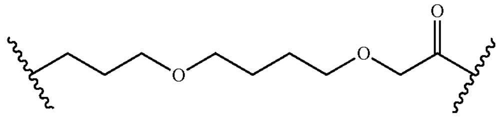
;

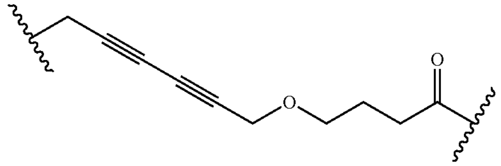
;

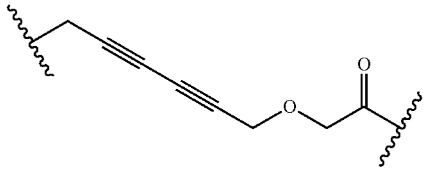
;

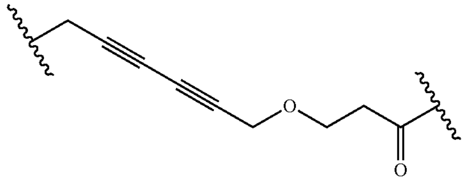
;

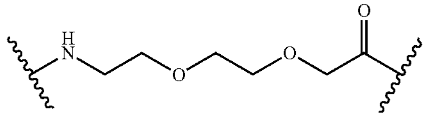
;

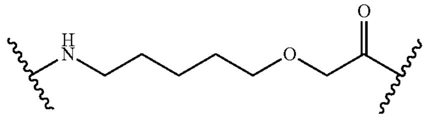
;

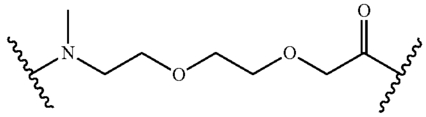
;

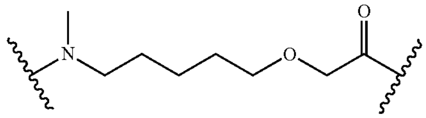
;

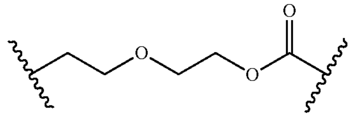
;

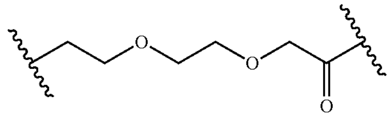
;

-continued
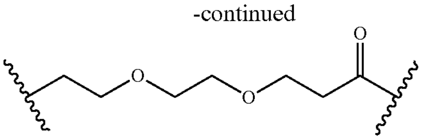
;
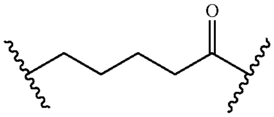
;
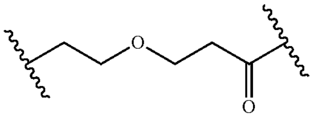
;
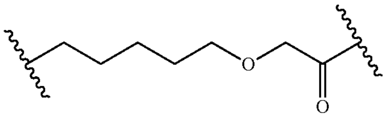
;
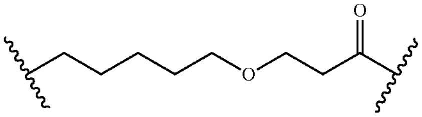
;
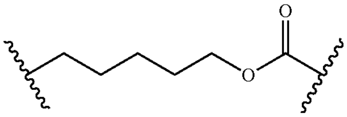
;
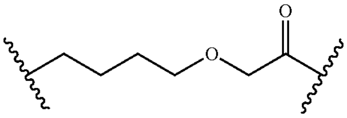
;
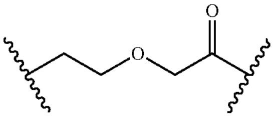
;
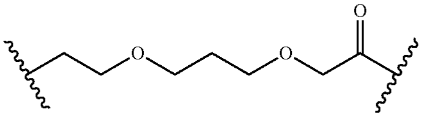
;
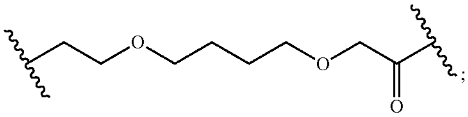
;
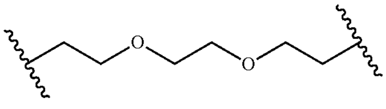
;
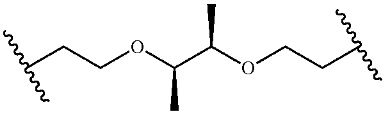
;
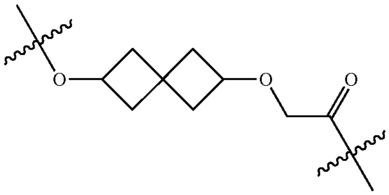
;
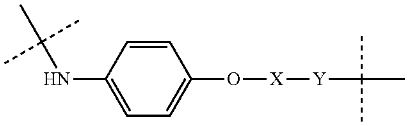
-continued
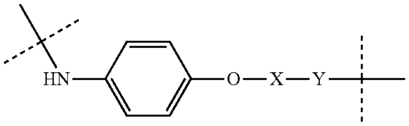
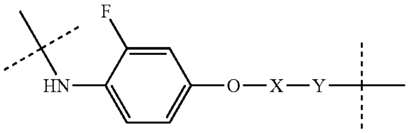
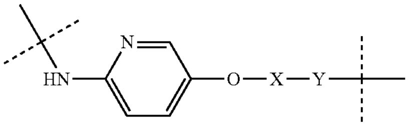
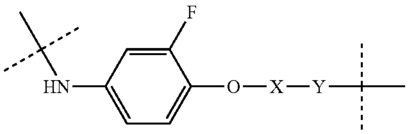
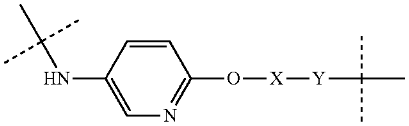
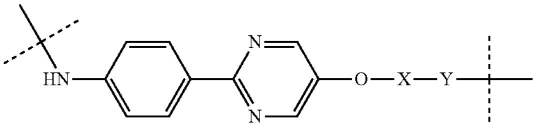
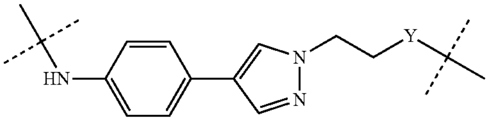
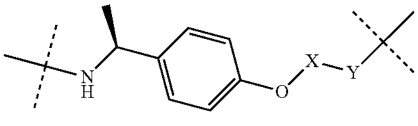
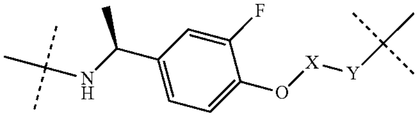
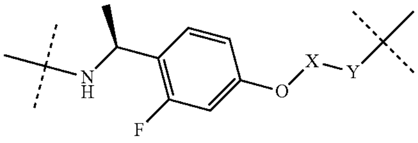
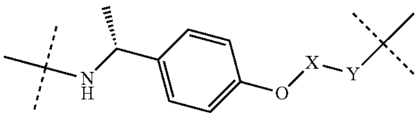
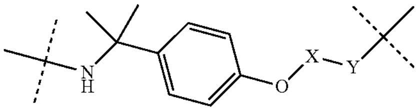
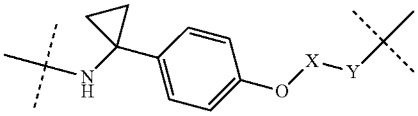

-continued

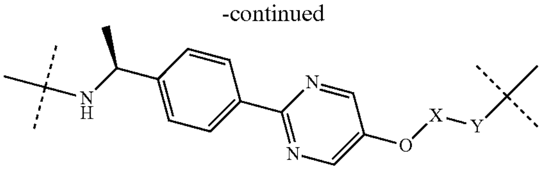

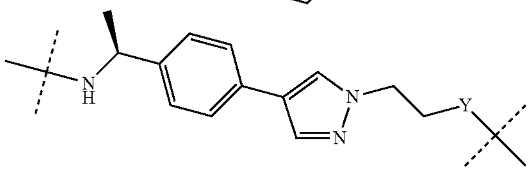

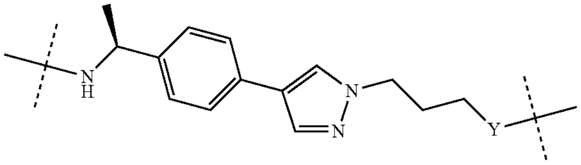

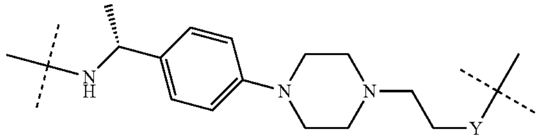

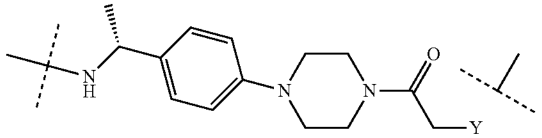

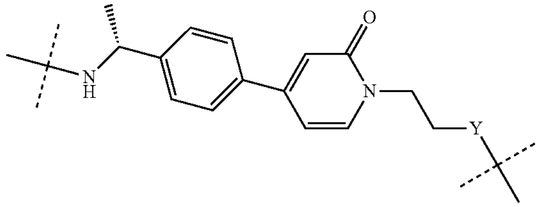

wherein:

"X" is a linear chain with atoms ranging from 2 to 14 with heteroatoms optionally; and "Y" is O, N and $S(O)_n$ wherein, (n=0, 1, 2).

In any of the aspects or embodiments described herein, the PTM group is a protein target moiety that binds to bromodomain-containing protein 4 (BRD4).

In any of the aspects or embodiments described herein, the PTM is a protein target moiety that binds to a human BET Bromodomain-containing protein is selected from the structure consisting of:

BRD-PTM-1

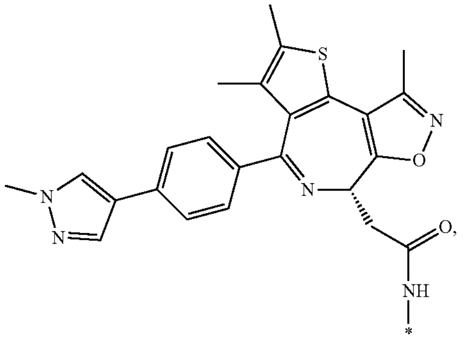

-continued

BRD-PTM-2

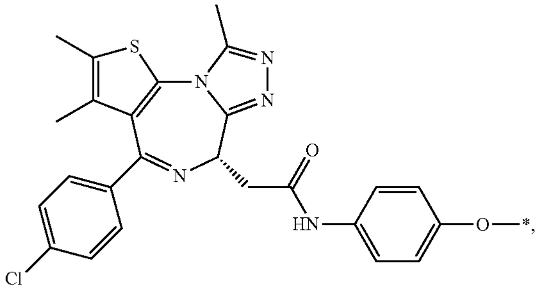

BRD-PTM-3

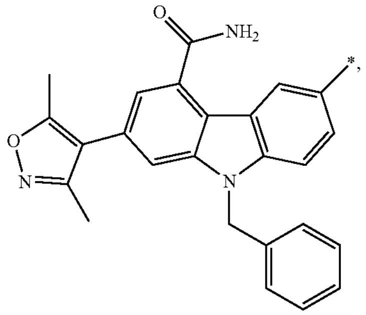

BRD-PTM-4

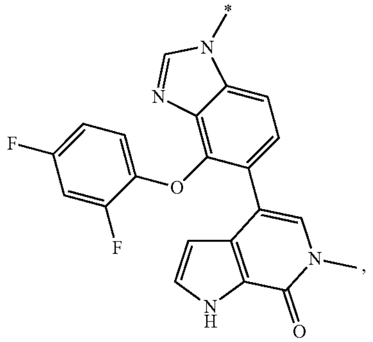

BRD-PTM-5

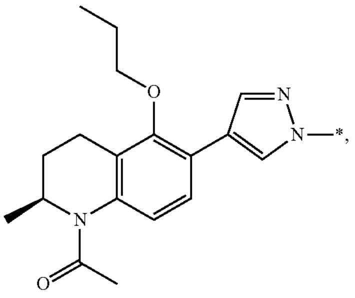

and

BRD-PTM-6

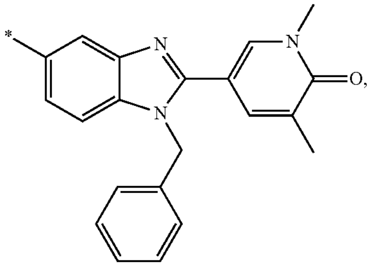

wherein * indicates the point of attachment of the linker.

In any of the aspects or embodiments described herein, the PTM is a protein target moiety selected from the structure consisting of:

AR-PTM-1

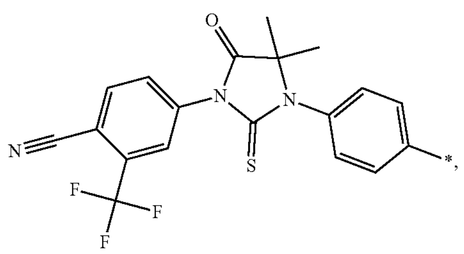

AR-PTM-2

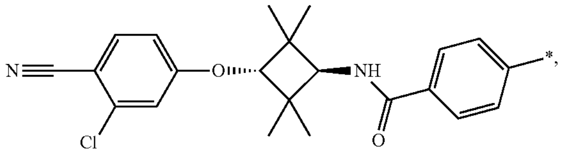

EZH2-PTM

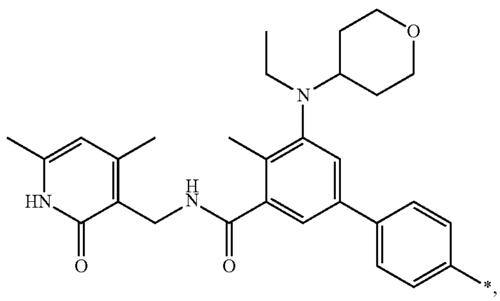

and

JNK-PTM

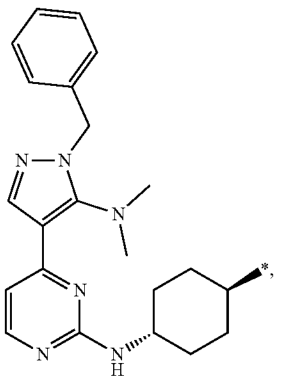

wherein * indicates the point of attachment of the linker.

In some embodiments, the MLM comprises part of structural feature as in at least one of RG7112, RG7388, SAR405838, AMG-232, AM-7209, DS-5272, MK-8242, or NVP-CGM-097, and analogs or derivatives thereof.

In any of the aspects or embodiments described herein, the description provides a compound selected from the group consisting of chemical formula:

4-(3-{4-[2-(2-{4-[2-(4-tert-butyl-2-ethoxyphenyl)-4,5-bis(4-chlorophenyl)-4,5-dimethyl-4,5-dihydro-1H-imidazole-1-carbonyl]piperazin-1-yl}ethoxy)ethoxy]phenyl}-4,4-dimethyl-5-oxo-2-sulfanylideneimidazolidin-1-yl)-2-(trifluoromethyl)benzonitrile;

4-(3-{4-[(17-{4-[2-(4-tert-butyl-2-ethoxyphenyl)-4,5-bis(4-chlorophenyl)-4,5-dimethyl-4,5-dihydro -1H-imidazole- 1-carbonyl]piperazin-1-yl}-3,6,9,12,15-pentaoxaheptadecan-1-yl)oxy]phenyl}-4,4-dimethyl-5-oxo-2-sulfanylideneimidazolidin-1-yl)-2-(trifluoromethyl)benzonitrile;

N-(17-{[3-(3-chloro -2-fluorophenyl)-4-(4-chloro -2-fluorophenyl)-4-cyano -5-(2,2-dimethylpropyl)pyrrolidin-2-yl]formamido}-3,6,9,12,15-pentaoxaheptadecan-1-yl)-2-[9S)-7-(4-chlorophenyl)-4,5,13-trimethyl-3-thia-1,8,11,12-tetraazatricyclo[8.3.0.$0^{2,6}$]trideca-2(6),4,7,10,12-pentaen-9-yl]acetamide;

N-(2-{2-[2-(2-{[3-(3-chloro-2-fluorophenyl)-4-(4-chloro-2-fluorophenyl)-4-cyano-5-(2,2-dimethylpropyl)pyrrolidin-2-yl]formamido}ethoxy)ethoxy]ethoxy}ethyl)-2-[(9S)-7-(4-chlorophenyl)-4,5,13-trimethyl-3-thia-1,8,11,12-tetraazatricyclo[8.3.0.$0^{2,6}$]trideca-2(6),4,7,10,12-pentaen-9-yl]acetamide;

N-(14-{[3-(3-chloro -2-fluorophenyl)-4-(4-chloro -2-fluorophenyl)-4-cyano -5-(2,2-dimethylpropyl)pyrrolidin-2-yl]formamido}-3,6,9,12-tetraoxatetradecan-1-yl)-2-[(9S)-7-(4-chlorophenyl)-4,5,13-trimethyl-3-thia-1,8,11,12-tetraazatricyclo[8.3.0.$0^{2,6}$]trideca-2(6),4,7,10,12-pentaen-9-yl]acetamide;

3-(3-chloro-2-fluorophenyl)-4-(4-chloro-2-fluorophenyl)-4-cyano-5-(2,2-dimethylpropyl)-N-{2-[2-(4-{[(1,3-trans)-3-(3-chloro-4-cyanophenoxy)-2,2,4,4-tetramethylcyclobutyl]carbamoyl}phenoxy)ethoxy]ethyl}pyrrolidine-2-carboxamide; 3-(3-chloro-2-fluorophenyl)-4-(4-chloro-2-fluorophenyl)-4-cyano-5-(2,2-dimethylpropyl)-N-[1-(4-{[(1,3-trans)-3-(3-chloro-4-cyanophenoxy)-2,2,4,4-tetramethylcyclobutyl]carbamoyl}phenyl)-1,4,7,10-tetraoxadodecan-12-yl]pyrrolidine-2-carboxamide;

3-(3-chloro -2-fluorophenyl)-4-(4-chloro-2-fluorophenyl)-4-cyano -5-(2,2-dimethylpropyl)-N-(2-{2-[2-(4-{[(1,3-trans)-3-(3-chloro-4-cyanophenoxy)-2,2,4,4-tetramethylcyclobutyl]carbamoyl}phenoxy)ethoxy]ethoxy}ethyl)pyrrolidine-2-carboxamide;

3-(3-chloro -2-fluorophenyl)-4-(4-chloro-2-fluorophenyl)-4-cyano -5-(2,2-dimethylpropyl)-N-[1-(4-{[(1,3-trans)-3-(3-chloro-4-cyanophenoxy)-2,2,4,4-tetramethylcyclobutyl]-carbamoyl}phenyl)-1,4,7,10,13,16-hexaoxaoctadecan-18-yl]pyrrolidine-2-carboxamide;

3-(3-chloro -2-fluorophenyl)-4-(4-chloro-2-fluorophenyl)-4-cyano -5-(2,2-dimethylpropyl)-N-[1-(4-{[(1,3-trans)-3-(3-chloro-4-cyanophenoxy)-2,2,4,4-tetramethylcyclobutyl]carbamoyl}phenyl)-1,4,7,10,13-pentaoxapentadecan-15-yl]pyrrolidine-2-carboxamide;

(2R,3S,4R,5S)-3-(3-chloro -2-fluorophenyl)-4-(4-chloro-2-fluorophenyl)-4-cyano -5-(2,2-dimethylpropyl)-N-[1-(4-{[(1,3-trans)-3-(3-chloro-4-cyanophenoxy)-2,2,4,4-tetramethylcyclobutyl]carbamoyl}phenyl)-1,4,7,10,13-pentaoxapentadecan-15-yl]pyrrolidine-2-carboxamide;

(2S,3R,4S,5R)-3-(3-chloro-2-fluorophenyl)-4-(4-chloro-2-fluorophenyl)-4-cyano-5-(2,2-dimethylpropyl)-N-[1-(4-{[(1r,3r)-3-(3-chloro-4-cyanophenoxy)-2,2,4,4-tetramethylcyclobutyl]carbamoyl}phenyl)-1,4,7,10,13-pentaoxapentadecan-15-yl]pyrrolidine-2-carboxamide;

3-(3-chloro-2-fluorophenyl)-4-(4-chloro-2-fluorophenyl)-N-{4-[(2-{2-[2-(2-{2-[(9S)-7-(4-chlorophenyl)-4,5,13-trimethyl-3-thia-1,8,11,12-tetraazatricyclo[8.3.0.$0^{2,6}$]trideca-2(6),4,7,10,12-pentaen-9-yl]acetamido}ethoxy)ethoxy]ethoxy}ethyl)carbamoyl]-2-methoxyphenyl}-4-cyano-5-(2,2-dimethylpropyl)pyrrolidine-2-carboxamide;

3-(3-chloro-2-fluorophenyl)-4-(4-chloro-2-fluorophenyl)-N-[4-({2-[2-(2-{(9S)-7-(4-chlorophenyl)-4,5,13-trimethyl-3-thia-1,8,11,12-tetraazatricyclo[8.3.0.$0^{2,6}$]trideca-2(6),4,7,10,12-pentaen-9-yl]acetamido}ethoxy)ethoxy]

ethyl}carbamoyl)-2-methoxyphenyl]-4-cyano -5-(2,2-dimethylpropyl)pyrrolidine-2-carboxamide; (2R,3S,4R,5S)-3-(3-chloro-2-fluorophenyl)-4-(4-chloro-2-fluorophenyl)-N-[4-({2-[2-(2-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}ethoxy)ethoxy]ethyl}carbamoyl)-2-methoxyphenyl]-4-cyano-5-(2,2-dimethylpropyl)pyrrolidine-2-carboxamide;

(2S,3R,4S,5R)-3-(3-chloro-2-fluorophenyl)-4-(4-chloro-2-fluorophenyl)-N-[4-({2-[2-(2-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}ethoxy)ethoxy]ethyl}carbamoyl)-2-methoxyphenyl]-4-cyano-5-(2,2-dimethylpropyl)pyrrolidine-2-carboxamide;

(2R,3S,4R,5S)-3-(3-chloro-2-fluorophenyl)-4-(4-chloro-2-fluorophenyl)-N-{4-[(2-{2-[2-(2-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}ethoxy)ethoxy]ethoxy}ethyl)carbamoyl]-2-methoxyphenyl}-4-cyano-5-(2,2-dimethylpropyl)pyrrolidine-2-carboxamide;

(2S,3R,4S,5R)-3-(3-chloro-2-fluorophenyl)-4-(4-chloro-2-fluorophenyl)-N-{4-[(2-{2-[2-(2-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}ethoxy) ethoxy]ethoxy}ethyl)carbamoyl]-2-methoxyphenyl}-4-cyano-5-(2,2-dimethylpropyl)pyrrolidine-2-carboxamide;

3-(3-chloro-2-fluorophenyl)-4-(4-chloro-2-fluorophenyl)-N-{4-[(14-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}-3,6,9,12-tetraoxatetradecan-1-yl)carbamoyl]-2-methoxyphenyl}-4-cyano-5-(2,2-dimethylpropyl)pyrrolidine-2-carboxamide;

3-(3-chloro -2-fluorophenyl)-4-(4-chloro-2-fluorophenyl)-4-cyano -5-(2,2-dimethylpropyl)-N-[4-({2-[2-({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methoxy)ethoxy]ethyl}carbamoyl)-2-methoxyphenyl]pyrrolidine-2-carboxamide;

3-(3-chloro-2-fluorophenyl)-4-(4-chloro-2-fluorophenyl)-N-(4-{[2-(2-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}ethoxy)ethyl]carbamoyl}-2-methoxyphenyl)-4-cyano-5-(2,2-dimethylpropyl)pyrrolidine-2-carboxamide;

(2S,3R,4S,5R)-3-(3-chloro-2-fluorophenyl)-4-(4-chloro-2-fluorophenyl)-N-(4-{[2-(2-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}ethoxy)ethyl]carbamoyl}-2-methoxyphenyl)-4-cyano-5-(2,2-dimethylpropyl)pyrrolidine-2-carboxamide;

(2R,3S,4R,5S)-3-(3-chloro-2-fluorophenyl)-4-(4-chloro-2-fluorophenyl)-N-(4-{[2-(2-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}ethoxy)ethyl]carbamoyl}-2-methoxyphenyl)-4-cyano-5-(2,2-dimethylpropyl)pyrrolidine-2-carboxamide;

(2R,3S,4R,5S)-3-(3-chloro-2-fluorophenyl)-4-(4-chloro-2-fluorophenyl)-N-{4-[(14-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}-3,6,9,12-tetraoxatetradecan-1-yl)carbamoyl]-2-methoxyphenyl}-4-cyano-5-(2,2-dimethylpropyl)pyrrolidine-2-carboxamide;

(2S,3R,4S,5R)-3-(3-chloro-2-fluorophenyl)-4-(4-chloro-2-fluorophenyl)-N-{4-[(14-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}-3,6,9,12-tetraoxatetradecan-1-yl)carbamoyl]-2-methoxyphenyl}-4-cyano-5-(2,2-dimethylpropyl)pyrrolidine-2-carboxamide;

3-(3-chloro -2-fluorophenyl)-4-(4-chloro-2-fluorophenyl)-4-cyano -5-(2,2-dimethylpropyl)-N-{4-[(1-{[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}-2,5,8,11-tetraoxatridecan-13-yl)carbamoyl]-2-methoxyphenyl}pyrrolidine-2-carboxamide;

(2R,3S,4R,5S)-3-(3-chloro -2-fluorophenyl)-4-(4-chloro-2-fluorophenyl)-4-cyano -5-(2,2-dimethylpropyl)-N-{4-[(1-{[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}-2,5,8,11-tetraoxatridecan-13-yl)carbamoyl]-2-methoxyphenyl}pyrrolidine-2-carboxamide;

(2S,3R,4S,5R)-3-(3-chloro-2-fluorophenyl)-4-(4-chloro-2-fluorophenyl)-4-cyano-5-(2,2-dimethylpropyl)-N-{4-[(1-{[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}-2,5,8,11-tetraoxatridecan-13-yl)carbamoyl]-2-methoxyphenyl}pyrrolidine-2-carboxamide;

(2R,3S,4R,5S)-3-(3-chloro -2-fluorophenyl)-4-(4-chloro-2-fluorophenyl)-4-cyano -5-(2,2-dimethylpropyl)-N-[4-({2-[2-({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methoxy)ethoxy]ethyl}carbamoyl)-2-methoxyphenyl]pyrrolidine-2-carboxamide;

(2S,3R,4S,5R)-3-(3-chloro-2-fluorophenyl)-4-(4-chloro-2-fluorophenyl)-4-cyano-5-(2,2-dimethylpropyl)-N-[4-({2-[2-({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methoxy)ethoxy]ethyl}carbamoyl)-2-methoxyphenyl]pyrrolidine-2-carboxamide;

3-(3-chloro -2-fluorophenyl)-4-(4-chloro-2-fluorophenyl)-4-cyano-5-(2,2-dimethylpropyl)-N-{4-[(2-{2-[2-({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methoxy)ethoxy]ethoxy}ethyl)carbamoyl]-2-ethoxyphenyl}pyrrolidine-2-carboxamide;

(2R,3S,4R,5S)-3-(3-chloro -2-fluorophenyl)-4-(4-chloro-2-fluorophenyl)-4-cyano -5-(2,2-dimethylpropyl)-N-{4-[(2-{2-[2-({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methoxy)ethoxy]ethoxy}ethyl)carbamoyl]-2-methoxyphenyl}pyrrolidine-2-carboxamide;

(2S,3R,4S,5R)-3-(3-chloro-2-fluorophenyl)-4-(4-chloro-2-fluorophenyl)-4-cyano-5-(2,2-dimethylpropyl)-N-{4-[(2-{2-[2-({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methoxy)ethoxy]ethoxy}ethyl)carbamoyl]-2-methoxyphenyl}pyrrolidine-2-carboxamide;

3-(3-chloro -2-fluorophenyl)-4-(4-chloro-2-fluorophenyl)-4-cyano-N-(3-{[5-(4-{3-[4-cyano-3-(trifluoromethyl)phenyl]-5,5-dimethyl-4-oxo-2-sulfanylideneimidazolidin-1-yl}phenoxy)pentyl]oxy}propyl)-5-(2,2-dimethylpropyl)pyrrolidine-2-carboxamide 3-(3-chloro -2-fluorophenyl)-4-(4-chloro-2-fluorophenyl)-4-cyano-N-{4-[(3-{[5-(4-{3-[4-cyano -3-(trifluoromethyl)phenyl]-5,5-dimethyl-4-oxo -2-sulfanylideneimidazolidin-1-yl}phenoxy)pentyl]oxy}propyl)carbamoyl]-2-methoxyphenyl}-5-(2,2-dimethylpropyl)pyrrolidine-2-carboxamide;

3-(3-chloro-2-fluorophenyl)-4-(4-chloro -2-fluorophenyl)-4-cyano-5-(2,2-dimethylpropyl)-N-(2-methoxy-4-{[2-(2-{[(1,4-trans)-4-({4-[1-benzyl-5-(dimethylamino)-1H-pyrazol-4-yl]pyrimidin-2-yl}amino)cyclohexyl]oxy}ethoxy)ethyl]carbamoyl}phenyl)pyrrolidine-2-carboxamide;

3-(3-chloro-2-fluorophenyl)-4-(4-chloro -2-fluorophenyl)-4-cyano-5-(2,2-dimethylpropyl)-N-[2-methoxy-5-({2-[2-(2-{[(1,4-trans)-4-({4-[1-benzyl-5-(dimethylamino)-1H-pyrazol-4-yl]pyrimidin-2-yl}amino)cyclohexyl]oxy}ethoxy)ethoxy]ethyl}carbamoyl)phenyl]pyrrolidine-2-carboxamide;

3-(3-chloro-2-fluorophenyl)-4-(4-chloro-2-fluorophenyl)-4-cyano-N-[4-({1-[4-(3-{[(4,6-dimethyl-2-oxo-1,2-dihydropyridin-3-yl)methyl]carbamoyl}-5-[ethyl(oxan-4-yl)amino]-4-methylphenyl)phenyl]-1,4,7,10-tetraoxadodecan-12-yl}carbamoyl)-2-methoxyphenyl]-5-(2,2-dimethylpropyl)pyrrolidine-2-carboxamide;

3-(3-chloro-2-fluorophenyl)-4-(4-chloro -2-fluorophenyl)-4-cyano-5-(2,2-dimethylpropyl)-N-[2-methoxy-4-({1-[(1,4-trans)-4-({4-[1-benzyl-5-(dimethylamino)-1H-pyrazol-4-yl]pyrimidin-2-yl}amino)cyclohexyl]-1,4,7,10-tetraoxadodecan-12-yl}carbamoyl)phenyl]pyrrolidine-2-carboxamide;

3-(3-chloro-2-fluorophenyl)-4-(4-chloro -2-fluorophenyl)-4-cyano-5-(2,2-dimethylpropyl)-N-[2-methoxy-5-({1-[(1,4-trans)-4-({4-[1-benzyl-5-(dimethylamino)-1H-pyrazol-4-yl]pyrimidin-2-yl}amino)cyclohexyl]-1,4,7,10,13-pentaoxapentadecan-15-yl}carbamoyl)phenyl]pyrrolidine-2-carboxamide; and 3-(3-chloro-2-fluorophenyl)-4-(4-chloro-2-fluorophenyl)-4-cyano-N-[4-({1-[4-(3-{[(4,6-dimethyl-2-oxo-1,2-dihydropyridin-3-yl)methyl]carbamoyl}-5-[ethyl(oxan-4-yl)amino]-4-methylphenyl)phenyl]-1,4,7,10,13,16-hexaoxaoctadecan-18-yl}carbamoyl)-2-methoxyphenyl]-5-(2,2-dimethylpropyl)pyrrolidine-2-carboxamide, or a pharmaceutically acceptable salt, enantiomer, stereoisomer, solvate, polymorph or prodrug thereof.

In an additional aspect, the description provides a composition comprising an effective amount of a compound as disclosed herein.

In an additional aspect, the description provides a pharmaceutical composition comprising an effective amount of a compound as described herein and a pharmaceutically acceptable carrier, additive, and/or excipient.

In certain embodiments the compositions described herein comprise an additional bioactive agent, e.g., an anticancer agent.

In any of the aspects or embodiments described herein, the described bifunctional compounds or compositions can comprise an anticancer agent is selected from the group consisting of everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, an mTORC1/2 inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdRi KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolylj-quinolone, vatalanib, AG-013736, AVE-0005, the acetate salt of [D-Ser(Bu t) 6, Azgly 10] (pyro-Glu-His-Trp-Ser-Tyr-D-Ser(Bu t)-Leu-Arg-Pro-Azgly-$NH_2$ acetate $[C_{59}H_{84}N_{18}Oi_4$ —$(C_2H_4O_2)_X$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, lonafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevac, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

In an additional aspect, the description provides a method for inducing degradation of a target protein in a cell comprising administering an effective amount of the compounds disclosed in any of the aspects to the cell.

In yet another aspect, the description provides a method for treating a disease state or condition in a patient wherein dysregulated protein activity is responsible for said disease state or condition, said method comprising administering an effective amount of a compound disclosed in any of the aspects, wherein the disease state or condition is cancer.

In certain embodiments of the above mentioned aspect, the cancer is squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; multiple myeloma, sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor or teratocarcinomas, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

Protein Degradation Biological Assays

The following biological assays were performed to evaluate the protein degradation in various cell types using representative compounds disclosed. In each assay, cells were treated with varying amounts of compounds encompassed by the current disclosure as shown in the Table. The degradation of the following proteins were evaluated: bromodomain-containing protein 4 (BRD4), androgen receptor (AR), c-Myc, c-Jun N-terminal kinases (JNK), and enhancer of zeste homolog 2 (EZH2).

BRD4 Western Blot

VCaP cells were chased from ATCC and cultured in Dulbecco's Modified Eagle's Medium (ATCC), supplemented with 10% FBS (ATCC) and Penicillin/Streptomycin (Life Technologies). DMSO control and compound treatments (0.03 μM to 1 μM) were performed in 12-well plates for 16 h. cells were harvested, and lysed in RIPA buffer (50 mM Tris pH8, 150 mM NaCl, 1% Tx-100, 0.1% SDS, 0.5% sodium deoxycholate) supplemented with protease and phosphatase inhibitors. Lysates were clarified at 16,000 g for 10 minutes, and protein concentration was determined. Equal amount of protein (20 μg) was subjected to SDS-PAGE analysis and followed by immunoblotting according to standard protocols. The antibodies used were BRD4 (Cell signaling #13440), and Actin (Sigma #5441). Detection reagents were Clarity Western ELC substrate (Bio-rad #170-5060).

AR ELISA Assay

VCaP cells were chased from ATCC and cultured in Dulbecco's Modified Eagle's Medium (ATCC), supplemented with 10% FBS (ATCC) and Penicillin/Streptomycin (Life Technologies). DMSO control and compound treatments (0.0001 μM to 1 μM) were performed in 96-well plates for 16 h. cells were harvested, and lysed with Cell Lysis Buffer (catalog #9803) (20 mM Tris-HCl, pH 7.5, 150 mM NaCl, 1 mM $Na_2EDTA$, 1 mM EGTA, 1% Triton, 2.5 mM sodium pyrophosphate, 1 mM B-glycerophosphate, 1 mM $Na_3VO_4$, 1 μg/mL leupeptin. Lysates were clarified at 16,000 g for 10 minutes, and loaded into PathScan AR ELISA (Cell Signaling Catalog #12850). The PathScan Total Androgen Receptor Sanwich ELISA Kit is a solid phase sandwich enzyme-linked immunosorbent assay (ELISA) that detects endogenous levels of total androgen receptor protein. An Androgen Receptor Rabbit mAb has been coated onto the microwells. After incubation with cell lysates, androgen receptor protein is captured by the coated antibody. Following extensive washing, an Androgen receptor Mouse Detection mAbis added to detect the captured androgen receptor protein. Anti-mouse IgG, HRP-linked Antibody is then used to recognize the bound detection antibody. HRP substrate, TMB, is added to develop color. The magnitude of absorbance for the developed color is proportional to the quantity of total androgen receptor protein.

c-Myc ELISA Assay

22Rv-1 cells were purchased from ATCC and cultured in RPMI with 10% FBS. Cells were harvested using trypsin (Gibco #25200-114), counted and seeded at 30,000 cells/well at a volume of 75 μL/well in RPMI with 10% FBS in 96-well plates. Cells were dosed with compounds diluted in 0.1% DMSO, incubated for 18 h, then washed and lysed in 50 μL RIPA buffer (50 mM Tris pH 8, 150 mM NaCl, 1% Tx-100, 0.1% SDS, 0.5% sodium deoxycholate) supplemented with protease and phosphatase inhibitors. The lysates were clarified at 4000 rpm at 4° C. for 10 minutes. Aliquots were added into a 96-well ELISA plate of Novex Human c-Myc ELISA kit from Life Technologies (catalog #KH02041). Into each well was added 50 μL of c-Myc detection antibody. Plates were incubated at room temperature for 3 h, washed with ELISA wash buffer, followed by addition of 100 μL of the anti-rabbit IgG-HRP secondary antibody and 30 minutes of incubation. The plates were washed with ELISA wash buffer followed by addition of 100

μL of TMB to each well. Color change was monitored every 5 minutes. Stop solution (100 μL) was added and plates were read at 450 nM.

JNK and EZH2 Western Blot Assay

Cells were purchased from ATCC and cultured in Dulbecco's Modified Eagle's Medium (ATCC), supplemented with 10% FBS (ATCC) and Penicillin/Streptomycin (Life Technologies). DMSO control and compound treatments (0.003 μM, 0.01 μM, 0.03 μM and 0.1 μM) were performed in 12-well plates for 16 h. Cells were harvested, and lysed in RIPA buffer (50 mM Tris pH8, 150 mM NaCl, 1% Tx-100, 0.1% SDS, 0.5% sodium deoxycholate) supplemented with protease and phosphatase inhibitors. Lysates were clarified at 16,000 g for 10 minutes, and protein concentration was determined. Equal amount of protein (20 μg) was subjected to SDS-PAGE analysis and followed by immunoblotting according to standard protocols.

Figure 1B:
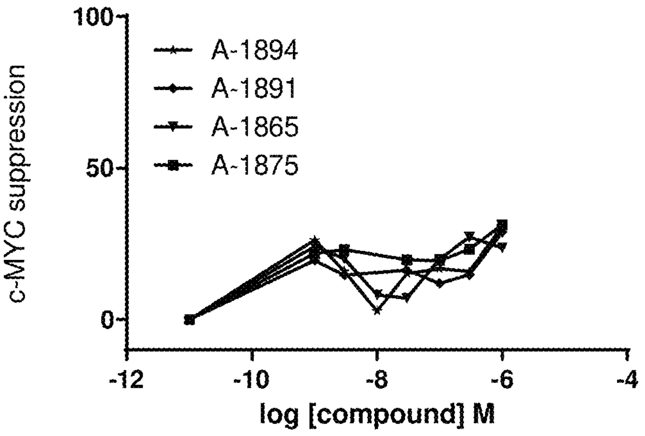

Synthesized molecules were assayed for protein degradation, suppression, and regulation and growth inhibition of cancer cells (FIGS. 1A and 1B). c-Myc suppression was observed in 22rv1 cells by chimeric molecules, where BRD4 ligand is connected through linkers to MDM2 ligands using partial structural motif in RG7388. Chimeric molecules with inactive MDM2 ligand (enantiomer of the active counterpart) demonstrated no c-Myc suppression across a range of concentrations, while chimeric molecules with active MDM2 ligand showed dose dependent c-Myc suppression, suggesting BRD4 degradation mediated by MDM2 E3 ligase ubiquitination mechanism, as c-Myc is directly regulated by the level of BRD4. Chimeric molecules with MDM2 ligand as a racemate displayed similar c-Myc suppression as observed in those containing active MDM2 ligand.

Figure 2:
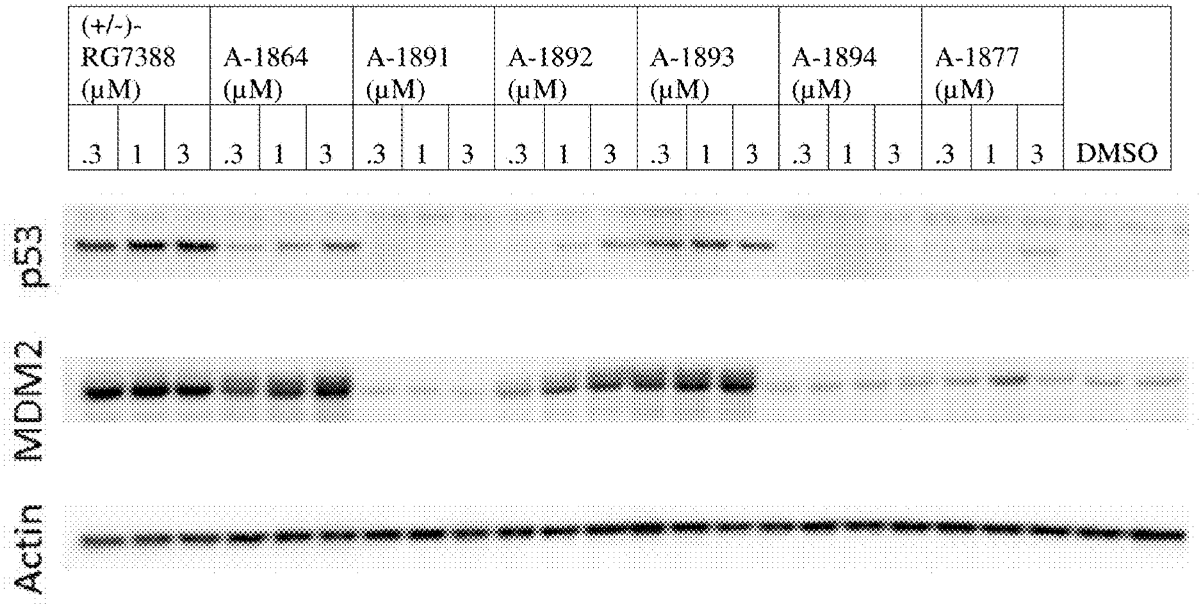
FIG. 2: Western blot of HCT116 cells treated with chimeric molecules, where BRD4 ligand is connected through linkers to MDM2 ligands using partial structural motif in RG7388. Chimeric molecules with inactive MDM2 ligand (A-1891, A-1894) demonstrated no p53 level increase and no MDM2 up-regulation, while chimeric molecules with active MDM2 ligand (A-1864, A1892 and A-1893, A-1877 carried a racemic MDM2 binding ligand) showed dose dependent p53 level increase and up-regulation of MDM2, suggesting chimeric molecules with BRD4 binding fragment and MDM2 binding fragment connected through a linker can function as small molecule MDM2 antagonist in stabilizing p53. The less significant MDM2 up regulation and p53 level increase is due to the chimeric molecule action mechanism of not only binding to MDM2 to block p53-MDM2 interaction but also degrading MDM2. Therefore, the net MDM2 up-regulation is significantly less, which also translated to p53 level due to MDM2-p53 feedback loop.

Western blot of HCT116 cells treated with chimeric molecules was performed, where BRD4 ligand is connected through linkers to MDM2 ligands using partial structural motif in RG7388 (FIG. 2). Chimeric molecules with inactive MDM2 ligand (A-1891, A-1894) demonstrated no p53 level increase and no MDM2 up-regulation, while chimeric molecules with active MDM2 ligand (A-1864, A1892 and A-1893, A-1877 carried a racemic MDM2 binding ligand) showed dose dependent p53 level increase and up-regulation of MDM2, suggesting chimeric molecules with BRD4 binding fragment and MDM2 binding fragment connected through a linker can function as small molecule MDM2 antagonist in stabilizing p53. The less significant MDM2 up regulation and p53 level increase is due to the chimeric molecule action mechanism of not only binding to MDM2 to block p53-MDM2 interaction but also degrading MDM2. Therefore, the net MDM2 up-regulation is significantly less, which also translated to p53 level due to MDM2-p53 feedback loop.

Figure 3:
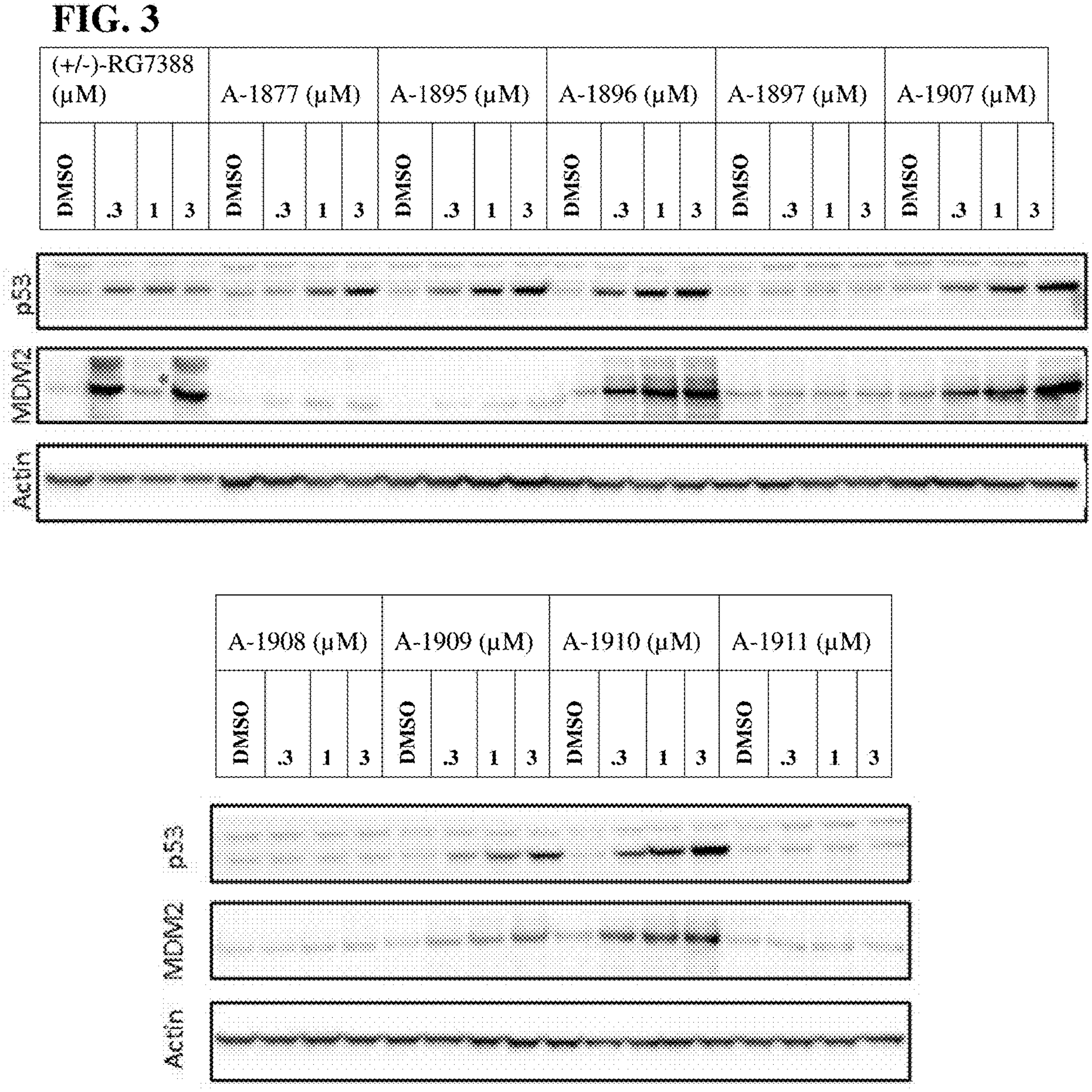
FIG. 3: Western blot of HCT116 cells treated with chimeric molecules, where MDM2 ligand (using partial structural motif of RG7388) is connected through linkers to VHL ligand. Chimeric molecules with inactive MDM2 ligand (A-1897, A1908, and A-1911) demonstrated no p53 level increase and no MDM2 up-regulation, while chimeric molecules with active MDM2 ligand (A-1896, A-1907, and A-1910, with A-1877, A-1895, and A-1909 carrying a racemic MDM2 binding ligand) showed dose dependent p53 level increase.

Western blot of HCT116 cells treated with chimeric molecules (FIG. 3), where MDM2 ligand (using partial structural motif of RG7388) is connected through linkers to VHL ligand. Chimeric molecules with inactive MDM2 ligand (A-1897, A1908, and A-1911) demonstrated no p53 level increase and no MDM2 up-regulation, while chimeric molecules with active MDM2 ligand (A-1896, A-1907, and A-1910, with A-1877, A-1895, and A-1909 carrying a racemic MDM2 binding ligand) showed dose dependent p53 level increase.

Figure 4:
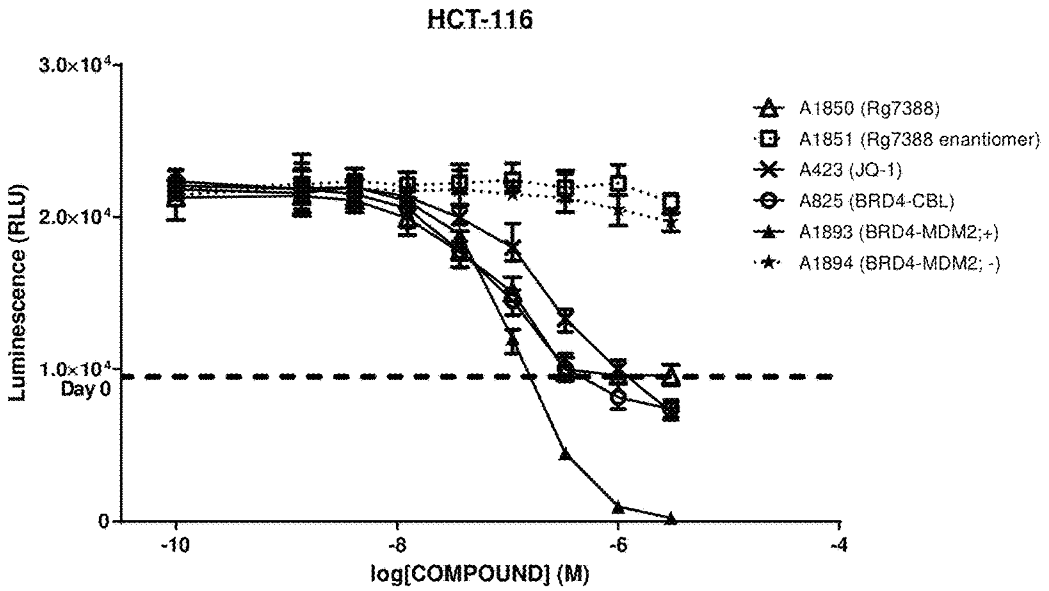
FIG. 4: Inhibition of cell proliferation in HCT116 and 22rv1 cells by chimeric molecules containing MDM2 binding motif. In $p53^{WT}$ HCT-116 colon cancer cell lines, MDM2-recruiting BRD-4 PROTAC with active MDM2 binding moiety (A-1893) caused very potent growth inhibition in comparison with the MDM2-recruiting BRD-4 PROTAC with inactive MDM2 binding moiety (A-1894). In this cell growth assay, BRD4-Cereblon PROTAC A-825, MDM2 antagonist RG7388 (A-1850), the racemate of RG7388 (A-1851) and JQ1 were included as a direct comparison.

In $p53^{WT}$ HCT-116 colon cancer cell lines, MDM2-recruiting BRD-4 PROTAC with active MDM2 binding moiety (A-1893) caused very potent growth inhibition in comparison with the MDM2-recruiting BRD-4 PROTAC with inactive MDM2 binding moiety (A-1894) (FIG. 4). In this cell growth assay, BRD4-Cereblon PROTAC A-825, MDM2 antagonist RG7388 (A-1850), the racemate of RG7388 (A-1851) and JQ1 were included as a direct comparison.

Figure 5:
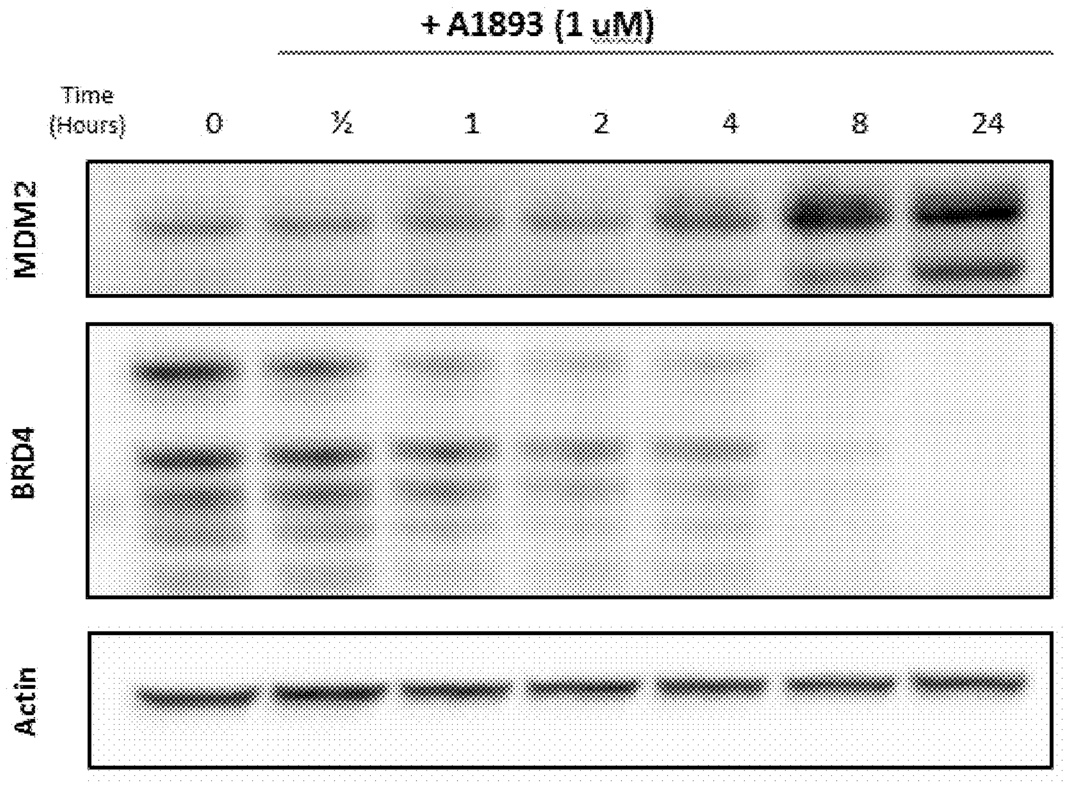
FIG. 5: Time course of BRD4 degradation caused by BRD4-MDM2 chimeric compound (A-1893) in human colon cancer cell line HCT116.
Figure 6:
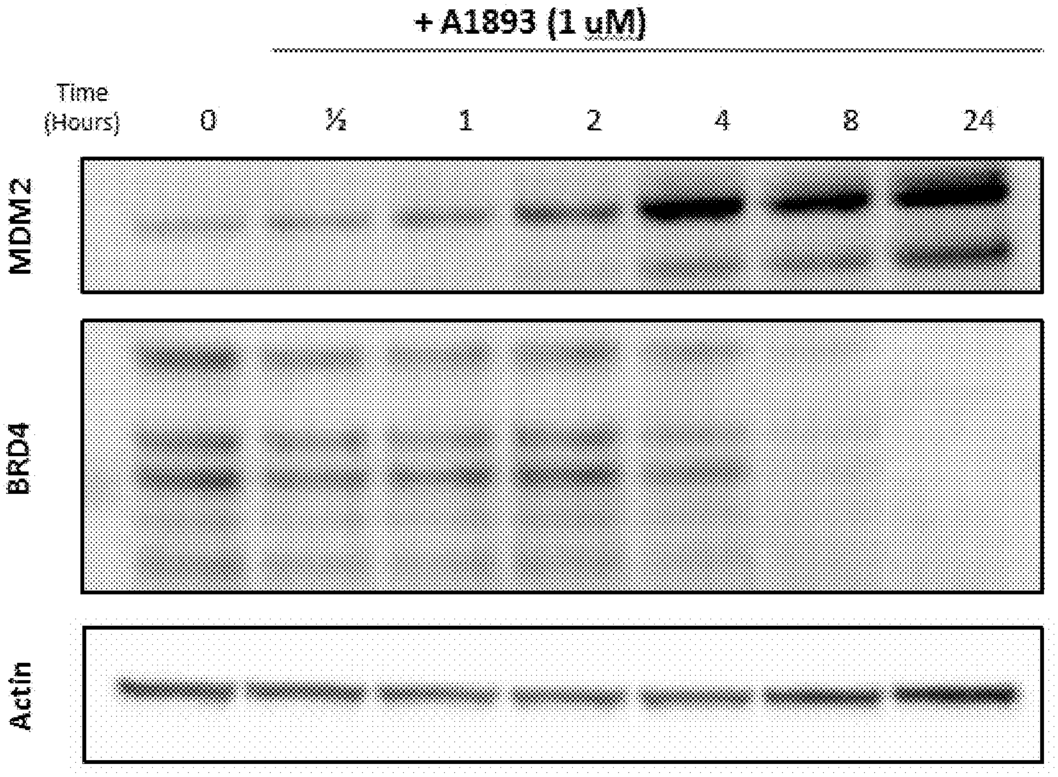
FIG. 6: Time course of BRD4 degradation caused by BRD4-MDM2 chimeric compound (A-1893) in human lung cancer cell line A549.

Time course of BRD4 degradation caused by BRD4-MDM2 chimeric compound (A-1893) in human colon cancer cell line HCT116 (FIG. 5) and human lung cancer cell line A549. (FIG. 6)

Following table is a representative of the degradation activity of some exemplary compounds. The degradation activities for target proteins are categorized as following: A (0 to 25% degradation at 1 μM); B (25 to 50% degradation at 1 μM) and C (larger than 50% degradation at 1 μM).

| | Observed (m/z) from | Degradation activity | | | | |
|---|---|---|---|---|---|---|
| Example | LC/MS | BRD4 | AR | JNK | EZH2 | ChemicalName |
| A680 | 1082 | | A | | | 4-(3-{4-[2-(2-{4-[2-(4-tert-butyl-2-ethoxyphenyl)-4,5-bis(4-chlorophenyl)-4,5-dimethyl-4,5-dihydro-1H-imidazole-1-carbonyl]piperazin-1-yl}ethoxy)ethoxy]phenyl}-4,4-dimethyl-5-oxo-2-sulfanylideneimidazolidin-1-yl)-2-(trifluoromethyl)benzonitrile |
| A702 | 1260 | | B | | | 4-(3-{4-[(17-{4-[2-(4-tert-butyl-2-ethoxyphenyl)-4,5-bis(4-chlorophenyl)-4,5-dimethyl-4,5-dihydro-1H-imidazole-1-carbonyl]piperazin-1-yl}-3,6,9,12,15-pentaoxaheptadecan-1-yl)oxy]phenyl}-4,4-dimethyl-5-oxo-2-sulfanylideneimidazolidin-1-yl)-2-(trifluoromethyl)benzonitrile |
| A1283 | 1135, 1137 (M + Na) | B | | | | N-(17-{[3-(3-chloro-2-fluorophenyl)-4-(4-chloro-2-fluorophenyl)-4-cyano-5-(2,2-dimethylpropyl)pyrrolidin-2-yl]formamido}-3,6,9,12,15-pentaoxaheptadecan-1-yl)-2-[(9S)-7-(4-chlorophenyl)-4,5,13-trimethyl-3-thia-1,8,11,12-tetraazatricyclo-[8.3.0.0$^{2}$,$^{6}$]trideea-2(6),4,7,10,12-pentaen-9-yl]acetamide |

-continued

| Example | Observed (m/z) from LC/MS | Degradation activity BRD4 | AR | JNK | EZH2 | ChemicalName |
|---|---|---|---|---|---|---|
| A1306 | 1025, 1027 | B | | | | N-(2-{2-[2-(2-{[3-(3-chloro-2-fluorophenyl)-4-(4-chloro-2-fluorophenyl)-4-cyano-5-(2,2-dimethylpropyl)pyrrolidin-2-yl]formamido}ethoxy)ethoxy]ethoxy}ethyl)-2-[(9S)-7-(4-chlorophenyl)-4,5,13-trimethyl-3-thia-1,8,11,12-tetraazatricyclo[8.3.0.0$^{2}$,$^{6}$]trideca-2(6),4,7,10,12-pentaen-9-yl]acetamide |
| A1307 | 1069, 1071 | C | | | | N-(14-{[3-(3-chloro-2-fluorophenyl)-4-(4-chloro-2-fluorophenyl)-4-cyano-5-(2,2-dimethylpropyl)pyrrolidin-2-yl]formamido}-3,6,9,12-tetraoxatetradecan-1-yl)-2-[(9S)-7-(4-chlorophenyl)-4,5,13-trimethyl-3-thia-1,8,11,12-tetraazatricyclo-[8.3.0.0$^{2}$,$^{6}$]trideca-2(6),4,7,10,12-pentaen-9-yl]acetamide |
| A1571 | 934, 936 | | A | | | 3-(3-chloro-2-fluorophenyl)-4-(4-chloro-2-fluorophenyl)-4-cyano-5-(2,2-dimethylpropyl)-N-{2-[2-(4-{[(1,3-trans)-3-(3-chloro-4-cyanophenoxy)-2,2,4,4-tetramethylcyclobutyl]carbamoyl}phenoxy)ethoxy]ethyl}pyrrolidine-2-carboxamide |
| A1603 | 1024, 1026 | | A | | | 3-(3-chloro-2-fluorophenyl)-4-(4-chloro-2-fluorophenyl)-4-cyano-5-(2,2-dimethylpropyl)-N-[1-(4-{[(1,3-trans)-3-(3-chloro-4-cyanophenoxy)-2,2,4,4-tetramethylcyclobutyl]carbamoyl}phenyl)-1,4,7,10-tetraoxadodecan-12-yl]pyrrolidine-2-carboxamide |
| A1621 | 980, 982 | | A | | | 3-(3-chloro-2-fluorophenyl)-4-(4-chloro-2-fluorophenyl)-4-cyano-5-(2,2-dimethylpropyl)-N-(2-{2-[2-(4-{[(1,3-trans)-3-(3-chloro-4-cyanophenoxy)-2,2,4,4-tetramethylcyclobutyl]carbamoyl}phenoxy)ethoxy]ethoxy}ethyl)pyrrolidine-2-carboxamide |
| A1688 | 1112, 1114 | | A | | | 3-(3-chloro-2-fluorophenyl)-4-(4-chloro-2-fluorophenyl)-4-cyano-5-(2,2-dimethylpropyl)-N-[1-(4-{[(1,3-trans)-3-(3-chloro-4-cyanophenoxy)-2,2,4,4-tetramethylcyclobutyl]-carbamoyl}phenyl)-1,4,7,10,13,16-hexaoxaoctadecan-18-yl]pyrrolidine-2-carboxamide |
| A1717 | 1068, 1070 | | B | | | 3-(3-chloro-2-fluorophenyl)-4-(4-chloro-2-fluorophenyl)-4-cyano-5-(2,2-dimethylpropyl)-N-[1-(4-{[(1,3-trans)-3-(3-chloro-4-cyanophenoxy)-2,2,4,4-tetramethylcyclobutyl]carbamoyl}phenyl)-1,4,7,10,13-pentaoxapentadecan-15-yl]pyrrolidine-2-carboxamide |
| A1720 | 1068, 1070 | | B | | | (2R,3S,4R,5S)-3-(3-chloro-2-fluorophenyl)-4-(4-chloro-2-fluorophenyl)-4-cyano-5-(2,2-dimethylpropyl)-N-[1-(4-{[(1,3-trans)-3-(3-chloro-4-cyanophenoxy)-2,2,4,4-tetramethylcyclobutyl]carbamoyl}phenyl)-1,4,7,10,13-pentaoxapentadecan-15-yl]pyrrolidine-2-carboxamide |
| A1735 | 1068, 1070 | | A | | | (2S,3R,4S,5R)-3-(3-chloro-2-fluorophenyl)-4-(4-chloro-2-fluorophenyl)-4-cyano-5-(2,2-dimethylpropyl)-N-[1-(4-{[(1r,3r)-3-(3-chloro-4-cyanophenoxy)-2,2,4,4-tetramethylcyclobutyl]carbamoyl]phenyl)-1,4,7,10,13-pentaoxapentadecan-15-yl]pyrrolidine-2-carboxamide |

-continued

| Example | Observed (m/z) from LC/MS | Degradation activity BRD4 | AR | JNK | EZH2 | ChemicalName |
|---|---|---|---|---|---|---|
| A1829 | 1174, 1176 | B | | | | 3-(3-chloro-2-fluorophenyl)-4-(4-chloro-2-fluorophenyl)-N-{4-[(2-{2-[2-(2-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}ethoxy)ethoxy]ethoxy}ethyl)carbamoyl]-2-methoxyphenyl}-4-cyano-5-(2,2-dimethylpropyl)pyrrolidine-2-carboxamide |
| A1863 | 1130, 1132 | B | | | | 3-(3-chloro-2-fluorophenyl)-4-(4-chloro-2-fluorophenyl)-N-[4-({2-[2-(2-{2-[(9S)-7-(4-chlorophenyl)-4,5,13-trimethyl-3-thia-1,8,11,12-tetraazatricyclo-[8.3.0.0$^{2,6}$]trideca-2(6),4,7,10,12-pentaen-9-yl]acetamido}ethoxy)ethoxy]-ethyl}carbamoyl)-2-methoxyphenyl]-4-cyano-5-(2,2-dimethylpropyl)pyrrolidine-2-carboxamide |
| A1864 | 1130 , 1132 | B | | | | (2R,3S,4R,5S)-3-(3-chloro-2-fluorophenyl)-4-(4-chloro-2-fluorophenyl)-N-[4-({2-[2-(2-{2-[(9S)-7-(4-chlorophenyl)-4,5,13-trimethyl-3-thia-1,8,11,12-tetraazatricyclo-[8.3.0.0$^{2,6}$]trideca-2(6),4,7,10,12-pentaen-9-yl]acetamido}ethoxy)ethoxy]ethyl}-carbamoyl)-2-methoxyphenyl]-4-cyano-5-(2,2-dimethylpropyl)pyrrolidine-2-carboxamide |
| A1865 | 1130 , 1132 | A | | | | (2S,3R,4S,5R)-3-(3-chloro-2-fluorophenyl)-4-(4-chloro-2-fluorophenyl)-N-[4-({2-[2-(2-{2-[(9S)-7-(4-chlorophenyl)-4,5,13-trimethyl-3-thia-1,8,11,12-tetraazatricyclo-[8.3.0.0$^{2,6}$]trideca-2(6),4,7,10,12-pentaen-9-yl]acetamido}ethoxy)ethoxy]ethyl}-carbamoyl)-2-methoxyphenyl]-4-cyano-5-(2,2-dimethylpropyl)pyrrolidine-2-carboxamide |
| A1874 | 1172, 1174 | B | | | | (2R,3S,4R,5S)-3-(3-chloro-2-fluorophenyl)-4-(4-chloro-2-fluorophenyl)-N-{4-[(2-{2-[2-(2-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}ethoxy)ethoxy]ethoxy}ethyl)carbamoyl]-2-methoxyphenyl}-4-cyano-5-(2,2-dimethylpropyl)pyrrolidine-2-carboxamide |
| A1875 | 1172, 1174 | A | | | | (2S,3R,4S,5R)-3-(3-chloro-2-fluorophenyl)-4-(4-chloro-2-fluorophenyl)-N-{4-[(2-{2-[2-(2-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}ethoxy)ethoxy]ethoxy}ethyl)carbamoyl]-2-methoxyphenyl}-4-cyano-5-(2,2-dimethylpropyl)pyrrolidine-2-carboxamide |

-continued

| Example | Observed (m/z) from LC/MS | Degradation activity BRD4 | AR | JNK | EZH2 | ChemicalName |
|---|---|---|---|---|---|---|
| A1876 | 1216, 1218 | C | | | | 3-(3-chloro-2-fluorophenyl)-4-(4-chloro-2-fluorophenyl)-N-{4-[(14-{2-[(9S)-7-(4-chlorophenyl)-4,5,13-trimethyl-3-thia-1,8,11,12-tetraazatricyclo[8.3.0.0$^{2,6}$]-trideca-2(6),4,7,10,12-pentaen-9-yl]acetamido}-3,6,9,12-tetraoxatetradecan-1-yl)carbamoyl]-2-methoxyphenyl}-4-cyano-5-(2,2-dimethylpropyl)pyrrolidine-2-carboxamide |
| A1877 | 1173, 1175 | | | | | 3-(3-chloro-2-fluorophenyl)-4-(4-chloro-2-fluorophenyl)-4-cyano-5-(2,2-dimethylpropyl)-N-[4-({2-[2-({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methoxy)ethoxy]ethyl}carbamoyl)-2-methoxyphenyl]pyrrolidine-2-carboxamide |
| A1890 | 1084, 1086 | C | | | | 3-(3-chloro-2-fluorophenyl)-4-(4-chloro-2-fluorophenyl)-N-(4-{[2-(2-{2-[(9S)-7-(4-chlorophenyl)-4,5,13-trimethyl-3-thia-1,8,11,12-tetraazatricyclo[8.3.0.0$^{2,6}$]-trideca-2(6),4,7,10,12-pentaen-9-yl]acetamido}ethoxy)ethyl]carbamoyl}-2-methoxyphenyl)-4-cyano-5-(2,2-dimethylpropyl)pyrrolidine-2-carboxamide |
| A1891 | 1084, 1086 | A | | | | (2S,3R,4S,5R)-3-(3-chloro-2-fluorophenyl)-4-(4-chloro-2-fluorophenyl)-N-(4-{[2-(2-{2-[(9S)-7-(4-chlorophenyl)-4,5,13-trimethyl-3-thia-1,8,11,12-tetraazatricyclo[8.3.0.0$^{2,6}$]-trideca-2(6),4,7,10,12-pentaen-9-yl]acetamido}ethoxy)ethyl]carbamoyl}-2-methoxyphenyl)-4-cyano-5-(2,2-dimethylpropyl)pyrrolidine-2-carboxamide |
| A1892 | 1084, 1086 | C | | | | (2R,3S,4R,5S)-3-(3-chloro-2-fluorophenyl)-4-(4-chloro-2-fluorophenyl)-N-(4-{[2-(2-{2-[(9S)-7-(4-chlorophenyl)-4,5,13-trimethyl-3-thia-1,8,11,12-tetraazatricyclo[8.3.0.0$^{2,6}$]-trideca-2(6),4,7,10,12-pentaen-9-yl]acetamido}ethoxy)ethyl]carbamoyl}-2-methoxyphenyl)-4-cyano-5-(2,2-dimethylpropyl)pyrrolidine-2-carboxamide |
| A1893 | 1216, 1218 | C | | | | (2R,3S,4R,5S)-3-(3-chloro-2-fluorophenyl)-4-(4-chloro-2-fluorophenyl)-N-{4-[(14-{2-[(9S)-7-(4-chlorophenyl)-4,5,13-trimethyl-3-thia-1,8,11,12-tetraazatricyclo[8.3.0.0$^{2,6}$]-trideca-2(6),4,7,10,12-pentaen-9-yl]acetamido}-3,6,9,12-tetraoxatetradecan-1-yl)carbamoyl]-2-methoxyphenyl}-4-cyano-5-(2,2-dimethylpropyl)pyrrolidine-2-carboxamide |
| A1894 | 1216, 1218 | A | | | | (2S,3R,4S,5R)-3-(3-chloro-2-fluorophenyl)-4-(4-chloro-2-fluorophenyl)-N-{4-[(14-{2-[(9S)-7-(4-chlorophenyl)-4,5,13-trimethyl-3-thia-1,8,11,12-tetraazatricyclo[8.3.0.0$^{2,6}$]-trideca-2(6),4,7,10,12-pentaen-9-yl]acetamido}-3,6,9,12-tetraoxatetradecan-1-yl)carbamoyl]-2-methoxyphenyl}-4-cyano-5-(2,2-dimethylpropyl)pyrrolidine-2-carboxamide |

-continued

| Example | Observed (m/z) from LC/MS | Degradation activity BRD4 | AR | JNK | EZH2 | ChemicalName |
|---|---|---|---|---|---|---|
| A1895 | 1261, 1263 | | | | | 3-(3-chloro-2-fluorophenyl)-4-(4-chloro-2-fluorophenyl)-4-cyano-5-(2,2-dimethylpropyl)-N-{4-[(1-{[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}-2,5,8,11-tetraoxatridecan-13-yl)carbamoyl]-2-methoxyphenyl}pyrrolidine-2-carboxamide |
| A1896 | 1261, 1263 | | | | | (2R,3S,4R,5S)-3-(3-chloro-2-fluorophenyl)-4-(4-chloro-2-fluorophenyl)-4-cyano-5-(2,2-dimethylpropyl)-N-{4-[(1-{[(2S)-1-[(2S,4R)-4-hydroxy-2-({[4-(4-methyl-1,3-thiazol-5-yl)phenyl]methyl}-carbamoyl)pyrrolidin-1-yl]-3,3-dimethyl-1-oxobutan-2-yl] carbamoyl}-2,5,8,11-tetraoxatridecan-13-yl)carbamoyl]-2-methoxyphenyl}pyrrolidine-2-carboxamide |
| A1897 | 1261, 1263 | | | | | (2S,3R,4S,5R)-3-(3-chloro-2-fluorophenyl)-4-(4-chloro-2-fluorophenyl)-4-cyano-5-(2,2-dimethylpropyl)-N-{4-[(1-{[(2S)-1-[(2S,4R)-4-hydroxy-2-({[4-(4-methyl-1,3-thiazol-5-yl)phenyl]methyl}-carbamoyl)pyrrolidin-1-yl]-3,3-dimethyl-1-oxobutan-2-yl] carbamoyl}-2,5,8,11-tetraoxatridecan-13-yl)carbamoyl]-2-methoxyphenyl}pyrrolidine-2-carboxamide |
| A1907 | 1173, 1175 | | | | | (2R,3S,4R,5S)-3-(3-chloro-2-fluorophenyl)-4-(4-chloro-2-fluorophenyl)-4-cyano-5-(2,2-dimethylpropyl)-N-[4-({2-[2-{[(2S)-1-[(2S,4R)-4-hydroxy-2-({[4-(4-methyl-1,3-thiazol-5-yl)phenyl]methyl}-carbamoyl)pyrrolidin-1-yl]-3,3-dimethyl-1-oxobutan-2-yl]carbamoyl}methoxy)-ethoxy]ethyl}carbamoyl)-2-methoxyphenyl]pyrrolidine-2-carboxamide |
| A1908 | 1173, 1175 | | | | | (2S,3R,4S,5R)-3-(3-chloro-2-fluorophenyl)-4-(4-chloro-2-fluorophenyl)-4-cyano-5-(2,2-dimethylpropyl)-N-[4-({2-[2-{[(2S)-1-[(2S,4R)-4-hydroxy-2-({[4-(4-methyl-1,3-thiazol-5-yl)phenyl]methyl}-carbamoyl)pyrrolidin-1-yl]-3,3-dimethyl-1-oxobutan-2-yl]carbamoyl}methoxy)-ethoxy]ethyl}carbamoyl)-2-methoxyphenyl]pyrrolidine-2-carboxamide |
| A1909 | 1217, 1219 | | | | | 3-(3-chloro-2-fluorophenyl)-4-(4-chloro-2-fluorophenyl)-4-cyano-5-(2,2-dimethylpropyl)-N-{4-[(2-{2-[2-({[(2S)-1-[2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methoxy)ethoxy]ethoxy}ethyl)carbamoyl]-2-methoxyphenyl}-pyrrolidine-2-carboxamide |

-continued

| Example | Observed (m/z) from LC/MS | Degradation activity BRD4 | AR | JNK | EZH2 | ChemicalName |
|---|---|---|---|---|---|---|
| A1910 | 1217, 1219 | | | | | (2R,3S,4R,5S)-3-(3-chloro-2-fluorophenyl)-4-(4-chloro-2-fluorophenyl)-4-cyano-5-(2,2-dimethylpropyl)-N-{4-[(2-{2-[2-({[(2S)-1-[(2S,4R)-4-hydroxy-2-({[4-(4-methyl-1,3-thiazol-5-yl)phenyl]methyl}-carbamoyl)pyrrolidin-1-yl]-3,3-dimethyl-1-oxobutan-2-yl]carbamoyl}methoxy)-ethoxy]ethoxy}ethyl)carbamoyl]-2-methoxyphenyl}pyrrolidine-2-carboxamide |
| A1911 | 1217, 1219 | | | | | (2S,3R,4S,5R)-3-(3-chloro-2-fluorophenyl)-4-(4-chloro-2-fluorophenyl)-4-cyano-5-(2,2-dimethylpropyl)-N-{4-[(2-{2-[2-({[(2S)-1-[(2S,4R)-4-hydroxy-2-({[4-(4-methyl-1,3-thiazol-5-yl)phenyl]methyl}-carbamoyl)pyrrolidin-1-yl]-3,3-dimethyl-1-oxobutan-2-yl]carbamoyl}methoxy)-ethoxy]ethoxy}ethyl)carbamoyl]-2-methoxyphenyl}pyrrolidine-2-carboxamide |
| A2434 | 997, 999 | | C | | | 3-(3-chloro-2-fluorophenyl)-4-(4-chloro-2-fluorophenyl)-4-cyano-N-(3-{[5-(4-{3-[4-cyano-3-(trifluoromethyl)phenyl]-5,5-dimethyl-4-oxo-2-sulfanylideneimidazolidin-1-yl}phenoxy)pentyl]oxy}propyl)-5-(2,2-dimethylpropyl)pyrrolidine-2-carboxamide |
| A2435 | 1146, 1148 | | C | | | 3-(3-chloro-2-fluorophenyl)-4-(4-chloro-2-fluorophenyl)-4-cyano-N-{4-[(3-{[5-(4-{3-[4-cyano-3-(trifluoromethyl)phenyl]-5,5-dimethyl-4-oxo-2-sulfanylideneimidazolidin-1-yl}phenoxy)pentyl]oxy}propyl)carbamoyl]-2-methoxyphenyl}-5-(2,2-dimethylpropyl)pyrrolidine-2-carboxamide |
| A2720 | 1077 | | | A | | 3-(3-chloro-2-fluorophenyl)-4-(4-chloro-2-fluorophenyl)-4-cyano-5-(2,2-dimethylpropyl)-N-(2-methoxy-4-{[2-(2-{[(1,4-trans)-4-({4-[1-benzyl-5-(dimethylamino)-1H-pyrazol-4-yl]pyrimidin-2-yl}amino)cyclohexyl]oxy}ethoxy)ethyl]carbamoyl}phenyl)pyrrolidine-2-carboxamide |
| A2766 | 1121 | | | A | | 3-(3-chloro-2-fluorophenyl)-4-(4-chloro-2-fluorophenyl)-4-cyano-5-(2,2-dimethylpropyl)-N-[2-methoxy-5-({2-[2-(2-{[(1,4-trans)-4-({4-[1-benzyl-5-(dimethylamino)-1H-pyrazol-4-yl]pyrimidin-2-yl}amino)cyclohexyl]oxy}ethoxy)ethoxy]ethyl}carbamoyl)phenyl]pyrrolidine-2-carboxamide |
| A2790 | 1264 | | | | A | 3-(3-chloro-2-fluorophenyl)-4-(4-chloro-2-fluorophenyl)-4-cyano-N-[4-({1-[4-(3-{[(4,6-dimethyl-2-oxo-1,2-dihydropyridin-3-yl)methyl]carbamoyl}-5-[ethyl(oxan-4-yl)amino]-4-methylphenyl)phenyl]-1,4,7,10-tetraoxadodecan-12-yl}carbamoyl)-2-methoxyphenyl]-5-(2,2-dimethylpropyl)pyrrolidine-2-carboxamide |

-continued

| Example | Observed (m/z) from LC/MS | Degradation activity BRD4 | AR | JNK | EZH2 | ChemicalName |
|---|---|---|---|---|---|---|
| A2791 | 1165 | | | A | | 3-(3-chloro-2-fluorophenyl)-4-(4-chloro-2-fluorophenyl)-4-cyano-5-(2,2-dimethylpropyl)-N-[2-methoxy-4-({1-[(1,4-trans)-4-({4-[1-benzyl-5-(dimethylamino)-1H-pyrazol-4-yl]pyrimidin-2-yl}amino)cyclohexyl]-1,4,7,10-tetraoxadodecan-12-yl}carbamoyl)phenyl]pyrrolidine-2-carboxamide |
| A2792 | 1209 | | | A | | 3-(3-chloro-2-fluorophenyl)-4-(4-chloro-2-fluorophenyl)-4-cyano-5-(2,2-dimethylpropyl)-N-[2-methoxy-5-({1-[(1,4-trans)-4-({4-[1-benzyl-5-(dimethylamino)-1H-pyrazol-4-yl]pyrimidin-2-yl}amino)cyclohexyl]-1,4,7,10,13-pentaoxapentadecan-15-yl}carbamoyl)phenyl]pyrrolidine-2-carboxamide |
| A2844 | 1352 | | | | A | 3-(3-chloro-2-fluorophenyl)-4-(4-chloro-2-fluorophenyl)-4-cyano-N-[4-({1-[4-(3-{[(4,6-dimethyl-2-oxo-1,2-dihydropyridin-3-yl)methyl]carbamoyl}-5-[ethyl(oxan-4-yl)amino]-4-methylphenyl)phenyl]-1,4,7,10,13,16-hexaoxaoctadecan-18-yl}carbamoyl)-2-methoxyphenyl]-5-(2,2-dimethylpropyl)pyrrolidine-2-carboxamide |

What is claimed is:

1. A compound selected from the group consisting of:

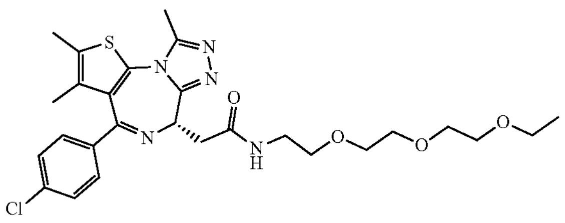

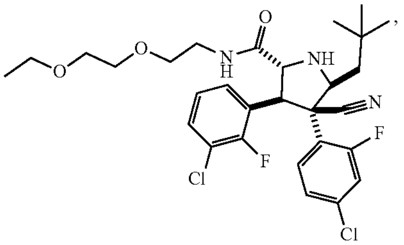

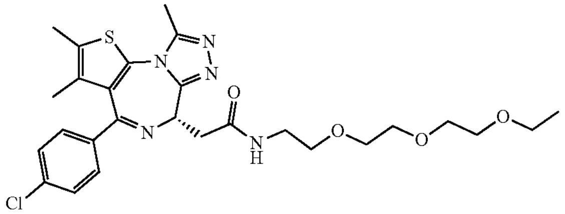

-continued

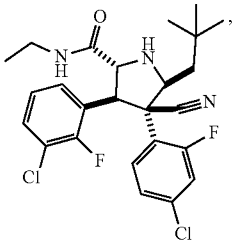

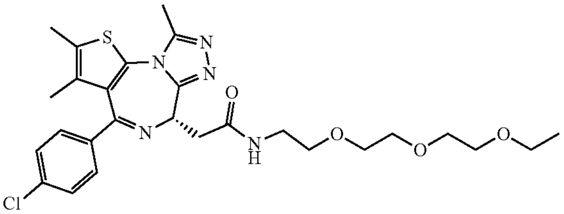

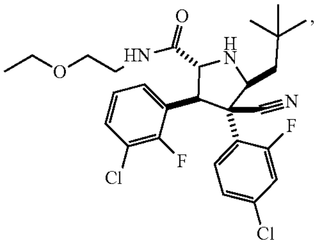

-continued
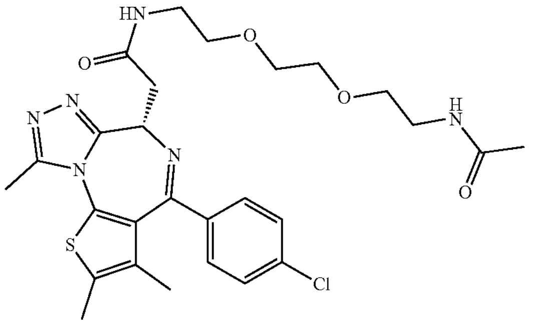
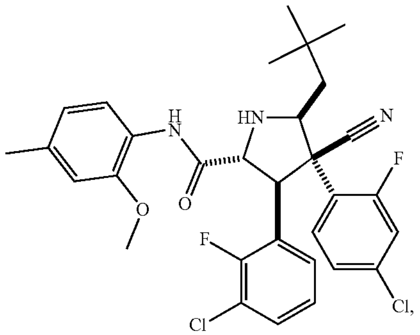
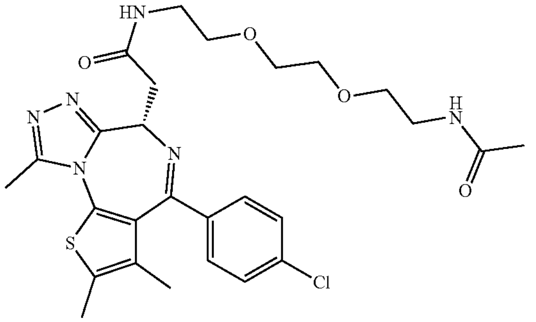
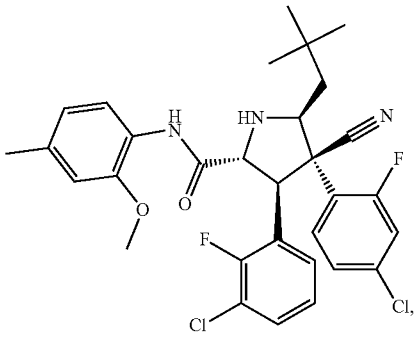
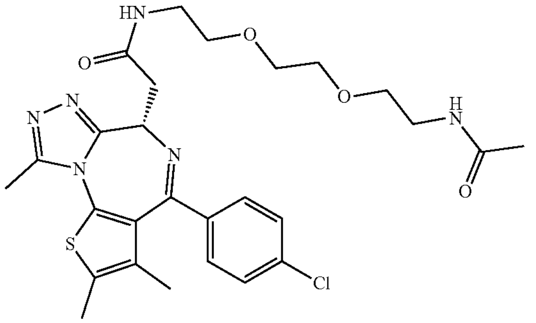
-continued
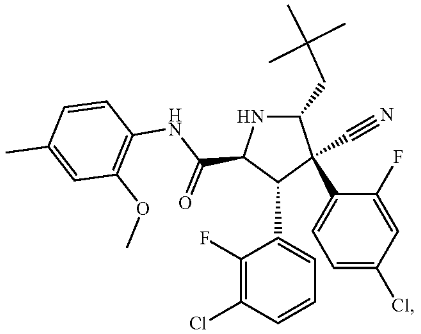
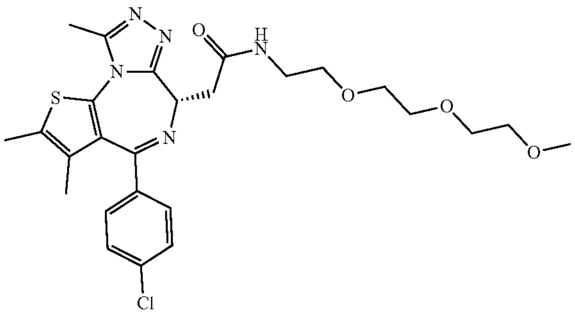
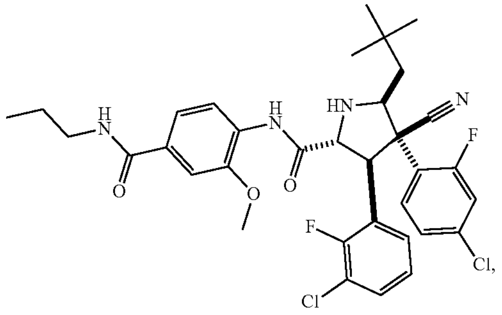
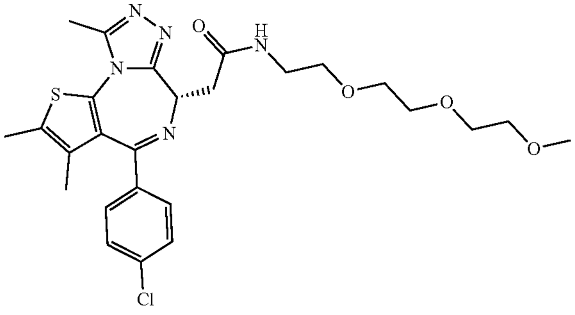
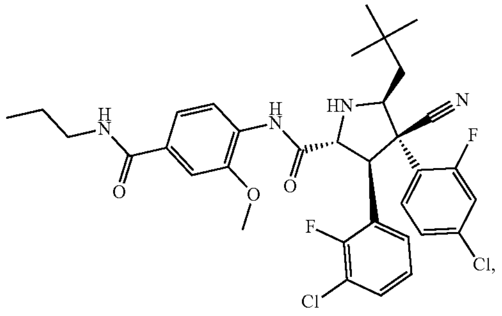

-continued
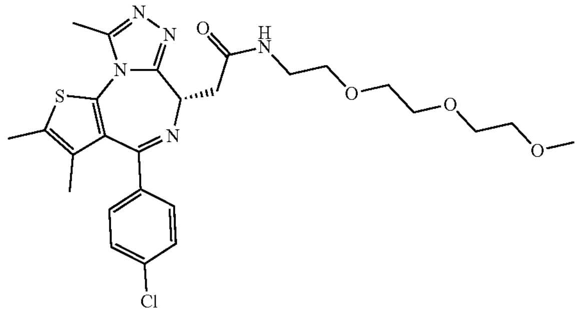
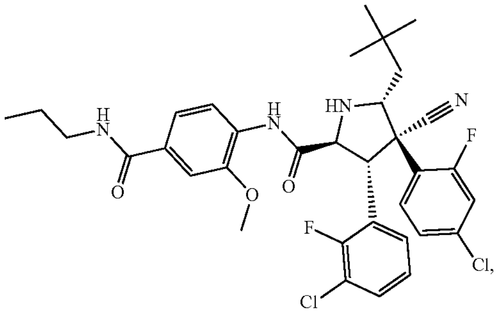
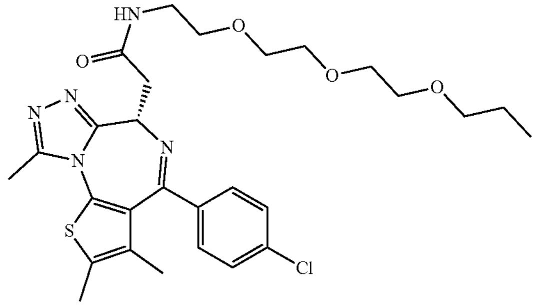
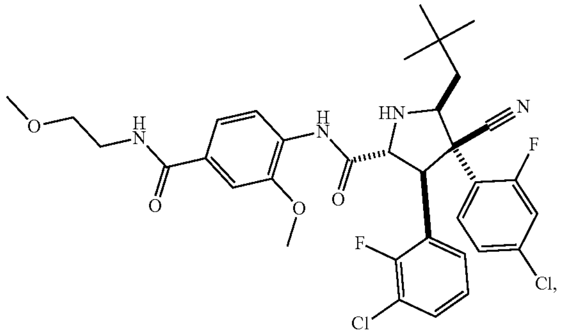
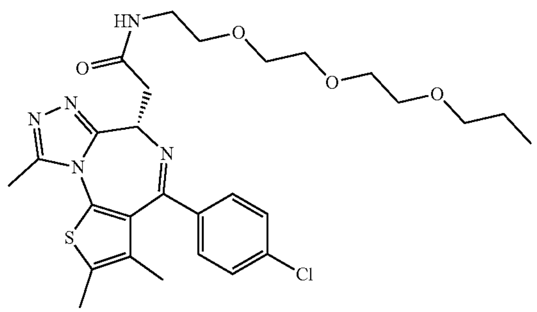
-continued
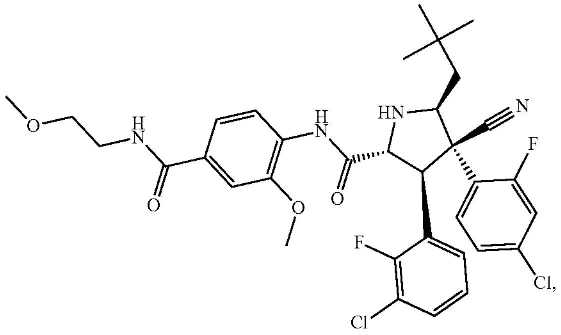
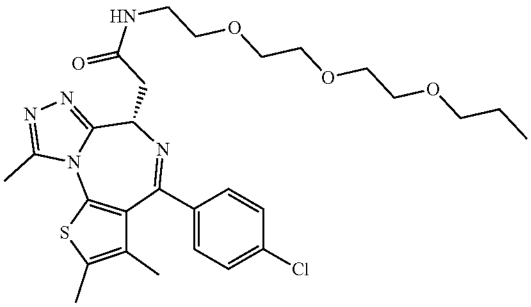
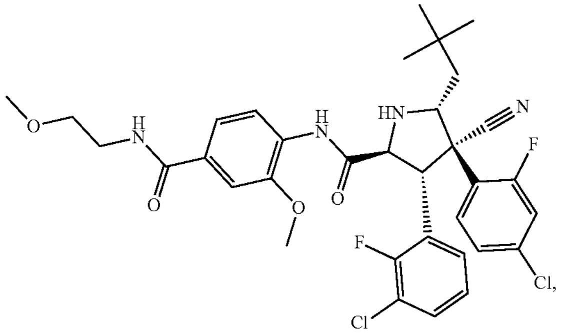
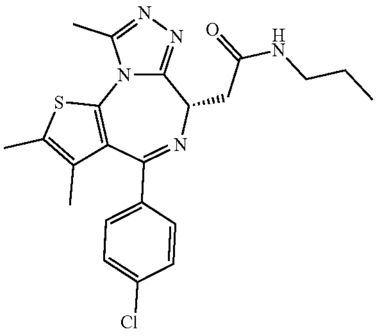
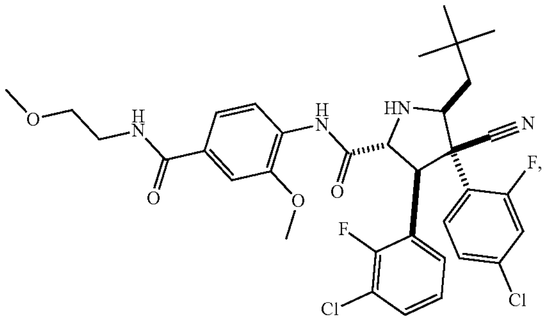

-continued

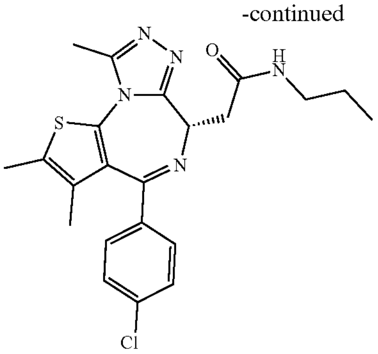

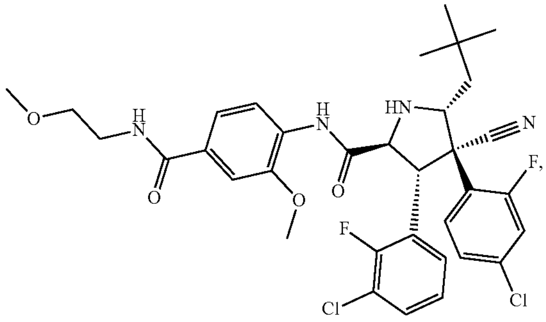

and

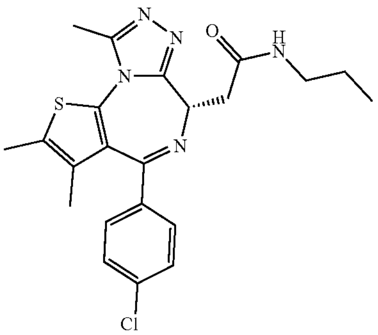

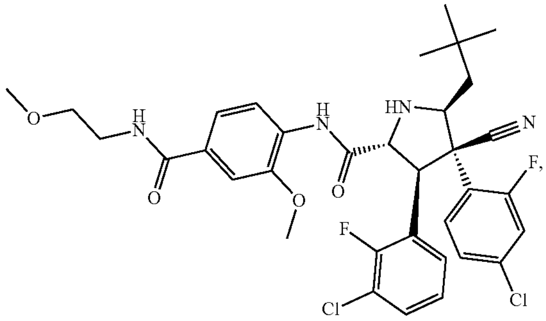

or a pharmaceutically acceptable salt thereof.

2. A pharmaceutical composition comprising an effective amount of a compound of claim 1 and a pharmaceutically acceptable carrier, additive, and/or excipient.

3. The pharmaceutical composition of 2, further comprising an additional bioactive agent, wherein the additional bioactive agent is an anticancer agent.

4. The composition according to 2, wherein said anticancer agent is selected from the group consisting of everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, an mTORC1/2 inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, dasatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl) ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolyl -quinolone, vatalanib, AG-013736, AVE-0005, the acetate salt of [D-Ser (t-Bu)$^6$, Azgly$^{10}$](pyro-Glu-His-Trp-Ser-Tyr-D-Ser(t-Bu)-Leu-Arg-Pro-Azgly-NH$_2$ acetate $[C_{59}H_{84}N_{18}O_4—(C_2H_4O_2)_X$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, Bacillus Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevac, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxy-ethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

* * * * *